(12) United States Patent
Carver, III et al.

(10) Patent No.: US 12,178,866 B2
(45) Date of Patent: *Dec. 31, 2024

(54) POLYPEPTIDES OF FUSOBACTERIUM AND METHODS OF USE

(71) Applicant: VAXXINOVA US, INC., Willmar, MN (US)

(72) Inventors: Charles Nelson Carver, III, Spicer, MN (US); Daryll A. Emery, New London, MN (US)

(73) Assignee: Vaxxinova US, Inc., Willmar, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/144,568

(22) Filed: May 8, 2023

(65) Prior Publication Data
US 2023/0338499 A1 Oct. 26, 2023

Related U.S. Application Data

(63) Continuation of application No. 17/888,916, filed on Aug. 16, 2022, which is a continuation of application No. 16/921,243, filed on Jul. 6, 2020, now Pat. No. 11,439,699, which is a continuation of application No. 15/774,168, filed as application No. PCT/US2016/061108 on Nov. 9, 2016, now Pat. No. 11,235,049.

(60) Provisional application No. 62/252,951, filed on Nov. 9, 2015.

(51) Int. Cl.
| | | |
|---|---|---|
| *A61K 39/02* | (2006.01) | |
| *A61K 39/114* | (2006.01) | |
| *A61K 39/39* | (2006.01) | |
| *A61P 31/04* | (2006.01) | |
| *C07K 14/195* | (2006.01) | |
| *G01N 33/569* | (2006.01) | |

(52) U.S. Cl.
CPC ............ *A61K 39/114* (2013.01); *A61K 39/39* (2013.01); *A61P 31/04* (2018.01); *C07K 14/195* (2013.01); *G01N 33/56911* (2013.01); *C12N 2500/24* (2013.01)

(58) Field of Classification Search
None
See application file for complete search history.

(56) References Cited

U.S. PATENT DOCUMENTS

| | | |
|---|---|---|
| 5,455,034 A | 10/1995 | Nagaraja et al. |
| 5,538,733 A | 7/1996 | Emery et al. |
| 6,027,736 A | 2/2000 | Emery et al. |
| 6,241,992 B1 | 6/2001 | Morck et al. |
| 6,632,439 B2 | 10/2003 | Liem et al. |
| 6,669,940 B2 | 12/2003 | Nagaraja et al. |
| 6,962,990 B1 | 11/2005 | Attarian et al. |
| 8,329,192 B2 | 12/2012 | Straub et al. |
| 9,308,247 B2 | 4/2016 | Narayanan et al. |
| 2002/0114817 A1 | 8/2002 | Liem et al. |
| 2003/0206922 A1 | 11/2003 | Emery |
| 2003/0211118 A1 | 11/2003 | Emery |
| 2004/0037851 A1 | 2/2004 | Liem et al. |
| 2004/0047871 A1 | 3/2004 | Nagaraja et al. |
| 2004/0197350 A1 | 10/2004 | Emery |
| 2004/0197869 A1 | 10/2004 | Emery |
| 2004/0265329 A1 | 12/2004 | Emery |
| 2005/0095682 A1 | 5/2005 | Straub et al. |
| 2005/0186217 A1 | 8/2005 | Emery et al. |
| 2006/0024323 A1 | 2/2006 | Emery et al. |
| 2006/0083753 A1 | 4/2006 | Straub et al. |

FOREIGN PATENT DOCUMENTS

| | | |
|---|---|---|
| WO | 1996/001620 | 1/1996 |
| WO | 2001/037810 | 5/2001 |
| WO | 2006/026373 | 3/2006 |
| WO | 2006/079076 | 7/2006 |
| WO | 2014/084964 | 6/2014 |

OTHER PUBLICATIONS

Ward et al (Submitted Feb. 2009; EMBL/Genbank databases; Accession No. E5BGP3_9FUSO).*
Oliw E.H. (Submitted (Jan. 2016) to the EMBL/GenBank/DDBJ databases. Accession No. A0A133NK58).*
Rae, "Injection Site Reactions," undated. Retrieved from internet Jun. 25, 2018. Online: animal.ifas.ufl.edu/beef_extension/bcsc/1994/docs/rae.pdf.
Rogers, "An aminopeptidase nutritionally important to Fusobacterium nucleatum," 1998 Microbiology, 144:1807-1813.
Rudinger et al. (Jun. 1976. Peptide Hormones. Biol. Council. pp. 5-7).
Saginala, "Effect of Fusobacterium necrophorum leukotoxoid vaccine on susceptibility to experimentally induced liver abscesses in cattle" Apr. 1997 J. Anim. Sci., 75, 1160-1166.
Smith, "Pathogenicity of Fusobacterium necrophorum strains from man and animals" Jun. 1993 Epidemiol Infect., 110(3):499-506.
Summons to Attend Oral Proceedings for European Application No. 16798901.1-1111 dated Oct. 19, 2022 (9 pages).
Tan, "Biological and biochemical characterization of Fusobacterium necrophorum leukotoxin" Apr. 1994 Am. J. Vet. Res., 55:515.
Tan, "Factors affecting the leukotoxin activity of Fusobacterium necrophorum," Vet. Microbial., Jul. 1992; 32(1):15-28.
Tan, "Fusobacterium necrophorum infections: virulence factors, pathogenic mechanism, and control measures" 1996 Vet Res. Commun. 20:113-140.
Tan, "Purification and quantification of Fusobacterium necrophorum leukotoxin by using monoclonal antibodies" Nov. 1994 Vet. Microbiol., 42:121-133.

(Continued)

*Primary Examiner* — Jennifer E Graser
(74) *Attorney, Agent, or Firm* — Mueting Raasch Group

(57) ABSTRACT

The present invention provides isolated polypeptides isolatable from a *Fusobacterium* spp. Also provided by the present invention are compositions that include one or more of the polypeptides, and methods for making and methods for using the polypeptides.

16 Claims, 49 Drawing Sheets

Specification includes a Sequence Listing.

(56) References Cited

OTHER PUBLICATIONS

Tatusova, "Blast 2 Sequences, a new tool for comparing protein and nucleotide sequences" 1999 FEMS Microbial Lett, 174:247-250.
Tatusova, "RefSeq microbial genomes database: new representation and annotation strategy" Dec. 2013 Nucleic Acids Res., 42:D553-D559.
Trivier, "Influence of iron depletion on growth kinetics, siderophore production, and protein expression of *Staphylococcus aureus*" Apr. 1995 FEMS Microbiol. Lett., 127:195-199.
Vasstrand, "Composition of Peptidoglycans in Bacteroidaceae: Determination and Distribution of Lanthionine," Infection and Immunity, Apr. 1982; 36(1):114-122.
Vasstrand, "Demonstration of Lanthionine as a Natural Constituent of the Peptidoglycan of Fusobacterium nucleatum," Sep. 1979 Infection and Immunity, 25(3):775-780.
Waldron, "How do bacterial cells ensure that metalloproteins get the correct metal?" 2009 Nature Reviews Microbiology, 7:25-35.
Ward et al "The Genome Sequence of *Fusobacterium* sp. 3_1_5R."; Submitted (Feb. 2009) to the EMBL/GenBank/DDBJ databases; Accession No. E5BGP3).
Watson, "Endotoxins and Their Detection with the Limulus and Amebocyte Lysate Test," John Wiley & Sons Inc., Alan R. Liss, Inc., New York NY: 1982. Cover page, title page and table of contents.
Benahmed et al., submitted Aug. 2013; EMBL/GenBank/DDBJ databases; Accession No. A0A017H636.
Durkin et al., submitted Jul. 2012 to the EMBL/GenBank/DDBJ databases; Accession No. J5W3E6.
"HMPREF1127_0553—Outer membrane efflux protein—Fusobacterium necrophorum subsp. *funduliforme* Fnf 1007—HMPREF1127 0553 gene & protein," UniprotKB, Oct. 31, 2012 (Oct. 31, 2012), pp. 1-4, XP055341300, Retrieved from the Intenet:http://www.uniprot.org/uniprot/J8W5G4 [retrieved on Feb. 1, 2017].
Abe, "Fusobacterium necrophorum infection in mice as a model for the study of liver abscess formation and induction of immunity" May 1976 Infect. Immun., 13(5): 1473-1478.
Afra, "Incidence, risk factors, and outcomes of Fusobacterium species *bacteremia*" 2013 Infectious Diseases, 13: 264.
Ainsworth, "Outer membrane proteins of Fusobacterium necrophorum biovars A, AB and B: their taxonomic relationship to F. necrophorum subspecies *necrophorum* and *F. necrophorum* subspecies funduliforme" Apr. 1993 J Vet Diagn Invest., 5:282-283.
Bachrach, "Identification of a Fusobacterium nucleatum 65 kDa Serine Protease," 2004 Oral Microbiolozy Immunolozy, 19:155-159.
Bakken, "Outer membrane proteins as major antigens" 1989 FEMS Microbiology Immunology, 47: 473-484.
Bakken, "Outer membrane proteins of Fusobacterium nucleatum Fev1" 1986 Journal of General Microbiology, 132: 1069-1078.
Bolstad, "Molecular characterization of a 40-kDa outer membrane protein, FomA, of Fusobacterium periodonticum and comparison with Fusobacterium nucleatum," Oct. 1995 Oral Microbiol Immunol., 10(5):257-264.
Bolstad, "Taxonomy, Biology, and Periodontal Aspects of Fusobacterium nucleatum," Jan. 1996 Clinical Microbiology Reviews, 9(1):55-71.
Chothia et al (The EMBO Journal, 1986, 5/4:823-26).
Conlon, "Evaluation of experimentally induced Fusobacterium necrophorum infections in mice" 1977 Infect. Immun, 15, 510-517.
Coyle, "Correlations between leukocidin production and virulence of two isolates of Fusobacterium necrophorum" 1979 Am. J Vet. Res., 40, 274-276.
E-Toxate® (Technical Bulletin No. 210). SIGMA Chemical Company, St. Louis, MO, 1998. pp. 1-4.
Emery, "Generation of immunity against Fusobacterium necrophorum in mice inoculated with extracts containing eukotoxin" Sep. 1986 Vet. Microbial, 12, 255-268.
Faraldo-Gomez, "Acquisition of Siderophores in Gram-Negative Bacteria," Feb. 2003 Nature Reviews Molecular Cell Biology, 4: 105-116.

Garcia, "Intraperitoneal immunization against necrobacillosis in experimental animals" 1978 Can. J Comp. Med, 42, 121-127.
Greenspan et al (Nature Biotechnology 7: 936-937, 1999).
Haake, "Cloning and expression of FOMA, the Major Outer-Membrane Protein Gene from Fusobacterium Nucleatum T18" Jan. 1997 Arch Oral Biol., 42(1): 19-24.
Harlow, Antibodies, A Laboratory Manual, Cold Spring Harbor Laboratory, Cold Spring Harbor, New York, NY: 1988. Cover page, publisher's page, and Chapter 5. 94 pages.
Hauptmeier, "Footrot In Beef Cattle," Iowa Beef Center, Mar. 1997, 2 pgs. Online at http:www.ioawbeef.org/Publications.footrot.pdf.
Heinrichs, "Identification and Characterization of SirA, an Iron-Regulated Protein from *Staphylococcus aureus*" 1999 J Bacterial., 181, 1436-1443.
Hussain, "A Lithium Chloride-Extracted, Broad-Spectrum-Adhesive 42-Kilodalton Protein of *Staphylococcus epidermidis* Is Ornithine Carbamoyltransferase" 1999 Infect. Immun., 67:6688-6690.
International Patent Application No. PCT/US2016/061108, filed Nov. 9, 2016; International Preliminary Report on Patentability issued May 24, 2018; 7 pages.
International Patent Application No. PCT/US2016/061108, filed Nov. 9, 2016; International Search Report/ Written Opinion issued Feb. 14, 2017; 15 pages.
International Search Report and Written Opinion for PCT application No. PCT/US2005/030290, Dec. 20, 2005; 6 pages.
Kapatral, "Genome Analysis of *F. nucleatum* sub spp *vincentii* and Its Comparison With the Genome of F. nucleatum ATCC 25586" 2003 Genome Res., 13:1180-1189.
Kapatral, "Genome sequence and analysis of the oral bacterium *Fusobacterium nucleatum* strain ATCC 25586" 2002 J. Bacteriol., 184:2005-2018.
Keler, "Metachromatic assay for the quantitative determination of bacterial endotoxins" 1986 Analyt. Biochem., 156:189.
Kittichotirat et al "Comparative genomics of Fusobacterium necrophorum wild isolates"; Submitted (Jan. 2014) to the EMBL/GenBank/DDBJ databases; Accession Nos. A0A064A2K7, A0A0E2V0S3, A0A064AI82 and A0A064AI94).
Kleivdal, "Identification of positively charged residues of FomA porin of Fusobacterium nucleatum which are important for pore function," Mar. 1999 Eur. J. Biochem., 260(3):818-824.
Kleivdal, "The Fusobacterium nucleatum major outer-membrane protein (FomA) forms trimeric, water-filled channels in lipid bilayer membranes," Oct. 1995 Eur. J. Biochem., 233(1):310-316.
Kleivdal, "Topological investigations of the FomA porin from Fusobacterium nucleatum and identification of the constriction loop L6," Apr. 2001 Microbiology, 147(4): 1059-1067.
Kumar, "New bacterial species associated with chronic periodontitis" May 2003, J Dent Res., 82(5):338-44.
Langworth, "Fusobacterium necrophorum: its characteristics and role as an animal pathogen" 1977 Bacteriol. Rev., 41:373-390.
Lechtenberg, "Hepatic ultrasonography and blood changes in cattle with experimentally induced hepatic abscesses" 1991 Am J Vet Res., 52(6)803-9.
Machado, "Subcutaneous immunization with inactivated bacterial components and purified protein of *Escherichia coli*, Fusobacterium necrophorum and Trueperella pyogenes prevents puerperal metritis in Holstein dairy cows" Mar. 2014 PLoS One, 9(3):e91734.
Mandell (Eds.), Principles and Practice of Infectious Diseases, Second Edition, John Wiley and Sons, New York, 1979, Title page, Publication pages and pp. 1377-1378.
Mikayama et al. (Nov. 1993. Proc.Natl.Acad.Sci. USA, vol. 90: 10056-10060).
Munson, "Molecular and cultural analysis of the microflora associated with endodontic infections" 2002 J. Dent Res., 81:761.
Nagaoka, "Establishment of a new murine model of liver abscess induced by Fusobacterium necrophorum injected Into the caudal vein" 2013 J Med Micriobiol., 62(11):1755-1759.
Narayanan, "Cloning, Sequencing, and Expression of the Leukotoxin Gene from Fusobacterium necrophorum" 2001 Infect. Immun., 69:5447-5455.

(56) References Cited

OTHER PUBLICATIONS

Narayanan, "Fusobacterium necrophorum Leukotoxin Induces Activation and Apoptosis of Bovine Leukocytes" 2002 Infect. Immun., 70, 4609-4620.

Narayanan, "Immunogenicity and protective effects of truncated recombinant leukotoxin proteins of Fusobacterium hecrophorum in mice" 2003 Vet. Micro., 93:335-347.

Nikaido, "Outer membrane" in: Neidhardt (Ed.), *Escherichia coli and Salmonella*:cellular and molecular biology. 1987. Cover page, publisher's page and Chapter 5; 35 pages.

Paster, "The breadth of bacterial diversity in the human periodontal pocket and other oral sites" 2006 Periodontology 2000, 42:80.

Porcheron, "Iron, copper, zinc, and manganese transport and regulation in pathogenic Enterobacteria: correlations between strains, site of infection and the relative importance of the different metal transport systems for virulence" Dec. 2013 Frontiers in Cellular and Infection Microbiology 3: 172-194.

Product data sheet: "Dairy Quality University - Volar Use in a Dairy Herd With Footrot" datasheet [online]. Bayer Corporation, Shawnee Mission, KS, 1996 [retrieved on 2004-07-08]. Retrieved from the Internet: http://dqacenter.org/university/moreinfo/rh48.htm; 2 pgs.

Product data sheet: "Merck Vet. Edition—Liver Abscesses In Cattle: Introduction" datasheet [online]. Merck & Co., Inc., Whitehouse Station, New Jersey, 2003 [retrieved on Jun. 24, 2004]. Retrieved from the Internet: http://www.merckvetmanual.com/mvm/index.jsp?cfile=htm/bc/23500.htm; 2 pgs.

Puntervoll, "Structural characterization of the fusobacterial non-specific porin FomA suggests a 14-stranded topology, unlike the classical porins," Nov. 2002 Microbiology, 148(11):3395-3403.

Quinde-Axtell, "Phenolic Compounds of Barley Grain and Their Implication in Food Product Discoloration" 2006 J. Azric. Food Chem., 54(26):9978-9984.

\* cited by examiner

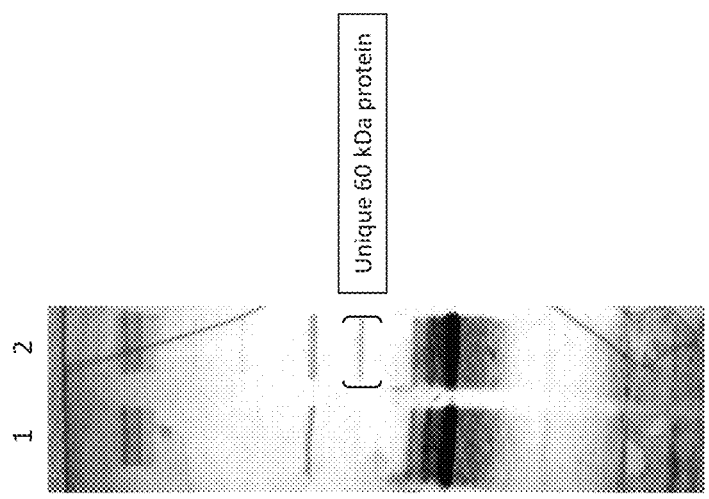
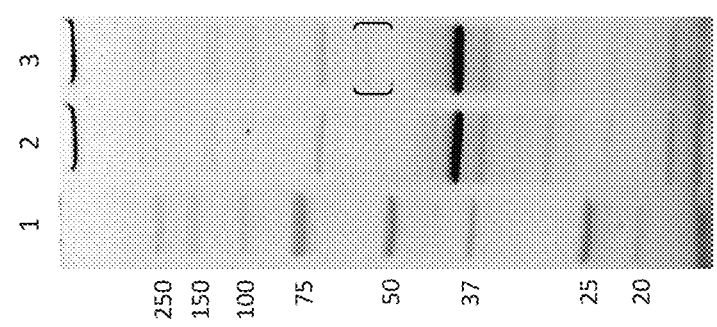

FIG. 14

| *Fusobacterium necrophorum* 1694 FQ (rCopper) Gene Sequence (SEQ ID NO:1) |
|---|
| atgaaaaagctatggatattattttttcctgctggggagtgttgcttttggaagagaagttactttggaagaagcgattcaagc gtcaatggagaatagcaaggcggtcaaaatttcagataagcagttagaaatttcaaaactaaaaatgaatcaggcaattaaaa agcactgccaagcgtagtgtacagtgccaactatcaacgtggagaatatgagagaaatatttataagaataaatcttctatg gaatcggaaaaaggcggttacaaacaatcgattacaatcagccaacctattttcaaggaggagccattcttgccggaattca agggcaaaagcctataaaaccatagcagatttgtcctatgttcaagagacactaaatactcgtttgaagacgattcgaactt tttcgaatattgtcaacagcaaaagaaatttacaagctttggaatattccgagaaacaattgcaaaatcgatataaaaagcag gaagctcaattggagttgcgactgattacgaagacggatttattgaaaacggaatactctttattggaagtacaatctttaat ttccaaagcgaaaagtaatattgaagtacagacggaagatttaaaatttcaaatgggagtggacaaaaaagaagcattggaag tcaaggaatttatcgttcccaatcatttgacagaacgtattacatttgaaaaagataaagagagggcattggaatccagtatt caggctttgattgcaaaatctcaagtgaagatagcaaaggcacaggaaacggcagcactgggaaatatgcttcctaaggtaaa tgcctttgtgagttatggagtggcttcggagagaacacattggaaacaaacgaaagaagatgcggaatggatgggaggtttgt ctgtttcttggaatgtctttctttgggagtgactatgatgcttatcaaattgcaaaattggaaaaagagtccaaagagtta tcagaaacgacagctcaggacaatatagctttgagccttaagacagcttatttggaattgcaagattggaaattttaagaga gtccagaaagagaggattggaagcggcagaattgaattttacaatggatcaagaaaaatttgatgcaggcttgctttccacag tggattatttatcatcggaaacacaattgcgggaagcaagagtgaattattaccaagcagaattagattattactatgcttt gaatattatagatcgttgttagtataa |

| *Fusobacterium necrophorum* 1694 FQ (rCopper) amino acid sequence (SEQ ID NO:2) |
|---|
| MKKLWILFFLL

FIG. 15

| *Fusobacterium necrophorum* 1694 FT (rZinc) Gene Sequence (SEQ ID NO:3) |
|---|
| atgaaaaaagtggtatttgggatttacagtatcttaatgtcctctgctatgcttggagcagaaattgatcttggaacacagaa
tatctattcggaaaccggatttgaaacgagtcttcgaagctctgtttcttcttatatcgttacttcaaaagaaatcaaag
aaaaacattataccccgtgtttctgaaattttgagagatattccgcatatctacatcggtcccggtggcagtgtagatatgcgt
ggtcagggaagtgctcatgccagaacaacagttcaactgttaattgatggagttcctgccaattttttggatacttcccacat
caatcttcctatcgatactttaaatccagaagatattaagagaattgaagtcatccctggaggaggagctgttttatatggaa
gtggaacttccggaggagtgatcaacatcattaccaaaaaatacacgggaaactatgcaaaggcaagctatcaaataggaagc
tatcacaatcataaatatgacgtagctgccggaacttctttgggaaattttgacattaacctaagttattcaaaaaataatag
ggatggatatcgtaaaaaagcttttccgattccgatttcttctccggaaaattacgttatcacttcaatccacagacagtc
ttgaattcaaatatagctattttgataataagttcagaggtgttaaatccctaaccagagaacaagtcgagaaagatcgaagg
caaagtggtcttctcctgaagacaatttgaaaaataccatccgaaaagaagaatggaatttaacttacgatgcaaaatggac
aagctggctggaacacaaatccaatcttttctatcagtccacagaaataaaatctagtgaatatgaagatgctcttcctttct
atcaatatcaaatttcttcttatcaaaaaatgcttactatgccagggattcctcctatgatgcaagcacaattgaaaaagcag
ataaaagccctacaaaatttgataacgagtaatccaaggatggaattacatcaaggaagtcgtttcaaagatcaaaaattcgg
ttttaaaatgaagaataaaatttaagtatggagaaaatagtgattttatttaggtttgggatacattcacaacaaaatggatc
gagattcttgggcttatacgaaaaatacgcaaacgaatcaaacaatagcaactcttacaaatactaaaattccttaaatag
aaaacattcgaaattttcggattaaatacctatcgtcataatattgggaatttgttcaggcttacgctttgaaaagcgaa
atatatatggaaaaagacaatataaaatctggatatcctttaaagatcgtagcatgaataatgttgcggcaaatctggctg
tcaattatctctattccgatacaggaaatgtctatgtaaaatatgaagaggatttacttctcctgctcctgcacagttaatg
gataaaatcagaaaaggaggagtgaacgattatgtcaataatgattttaaaatctgaaaaatcaaactcctttgaagttggatg
gaatgactatctcttccattctttagtcagtgctgatgttttttcagtgaaacgaaagatgaaatttctaccatattctcgg
gagggcatgggacaacattcagcaatttgaaccttggtcaaacgaaacgatatggttttgatctaaaagccagtcaagttttt
gaaaagtggacattctcggaagcttacagttatatccatgcaaaaatcatgaaagataaaacaaaggcttatgaaggaaaata
tatcagttatgttccaaggcataaatttctttgaatgctgattatgcaatcactccaaaatggactcttgggggagaatatc
aatacagttcttccgtatatctggacaatgcaaataaaaatggaaaagatggagcgagatctgttttaatcttcaaacctct
tatgagttcaattcacattttttctatctatgcaggaattaaaaatgtgttaaatcataagtattatgaatctgtcagtgcagg
ttccagtcaaaagtattatagtccggctccggaaagaaattactatgccggattccgttatcaatttaa |

| *Fusobacterium necrophorum* 1694 FT (rZ

FIG. 16

| *Fusobacterium necrophorum* 1694 FN rHemin TonB-dependent receptor. Gene Sequence (SEQ ID NO:5) |
|---|
| atgaaaaaaattttgtttttagttggggctttgttttctatttctgcttttgcggagcagactatagaattaggaagtacttc<br>cataaaaggaaatagaaagacagattatacttttaacaccaaaagagtataaaaatacatataccattacgcaagaaaaaattc<br>aagaacgaaactataaaaatgtagaagatgttttacgagatgctcctggtattgttgttcaaaatacagcatttggacctcga<br>attgatatgagagggagtggggagaaatctttgtcaagagtaaaggttcttgtggatggaattagtatcaatcctacagagga<br>aacgatggcgagtttaccaattaattcgattcccattgaaagtgttaaaaagattgaaattattccaggaggaggagctactt<br>tatatggaagtggctctgtaggaggagttgtcagtatttctacgaattccaatgtaacgaagaataatttctttatggatttg<br>aactatggttcttttgataatagaaactttggattgcaggaggatataatgtaagtgacaaattatatgtgaactatggttt<br>taattatttgaacagtgaagattatagagaacatgaggagaaggaaaataaaatttatttgttgggttttgactataaaatca<br>acccaaagaatcgtttcagagtacaaacaagatatagtaaaatgaagcatgatggaagtaactggctaagtcaggaggaatta<br>aagatttcgcgaaagaaagctggattgaatttggacctagatacaacagataaaagttacacttttcgattatgagtatagatc<br>tagtcaaaatttaacgctagccgctactgcctataaacaacaacaagatagagacattacaaacgatgatattcgagatattg<br>aaattatagcttctaaccgaaactacactgatttaaaagaatatatgactttttatgatgtaaaatctactttaaaggcaaag<br>tttaaagaaaaaaatatggactaaaattaaaaggaaaatacgagtatggaagaggggaagttatttcgggtatgattatca<br>agattctaacaataaaagaaactctcttgtacaatcagagactttaaaaacttataatgacaaaatcagtgacttaaatttat<br>ctcctgaagatagaaagccaatcatcaatagagtcaacattgatttaacaaagaaatctcacggttttttatgtgtttaataag<br>ttagaattaacagataaatggattttacgacaggatttagaaccgaaattacaaaatataatggatatcgaaaaatgggcc<br>aaataccatgccaatcgtctctccgaaagtaaatgaaatcagaacagacgagaagatgacaaactatgcgggagaagcaggaa<br>tgttgtacaagtatagtgacacaggaagagcctttgttcgatatgaaagaggatttgtaacaccgtttgcaaaccagttgaca<br>gataaaattcatgatacaaaattaaaaagtccagctggatttttcaccccaccaattgtgaacgtttcttctttgtatgtagc<br>aaataacttgaaatcagaaatcacagatactatagaagtggggattccgagattatattttaattccttaatcagtgcttcct<br>tctttgcaacggacactaccgatgaaattacacttatcagttccggaattacgaatccggcagtcaatagatggaaatttcga<br>aatataggaaaacaagaagattaggaattgaattggaacggaacaaaaatggggaaaatttgatttcagtcaatcgctaac<br>ttttgtagatacaaaagtattaaaaacagatgcagaatccagaattttttagaggagataaggttccaatggttcctagaatca<br>aagcaacattaggattaaaaatataatgtgacagataacttggctttgattggaacttatacgtatttgagtaaacgggaaacc<br>agagaattggatgaaaaagataaggtatataaacatactatcaaaggatatggaacagcggatttggaatatattgtataaggt<br>ggacaagtattcaaactttaaagtgggggcaaagaatatttttggaaagaaatataatttacgagagacaaaattagaagcat<br>tgccagcaccggaaagaaattactatttagaatttaatgtcaaatttaactaa |
| *Fusobacterium necrophorum* 1694 FN rHemin TonB-dependent receptor amino acid sequence (SEQ ID NO:6) |
| MKKILFLVGALFSISAFAEQTIELGSTSIKGNRKTDYTLTPKEYKNTYTITQEKIQERNYKNVEDVLRDAPGIVVQNTAFGPR<br>IDMRGSGEKSLSRVKVLVDGISINPTEETMASLPINSIPIESVKKIEIIPGGGATLYGSGSVGGVVSISTNSNVTKNNFFMDL<br>NYGSFDNRNFGFAGGYNVSDKLYVNYGFNYLNSEDYREHEEKENKIYLLGFDYKINPKNRFVQTRYSKMKHDGSNWLSQEEL<br>KISRKKAGLNLDLDTTDKSYTFDYEYRSSQNLTLAATAYKQQQDRDITTDDIRDIEIIASNRNYTDLKEYMTFYDVKSTLKAK<br>FKEKKYGLKLKGKYEYGRGEVIFGYDYQDSNNKRNSLVQSETLKTYNDKISDLNLSPEDRKFIINRVNIDLTKKSHGFYVFNK<br>LELTDKWDFTTGFRTEITKYNGYRKNGFNTMPIVSPKVNEIRTDEKMTNYAGEAGMLYKYSDTGRAFVRYERGFVTPFANQLT<br>DKIHDTKLKSPAGFFTPPIVNVSSLYVANNLKSEITDTIEVGFRDYIFNSLISASFFATDTTDEITLISSGITNPAVNRWKFR<br>NIGKTRRLGIELEAEQKWGKFDFSQSLTFVDTKVLKTDAESPIFRGDKVPMVPRIKATLGLKYNVTDNLALIGTYTYLSKRET<br>RELDEKDKVYRHTIKGYGTADLGILYKVDKYSNFKVGAKNIFGKKYNLRETKLEALPAPERNYYLEFNVKFN |

FIG. 17

| Fusobacterium necrophorum 1694 Hemin receptor Gene Sequence (SEQ ID NO:7) |
|---|
| atgaaaacaaacatttattttaacatttttattttgtaatactgtttcttttgcagaaacaaccattcatctaccagaaag<br>caatattcaatccgattatgtggaaatcaataagatgaaaaatctcaaaaatataattgtgattgaaaaaaaagaaattcagg<br>agaaagggtatacaaatttatccgccgtattgcaagatatcccaaatattcatgtcggaacaaccggttggggagaaattgat<br>attcgaggtcaggagaaggaaatgcagcaaaaatttgcaggtgttaatcgatggagctccgattaccactttggtaaacca<br>tcctttgcaaacgaattacgacgtagttccggtagaaaatattgaaagaattgaaattattccggaggaggttccatcattt<br>atggttccgggacagctggaggagttatcaatattactaccaatctaagtcgtttacacagaccaataaacattgtagaagtt<br>tccgccggaaccggtggagaaaaatataatcttgcctttggtcatagagttactaagaaactaaacgtacaattatcatatct<br>tcgaataatcagaatctatatttcaaagatacctatcgacatagcaactatttcacggcaggattacattatcaaatctccg<br>acagacaaaatttgtctctgcgatatagtactctcacagaagacggaaaattgttcgaaatattttatataaaaaattgaat<br>caggatggaaaaaattatcgaccggaaaagaaaaagtaaccgccggtttggacaaagacggacataaaattgaaaaatggat<br>ggacggatattccaatgccaagagaaatatggacagcttcaatctaagttatcgtttccgacttggggaaaactcaacttatc<br>ttatggatgccttttacaataagggacatttttccaatatggctttgagtgatcagaccatgtatcatcatacctacggagtt<br>aaaaataaattggactttttctatgcaaagaatagtgcttttgacggaagtagcttgttgattggattggattcttaccaaca<br>ggatgcaaaattggaatacaatgattacaaattttagattacaaaagaaaacttattacatcagacgcgtttccttttaaat<br>ataaaaagaaaaccaatgcttttatctattgaatactctaaaatatggaaattgggagtcttcacaagaattcgaagagat<br>tatacctattggcatttgacaaggttacttccaaaaatgaaggaaaagaaaaccagccatcgtcacaataccaattacgaatt<br>cagtcttgcctataaatatcgtgataccggaaggatctatgctcgttacgaagaggctttacttcccctgatggtctagaaa<br>ttacagatgactttccaaacaagacattaagcctacaaaaggaaaagatgaaatctatgacttatatgaaatcggttggaga<br>gaatacttcggatttactaccataaaacttaactgcattctattcttttacagacaatgaaatgagccgaaattatgttttcaa<br>tgaactaggattcggaaggaaaaccatcaacattctaaaaaccaaagaaaaggaatagaattaagtctattccaaaaattag<br>gaaatttggaattaaaagaaagttacgcttatttaaaaggaaaaagaacttacaacggaaaagaatctcaattcttagatccg<br>gatgactatgtagattggtccaatacgggacttcccaaagtcccaaaacagtctctaaccttggaagcaaaatatcatttttag<br>cccaaaaatttcagtcggtttacgatataaatacaatggaaaatatagtaatttcagtgatttaagacaaaagaagaagaag<br>gatacatcaaatctcattctgtaacggacttatctttacattatcaaaatgaaaaaggatttcatctgtatggaggaatcaat<br>aatgtattcaatgaaaaatattttgaatataccggttctaaaatgtataccatcatccctgcggaagaaagaacattcttttgt<br>gggagcgaaatatcaattttaa |
| Fusobacterium necrophorum 1694 Hemin receptor amino acid sequence (SEQ ID NO:8) |
| MKTNILFLTFLFCNTVSFAETTIHLPESNIQSDYVEINKMKNLKNIIVIEKKEIQEKGYTNLSAVLQDIPNIHVGTTGWGEID<br>IRGQGEGNAAKNLQVLIDGAPITTLVNHPLQTNYDVVPVENIERIEIIPGGGSIIYGSGTAGGVINITTNLSRLHRPINIVEV<br>SAGTGGEKYNLAFGHRVTKKLNVQLSYLRNNQNLYFKDTYRHSNYFTAGLHYQISDRQNLSLRYSTLTEDGKFVRNILYKKLN<br>QDGKNYRPEKKKVTAGLDKDGHKIEKWMDGYSNAKRNMDSFNLSYRFRLGENSTYLMDAFYNKGHFSNMALSDQTMYHHTYGV<br>KNKLDFFYAKNSAFDGSSLLIGLDSYQQDAKLEYNDYKFLDYKKKTYYIRPLSFKYKKKTNAFYLLNTLKYGNWESSQGIRRD<br>YTYWHFDKVTSKNEGKETSHRHNTNYEFSLAYKYRDTGRIYARYERGFTSPDGLEITDDFSKQDIKPTKGKDEIYDLYEIGWR<br>EYFGFTTINLTAFYSFTDNEMSRNYVFNELGFSPKTINILKTKRKGIELSLFQKLGNLELKESYAYLKGKRTYNGKESQFLDP<br>DDYVDWSNTGLPKVPKQSLTLEAKYHFSPKISVGLRYKYNGKYSNFSDLRQKEEEGYIKSHSVTDLSLHYQNEKGFHLYGGIN<br>NVFNEKYFEYTGSKMYTIIPAEERTFFVGAKYQF |

FIG. 18

| |
|---|
| *Fusobacterium necrophorum* 1694 TonB-dependent receptor Gene Sequence (SEQ ID NO:9) |
| atgaaaaagtactttgttgcagtgtcgatttccttagcactttcgtatcagattttgcagaggaaaatcctgttatcaaatt aaatgaaactgttataacttctgaaagttttggaacaaatattttgagaactccaaagaatattacagtaattactgcaagaa atattaaaattcaaggagcaaagaatatagaagatgctttaagaggggttgcaggcttaactgcttataataatatgggcggc tctgatcccaaaatttctcttcgaggaatggctccgggaaaagaagaacaaagtattctgtttttattagatggaatcccta taacagtacagtagatactggagcggtaaatctgaatttgattcctattgacatcgtagagagaattgaaattattcctaatg ggggaaacgtagtttatggagaaggagctgtcggaggagttatcaatattatcactaaaaaaggaaaaaataaaaaatattac ggttcttttcaatagatggaggatcttatgatttaaaggagtataaggtaaatttggggagcaacctgacggagcagcttc tctagatttgaaatataataatagaaggcaaaaaattaccgggatcaccacacaagagacattgaatatatcaatttgggaa tggaatataaagaaaatgagcacagtatttatttcgatttcagaattcagaaacagaatatcgttctcctggttatctgaca aagaaacaaatagaagaggtaagattaaaaaatcaacaggaaatataaagggaaaagaaaaattaagaatttaccgtgcaaa atacgagggaaatgggctaaaaatttatttttaatattgcaggagatttaaagataaattatataagtccattgatgaaa aaacaaataccgtcagtaccataagagatacggaatcttttacatcagtccacaaatcaaatatcaatatatgccgaattct tactttatactaggaggagatttcctgaaagggaaatcaaaatatagatataaaagacattaaaagcattaaaaaaaatcaagt atctgtcggagtgtttcttaccaataataaaatgggaaaatttatatttacacagggtatcgacatcaaaaatcaagt atgatgtaaaggataagttgtatccttcccaaaccataaacaaaaattctattggataaaactttccaacaggattcctat gaactgacagcaaattatcttttgtcggatacaggtagtatatacgcttcttacacaaaagctttcagagcccctactgcaga tgaagcaggtagatggcgaaaaggatacgatgtaaaaatacaagaagcggatacttttgaagttggaggaaagcttgcttgga agaactggtatatatctggttctatctttcataccagaaccgaaatgagattctatatattgcctatgaagatggaaagctg ggtaaaaattataacttgccggaaagaatataagcagggaattgagcttctctggaacaatacttagaaaaattaacgtt acgggaaagtttccattatttaaaacataaaatcaaaaaggaacttcgccggaaataagattccaggagtccctcagtaca tttatagtttaggtatggattatagaatattagatcatgttatctggagtaattcttttcattatatggaagtgcctatgga aattatgattatcataataaatttggaaaacagaaagggcatacggaattaaacaccagtcttcgctatgaaatgaaaaacgg cttgagttttatggagggattcacaatcttctggataaggaatattttactccaaaattaaatgcggccggaacagggatga attattattatggcagcagaagaaattactatattggattccagtatacttctaa |
| *Fusobacterium necrophorum* 1694 TonB-dependent receptor amino acid sequence (SEQ ID NO:10) |
| MKKYFVAVSISLALSYQIFAEENPVIKLNETVITSESFGTNILRTPKNITVITARNIKIQGAKNIEDALRGVAGLTAYNNMGG SDPKISLRGMAPGKEEQSILFLLDGIPYNSTVDTGAVNLNLIPIDIVERIEIIPNGGNVVYGEGAVGGVINIITKKGKNKKYY GSFSIDGGSYDLKEYKVNLGSNLTEQLSLDLKYNNRRQKNYRDHHTRDIEYINLGMEYKENEHSIYFDFQNSETEYRFPGYLT KKQIEEGKIKKSTGNIKGKEKLRIYRAKYEGKWAKNLFFNIAGDFKDKLYKSIDEKTNTVSTIRDTESFYISPQIKYQYMPNS YFILGGDFLKGKSKYRYKKDIKTETSRKSVGVFLTNNIKWENFIFTQGYRHQKIKYDVKDKLYPSPNHKQKILLDKTFQQDSY ELTANYLLSDTGSIYASYTKAFRAPTADEAGRWRKGYDVKIQEADTFEVGGKLAWKNWYISGSIFHTPTENEILYIAYEDGKL GKNYNLPGKNIRQGIELSLEQYLEKLTLRESFHYLKHKIKKGTFAGNKIPGVPQYIYSLGMDYRILDHVIWSNSFHYYGSAYG NYDYHNKFGKQKGHTELNTSLRYEMKNGLSFYGGIHNLLDKEYFTPKLNAAGTGMNYYYGSRRNYYIGFQ |

FIG. 19

| Fusobacterium necrophorum 1694 Hemin receptor Gene Sequence (SEQ ID NO:11) |
|---|
| atgaaaaaaattttatggtaacagcaattttagcaacagcttccggtcttggttttgcaaaggagatttctcctattgaact |
| ggagcaaacagtcgtaacttctgaatctttcggaacatcaactcataggacagccaaaaatatacaggtaattacagcaagg |
| aaatggaagaaaaaggggcattaacagtagatgaagcattaaagggagtacccggagttatggtaagaaaaatggatggaga |
| actcctgttattgatttacgggggtcaggagcggcatccagtttcagttccagcatactcttgttggatggagttccgttaaa |
| cggtttggtgaaattggacatcaattccattcctctaagtgaaatcagtcgtatcgaattattcaaggaggaggagctgtta |
| tgtatggggatggctccacaggagggttgttaatattattacgaagagtccgaatacaaaaaacattatggaagtgcaggc |
| ttggaatacggttcttggaaaacaagtcgggcaagcttacattacggaacggctttaacagataaattatccgtcagtgcttc |
| ctattccggatatgcttctatggaataccgagatcgaggacatggaaaacttggagcgggagaaagtttcgattacagaaata |
| aaaaagataagaaatattccctttggttacaaggaaaatcaattggaagacggaagtatcggcttcaagtataatcataac |
| gaaagaaaggattattacaccggatatttggaaaagaaacagtatgaagaaaatcctaaacaaataggaagttattcaggtaa |
| aatacaggatgtgacggatatttataatctttcttatcaaacaaagttgacagatacctiggaatttttagtttacggaggat |
| attatcgaggaagagcatcgaccaaatcagcttaccagtgaatatttataaaacctcaattcaaatatacttacggagaa |
| aacagctatgttattaggtggggattaccgagatggaaagcgggaattcaaagaaaaagttctggtaaacgaaggatgca |
| aaaagctcccaacgatgaaagagaatccaaagcaatctatgttatgaataaaacttctttgggaaactgggaattttctcaag |
| gatatcgttatgaaaggtggattataaatacagttccaaatttatggaccaggctggtcattatccgaaattaaaccgatg |
| aattcaaaatattctcataatgacagctttgaattgggagtgaattatctatattccgatacgggaaatgtatatttcaatta |
| taccaaagcgatgagaactccgacaattggagaggcaggagcttggtacggagatgtaaagacacagaaaatgatatttttg |
| aaataggattaagggattatttcaaaaatacacaaatctcttcctctatttctatattacttccaaaatgaagtctactat |
| gataaaacgaatccgaataattcaaataacagaaactttgacggaagggtaagaagaacgggggcacaattgtcttgaccca |
| ttatttggataaattaagtgtaagagaaagaatttcttacatccatccaaaagtatccagtggaatttatagcggaaaaactt |
| ttgcaggagttccaaaatggacttttaaatctaggggcaacttatcatgttacggataagtttttagtaaatacagatttatat |
| tatcaatccaaagcttatgcagaagatgattttgacaactattttaagaaggataattcttatgcaactttggatatcaatac |
| ttcttatgcgtttgaaaatggaatggaagtatacggaggagtcaaaaatgtatttgataaaaaatatgccaatacgataacttt |
| ctagcagaagcacatggtctccgggacctagaactgtgttctatcctgcagatggaaagagtgtttatgtaggattcaaatat |
| catttttaa |

| Fusobacterium necrophorum 1694 Hemin receptor amino acid sequence (SEQ ID NO:12) |
|---|
| MKKIFMVTAILATASGLGFAKEISPIELEQTVVTSESFGTSTHRTAKNIQVITAKEMEEKGALTVDEALKGVPGVMVRKMDGG |
| TPVIDLRGSGAASSFSSSILLLDGVPLNGLVKLDINSIPLSEISRIEIIQGGGAVMYGDGSTGGVVNIITKSPKYKKHYGSAG |
| LEYGSWKTSRASLHYGTALTDKLSVSASYSGYASMEYRDRGHGKTWSGESFDYRNKKDKKYSLWLQGKYQLEDGSIGFKYNHN |
| ERKDYTGYLEKKQYEENPKQIGSYSGKIQDVTDIYNLSYQTKLTDTLEFLVYGGYYRGKSIDQNQLTSEYFIKPQFKYTYGE |
| NSYVILGGDYRDGKREFKEKVLVNGRMQKAPNDERESKAIYVMNKTSLGNWEFSQGYRYEKVDYKYSSKIYGPGWSLSEIKPM |
| NSKYSHNDSFELGVNYLYSDTGNVYFNYTKAMRTPTIGEAGAWYGDVKTQKNDIFEIGLRDYFKNTQISSSIFYITSKNEVYY |
| DKTNPNNSNNRNFDGRVRRTGAQLSLTHYLDKLSVRERISYIHPKVSSGIYSGKTFAGVPKWTLNLGATYHVTDKFLVNTDLY |
| YQSKAYAEDDFDNYFKKDNSYATLDINTSYAFENGMEVYGGVKNVFDKKYANTITSSRSTWSPGPRTVFYPADGKSVYVGFKY |
| HF |

FIG. 20

| *Fusobacterium necrophorum* 1694 Hemin uptake system outer membrane receptor gene sequence (SEQ ID NO:13) |
|---|
| atggaagaaaacaatggaacgattgtcatcacggaagaaatgatacaaaagaagcattatgacagcgttgccaaaattttga<br>agattctccggtttccgtcgtaagacatacggcattcggacgattgtcgatttgcgaggaagcggagagagaaccatcagtc<br>gagtgaaagtgatgattgatggcacaccgatcaaccctttagaagaaactcacggaaccatcccttttgataccattccggtg<br>gaatccattgccaagatagaaattgttccgggaacaggaacgacaaaatatggaggaggaaccacaggagggtatatcaacat<br>tcatacgaaaaacagaaacagaataattacattacgatcaatgcggacaatgcctcttataatgccaagagtattggaattg<br>ctgcgggaatgaatgtaaccaagaaattatttgtttatgcgggagaagcctatcaaagaaaagacggctatcgaaagaaagac<br>cattcggacagaaacaattttttaggaggctttgattatcaaatcaatgcaaacataggatcaaaggacaaggaaatctcta<br>ccgagaggatttaaaatccacaacggaagtaactcatgaagaattgaaagaagatagaagaaagcgggagaagatacaaaga<br>tagaaatggatcgagattttgcttcttggactatgaatacacacctacttccattttaaattaagaaccaatgtcaatcga<br>gctcattttacaagagatgtatctatgaatgcgaagcaggatcaacttgttcttgcttttatgccaagagatgaacaaggata<br>ttttttgcatttgatgcaggattattggcagatcctaagttatctgatgtaaggccggttcttctggattttgaatctacta<br>tggaaggaaaattcaaggaaaaaaatcaggagggaaagctggacggagaatggaaatacaatcaaggaaaagggcatttacaa<br>tttggatatagttataatgagaagaaattgaatcaagatttaaaatcaatttccaaaccttttactttaaaaaatcaattggg<br>atatttgattcaaggtgaccccggctccgaaaggatatgaagattacaccggaaaaattattgcccggaagaaatgtttaaaa<br>taaaatttaaagattttcctcaaatactggaaactttttaggacttaggagagaaggcgtcgaaaaggaaaaaattgattttt<br>caaaattataataaaattgatgcttttaaggatactcatgccttgtatttgttaaatgattacaaattaactccaaaatttaa<br>ttttagagcaggtttaagatggaggaacattcagaatatggttctgatagaaaaaataaataatgatttttgggagttcataatgcac<br>aatcatcaggaatggcaaatagaatggcaattgcgggtcttcttaatgagtatcaaatggaggcttatgtacaaggaaaatta<br>tcctacttggatgttgatttatctttgaaagaaactcatgtcaaagataggagtgataatttcggaggagagcttggatttac<br>ttatcaatatcatcgaaaaggaagtgtattttccgatatgaagaggattttttatctccattgccttccaacttaccaata<br>aggattcttaacaggaatttattatccaagtcatgtcaaatcggaaaaagtagacactattgaaatgggaatcaaacattct<br>ctatggaacaatactcatatcgaagccactactttcttttcttttgacaaaagatgaaattacaaatatgcgatacaatgcgaa<br>caaccatatgaatatgcgttgggcatatgccaatatttctaaaacaagaagattgggattggaattgaatgcggaacatattt<br>tcgacaaattaaagattcgagagtccttcagttatgtggatgctaagatagcaaaagataccggattcaaagattactatcat<br>tccgattacaaagtgaaatcggaaaaagaatttaaagacgccccctatattataaaaaaggacaacaagtacctcttgtttc<br>taaggtcaaagtgacggtaggagcagaatatcaatttacagataaattgagtttaggaggaaactataactatgtcagtggct<br>atgatacccgagaaccgggcgaaggcttccaagcaaagacctataaagtaaaggccatggaactttggacctgtttggaaga<br>tattctttcacagactatgcctatgtacgatttggagtgaataatgtgctaggagaaaaatacaatttacgagaagactctca<br>ctatgcagtaccggctccaaaacaaaattattatgcaggatttagttataagttctaa |
| *Fusobacterium necrophorum* 1694 Hemin uptake system outer membrane receptor amino acid sequence (SEQ ID NO:14) |
| MEENNGTIVITEEMIQKKHYDSVAKIFEDSPVSVVRHTAFGPIVDLRGSGERTISPVKVMIDGTPINPLEETHGTIPFDTIPV<br>ESIAKIEIVPGTGTTKYGGGTTGGYINIHTKKQKQNNYITINADNASYNAKSIGIAAGMNVTKKLFVYAGEAYQRKDGYRKKD<br>HSDRNNFLGGFDYQINAKHRIKGQGNLYREDLKSTTEVTHEELKEDRRKAGEDTKIEMDRDFASLDYEYTPTSHFKLRTNVNR<br>AHFTRDVSMNAKQDQLVLAFMPRDEQGYFLHFDAGLLADPKLSDVRPVLLDFESTMEGKFKEKNQEGKLDGEWKYNQGKGHLQ<br>FGYSYNEKKLNQDLKSISKPFTLKNQLGYLIQGDPAPKGYEDYTGKIIAPEEMFKIKFKDFPQILETFLGLRREGVEKEKIDF<br>QNYNKIDAFKDTHALYLLNDYKLTPKFNFRAGLRWEHSEYGSDRKNRMILGVHNAQSSGMANRMAIAGLLNEYQMEAYVQGKL<br>SYLDVDLSLKETHVKDRSDNFGGELGFTYQYHRKGSVFFRYERGFLSPLPSQLTNKDFLTGIYYPSHVKSEKVDTIEMGIKHS<br>LWNNTHIEATTFFSLTKDEITNMRYNANNHMNMRWAYANISKTRRLGLELNAEHIFDKLKIRESFSYVDAKIAKDTGFKDYYH<br>SDYKVKSEKEFKDAPLYYKKGQQVPLVSKVKVTVGAEYQFTDKLSLGGNYNYVSGYDTREPGEGFQAKTYKVKGHGTLDLFGR<br>YSFTDYAYVRFGVNNVLGEKYNLREDSHYAVPAPKQNYYAGFSYKF |

FIG. 21

| Fusobacterium necrophorum 1694 TonB-dependent receptor Gene Sequence (SEQ ID NO:15) |
|---|
| atgaaaaagaaaatacgggtatgtggcaaaggattttgaaaatcggtatgttaagtataatactcttatactggacagactc |
| tctatatgcaatagagactagcgagaatatgcagtcgacaacgatgtcggtttccggagaaacggtaaacttcaaaatggaag |
| gaattaccgtggaggcaaaaagaccggattgggaatcgaaattatcaccgggaacagtgacggtcattcgtccggatgattat |
| aaaggagagcaaaaagatttacctgattttttgaaaatggttccggagttcatgtgcgggaaatcaatggaaaagggcagta |
| caccacagtcagtgttcgtggttccactgcgggctcaggtcggagtgtttgtagacggagttcttttaatctcggaggagatg |
| cggcagctgatatttcaacaattcccgtgcataatgtggaaagaattgaagtgtatcgtggatatattcctgcacgtttcggt |
| ggaacttttatgggaggagttatcaatatcgttaccaaaaaaccgaatcgaggaaatgtgagcgcaagcgtcggacgaagttc |
| ttttggcggtaaaaaagcaaatttgcagtttgatcttccttgggaagcggaactttaatggtcggaatcaatcatgatgaaa |
| gcaaaggaaatttcaaatataaaaacttctctatgatagaagataaagagtatcaaaaggaagtgaaaatgcaaaaagttcg |
| gaacgaggagcaatagataattataataaggcatttaaagaattaaaaaaatacgattttacagatgatagcggaaatatatt |
| taaggttgatactctggaagaagcaactcagattgtcaaaaataatcaggatcgttgggaaaagtctttgcaggaagctaaaa |
| atgacattgataataattttttaaaaagaaacatattatagcaagattcccgggaattcccaaagaagagattcttcctctt |
| cttagaagtactcatattgatgcagagcaagctctttatgaatctgcttttaaagaatactctgtaaatcaaggcaataattt |
| tattccaaaatggaaagattccagtggtaactggggttgtccctgatagagtggaagattatgttgaagcttataataagagtc |
| atgaaataggatatcaacattttcaacagattatagcaaagggtgtgcaggagatatagaaaagatggatagcaaaatatgga |
| aaagctatgctgttaattatgcacaacaggcggagtatagtgtcaaagaaatggaaaaacataaaaaacaggcggaagcgt |
| gaaagaccactatagacgaagaaaagccaatgattataaaaatatggatatattttaaaatggcaggatgaacattggatgg |
| cgaaggcaacttggaaaagaatcaaaagacatctgccgtttcctattgatgagaactatggtaatgcaccatatatagatacc |
| gaccttatggcaaataatccgctctctatcttttatcatcgaaatcagaaattgaccgttcaggaatttcttttcggaagacg |
| ggatactttcaggaatcttgaatgggctggagtgttaattatctaaaacaagagaaagattactatgttgatgattgggaat |
| ggttggaaaaaatacgggaagtctcttaaacagctatcgtccaaacactctgtggagtaaatatgacagtcatcgctggggt |
| gcaaattggatggaagctacaaaagcggagaacgtcatatcatagaatttatggtaaacgcttccaaagaaaaaatggatat |
| tgacggctggcgtatgaaggatttcagttctcacagtttcagatacacttgccagatggagaattattatgagcaggatattt |
| tcaatgcacagcttcaggataccatcactttaaatcggaaggagatctgtggttaaccccgagcattcgttataatcgttct |
| acaatactcggacgcagtgaacgctacgataaaaagaaagatccgcaaagtggaaattttcagccgggaagacaaacaaac |
| cgatgataaagtgacttggcaagtcgcaatcaaaaaacaattcaatgagcatttcaccttgcgtgctaccggaggaagctatt |
| atcgtctgttgaatatgtatgaaattgcggagacggagcaggaattatccctatgccaatatcaaaggggatggaagtatc |
| gaagaaggaggaaaactcatgttttcctatgccggaagaagagaaaacaatggatgtcagtgctatctgggacggagctgc |
| attgggagcaaaggcggccaagcttcaactgacatatttcggacgagattccaaaagaatttggaactgggttcctggaatc |
| gttttttctttgtttataccaatgccatcagtgccaaggttcacggagcggaaatacaggcggatttatcttggaaaaatgg |
| gatctcaacctacaggcaacttataccagacccagaaatgtagtgtatgacaatagtgctctgccggaagctatattctggaa |
| tggaggagtctttaagggcttttctgacatatcagccgaaatggaagggacggcaagaattacctatcgtccgaatccacgtt |
| ggagtatcttttctcaatttcgttatgtcggagaaatgattacgagcagaattcctttggcaacgggagattttatgcatcag |
| tcttcactgacagcttgggatttgggaatcaagtgtaaactaacggaacattttcaaatcgctcttggagtgaatgatctatt |
| caataaagcagatatgtatcataaatataaaagcatcaattatcagaccaacattcaatatcctattcagggaagaagct |
| actatgcaagctttcaatacaaatttttaa |

| Fusobacterium necrophorum 1694 TonB-dependent receptor amino acid sequence (SEQ ID NO:16) |
|---|
| MKKENTGMWQRILKIGMLSIILLYWTDSLYAIETSENMQSTTMSVSGETVNFKMEGITVEAKRPDWESKLSPGTVTVIRPDDY |
| KGEQKDLPDFLKMVPGVHVREINGKGQYTTVSVRGSTAAQVGVFVDGVLFNLGGDAAADISTIPVHNVERIEVYRGYIPARFG |
| GTFMGGVINIVTKKPNRGNVSASVGRSSFGGKKANLQFDLPLGSSTLMVGINHDESKGNFKYKNFSYDRDKEYQKEVENAKSS |
| ERGAIDNYNKAFKELKKYDFTDDSGNIFKVDTLEEATQIVKNNQDRWEKSLQEAKNDIDNNFLKKKHIIARFPGIPKEEILPL |
| LRSTHIDAEQALYESAFKEYSVNQGNNFIPKWKDSSGNWVVPDRVEDYVEAYNKSHEIGYQHFQQIIAKGVQGDIERWIAKYG |
| KSYAVNYAQQAEYSVKEMEKHKKQAEAVKDHYRRRKANDYKNMDIILKWQDEHWMAKATWKRIKRHLPFPIDENYGNAPYIDT |
| DLMANNPLSIFYHRNQKLTVQEFLFGRRDTFRNLEWGWSVNYLKQEKDYYVDDWEWLEKNTGSLLNSYRPNTLWSKYDSHRWG |
| AKLDGSYKAGERHIIEFMVNASKEKMDIDGWRMKDFSSHSSDTLARWRRNYYEQDIFNAQLQDTITLNRKGDLWLTPSIRYNRS |
| TILGRSERYDKKKDPQKWKFFSREDKQTDDKVTWQVAIKKQFNEHFTLRATGGSYYRLLNMYEIAGDGAGIIPMPNIKGDGSI |
| EEGGKTHVFPMPEEGKQWDVSAIWDGAALGAKAAKLQLTYFGRDSKRILELGSWNRFFFVYTNAISAKVHGAEIQADLSWKKW |
| DLNLQATYTRPRNVVYDNSALPEAIFWNGGVFKGFLTYQPKWEGTARITYRPNPRWSIFSQFRYVGEMITSRIPLATGDFMHQ |
| SSLTAWDLGIKCKLTEHFQIALGVNDLFNKANDMYHKYKSINYQTNIQYPIQGRSYYASFQYKF |

FIG. 22

| *Fusobacterium necrophorum* 1694 Hemin receptor Gene Sequence (SEQ ID NO:17) |
|---|
| atgagaaaaaatttttttattggcaagttttttggtatttggagtaaatatagcttttgcggaagaaaacccggtgttgacatt |
| ggaacaaacgattgtgagtacggaatcctttggaacatctgctcgaaagacaccaagaaatgtaagagtgatgacagagaaag |
| aaattaaagagaaaggagccttgaccatagaggaagctctcaaaggacttccgggagtgatagtcagaagaatagatggctct |
| gctcctattattgacttaagaggaacaggtatggcttccagtatcagttccagtcttcttcttttaaacggagttccttaaa |
| tggacttattgtatttgatattaattccattcctatcaacgaagtggaaagaattgaaattattcaaggaggaggagctctga |
| tgtatggggatgtgccgttggtggaatgataaatatcatcacaaaatctcctaagaataagaaatattttggaagtgtcaat |
| ctggaacttggttcttggaagactaaacgagccaatatcaattatggaaagtgggagaaaaattatcggtgaatgcttc |
| ctattctggatattcctctatggattatcgggacaggtatcatgaatggattggacaggacagtaccttgattaccgaaatc |
| gagcggataagaaatattctgtttggtttagcggaaagtatgacttacaagatggaaatatagaattacgctacaatcatact |
| gaaaatagagacatctttgccggttctttggataaaaaacaatttcaagacaatccaaaacaaacggcggttttggaaggga |
| agtgaaaaatatatctgatgtttggaatctatcttatcagaaagcattgaaagaaaatttagaattttcacttattggaggac |
| atcaccaagacaagagtatccttttgaatcaaatttcttccgagtatttttatcaaaccacaattaaaatatcgctatggaaaa |
| aatagttatcttattttggaggagattataaaaatggaaaacgtgtctttaagcacacccttattacaaatcataaaaaagc |
| cccagatgataagagaaaagctatggcattctatttatgaataaattttccaatggaaaatgggaattttcacaaggataca |
| gaagagaaagagtagaatgattatacttccaaagcctatagaaatctttactatttatcagaagcaaatccagtttcttcg |
| cgttcttctaataacaatagttttgaattgggagtaaattatttatattctgatacaggaaatatgtatttcaattcacaag |
| ggctgttagaactccaacaatagaagatgctaaaatttggtatggagaggtaaagagtaaaaaagtgatattttgagatag |
| gaatgagagactatttcaaaaatacCttaatctcctcctctatttttatatgaatgcaaaaatgaagtttattatgatacg |
| agagatatgttgcgtatcaaaagtagaaattttgatggaacagtaagacggattgggcacagttagcattaagccattatct |
| tgggaaattcgtttgaaagaaaatattttcttatgttaatcccaaaattgtgagtggacctatagggaaaagctttgtta |
| cggtgccaaattggatttgaatctgggggcagcttatcgttttcagaacaatttttaataatgcagacttatattatcaa |
| tccaaaatgtatgcagaagatgatttcgagaatattcttggaaaagataattcctatgtaactttgaatatgaacgcatccta |
| taagtttgataatggaattgagatttatggaggaattaaaaatctgttgaatgaaagatatgcggatacgatagcgataaatc |
| cttatccaagccctaaaatagcatattatccgggagatgggagaaatttttatatgggatttcgatatcagttttag |

| *Fusobacterium necrophorum* 1694 Hemin receptor amino acid sequence (SEQ ID NO:18) |
|---|
| MRKNFLLASFLVFGVNIAFAEENPVLTLEQTIVSTESFGTSARKTPRNVRVMTEKEIKEKGALTIEEALKGLPGVIVRRIDGS APIIDLRGTGMASSISSSLLLLNGVPLNGLIVFDINSIPINEVERIEIIQGGGALMYGDGAVGGMINIITKSPKNKKYFGSVN LELGSWKTKRANINYGMKVGEKLSVNASYSGYSSMDYRDRYHGMDWTGQYLDYRNRADKKYSVWFSGKYDLQDGNIELRYNHT ENRDIFAGSLDKKQFQDNPKQTGGFGREVKNISDVWNLSYQKALKENLEFSLIGGHHQDKSILLNQISSEYFIKPQLKYRYGK NSYLIFGGDYKNGKRVFKTPLITNHKKAPDDKFKAMAFYFMNKFSNGKWEFSQGYRRERVEYDYTSKAYRNLYYLSEANPVSS RSSNNRSFELGVNYLYSDTGNMYFNYTRAVRTPTIEDAKIWYGEVKSKKSDIFEIGMRDYFKNTLISSSIFYMNAKNEVYYDT RDMLRIKSRNFDGTVRRIGAQLALSHYLGKFVLKENISYVNPKIVSGPYKGKSFVTVPNWILNLGAAYRFSEQFLINADLYYQ SKMYAEDDFENILGKDNSYVTLNMNASYKFDNGIEIYGGIKNLLNERYADTIAINPYPSPKIAYYPGDGRNFYMGFRYQF |

FIG. 23

| |
|---|
| *Fusobacterium necrophorum* Hemin uptake system out

FIG. 24A

| *Fusobacterium necrophorum* Hemin uptake system outer membrane receptor Gene Sequence (SEQ ID NO:21) |
|---|
| atgagaaaagaaatgcttttgacattgttgtgttttgtttctttgcatgctatggcagcaacacaggaagtggagttgaaccc |
| gacaaaaattcgaggagggggggcgacctataatggctcggttctctccaatgaaaagaaaaatgtaatcatcattacgaaag |
| cagatattgaaaagaaaaattatagagatttggaatctattttaaggattctccggttacttctgtcgtttatacggaggcg |
| ggtcctttggtcaccttaagaggaagtggacaaaagacggcaatgagagttaaagtactcttagatggcgtttccatcaatac |
| cgtggatgattctatgggagtgattcctttcaacgccattccggttgccagtattgaaaaaattgaaattattccggggaggag |
| ggattactcttcacggttccggaacttccagcggagtcatcaacatcgtgacgggaaaatcgagtaagaaagattatggagag |
| cttggtttttactgtaagttctttcaatacttacaatacaaccttcataagggaatttcctttggagataagctgtattggaa |
| tattggagtggaagcgaaaaggaaaggcatatcgagagaaagaggatagtaaaagataaatctgctgtccggaatcaact |
| ataaaatcaatgaaaaacatcaaattaaattacatgaagtaaatattggtcggattttaacggaacaaatgaattggatctt |
| atcagtttgcaaaaaaatcgaagagggggcaggaaaatcagatgccgaagtaaagtcaaatcgatattcccttctttcgatta |
| tgaatataaacctacgaagatttgaccgttacttccggatacaatcaacaaaaatttcgaaggaattttacacagaacaaca |
| aaccttatcttactttcttatcgtcggaatgggtggaagatatgtttggaattcccgacggaatgaatgcagatttagtcatt |
| aaaaatgtaaataaccatttaacgggacgtattgaagaaaaataaaaaatggaaaagtcaaagtggactggaaacagtaa |
| caatcgtggaaaattaacttttggatatgattattcttctcatgaattaaaacgaagaatgaatgtacaagttgatgcttta |
| atccgatcgataataattacttttttgagaaaaaagaggagagaattatcaatgaagaaattttagaacaacatccggat |
| cagttaatgcattttttcgataacacttttagcggcaattctaatatttgatcctgattctatggatagttatgggctagattc |
| tgttaaactaaagaaaaaaatagacgaactctattcatttgactacttcggaaaagataagaaaaaatatgaaatggag |
| aagaaaatccttgggattattgggaaaccatcaaaccgaatatgtggaaaatgatttatcatttgacagaagaaaagattcaa |
| gagtatgcaaagacggaaaaaatattcttaagagaagatgaaatgattgggattctgaaccaagcgttcaggttccgat |
| tgaggggaaaaatttaaagaatttttaagattgattattcctagtatgtatgacccgattttagtatgacaccaatcacgc |
| aaagtatggtagatgtgaagaagacaacgaattccttttatctatttgacagctataaacttactgatcgtttagaaatcaat |
| ggaggtttgcgatatgaaaaagcaaaatactccggaaatcgttatacaaaaacggaacaatttatcaaaggaatgcggagaa |
| taaatctaccaactctatgatagcgatgtatacggaattgtcagaagcggaatcggcaaagaaaaacataggagatactcatc |
| actggaatggaaatgatacttccaaagaaaaataaaagaactgaaagaaaaggatatactaccatttaatgacggattta |
| actcgaaaagagaaaagagaagaggaaaatctggaggagaaattgggattaattaccgtttcaatgatacagacacagtata |
| tttaaaatatgaagaggctttaatactcctcttcctacacaattgaccaataaaacctttgatccgaaaaccaagataaaag |
| catattgggaaagcaatataaagacagaaaaaatagacaatgtagaactggaattcgaggaatgttacacccaaagtgacc |
| tattctttgacaggatttatcagtgatactcaaaatgaaattctatccattgtgaagaatggaagttctcatatgctccgaga |
| atggagatttatcaatattgataaaacgagaagaatgggactggagttccaatctcaacaaaatttgataaattgactttaa |
| aagaatctcttacttatgtggatccaaagtctctatccaatgattatgaaaaacaggttcataaaattggagtggacagagcg |
| gaggaaatgtaccaaaacaatcaaaaagtacggatggacaattgaaaaatatcagatttcatgaaaatggcttacaattcc |
| ggcaggaacttcggaagaagaaattgtaaaaatgaaggcggagtccaagcgattgggaaaagaagcggttaaaatcattcaaa |
| aactaagagagacaggagtaaaagtggactatagtgcacgagatgccaaactgaaagaaattgttccgggaatgtcttctgcc |
| gaacaatctaagattagaatggaagcttcaaaattagcacaagaagctgaaaatagagctgtggcagaacctagaaaagcctt |
| ggaagatcttcttgcaaactcagcttatcctgacattttaaagaaaaattgcgttcattcaataaccataccttaattcagg |
| aaggaacgatgaaagaaattatttatgaacatttgaaaagagataaagtcttcttatacgaaaggaaccttagaaagga |
| agcagaatcccgctttctccaaaatggaaaggaacttcagtgcggactatcaattcacggataggttaaaattaggaatgaa |
| tactacttatataggaagctatgattccgcggaaccgggaaaaggatatgaaattgtaatgacaaaagtaccgcatcatatgg |
| tagccgatttctatggaagttatgatattcaggaagattttccattaaattcggaattaacaatgtatttaatcatcaatat |
| tatttacgacaagattccagaacggcaactccggcacccggaagaacctacagtgcgggattcagttatcgattttaa |

FIG. 24B

*Fusobacterium necrophorum* Hemin uptake system outer membrane receptor amino acid sequence (SEQ ID NO:22)

MRKEMLLTLLCFVSLHAMAATQEVELNPTKIRGGGATYNGSVLSNEKKNVIIITKADIEKKNYRDLESIFKDSPVTSVVYTEA
GPLVTLRGSGQKTAMRVKVLLDGVSINTVDDSMGVIPFNAIPVASIEKIEIIPGGGITLHGSGTSSGVINIVTGKSSKKDYGE
LGFTVSSFNTYNTTFNKGISFGDKLYWNIGVEAEKGKAYREKEDSKKINLLSGINYKINEKHQIKLHGSKYWSDFNGTNELDL
ISLQKNRRGAGKSDAEVKSNRYSLSFDYEYKPTEDLTVTSGYNQQKFRRNFTQNNKPYLTFLSSEWVEDMFGIPDGMNADLVI
KNVNNHLTGRIEEKIKNGKVKVDWKHSNNRGKLTFGYDYSSHELKRRMNVQVDAFNPIDNNYFFLRKKEERIINEEILEQHPD
QLMHFFDNTLAAILIFDPDSMDSYGLDSVKLKKKIDELYYHLTTSEKDKKKYENGEENPWDYWETIKPNMWKMIYHLTEEKIQ
EYAKDGKNILKREDENDWDSEPSVQVPIEGKKFKEFLRLIIPSMYDPDFSMTPITQSMVDVKKTTNSFYLFDSYKLTDRLEIN
GGLRYEKAKYSGNRYTKTEQFIKGNAENKSTNSMIAMYTELSEAESAKKNIGDTHHWNGNDTSKEKIKELKEKGYTTILMTDL
TRKEKREEENLGGEIGINYRFNDTDTVYLKYERGFNTPLPTQLTNKTFDPKTKIKAYWESNIKTEKIDNVELGIRGMLHPKVT
YSLTGFISDTQNEILSIVKNGSSHMLREWRFINIDKTRRMGLEFQSQQNFDKLTLKESLTYVDPKILSNDYEKQVHKIGVDRA
EEMYQNNQKVRDWTIENIRFHENGFTIPAGTSEEEIVKMKAESKRLGKEAVKIIQKLRETGVKVDYSARDAKLKEIVPGMSSA
EQSKIRMEASKLAQEAENRAVAEPRKALEDLLANSAYPDIFKEKLRSFNNHTLIQEGTMKEIIYEHFEKEIKSSYTKGTLEKG
SRIPLSPKWKGTFSADYQFTDRLKLGMNTTYIGSYDSAEPGKGYEIVMTKVPHHMVADFYGSYDIQEDFSIKFGINNVFNHQY
YLRQDSRTATPAPGRTYSAGFSYRF

FIG. 25

| Fusobacterium necrophorum Hemin Receptor Gene Sequence (SEQ ID NO:23) |
|---|
| atgaaaaaaaagttaatgattttggcaattttaagtatttcagtttcagcatttgctatgaaggaggaaattcctgtgcaaag
attaaatgaaacagtaataacaactcctgaaagattcggtacaaaggttagaaatatatcaaaaaatatacaaataattacaa
aaaaagatatgaaggaaaagggggcaaaaaaccttttttgaggcattgagaggactcccaggagtagttatacgtagagatgga
ggaggacatatagatcttcgtggttctggagaaaatgataaaaaaaatatgatattttttaatagatggaatacccctatagtgg
attaagtatatttgacattaattctatctcaatggaagaaattgaaagaattgaaattatccaaagtggtggtgtttatatg
gagatggagctataggaggagttataaatttagttactaagcctattactactggaaaatacagcaatagcattggtttggaa
tacggctcttgggaaacggctaaattaaatgtaaatgtcggaactaaattaacagataattttgttgtaagtgtttcttactc
tggtgaacaaactgaagaatataaaaatagaagcatagatttcaaagataaaaaagatagccggaatctatttggttaaaaa
ctaaatataatttaaatgatggggaaattgagttaaaatataatcatttgaaaaacaatgactacatcacaggacttctatca
gcaaaagactttaaagaaaatcctaaaaaagcaggtacaacaaatgcttcttttaaagctgaatcagatttatggaacctatc
ttttaataaaaaattaaatagtaagtttgaagttttcttacaaggtggatattatactgatgaaacaaaatactatgaaatag
gtccaggatatgcagattttcaaaaaatggaaataaaagtcattttataagacctcaaataaaatataattatatggaagat
agttgcatcatattaggaggagatagaaaaaaagaaactgttactaataaattatctccaaattctcctaaaactataaggaa
aaaagaatctatttacttattaaatagtaataagataggaaactttgaaattacagaaggatatagaatagaaaaaattgatt
taaaagaaagaatagagctaaagactttaaagaagatggaatggaattaggaataaactatctttattcagatactggaaat
ctttatttaattacacaaaaggatttagagtacctacattgggtgaaatgaatagttgggttggtgatatgaaatcacataa
aaatcatactttgaattaggtttaagagatgtatatgaaaatacttctataaatacttctattttcacattgtattccaaag
atgaaatcttttatgatagtttagttgcaaacccttcaccaaaaaatcctaatagaaaaggagcaaatagaaactttgaaggt
aaggttagaagaataggtgcacagttagctttagaacacaatattggtaaattatcattaagagaaaaaatttcttacatgga
tcctaaaataattgatgatatttataaagagaaagttttcccgggagttcctaaattaacagcagcactaggtttaacttata
attttgaaaattcccttaaattaaatattgatgggtattatcaagaaaaaattatgccggaactgattttttaaataaatat
ggtaaacacaatagttatacagtagtagatgctaatatttcatatacttttgaaaatggtttggaactttatggtggagttaa
aaacttatttgataaaacatatgctactgccttttttcccaagagcaacaggagaattaagatatgatccagataatggaagaa
gttttttacactgggttttaagtatacttttttaa |
| Fusobacterium necrophorum Hemin Receptor amino acid sequence (SEQ ID NO:24) |
| MKKKLMILAILSISVSAFAMKEEIPVQRLNETVITTPERFGTKVRRISKNIQIITKKDMKEKGAKNLFEALRGLPGVVIRRDG
GGHIDLRGSGENDKKNMIFLIDGIPYSGLSIFDINSISMEEIERIEIIQSGGVLYGDGAIGGVINLVTKPITTGKYSNSIGLE
YGSWETAKLNVNVGTKLTDNFVVSVSYSGEQTEEYKNRSIDFKDKKDSRESIWLRTKYNLNDGEIELKYNHLKNNDYITGLLS
AKDFKENPKKAGTTNASFKAESDLWNLSFNKKLNSKFEVLQGGYYTDETKYYEIGPGYADFSKNGNKSHFIRPQIKYNYMED
SCIILGGDRKKETVTNKLSPNSPKTIRKKESIYLLNSNKIGNFEITEGYRIEKIDLKRKNRAKDFKEDGMELGINYLYSDTGN
LYFNYTKGFRVPTLGEMNSWVGDMKSHKNHTFELGLRDVYENTSINTSIFTLYSKDEIFYDSLVANPSPKNPNRKGANRNFEG
KVRRIGAQLALEHNIGKLSLREKISYMDPKIIDGYYKEKVFPGVPKLTAALGLTYNFENSLKLNIDGYYQEKIYAGTDFLNKY
GKHNSYTVVDANISYTFENGLELYGGVKNLFDKTYATAFFPRATGELRYDPDNGRSFYTGFKYTF |

FIG. 26

| |
|---|
| *Fusobacterium necrophorum* Heamin uptake system outer membrane receptor Gene Sequence (SEQ ID NO:25) |
| atgaaaaaaaattttttacttactgtctatttcatgttggcaactgttcaaacagttttttggaaaagaggatcccactgtgac<br>attggagcaaacaattgtcagtatggattcttttggaagttctccccacaggactgcaaaaaatgttcgtgtggttaccaaag<br>aagaaataaaagaaaaaggagctttgaatgtagaagatgctttgaagggaattccggggcttctcatacggaacttggatgga<br>gctcctccggtcattgatttaaggggagccggaatggcttccagtttgacttccactctgttgcttctcaatggagttcctt<br>aagtggagtcgagttttgatgtcaattccattcctgttctgaaattgagagaattgaaatcattcagggaggaggagctt<br>tgatgtatggagacggtgctgcgggaggagttgtcaacattatcacacagacgatgaagaataaaaaatattatggaaatgtc<br>gatttggaatatggttcttggaaaacgggaagaattcatttgggaataggaggtcaaatggagaaaaacttttctctccaagc<br>ttcctattcaggatattcttctatggattggagagatagagcacatgggattgacatgagcggaaagactttcgactacagac<br>ataaaaaagataggaaagacagttttggttgagtgggaaaaaggaagggaaagaccaaagtattgaattacgttacagtcat<br>atgaaaagcaaagactatttaccactttctgaacaaaaaacagtatgaagaaatccgaaacaagcgggaatgacaggtaa<br>ctacatagaggatgtcacggatatctggaatctatcctatcgtaaaaaatggaatgataagcttgattttttacttatggag<br>gctatcatcacgaaaaaatgaaaatcaacattttctaatggaagaatatttgtgactccgcagataaagtatctctacgga<br>aacaatagctatgtcatcgtcggtggggacattagaaacggaaaagggaatggaaggatacctcctatcgaatggaaaaaa<br>ggctccgacgataccagaaaatcgaaggctctctatctcatgaataaaattaccgttaagaattgggaatttacacaaggct<br>atcgaagagaaaggtaaattatgattacacttccaaagtttacggtcctgtttggaatttgttggaagcaaatcctgtatcc<br>tccacttcttccaataacaacagttttgaactgggagtcaattatctttattccgacagcggaaacttgtatttcaattacac<br>aaattcgatgagaactccaagtatcggggatatggaggcatgaccggagatgtgaaaacgaaaaagacagtatttatgaac<br>tgggatggcgagattatcttgcgaacactcttttctcgacttctattttctggatggatactcgaaatgaagtatattacgat<br>aaaacgggattgtatcaagtcaaaacaagaaattttgatgggaaaacaagaagaagggagctcaaatctccttgattcatta<br>tttggataagctgtccctacgagaaaatatctcctatatccatcccaagatagaaagtggaatctatcagggaaaacgttcc<br>cggaagttccgaaatggattgtgaatttgggagccagctatcatgttacagaacaatttcatatcaatacggatgtatattat<br>caatcgaaggcttatgctgacgacgatttaaaaatgaatttcaaaagaaaattcttacacaacatgggaccttcatcttc<br>ctaccgttttcaaaatggaatggaaatttatggggagctaaaaacctattcgataaaaaatatgctcacagtgtagcgatta<br>tgcgaagtccttttgcttctcagaaggtatatcatccggcaaatggaagaaatgtctatgtaggatttaaatatcgttttaa |
| *Fusobacterium necrophorum* Heam

FIG. 27

| *Fusobacterium necrophorum* Hemin uptake system outer membrane receptor Gene sequence (SEQ ID NO:27) |
|---|
| atgaaaaaattattcttactattttctttgattgctgttccaattcggtttactccgaaatcatccatttgggggcaagtga catttactctgatactggttatgcgaccaatataagaagtacgacttcatctcctttataataactgcaaaagaaattcagg aaaaaaggtttgcaagtctctctgaaattttggcaagtcttccgggaatcactatacgagagggatacgaactgaaattgat ttgagaggacagggatactcgaaagcaagggcaaccattcaggtcatgatagacggtgtgcctgtcaatatgctggattctc tcatagaaaagttcccttaaatactgtaaatccgaatcaaatcgaacgaatcgaagtcattccgggtggaggagctgttttat atgggaatggaacggcaggcggtgtcatcaatattcttactaaaaaacatcgaggaattttggaaatataggctatcgttat ggaagttttggagatcgtaaatacgatattgccgcaggaaccagtttaggaaactttgactttgctcttgattattccaatga agataaaaacggctacagaagaaattctccttccgattcggattattttttctgccagaattgcttataacttcaataaaaatg atacaattgctctaaaatacagagggatatagaacagagtataaacagtacaacggtttaagcaaaaagcaagtacaggaagac agaagacagaacggaatggccccggacaaaaaggttccactgatagaaagttggatgaatacagtttcaattttcataaaag agtaggaaaaaacaacgatcttagtttccatgcctataaactagaaagcgatataaaaacaagatcacaaactccaaaattaa cgagaattgtaaaagcggaagataatagatcaggagtaaaaatcaagatcaaattgaattatggaaatggtaacaacattatt atcggtgcaggttataccaatcataccatgttttttaagcaacataaaagtagagaaaaagactctggaaagcttcgccttgaa cacattgaaattcggaaaacttgaattttcacaaggattgagatttgaaaatccaaatatcaaggagatgcgcaaagctt tcggattaaaaagtggagaaacttctaaaacactggagaactatggtgcttccctagctcttaattatttgtattctcatgca ggaaatgtatatgtgaaatatgagagagctttaatactcctgcccttacaaaccataaaaaatattaactggcaaacta aacagtgatgcaaaatcagaaaaagtaatacctatgaaatcggcttccgagactatatctaaattccatagtcagtgctt ccgcttattatagtgaaacgcaaatgaattaaaaacagtttggttaggtagccattccatgatctttccaatttaatacc atcaactatggaaagacaaagagatacggattcgatttgaaggcggaacagaaatttgaaaaattcagaatttcagaatccta ttcctttgtaaatgctaaaatcataaaaagtggggaaactgccagtcaaaaagcaacggaaggaaaatatattcctgatgttc cgaaacacaagtttgtactttcgactgattatgattttaatgaaaaattctctattggagcaagctatcaataccaagctgct gcatatattgactctcgaaacagcttgggaaaagaagggaaaaatcaattgtgaatttgagagcaaactataaattcaatga tcatttccacatttatgccggaattaaaaatctatttaatgcaaaatactatgattctgtgggttatactactgccaaaccaa ataggatatataaggtttacaaccctgcaccaagcagaaattactatatgggatttgattataaattctaa |

| *Fusobacterium necrophorum* Hemin uptake system outer membrane

FIG. 28

| *Fusobacterium necrophorum* Hemin uptake system outer membrane receptor Gene sequence (SEQ ID NO:29) |
|---|
| atgaaaaaagtggtatttgggatttacagtatcttaatgtcctctgctatgcttggagcagaaattgatcttggaacacagaa tatctattcggaaaccggatttgaaacgagtcttcgaagctctgtttcttctccttatatcgttacttcaaaagaaatcaaag aaaaacattataccgtgtttctgaaatttgagagatattccgcatatctacatcggtcccggtggcagtgtagatatgcgt ggtcaggaagtgctcatgccagaacaacagttcaactgttaattgatggagttcctgccaattttttggatacttcccacat caatcttcctatcgatactttaaatccagaagatattaagagaattgaagtcatccctggaggaggagctgttttatatggaa gtggaacttccggaggagtgatcaacatcattaccaaaaaatacacgggaaactatgcaaaggcaagctatcaaataggaagc tatcacaatcataaatatgacgtagctgccggaacttctttgggaaattttgacattaacctaagttattcaaaaaataatag ggatggatatcgtaaaaaagcttttccgattccgatttcttctccggaaaattacgttatcacttcaatccacagacagtc ttgaattcaaatatagctattttgataataagttcagaggtgttaaatccctaaccagagaacaagtcgagaaagatcgaagg caaagtggtctttctcctgaagacaatttgaaaaataccatccgaaaagaagaatggaatttaacttacgatgcaaaatggac aagctggctggaacacaaatccaatctttttctatcagtccacagaaataaaatctagtgaatatgaagatgctcttcctttct atcaatatcaaatttcttcttatcaaaaaatgcttactatgccagggattcctcctatgatgcaagcacaattgaaaaagcag ataaagccctacaaaatttgataacgagtaatccaaggatggaattacatcaaggaagtcgtttcaaagatcaaaaattcgg tttaaaatgaagaataaatttaagtatggagaaaatagtgatttattttaggtttgggatacattcacaacaaatggatc gagattcttgggcttatacgaaaaaatcacaaaaatcaaacaatagcaactcttacaaatactaaaattccttaaataag aaaacattcgaaattttcggattaaatacctatcgtcataataattgggaatttgttcagggcttacgtttgaaaaagcgaa atataatggaaaagacaatataaaaatctggaatatccttaaaagatcgtagcatgaataatgttgcggcaaatctggctg tcaattatctctattccgatacaggaaatgtctatgtaaaatatgaaagaggatttacttctcctgctcctgcacagttaatg gataaaatcagaaaaggaggagtgaacgattatgtcaataatgatttaaaatctgaaaaatcaaactcctttgaagttggatg gaatgactatctcttccattcttagtcagtgctgatgttttttcagtgaaacgaaagatgaaattctaccatattctcgg gagggcatgggacaacattcagcaatttgaaccttggtcaaacgaaacgatatggttttgatctaaaagccagtcaagttttt gaaaagtggacattctcggaagcttacagttatatccatgcaaaaatcatgaaagataaaacaaaggcttatgaaggaaaata tatcagttatgttccaaggcataaatttctttgaatgctgattatgcaatcactccaaaatggactcttggggagaatatc aatacagttcttccgtatatctggacaatgcaaataaaatggaaaagatggagcgagatctgtttttaatcttcaaacctct tatgagttcaattcacattttctatctatgcaggaattaaaaatgtgttaaatcataagtattatgaatctgtcagtgcagg ttccagtcaaaagtattatagtccggctccggaagaaattactatgccggattccgttatcaattttaa |

| *Fusobacterium necrophorum* Hemin uptake system outer membrane receptor amino acid sequence (SEQ ID NO:30) |
|---|
| MKKVVFGIYSILMSSAMLGAEIDLGTQNIYSETGFETSLRSSVSSPYIVTSKEIKEKHYTRVSEILRDIPHIYIGPGGSVDMR GQGSAHARTTVQLLIDGVPANFLDTSHINLPIDTLNPEDIKRIEVIPGGGAVLYGSGTSGGVINIITKKYTGNYAKASYQIGS YHNHKYDVAAGTSLGNFDINLSYSKNNRDGYRKKAFSDSDFFSGKLRYHFNPTDSLEFKYSYFDNKFRGVKSLTREQVEKDRR QSGLSPEDNLKNTIRKEEWNLTYDAKWTSWLEHKSNLFYQSTEIKSSEYEDALPFYQYQISSYQKMLTMPGIPPMMQAQLKKQ IKALQNLITSNPRMELHQGSRFKDQKFGFKMKNKFKYGENSDFILGLGYIHNKMDRDSWAYTKNTQTNQTIATLTNTKIPLNK KTFEIFGLNTYRHNNWEFVQGLRFEKAKYNGKRQYKNLEYPLKDRSMNNVAANLAVNYLYSDTGNVYVKYERGFTSPAPAQLM DKIRKGGVNDYVNNDLKSEKSNSFEVGWNDYLFHSLVSADVFFSETKDEISTIFSGGHGTTFSNLNLGQTKRYGFDLKASQVF EKWTFSEAYSYIHAKIMKDKTKAYEGKYISYVPRHKFSLNADYAITPKWTLGGEYQYSSSVYLDNANKNGKDGARSVFNLQTS YEFNSHFSIYAGIKNVLNHKYYESVSAGSSQKYYSPAPERNYYAGFRYQF |

FIG. 29

| |
|---|
| *Fusobacterium necrophorum* TonB-dependent receptor Gene sequence (SEQ ID NO:31) |
| atgaatttaaaattaaaatgtatattacttagtagtctactaagcatgacagcatatggagcatccatagaccatattcaaac
gtatgcaccagaatatttaggaaatcaagctcaaaatggagcaattaacggagttctctccttattacaatcctgccggaacta
ctcagctagaagaaggattctatatcaatggtggattacaaatagcagctggacatgagcaatcagaatacaaagagaaagaa
tataaagctattttatacaacctgttccaagtattgcattgacgaaagtaaacaaagatagttcgacttattttacttttag
tgctattgcgggaggaggaacattaaactataaacatggagtagtaggaactgcaattattcctgatttagtggcaaatttaa
aagtcggatatttaaattcagctgcttttggtatgccaacaattccatctacattagctggaaaaaagtggcagttcaagtt
ttagatggaacaagagcaaaaggaagtaatctatacagtcaaatgacattaggaaaagcatttcaagtgaatgataaattatc
tctttctgcaggaattcgatttgtactggaagaagagatttagagggaaacattaaattaaaagcatattcccagattctc
caaatttgatcctgttttagcaaaattgcctttagaagcagaaattgattctaaaagaagagcaaaaggatttggatttgta
ttgggagcgaactacaaggtaaatgataagtggaatgttggaatgagatacgattctagagtaaaattaaatttcaaagcttc
tacaagcgaaaaagaaattagcattcctacagtaggggaataaagcatatcggatttacttctgatttatattatcctcaat
ataaagatggaaagaaagtaagaagggatttaccagctattttagcattaggaacaacttatcaggtatcagatacatggaaa
actggtctatctgtaaattattatttcaataaaaatgctaaaatggatggacaaaaatacaaaaatggctttgaagtggcttt
cggaaatgaatataaattaaatgaaaaatggacttgctagcttctattaactatgcaaaaacaggagcattaaaggaaagtt
atagtgatgtggaatatgctttggattctatcatgttaggaacaggagtgaaatatcaatatagccctactttagaattaaca
gcaactgtaggacactatttttatagatcggaagagggagatatcaaaggaagagttgctaaaaagacggattccatgataaa
acaattgcaaaatgtaaatgaacaacaaaaatacagaaaaagtattactgcttttgggcttggctttaccaaaaaattctag |
| *Fusobacterium necrophorum* TonB-dependent receptor Gene sequence (SEQ ID NO:32) |
| MNLKLKCILLSSLLSMTAYGASIDHIQTYAPEYLGNQAQNGAINGVSPYYNPAGTTQLEEGFYINGGLQIAAGHEQSEYKEKE
YKAIFIQPVPSIALTKVNKDSSTYFTFSAIAGGGTLNYKHGVVGTAIIPDLVANLKVGYLNSAAFGMPTIPSTLAGKKVAVQV
LDGTRAKGSNLYSQMTLGKAFQVNDKLSLSAGIRFVHGRRDLEGNIKLKAYSPDSPNLDPVLAKLPLEAEIDSKRRAKGFGFV
LGANYKVNDKWNVGMRYDSPVKLNFKASTSEKEISIPTVGGIKHIGFTSDLYYPQYKDGKKVRRDLPAILALGTTYQVSDTWK
TGLSVNYYFNRNAKMDGQKYKNGFEVAFGNEYKLNEKWTLLASINYAKTGALKESYSDVEYALDSIMLGTGVKYQYSPTLELT
ATVGHYFYRSEEGDIKGRVAKKTDSMIKQLQNVNEQQKYRKSITAFGLGFTKKF |

FIG. 30

| Fusobacterium necrophorum Cell surface Protein Gene sequence (YadA-like protein) (SEQ ID NO:33) |
|---|
| atggggaattttaatttaaaatttttaccatatctttattaattttattggtacaaaattcttttgcagaagatccggtaat aaaaagagggaaataaccaagatagtatagtagccggtctccataacaaagctgtaaacggatattccttagcttatggagatg ctaatgaggccactggagatgcagccagtgtagcttttggcttaaaaaatgtggcaagtgggaaaagtgcaacagcctttggt aatgccaataaggcgggtggagatacagcagcagcttttgggaacaataacacagcaggcggtcgttttagcttagcttttgg taataaaaatgaggtcagtggaacaagcagtgcagcttttggtttccaaaataaggctaaatctaaagaaagtgttgctgtag gtcatgagaatgaggtagaagcggactacggcattgctttgggtaatggaaatgaagtaaaatcacaaaaaggtgtagcagta ggatatcaaaatgaagcaaaaggtttttcaaattctgttttcggtattgaaagtagagtcagtgggacaagcagtacagttgt aggaaattcttatgaagtttcaggaactaaatcggtgcctttggagtgggagaagccggactaaagtcttcaggaataagct acaaatataaaaatgaggtaatgaatcttacactataggaaatagaaacagtatagcaacaaggacgaataataactttata ttgggaaatgatgttactataggtgacggaataaacggtgctgtagttttaggtaaaagttctaaggtaacggaaagcaatac agtttctgtcggttctgaaaacgaagaagaagaatagtatttgtggcggatggaactcaggatacagatgcggctactgtag ggcaagtcaagaaactaatttcttcaagtacagtactgggagctggaatgggaaatgtttatacaaaggctgagagtgatgct aaatttgctactaaagatgcaggtaatttgtcggcaagtgatgttgatgcttggagaagtaagttaggagttattgctaacac agcagcagatccaaaaagtacaagtataggaaataataataaagtgacggaacttattcaacagcggttggttacaaaaatg aagttagcggaaataaatctggagcttttggagatccaaatatagttacagggaatcgttcctatgccttggcaatgataat actattgcaggggatgataatttttgttttaggttctaatgtaaatataggagtggaatatcaaattctgttgcgcttggaaa taactcaaaagtaaaagcttctaatgaagtttctgtaggttcggtaggaaatgaaagaaagataacgaatatggcagatggag aagtttcatctacatgacagatgcaattacaggtagacaactatatcatgtaatgcaaaattcaggaacaacaggaatagaa aatttaagaaatgaagtaaatgaaaagttctcagatgttaaaaatgaagtgaaccatgtaggttccttgagcgcggcacttc tgccattaaatcctatgcagtatgatccgaaagctcctaatcaaatcatgcgcaggcttgggacattatagaaataaacaggctg ttgcagtaggactaagccatcatttcaataatagtgcgatgatgacagcagggcttgccttagggaatgagtcaaagataaaa gctatggcaaatcttggatttacaataagattgggaagaggcggagaaacttcggctgaaattcctcaaagtgtaattcaaaa tgaaatggcaagattagctagagagaatcaagaactaaaaaaagagttatttatcataagagagcagttagaagaattaataa acaaataa |
| Fusobacterium necrophorum Cell surface Protein amino acid sequence (YadA-like protein) (SEQ ID NO:34) |
| MGNFNLKFFTISLLILLVQNSFAEDPVIKRGNNQDSIVAGLHNKAVNGYSLAYGDANEATGDAASVAFGLKNVASGKSATAFG NANKAGGDTAAAFGNNNTAGGRFSLAFGNKNEVSGTSSAAFGFQNKAKSKESVAVGHENEVEADYGIALGNGNEVKSQKGVAV GYQNEAKGFSNSVFGIESRVSGTSSTVVGNSYEVSGTKSGAFGVGEAGLKSSGISYKYKNEGNESYTIGNRNSIATRTNNNFI LGNDVTIGDGINGAVVLGKSSKVTESNTVSVGSENERRIVFVADGTQDTAATVGQVKKLISSSTVLGAGMGNVYTKAESDA KFATKDAGNLSASDVDAWRSKLGVIANTAADPKSTSIGNNNKVTGTYSTAVGYKNEVSGNKSGAFGDPNIVTGNRSYAFGNDN TIAGDDNFVLGSNVNIGVGISNSVALGNNSKVKASNEVSVGSVGNERKITNMADGEVSSTSTDAITGRQLYHVMQNSGTTGIE NLRNEVNEKFSDVKNEVNHVGSLSAALSALNPMQYDPKAPNQIMAGLGHYRNKQAVAVGLSHHFNNSAMMTAGLALGNESKIK AMANLGFTIRLGRGGETSAEIPQSVIQNEMARLARENQELKKELFIIREQLEELINK |

FIG. 31

O-antigen polymerase, 60.6 kDa. (SEQ ID NO:35)

LGIFSFLGIIQFLIRNSSDQKMLILGIFFLYLSSLLFVYSFQSILKEKDMGLFFFLGILFPYYFQKHPYVFKDLMRESHNIRN
INYVYIFIFSIFFLKYFFYNTKKNWKEYLEVENIRNYLLYLMPFFILRAKDIKMIGFFYGIVVFVFCYKKDWNILLEKRKKIC
LLFLVLLFLFFSYMSNYVWGIPNQFGEQLLGNYVYNYFLLLILLLIPISEEMMKKIKMSIAISLFYPILLIVLEWMQNHYTLE
IAMGTEEWTSIWAVRAGLVSLISLFFYLSEKRKVYLFGVIFSLLSLFLGQGRGPILSFIASFCILFFFFYEKKTDRKKVFTSL
GIVLLLLFVIYNTENYIIKKFQLVFLGADSSTNTRIELYHGAIEQWKSQKWIGYGLGSYKETVELLKQEYLEKYDLIRIPHAH
NNILELLRSLGILGTFIYIFLNGYLCFWLLGKYWKTREKLYILPFVLIVNFELSGITDFSLMMYKSQLLLFFICSLSLSYTVS
MSTDVEYKI

FIG. 32

Membrane Spanning Protein, 26.8 kDa. (SEQ ID NO:36)

VEMFVLFGTSHMIMILIGVISVLLLIILGFLIRPQLLAKWISVSVLVIKLAEMYYRHRVLGEEIYRMLPFHLCNLTIILSLFM
MFFHSKFLFQLVYFWFVGAIFAILTPDIIFAYPNFWTISFFITHFYLVFSALFALIHFHFRPTKRGMLMAFLFINLWAVLMYF
VNQELGTNYLFVNRIPETTTLLSYFGAWPYYLLPVEGIYIIESILLYLPFRKSNIKFHF

FIG. 33

Outer membrane protein, 18.9 kDa. (SEQ ID NO:37)

MRANSIRINALEINIIEALKEELPEEMTIVLDDRALNFDFDKSVVKPKYNEMLTNLKEFITKNNYEVTIEGHTDYIASNEYNM
GLSKRRAEAVKAKLIELGLEPSRIVAILPKGEEEPIADNKTTEGRAKNRRVEFKLVKRDSVGEVNSEESRIIDVKKGVVEAEN

FIG. 34

Outer membrane porin F, 20.2 kDa. (SEQ ID NO:38)

MKKYLGMTVLLASFVLAACGKTSNTSVRDLSTEGNQNFAIEDIDTAKKPLEDIIVFNQDGVTIRREGNNLILSMPELILFDFD
KYEVKDGIKPSLRTLANALGANSDIKIKIDGYTDFIGSEGYNLELSVNRAKAIKSYLVNHGAIENNISIEGYGKQNPVASNAT
ESGRARNRRVEFIISRS

FIG. 35

Outer membrane protein, 19.7 kDa. (SEQ ID NO:39)

VGRKSTKIGILFFLFLFSLPSFAVQKLTTTQMRENSIRINALELKEMDIHLKKVTVVLDERALNFDFDKWNIKEQYYEVLENL
KEYILANDYEVVIEGHTDSIGTNAYNIGLSFKRANSTKEKLIEFGLPADRIVGISGKGEESPIATNETPEGRSQNRRVEFHLE
KIGDKE

FIG. 36

Hemin uptake system outer membrane receptor, 90.2 kD. (SEQ ID NO:40)

MEENNGTIVITEEMIQKKHYDSVAKIFEDSPVSVVRHTAFGPIVDLRGSGERTISRVKVMIDGTPINPLEETHGTIPFDTIPV
ESIAKIEIVPGTGTTKYGGGTTGGYINIHTKKDKQKNYITINADHASYHANSIGIAAGMNASKKLFVYAGEAYQRKDGYRKKD
HSDRNNFLGGFDYQINAKHRIKGQGNLYREDLKSTTEVTHEELKQDRRKAGEDTKIEMDRDFASLDYEYTPTSHFTLPANVNR
AHFTRDVSMDAKQEQLTLVNAFRFTHNMSMVDDEVKTLKPVLKDFQSTMEGKFKEENQEGKVDGEWKYNQGKGHLQFGYAYNK
KSLDQNLKIQSKPFNLGKSLYYLFPGDPAPHPFEDYAGKVLDQETMWRVIFNDLGYSQEYIDTHAPSMAGDNSGEILDLQNYN
QVDSFRNTHSLYLLNDYKITPKLNFRSGLRWEYSKYGSKRKNYMAIGIHKAQHSDLAASAGLAGLLDSYEKEALLLGKLDYVD
IELSIKDTDMKDSSHNFGGEVGFSYQYHKKGNLYFRYERGFLSPLPSQLTNKDFLTGNYYPSGVKSEKVDTIEIGIKHSLWNN
THIEANTFFSLTKDEITNMRYNANNHMNMRWAYANISKTRRLGFELNAEHIFDKLKIRESFSYVDAKIAKDTGFKDYYHSDYK
EGTKNEFKDAPLYYKKGQTVPLVSKVKVTVGAEYQCTDKLSLGGNYNYVSGYDTREPGEGFQAKTYKVKGHGTLDLFGRYYFT
DYAYVRFGVNNVLGEKYNLREDSHYAVPAPKQNYYAGFSYKF

FIG. 37

Outer membrane protein H precursor, 17.5 kDa. (SEQ ID NO:41)

MKKMLLVLGLVSAFSMSAFADKIAVVDSQEVIGRYSGTKGVEATLQKEVKRIENDVNQRQVALQKEEVALQAKGDKLTDAEKK
AFQAKVEGFYKYVNTSRESLAKMEQTKMSAIFTKANKAVQAVAAEGKYDYVLDRGAVLVGGEDITDKVIKKMETIK

FIG. 38

Major outer membrane protein, 42.9 kDa. (SEQ ID NO:42)

MKKLALVLGSLLVIGSAASAKEVMPAPMPEPEVKIVEKPVEVIVYRDRVVQAPAKWKPNGSVGVELRTQGKVENKGKKATEEN
ARKGWAGKEPNVRLETKASVNFTENQNLEVRTRQTHVLTKTDSDKEESNHKDTQVRIRHTYNFGKLGSSKVGFKVASQYLHDD
HVDSLRTRAVFDFADYIYSNSLFKTTALEIGPSYKYVWGGNDDRYYNALGLYANAEFELPYGFGFQAEFEDAFTYTSTGKGDG
KRDKAKLGHADFVLSHSLDLYKEGKHSLAFLNELEYETFWAWDKKDASMEEWPHVDGHGRVNSEGKNKKWGAYELTYTPKLQY
NYQATEFVKLYAAIGGEYVNRENNKSTARYWRWNPTAWAGMKVTF

FIG. 39

Outer membrane protein, 27.8 kDa. (SEQ ID NO:43)

MKKNFIIAIFCSFAAFSYAEEKMSGVNLGITASHAKEIYKVSAKEKYSVLPLISVNYKDFYINQSELGYQFQVHDNFLISGYF
DFLDGYPVKGKEMQKEYKSIQTRRSQIVGGGRITYFKDNFQTSIFAQGGKRGSSTGADLSLSFPLTEKLFFTTGLNYTIYSKN
FTNYYFGVHKEDFGGKLTKVYSPKASYSYGAEASLEYQITEPFSIFTSVSATNYSKEITNSPLVKDKTNISTTIGLQYSF

FIG. 40

Outer membrane protein tolC, 54.6 kDa. (SEQ ID NO:44)

MKQKWSFFLCLLFLSSCSSVNKEISETSLLQELKRKETETQRILTEQRLSLEEAIQIAKERNLELKTKQLEREISKIDSKIAF
GNFLPRISAFYTRSFWEEALSGQVDLPASLSQFPLIGPMLPKEIQGRLLDKSYSVYGLQASMPIFAPATWFLYSARRKGEEIQ
SLVLTLTEKMISIQVIQQYYWILALEAEEIQLKASLKSAEQLLHNMKIALDTQSILEWQYQKAQAYYKQKKLALAQNQRDLKL
AKMGLLSTLNLSPLSSVRLQKTQNITKRKEDNYEEVIYQALVHNDALGIQEKVLEVEKEKLKISFSRFLPVIGLQGFYGEHSL
SLLSSSHYLLGILGGVFSIFNGFQDISAYQKAKIEQRKAMLKKESLILQSIAETTNVYQKLQSSIEEEEIAEINEKAERGKFH
QKSLERKVGMIDELSYLQAVQSYEEAKSLALKAEYQSAVLQEILDTLVGRGRFVEEGENND

FIG. 41

Major outer membrane protein, 53.8 kDa. (SEQ ID NO:45)

MKKNVFMLGGFILLTSSVLAKEALVVPEQKPEILVVEKPVEVIVYRDRVLETPAKWRPNGSIDIQYRVYGKTENKVASPRTVP
PIPIEPPRIPLVPLEPPHIPLVPLEPPHIPLVFLLPPPTLEEDDGETHWQAASLLEGEGEVYDDEDVDDLSETVEIPPMQAAE
ALEEKEDEKTSKWARKKRYNTGRLQVEAKLNFTEKQSLEIRERVYHALRTTKVDENERYGKAAADEDELRLRHFYRFGNLGNS
KVNASSRLEYNTLHNSEKMSGSAYLAFDISSYLFQNNFIKTDYFRVGPTYTYAMKNKTNYSNQIGLLLESYFSLPYNFGLELN
VHPKYMAYNKEFEIGEGKTKKHEFYAEVEAKLFHSLNLYKNNKWRLDLNTEGGYDPYQFHQYKVVKNREKKVEKRAYSLYALP
TFQVSYQATEYVNVYATAGAEYRNWVDTAESTASHWRWQPTAWAGMKVTF

FIG. 42

Outer membrane protein TolC, 49.7 kDa. (SEQ ID NO:46)

MKKIAAIFFLTGTVLFAGEITLEEAIARALKHSREVQIAEKKFLSSKIKAKQAIKKALPSLVYSGSYQQSEYERMQAKNRTEK
QGEKIGYRQSVTLTQPLFQGGSIVAEIQGAKYYESLFEIEYLQKKIETRLKTIQIYSHIIRAKKELEALRYSKKQLEQRYEKQ
KVQLELQLITRTDLLKTEYHLLSVESQMEKAKNEIEVQMENLKIQMGLFKDEKIEIQEFFVPKQCSAKIDFDKDRKQAMETSM
SVLSAKYRLEIAKAEQRGRAGEMLPEINLFASYENVGERRTFNQSRKDMEWIGGVEVRWKLFSFGREYDSYKVATLEKETQEL
SQEKIQDSLRLKLREAYLDLCRLEILRDSKTKALETAELNFQMEQEKYDAGLISVVDYLDSEKQLREAKVSYYQTELEYYYAF
EYYQSLLV

FIG. 43

Outer membrane protein, 19.7 kDa. (SEQ ID NO:47)

VGRKSTKIGILFFLFLFSLPSFAVQKLTTTQMRENSIRINALELKEMDIHLKKVTVVLDERALNFDFDKWNIKEQYYEVLENL
KEYILANDYEVVIEGHTDSIGTNAYNIGLSFKRANSTKEKLIEFGLPADRIVGISGKGEESPIATNETPEGRSQNRRVEFHLE
KIGDKE

FIG. 44

Major outer membrane protein, 44.5 kDa. (SEQ ID NO:48)

MKKLALVLGSLLVIGSAASAKEVMPAPMPEPEVKIVEKPVEVIVYRDRVVQAPAKWKPNGSVDVQYRWYGETENKVDGQLKQE
GLAEGEHDWANDENNYGRLQTEAKINFTENQRLEIRTRNFHTWAQGKNTKDYSKAKAEDDKIRLRHFYNFGKIANTKVNATSR
LEWDQKSGDGAKKLEASVGFNFADYLFNNDFVKTTNFTVRPLYAHKWTAHRGGGRKGAEVLGLNLESNFEFPYGFELEFKLEP
TYTFYGTKQTISDKDGENQREKKPAFDMDVTLILSNSVNLYTQDKFALDFNFEGGYDPYSFHQYRIYDKEEKEVGVKRSYSLY
ALPTLEANYQATEFVKLYAGAGAEYRNWKIEDEDYATRWRWQPTAYAGMKVNF

FIG. 45

Putative hemolysin, 37.9 kDa. (SEQ ID NO:49)

VKTKNFVLESKQDTSERKDSSYGGSFSIDLGNFSNLSVTMNGRKGNGEKEWVEKQTSFIARNGGKIDTDSLTNIGAVIGSESE
TEKLKVSANQVIVKDLEDKNQYENMGGGISIGTSIPNISIKHDKIEKEQINRATAANTEFGISGKKTSAEDLGFNTDINKTQE
VTKNEEKHLDAELHADLIGEDKRNEIKYAFKKLGSLHEILDQKKFKESMEGVLVDKFKDEHQKEFHLIKDENLSLEDKQKLAQ
NLVEKYLRENGYQGIIPEVLLTEEAHSFTVDSKDKTTGAKRGEKIYFSIHDIANPDLAFSQLFGHEKAHMNTYDEGKYGEETS
FHCKLQ

FIG. 46

Exoprotein involved in heme utilization or adhesion of ShlA/HecA/FhaA family, 62.0 kDa. (SEQ ID NO:50)

VKGSVNNSKTIEATNIDITGENLVNSSSIKADNILATVKTTKNDGDILALKDITLNTKKLDNTKKIAALQNITANNTALTNSG
EIVSNHKIELNHSNISNTNKILSNTIDMKNTSNFNNTGTISGTDVTLTSVNDIHLIANLHGENSLIIEGKNIVNENSISANDL
HMNAKNLTNHDLIAAENNANINVKNKVTNTENSSIYAGNKLNIQASELFNDSAEILGTDVKLEANQITNHIGTLQALNTMHIK
AGKFENIGKVEDLDRYESYYETWDGQRIEANQIEDWKVHFSKSSSKRSNGSAGKTIRKRQREAYHEISEKMKNDKYASLLFPK
YDKLMRGYLGDRGEYTEKTGSARIQTVPLQEKLRSLGKTTHAKVLAGNNILIEKKSDSNNEVMNKDGILSAGNTIKIDANQVQ
NLVSVGDEKIKVKTGEESMYIKLERTGKKPRKKVKMEVSYDRDFANDYITKKIPKLDEKGRQVYQKKFGGRKKPVYEYVTEYV
GRYAYVTGQPSVIEGKNVVIDNASLVRQGIEEANGYIKSGKDVNIQNFTSKNFHTGLSNGN

FIG. 47

Outer membrane protein, 19.7 kDa. (SEQ ID NO:51)

VGRKSTKIGILFFLFLFSLPSFAVQKLTTTQMRENSIRINALELKEMDIRLKKVTVVLDERALNFDFDKWNIKEQYYEVLENL
KEYILANDYEVVIEGHTDSIGTNAYNIGLSFKRANSTKEKLIEFGLPADRIVGISGKGEESPIATNETPEGRSQNRRVEFHLE
KIGDKE

FIG. 48

Exoprotein involved in heme utilization or adhesion of ShlA/HecA/FhaA family, 27.8 kDa. (SEQ ID NO:52)

LEKKKKGLSLSISKNSFKVAYGKNQFNYDEKDKTNIKSNLVLGDGTVLNKGAEITATNFNHGDITINNGDVIYGARKDERDVK
TSTEKSSFGISANVSSPALERIKQGANALEQIGNGDALGGLVNVGNVVTGTVDGLASNIKTKDGKQATAKDVEDNKFTSNNSF
YVQAGGSAGYSKSKQKTKSHTEKAVVTNITGLDENAKITYNDNKNVKYQGTQTQNTTFVYNNXXXDSYIDGKLTTDSKAIYN
KYILESIGIFFF

FIG. 49A

| *Fusobacterium necrophorum* filamentous hemagglutinin gene sequence (SEQ ID NO:78) |
|---|
| atgaaaaaattaaaaaattttgaaaatgttttaaaatcgcatttaaaacaaagagtaagaattacgacagcattca
ttgttgcttttttaattcatgggatgctaagctttgatgttgaagcaagagatttaagagttaggaatcaaataac
tccgtcaaattcaaataatggcttaagaataacttcaagccaaaatgggaccgatgttattaatattgttgatcct
aataatggaatatctcacaataagtatgtagattttaatgttggggacaaaaataatgttattttaacaacagtc
aaaaaaatggaacttctgttacaggaggagaagtcagtgcaaacccaaatttaacaaactctgcttctgttatctt
gaatgaaattcaaggaaattctgcttcagaattaaacggaggacttgaagttttggggaaagagcagatcttgtt
attgccaatgaaaatggaataaatgtaaatggagcaagatttataaacacttcagctctaacattatcaacaggaa
aagtctcagtcgataataaaaaatttcttttaacacagctacaaataatgcaaagatagcagtaaaagaaaaagg
aatagaaacagattctgattacttgaatatcctttcaagaagggctgaactagatggagcaatcaactctgaacat
aataaaaatttaaatatcaatgttatagctggtgcaaatactgttacagctgtaaatgatactttcgaattaaatg
ctgaaaacgccaaagatggaattaccaatgtagaagctatttccgcttcaaaatttggagctatgtatggaaataa
cattttttatcttgagtactaataaaggcgaaggaatcaaatatgaaggaagcctaaaagcaaaggatgaagtggag
ataatctctgaaggaaaagttgtaagttctgacataaatggaaaagatatcaaaatatcgtctaaagaagaaatta
acaatattggaaaaatgaaagcggataaaaatgtcagtcttaatgctcctatcgtaaaaaatatgtccagattaga
aggaagtgttagattaaaatcaaatgaacataataaaaagtatcaaaatagagaaagaggaattatctattatgac
tattatttaaatgtgaaaaatatgtcagaagtggaaaatgaattaaaattagttaaatcgtctattgaagccggaa
ataatattgaaataaataataatcttgaaaatggaagttttgaaaatttatctggggatttaaaagcaggaaatga
tatcaaagtaaaaggaaattttaaaacaaaacatttgtcagaaggaataaagctagaagatcttttaaaagaata
aaagtagatcttcgttgggagcacagaagtctagttgataacgcatattaatggaaactcttctttaacagatg
gaagcttgttggatgctttaaaaataatgactcaaaagaaaaataagaatattacacagccttaaaacaaattga
tgaccctcaattaaataaagttttaagtggtttattagggctgattggagaacaagggaacgaataaaagatgaa
aaagattggaataaagaagcagccataagttttacaaatggaacttattcaatagaagcaggaaatgacttgaaag
cttctggaaagtgattgaacttggtggttctaatgttatgactaaaaagaaatatttgaagtagcatctacgaa
aacggaaagtttacaatcaacgatttcagatgttaaaaatgctaatataaaagcgaaaaatgtttatatggaagcc
gataatataacaaatgtaaatgcagatattgcagcggaagacagtgcgattctttattctaaaaacaatattgatg
tgaagggagctaaagtttctgctgataaaattcttcttgaagctggtaaagatataaatttatcttcagaacttgg
tttcaaatcttctggggaacatgcgattattaaagaaacagatgttactgcaaataaggctgttggaatcaaatcc
aagaacttaaatattatggtgcagatgtagaggcaaaagatggacttataaaaatagactctgataagttaaatg
taaaagatatcagtacaatcaatgcaaattataaggccgaattaatagaaggaaaaaaatatatttaagagatca
tcaatatacaaaagctttacaagctaaagtggaatctacaccttctaaaataattgctaataaaatttttatcact
gcaaaagatggtgctgctattgagggttcactgatttcaggaaaaaatgctgacagcataatccaaatcatttctg
agggaaatgtcaatatcaaaaatagcaataatattgattatagtaattttattcagatagcagaggaaaaaataa
aaaaggagtctacaaattattaaaaatagataaggcttcaaaagaaaatcttgacatagtaggaagcaacttaaaa
tcggaaggaaatataaatataaaatcaaaaaatttaactgttgtatcaagtaaaataaaagcaggaaaaaagtta
acttagaagccgaagaagatataaaattactagcttcttgaattctaagaagaggaattaaataagatggaatg
gggtagcggtgctatcaatagttataaaaagtctttggagaaaaagatgtagtgtctactatgattgaagctgga
gaaaaagcaaatgtacatgcaaaaagagatttgtataaacaatctgtttttgtgaaagctggaagcgtaactatga
atggtgaggcaaataattacagtgatgctttagcttcaacagaaataaaaaaagaaacagatgtgaaagctggctt
tggtgtagaaggaaagattgcttttgctggaatgggagcagctggggaagcaaacactttagataatacagcaaca
ggaaaaacttccgggataaaaggtctttagaaaagagaatgaatttaaaaaagcggaagccagagcgaaagttt
acgcaaaaatggaagttaataagagcataaaagaaagtaaaaattatgtaaataacaacattacctcggaaagtgg
tgatgtgactataggttctaatggggtcactgatataggaaataccgatatcaattctcaaaatgatgttaactta
agaggtaaaaagtagaaaccactacaaggaaaatgtaacgaaagaggttaatcataagcttgatctttctgtaa
aaggtgacatcgcttttctaatgaaaatgtcaataaattgaatgatttggcaaatgatgttctaaaaagtaaaga
gatgttagaaaagaaagatatactcgggttagctcaaaaagcagaagaaacaatcaaagatttaaaagaaacgatt
ccaaatctaactaaaaaagacatttaggaataaaatcaagtcagggagtagggtagaatacactaataaaactt |

FIG. 49B

```
tactttaaaaaacacttatttaaaagctcaagagtttaacacagaaactcctggaaaagttaatcttttagcaggg
aagaaaacgattcataaagaagaaaattctttaaaggttggtgtatcagttaacgaaaatgtaggagtcaatatag
cagatggagccaatgctaaaattggtgtaggtgttcaagctagttacaatggcggaactgatttgaataaaaaaag
tttaaatacaactgtagaggtaggaaaagtgaatcataaagctgcagctgtaaatgaagataataaaacagacttt
tattacaaagataaaagaggtgcaggagttgatgttgatttaaaaataggagttcttcgaatcatatagtagcgg
cagatggaaatgtaggaggaaatgtgaattattcttttgcggctggaaaatcaacaacagatgttgtaacaaataa
gacagaaagtactgatgtaaaagcaggggttggactgaaagcttctgttggaatagatggaaaaagtccagatttt
tcaatttcaacagaccaaattgaatataaaaaagatggaaaagtattagttaatattgacgcaaaagataaaatga
tcaccaaagagagaattgaacagatgagagataaggtaaaaaattggagaactccaacaaatagtgcggaaaaatt
aatctaa
```

*Fusobacterium necrophorum* filamentous hemagglutinin amino acid sequence, 154 kDa.
(SEQ ID NO:53)

```
MKKLKNFENVLKSHLQRVRITTAFIVAFLIHGMLSFDVEARDLRVRNQITPSNSNNGLRITSSQNGTDV
INIVDPNNGISHNKYVDFNVGDKNNVIFNNSQKNGTSVTGGEVSANPNLTNSASVILNEIQGNSASELNG
GLEVFGKRADLVIANENGINVNGARFINTSALTLSTGKVSVDNKKISFNTATNNAKIAVKEKGIETDSDY
LNILSRRAELDGAINSEHNKNLNINVIAGANTVTAVNDTFELNAENAKDGITNVEAISASKFGAMYGNNI
FILSTNKGEGIKYEGSLKAKDEVEIISEGKVVSSDINGKDIKISSKEEINNIGKMKADKNVSLNAPIVKN
MSRLEGSVRLKSNEHNKKYQNRERGIIYYDYYLNVKNMSEVENELKLVKSSIEAGNNIEINNNLENGSFE
NLSGDLKAGNDIKVKGNFKTKHLSEGIKLEDLLKRIKVDLRWEHRSLVDNAYFNGNSSLTDGSLLDALKI
MTQKKNKEYYTALKQIDDPQLNKVLSGLLGADWRTRERIKDEKDWNKEAAISFTNGTYSIEAGNDLKASG
KVIELGGSNVMTKKEIFEVASTKTESLQSTISDVKNANIKAKNVYMEADNITNVNADIAAAEDSAILYSKN
NIDVKGAKVSADKILLEAGKDINLSSELGFKSSGEHAIIKETDVTANKAVGIKSKNLNIYGADVEAKDGL
IKIDSDKLNVKDISTINANYKAELIEGKKYILRDHQYTKALQAKVESTPSKIIANKIFITAKDGAAIEGS
LISGKNADSIIQIISEGNVNIKNSNNIDYSNFYSDSRGKNKKGVYKLLKIDKASKENLDIVGSNLKSEGN
INIKSKNLTVVSSKIKAGKKVNLEAEEDIKLLASLNSKKEELNKMEWGSGAINSYKKSLEKKDVVSTMIE
AGEKANVHAKRDLYKQSVFVKAGSVTMNGEANNYSDALASTEIKKETDVKAGFGVEGKIAFAGMGAAGEA
NTLDNTATGKTSGIKGLLEKENEFKKAEARAKVYAKMEVNKSIKESKNYVNNNITSESGDVTIGSNGVTD
IGNTDINSQNDVNLRGKKVETTTKENVTKEVNHKLDLSVKGDIAFSNENVNKLNDLANDVLKSKEMLEKK
DILGLAQKAEETIKDLKETIPNLTKKDILGIKSSQGVGVEYTNKTSTTTETTASSLKAKGKLNIKADEGD
ITLKNTYLKAQEFNTETPGKVNLLAGKKTIHKEENSLKVGVSVNENVGVNIADGANAKIGVGVQASYNGG
TDLNKKSLNTTVEVGKVNHKAAAVNEDNKTDFYYKDKRGAGVDVDLKIGVSSNHIVAADGNVGGNVNYSF
AAGKSTTDVVTNKTESTDVKAGVGLKASVGIDGKSPDFSISTDQIEYKKDGKVLVNIDAKDKMITKERIE
QMRDKVKNWRTPTNSAEKLI
```

FIG. 50

Membrane protein, 79.4 kDa. (SEQ ID NO:54)

MKRTLVAMLLFLVSMVSFAAGGSLIVKKVEVLNNQEVPASIILNQMDLKEGKPFSTEIMLHDFQTLKKSKYLEDVLIQPQAYE
GGVNVVVNVIEKKDVQSLLREDGVISMSEQANVDKSLILSDIIISGNQFVSTADLKKVLSVKQGGYFSKTAIEDGQKALLATG
YFREVTPNTQKNGNGVKIIYTVVENPVIQGINIHGNTLFSTPDILKVLKTKIGEVLNINSLREDRDTIMNLYQDQGYTLSEIS
DMGLNDRGELEVVISEGIIRNVSFQKMVTKQRGNRRKPTDDILKTQDYVIQREIELQEGKIYNAKDYDNTVQNLMRLGVFKNI
KSEIRRVPGDPNGRDIVLLIDEDRTAILQGAISYGSETGLMGTLSLKDNNWKGRAQEFGVNFEKSNKDYTGFTIDFFDPWIRD
TDRISWGWSLYKFSYGDSDSALFNDIDTIGAKINVGKGFARNWRFSLGFKGEYVKEKANKGNFRQLPDGTWYYTGKNKNDASN
TPLPKDAVNDKYMVFSIFPYLTYDTRNNPWNATTGEYAKLQLETGYAGGYKSGSFSNVTLELRKYHRGFWKKNTPAYKVVGGV
MTQSTKEGQRFWVGGGNTLRGYDGGTFRGTQKLAATIENRTQINDILGIVFFADAGRAWKQNGRDPEYGNDEKFSKGIATTAG
VGLRLNTPMGPLRFDFGWPVGKSQDKYSNDRGMKFYFNMGQSF

```
MKKLWILFFLLGSVAFGREVTLEEAIQASMENSKAVKISDKQLEISKLKMNQAIKKALPS
MKKLWILFFLLGSVAFGREVTLEEAIQASMENSKAVKISDKQLEISKLKMNQAIKKALPS
MKKLWILFFLLGSVAFGREVTLEEAIQASMENSKAVKISDKQLEISKLKMNQAIKKALPS
MKKLWILFFLLGNVAFGREVTLEEAIQASMENSKAVKISDKQLEISKLKMNQAIKKALPS
MKKIWTMFFLVGSLAFAREITLEEAIQESMNHSKTLKISEKKLQISKLNRSQAIKKALPS
MKKILGLLLILSSSVFAREITLDQAIQMSLENSKEIKISEKDVEVSKLRVGMAFKDALPS
MKKILGLLLILSSSLFAREITLDQAIQMALENSKEIKVSEKDVEVSKLKVGIAFKDALPS
MKKILTIFMLMASVALARDLTLEQAIDLSLNNSKEMRISEKNLEISKLNVSKAFKNALPS
MKKTLGLLLLLSSSVFARELTLDQAIQMALDNSKEMQISQRDVETAKLNVGIAFKNALPS
MKKLLSIFFLLTGSLFARELTLDEAINLSLTNSKDIQISEKNLEISEINLQKAFKLALPT
```

```
***        *  **  **     **    *         *  *  ***
```

FQ

```
VVYSANYQRGEYERNI-YKNKS---SMES-------EKGGYKQSITISQPIFQGGAILAG
VVYSANYQRGEYERNI-YKNKS---SMES-------EKGGYKQSITISQPIFQGGAILAG
VVYSANYQRGEYERNI-YKNKS---SMES-------EKGGYKQSITISQPIFQGGAILAG
VVYSTNYQRGEYERNI-YKNKS---SMES-------EKGGYKQSITISQPIFQGGAILAG
VLYNTSYQRTEYERNI-SKNKS---SMQL-------EKGGYKQSITISQPIFQGGAIIAG
VVYSGTYTRGESDRKM-Y-----RHGWED----QVERKGGYTQTISISQPLFQGGAVLGG
VVYNGKYTRGEYERKM-Y------KHGWEE-----QVDRKGGYTQTISISQPLFQGGAILGG
VTYSGTYAVGEHERQILTQSER---NYAS--------KKRGYTQNLRLTQPLFTGGTITAG
VVYTGSYTRSEYDRKI-TAEERPNHRLEKNGSREVEAKGGYTQKITISQPIFQGGAILGG
VTYNGKYSRTNYDRKI-AIDD---HSSEK-------GRGSYSQSITIAQPLFAGGTIFAG
```

```
* *   *      *                         * *    ** * **        *
```

FQ

```
IQGAKAYKTIADLSYVQETLNTRLKTIRTFSNIVNSKRNLQALEYSEKQLQNRYKKQEAQ
IQGAKAYKTIADLSYVQETLNTRLKTIRTFSNIVNSKRNLQALEYSEKQLQNRYKKQEAQ
IQGAKAYKTIADLSYVQETLNTRLKTIRTFSNIVNSKRNLQALEYSEKQLQNRYKKQEAQ
IQGAKAYKTIADLSYVQETLNTRLKAIRTFSNIVNSKRNLQALEYSEKQLQNRYKKQEAQ
IQGAKAYETIADLSYVQEGLNTRLKTIRTFSNIVNSKRNLQALENSEKQLQKRYQKQEAQ
IKGAKAYKTIANLLYLGERRDTRLKTIQNYSNIVKYEKDLEALESSKRELQARYNKQKAQ
IKGAKAYKSIANLLYLGERRDTRLRTIQNYSNIVKYQKDLEALEASKKELQARYNKQKAQ
IKGAKAYENIASYSYLQSKIQNRLDTIKIFSDIINAERNLEALEYSENILQKRYQKQEEQ
IQYAKAYKSVANLMYLSSQRDVRLETIQIYSDIVKSEKDLEALMSSKEELKATYDKQKAQ
IKGAQAYENIANYNFLNSKIKMRIETIAAYFSLLNAEKDLNALKNSKSILQKRYDKQKVQ
```

```
LELRLITKTDLLKTEYSLLEVQSLISKAKSNIEVQTEDLKFQMGVDKKEALEVKEFIVPN
LELRLITKTDLLKTEYSLLEVQSLISKAKSNIEVQTEDLKFQMGVDKKEALEVKEFIVPN
LELRLITKTDLLKTEYSLLEVQSLISKAKSNIEVQTEDLKFQMGVNKKEALEVKEFIVPN
LELRLITKTDLLKTEYSLLEVQSLISKAKSNIEVQTEDLKFQMGVDKKEVLEVKEFIVPN
LELRLITKTDLLKTKYNLLEIQSLIAKAKSNIEVQTEDLKFQMGIDKEEQLEVKEFNVPN
LDLRLITKTDLLKTEYSLLEVESQIIGTKNGITIEKENLKIKTGIPKQEDVTVVDFNVPM
LDLRLITKTDLLKTEYSLLDVESQIIGTKNGITIEKENLKIKTGIPKHEDVSVVEFEVPM
LNLRLITRTDILQTEYSIEDIRAQMINAKNTIDTNMEKLYIRTGINKSESLNLIPFDIPN
LDLRLITKADLLKTEYSMLEVDSQIIGTQNQITVQKENLKLKLGLPKTEDLTVVEFDVPM
LELRLIRKSDISQTEYSLLNVESNIIAIKSQIDTYREQLRIKTGLAKNEFITVVDFNVPM
*  ****    *   * *             *       * *      * *       * *
```

FQ

```
HLTERITFEKDKERALESSIQALIAKSQVKIAKAQETAALGNMLPKVNAFVSYGVASERT
HLTERITFEKDKERALESSIQALIAKSQVKIAKAQETAALGNMLPKVNAFVSYGVASERT
HLTERITFEKDKERALESSIQALIAKSQVKIAKAQETAALGNMLPKVNAFVSYGVASERT
HLTERITFEKDKEKALESSIQALIAKSQVKIAKAQETAALGNMLPKVNAFVSYGVASERT
HLTDTIDFQKDKEKALESSIQSLIAKSQVEIAKAQETAALGNMLPKINAFASYGVATERT
YLSRNINFKADLDQAMNESINALVAKNYVEAADASKMVSRADMLPKVNAFASYGT-SERT
YLSRNINFKADLDQAMNESINALVAKNYVEAADASRIVSRADMLPKVNAFASYGT-SERT
NFSEKINLNNDLKQAINESLSAKVAEEQVKVASATRMAAVGDLLPQVNAYASYGTG-ERT
YLSRNIDFQADLNQALTESIDAMVANKYVDMADAQRKVARADMLPQVSAFASYGVDSDRR
NLSKNINIDKDLEQAINESLNAKIAEEMYKISEAQTIAAAGSILPKVSAFATYGT-TERT
       *    *    *    *      *             **    *   **      *
```

FQ

```
HWKQTKEDAEWMGGLSVSWNVFSFGSDYDAYQIAKLEKESKELSETTAQDNIALSLKTAY
HWKQTREDAEWMGGLSVSWNVFSFGSDYDAYQIAKLEKESKELSETTAQDNIALSLKTAY
HWKQTREDAEWMGGLSVSWNVFSFGSDYDAYQIAKLEKESKELSETTAQDNIALSLKTAY
HWKQTPEDAEWMGGLSVSWNVFSFGSDYDAYQIAKLEKESKELSEMTAQDSIALSLKTAY
KWKQTREDAEWMGGLSVSWNVFSFGSDYDNYQIAKLEKENKELSEMTAQDTIELTLKTAY
KYNPTIDEAEWRGGVQVTWNVFEFGKNYDSYKVAAIGKEQEILREKISKDSIDISVTDAY
KYNPTIDEAEWRGGIEVTWNVFEFGKNYDNYRVAAIGKEQEMLREKISKDSIDINVTDAY
SFERSYKDGEWTGGIEVSWKVFSFGSDLDSYRVAKLQEEQEELRETSTKEDIEVNVRSAY
KYNATMDDAEWRGGVQVTWNVFEFGKNYDTYKTAAIAKEQEELREKISKDTIDINVTDAY
KFENSYRDAKWVGGIQVTWNVFSFGSDIDEYRIAKLEEEQQKLKEISTKENIEIAVKSAY
    * **  * * ** **    * *   *     * *       *    **
```

```
LELQRLEILRESRKRGLEAAELNFTMDQEKFDAGLLSTVDYLSSETQLREARVNYYQAEL
LELQRLEILRESRKRGLEAAELNFTMDQEKFDAGLLSTVDYLSSETQLREARVNYYQAEL
LELQRLEILRESRKRGLEAAELNFTMDQEKFDAGLLSTVDYLSSETQLREARVNYYQAEL
LELQRLEILRESRKRGLEAAELNFTMDQEKFDAGLLSTVDYLSSETQLREARVNYYQAEL
SELQRLEILRESRKRGLEAAELNFSMDQEKFDSGLISTIDYLLSETQLREARVNYYQAEL
LELIRMEKERDSKERAMEAAIENFRMDQERYDAGLISTVDYLLSESQEREAKVSYNQIVI
LELIKMEKERDSKERAMEAAIENFRMDQERYDAGLISTVDYLLSESQVREATVAYNQIVI
LNVLSLEKQIDSQAKALEAAKVNFELNQEKYDAGLISTVDYLDFENTYRQARIAYNKVLL
LELVRMEKDRDSKGRALEAAMENYKIDKEKYTAGLISTIDFLASETQLREAKVAYNQVVI
FDLLRLEKLRESKSKALEVAKLNFEMDQERYDAGLISTIDYLDTENTYRNANIDYNKTLM
      *    *        * *        *    ** **  * *    *     * *    *
```

FQ

```
DYYYAFEYYRSLLV   (SEQ ID NO:4)
DYYYAFEYYRSLLV   F. necrophorum    (SEQ ID NO:63)
DYYYAFEYYRSLLV   F. necrophorum    (SEQ ID NO:64)
DYYYAFEYYRSLLV   F. necrophorum    (SEQ ID NO:65)
DYYYAFEYYRSLLV   F. gonidiaformans (SEQ ID NO:66)
DYLYAFEKYRSLLI   F. ulcerans       (SEQ ID NO:67)
DYLYAFEKYRSLLI   F. varium         (SEQ ID NO:68)
DYYYAFETYRSLLI   F. nucleatum      (SEQ ID NO:69)
DYLYAFEKYRSMLI   F. mortiferum     (SEQ ID NO:70)
DYYLAFEKYRSLII   F. russii         (SEQ ID NO:71)
 **  ***  ***
```

MKKVVFGIYSILMSSAMLGAEIDLGTQNIYSETGFETSLRSSVSSPYIVTSKEIKEKHYT
MKKVVFGICSILISSAMLGAEIDLGTQNIYSETGFETSLRSSVSSPYIVTSKEIKEKHYT
MKKVVFGICSILISSAMLGAEIDLGTQNIYSETGFETSLRSSVSSPYIVTSKEIKEKHYT
MKKVVFGICSILMSSAMLGAEIDLGTQNIYSETGFETSLRSSVSSPYIVTSKKIKEKHYT
MKKVIFGIYSILLSSAMLGAEIDLGTQNIYSETGFETSLRSSVSSPYIVTSKKIKEKHYT
MKKVVFGIYSILMSSAMLGAEIDLGTQNIYSETGFETSLRSSVSSPYIVTSKKIKEKHYT
MKKVVFGICSILMSSAMLGAEIDLGTQNIYSETGFETSLRSSVSSPYIVTSKKIKEKHYT
** * * **************************** ****

FT

RVSEILRDIPHIYIGPGGSVDMRGQGSAHARTTVQLLIDGVPANFLDTSHINLPIDTLNP
RVSEILRDIPHIYIGPGGSVDMRGQGSAHARTTVQLLIDGVPANFLDTSHINLPIDTLNP
RVSEILRDIPHIYIGPGGSVDMRGQGSAHARTTVQLLIDGVPANFLDTSHINLPIDTLNP
RVSEILRDIPNIYIGSGGSVDMRGQGSIHSRTTVQLLIDGVPANFLDTSHINLPIDTLNP
RVSEILRDIPNIYIGSGGSVDMRGQGSIHSRTTVQLLIDGVPANFLDTSHINLPIDTLNP
RVSEILRDIPNIYIGSGGSVDMRGQGSIHSRTTVQLLIDGVPANFLDTSHINLPIDTLNP
RVSEILRDIPNIYIGSGGSVDMRGQGSIHSRTTVQLLIDGVPANFLDTSHINLPIDTLNP
********  ******** * ******************************

FT

EDIKRIEVIPGGGAVLYGSGTSGGVINIITKKYTGNYAKASYQIGSYHNHKYDVAAGTSL
EDIKRIEVIPGGGAVLYGSGTSGGVINIITKKYTGNYAKASYQIGSYHNHKYDVAAGTSL
EDIKRIEVIPGGGAVLYGSGTSGGVINIITKKYTGNYAKASYQIGSYHNHKYDVAAGTSL
EDIERIEVIPGGGAVLYGSGTSGGVINIITKKYTGNYAKAGYQIGSYHNHKYDVAAGTSL
EDIERIEVIPGGGAVLYGSGTSGGVINIITKKYTGNYAKAGYQIGSYHNHKYDVAAGTSL
EDIERIEVIPGGGAVLYGSGTSGGVINIITKKYTGNYAKAGYQIGSYHNHKYDVAAGTSL
EDIERIEVIPGGGAVLYGSGTSGGVINIITKKYTGNYAKAGYQIGSYHNHKYDVAAGTSL
* ************************************ ****************

FT

GNFDINLSYSKNNRDGYRKKAFSDSDFFSGKLRYHFNPTDSLEFKYSYFDNKFRGVKSLT
GNFDINLSYSKNNRDGYRKKAFSDSDFFSGKLRYHFNPTDSLEFKYSYFDNKFRGVKSLT
GNFDINLSYSKNNRDGYRKKAFSDSDFFSGKLRYHFNPTDSLEFKYSYFDNKFRGVKSLT
GKFDINLSYSKNNRDGYRKKAFSDSDFFSGKLRYHFNPTDSLEFKYSYFDNKFRGVKSLT
GKFDINLSYSKNNRDGYRKKAFSDSDFFSGKLRYHFNPTDSLEFKYSYFDNKFRGVKSLT
GKFDINLSYSKNNRDGYRKKAFSDSDFFSGKLRYHFNPTDSLEFKYSYFDNKFRGVKSLT
GKFDINLSYSKNNRDGYRKKAFSDSDFFSGKLRYHFNPTDSLEFKYSYFDNKFRDVKSLT
* ******************************************************* ***

REQVEKDRRQSGLSPEDNLKNTIRKEEWNLTYDAKWTSWLEHKSNLFYQSTEIKSSEYED
REQVEKDRRQSGLSPEDNLKNTIRKEEWNLTYDAKWTSWLEHKSNLFYQSTEIKSSEYED
REQVEKDRRQSGLSPEDNLKNTIRKEEWNLTYDAKWTSWLEHKSNLFYQSTEIKSSEYED
REQVEKDRRQSDLSPEDNLKNTIRKEEWNLTYDAKWTSWLEHKSNLFYQSTEIKSSEYED
REQVEEDRRQSGLSPEDNLKNTIRKEEWNLTYDAKWTNWLEHKSNLFYQSSEIKSSDYED
GEQVEEDRRQSGLSPKDNLKNTIRKEEWNLTYDAKWTNWLEHKSNLFYQSSEIKSSDYED
REQVEEDRRQSGLSPKDNLKNTIRKEEWNLTYDAKWTNWLEHKSNLFYQSSEIKSSEYED
** * * ***************** ******** * *

FT

ALPFYQYQISSYQKMLTMPGIPPMMQAQLKKQIKALQNLITSNPRMELHQGSRFKDQKFG
ALPFYQYQISSYQKMLTMPGIPPMMQAQLKKQIKALQNLITSNPRMELHQGSRFKDQKFG
ALPFYQYQISSYQKMLTMPGIPPMMQAQLKKQIKALQNLITSNPRMELHQGSRFKDQKFG
ALPFYQYQISSYQKMLTMPGIPPMMQAQLKKQIKALQNLIMSNPRMELHQGSRFKDQKFG
AIPFYQARIAMYQQMLATPGIPPMMLEKLKKQIQIWENIITNNPKMELRQGSLFKDRKFG
AIPFYQARIAMYQQMLATPGIPPMMLEKLKKQIQIWENIITNNPKMELRQGSLFKDRKFG
AIPFYQARIAMYQQMLATPGIPSMMLEKLKKQIQFWENIITNNPKMELRQGSLFKDRKFG
* **** *   **    *****      *  *   * * * ***

FT

FKMKNKFKYGENSDFILGLGYIHNKMDRDSWAYTKNTQTNQTIATLTNTKIPLNKKTFEI
FKMKNKFKYGENSDFILGLGYIHNKMDRDSWAYTKNTQTNQTIATLTNTKIPLNKKTFEI
FKMKNKFKYGENSDFILGLGYIHNKMDRDSWAYTKNTQTNQTIATLTNTKIPLNKKTFEI
FKMKNKFKYGENSDFILGLGYIHNKMDRDSWAYTKNTQTNQTIATLTNTKIPLNKKTFEI
FKMKNKFKYGENSDFILGLGYIHNKMNRNSWAYTKNTQTNQTIETITDTKIPLNKKTFEI
FKMKNKFKYGENSDFILGLGYIHNKMNRNSWAYTKNTQTNQTIETITDTKIPLNKKTFEI
FKMKNKFKYGENSDFILGLGYIHNKMNRNSWAYTKNTQTNQTIETITDTKIPLNKKTFEI
************************* * ************* * * ************

FT

FGLNTYRHNNWEFVQGLRFEKAKYNGKRQYKNLEYPLKDRSMNNVAANLAVNYLYSDTGN
FGLNTYRHNNWEFVQGLRFEKAKYNGKRQYKNLEYPLKDRSMNNVAANLAVNYLYSDTGN
FGLNTYRHNNWEFVQGLRFEKAKYNGKRQYKNLEYPLKDRSMNNVAANLAVNYLYSDTGN
FGLNTYRHNNWEFVQGLRFEKAKYNGKRQYKNLEYPLKDRSMNNVAANLAVNYLYSDTGN
FGLNTYRHNNWEFVQGLRFEKAKYSGKRQYKNLEYPLKDRSMNNVAANLAVNYLYSDTGN
FGLNTYRHNNWEFVQGLRFEKAKYSGKRQYKNLEYPLKDRSMNNVAANLAVNYLYSDTGN
FGLNTYRHNNWEFVQGLRFEKAKYSGKRQYKNLEYPLKDRSMNNVAANLAVNYLYSDTGN
********************** *********************************

FT

VYVKYERGFTSPAPAQLMDKIRKGGVNDYVNNDLKSEKSNSFEVGWNDYLFHSLVSADVF
VYVKYERGFTSPAPAQLMDKIRKGGVNDYVNNDLKSEKSNSFEVGWNDYLFHSLVSADVF
VYVKYERGFTSPAPAQLMDKIRKGGVNDYVNNDLKSEKSNSFEVGWNDYLFHSLVSADVF
VYVKYERGFTSPAPAQLMDKIRKGGVNDYVNNDLKSEKSNSFEVGWNDYLFHSLVSADVF
VYVKYERGFTSPAPAQLMDKIKKGGVNDYVNNDLKSEKSNSFEVGWNDYLFHSLVSADVF
VYVKYERGFTSPAPAQLMDKVKKGGVNDYVNNDLKSEKSNSFEVGWNDYLFHSLVSADVF
VYVKYERGFTSPAPAQLMDKIKKGGVNDYVNNDLKSEKSNSFEVGWNDYLFHSLVSADVF
******************  ************************************

FSETKDEISTIFSGGHGTTFSNLNLGQTKRYGFDLKASQVFEKWTFSEAYSYIHAKIMKD
FSETKDEISTIFSGGHGTTFSNLNLGQTKRYGFDLKASQVFEKWTFSEAYSYIHAKIMKD
FSETKDEISTIFSGGHGTAFSNLNLGQTKRYGFDLKASQVFQKWTFSEAYSYIHAKIVKD
FSETKDEISTIFSGGHGTTFSNLNLGQTKRYGFDLKASQVFEKWTFSEAYSYIHAKIMKD
FSETKDEISTIFSGGHGTAFSNLNLGQTKRYGFDLKASQVFRKWTFSEAYSYIHAKIVKD
FSETKDEISTIFSGGHGTAFSNLNLGQTKRYGFDLKASQVFQKWTFSEAYSYIHAKIVKD
FSETKDEISTIFSGGHGTAFSNLNLGQTKRYGFDLKASQVFQKWTFSEAYSYIHAKIVKD
**************** ***************** ***********

FT

KTKAYEGKYISYVPRHKFSLNADYAITPKWTLGGEYQYSSSVYLDNANKNGKDGARSVFN
KTKAYEGKYISYVPRHKFSLNADYAITPKWTLGGEYQYSSSVYLDNANKNGKDGARSVFN
KNKAYEGKYISYVPRHKFSLNADYAITPKWTLGGEYQYSSSVYLDNANKNGKDGARAVFN
KTKAYEGKYISYVPRHKFSLNADYAITPKWTLGGEYQYSSSVYLDNANKNGKDGARSVFN
KNKAYEGKYISYVPRHKFSLNADYAITPKWTLGGEYQYSSSVYLDNANKNGKDGARAVFN
KNKAYEGKYISYVPRHKFSLNADYAITPKWTLGGEYQYSSSVYLDNANKNGKDGARAVFN
KNKAYEGKYISYVPRHKFSLNADYAITPKWTLGGEYQYSSSVYLDNANKNGKDGARAVFN
* ******************************************************* *

FT

LQTSYEFNSHFSIYAGIKNVLNHKYYESVSAGSSQKYYSPAPERNYY
LQTSYEFNSHFSIYAGIKNVLNHKYYESVSAGSSQKYYSPAPERNYY
LQTSYEFNSHFSIYAGIKNVLNHKYYESVTAGSGQKYYSPAPERNYY
LQTSYEFNSHFSIYAGIKNVLNHKYYESVSAGSSQKYYSPAPERNYY
LQTSYEFNSHFSIYAGIKNVLNHKYYESVTAGSGQKYYSPAPERNYY
LQTSYEFNSHFSIYAGIKNVLNHKYYESVTAGSGQKYYSPAPERNYY
LQTSYEFNSHFSIYAGIKNVLNHKYYESVTAGSGQKYYSPAPERNYY
*************************** * ************

FT

AGFRYQF          (SEQ ID NO:2)
AGFRYQF  F. necrophorum    (SEQ ID NO:72)
AGFRYQF  F. necrophorum    (SEQ ID NO:73)
AGFRYQF  F. necrophorum    (SEQ ID NO:74)
AGFHYQF  F. necrophorum    (SEQ ID NO:75)
AGFRYQF  F. necrophorum    (SEQ ID NO:76)
AGFRYQF  F. gonidiaformans (SEQ ID NO:77)
* *

```
---------------MKKILFLVGALFSISAFAEQTIELGSTSIKGN-RKTDYTLTPKEYKN
---------------MKKILFLVGALFSISAFAEQTIELGSTSIKGN-RKTDYTLTPKEYKN
---------------MKKILFLVGALFSISAFAEQTIELGSTSIKGN-RKTDYTLTPKEYKN
LKVNFIMKRESEKMKKILFLVGALFSISAFAEQTIELGSTSIKGN-RKTDYTLTPKEYKN
---------------MRKMLFLIGALLSISAFAEQTVELGSTSIKGN-RKADYTLTPKEYKN
---------------MRKTLLLFSILATL-AYAEQTVELGSSSIRSSAKKTDYTLIPKEYKN
---------------MKKLLVLLTILSSIIAHAEDTIELKETTVKSSPRSSDYTLIPKEQKN
---------------MKKLLVLLTILSSIIAYAEDTIELNQTTVKSSPRSSDYTLIPKEQKN
---------------MKKLLVLLTILTSIASFSEDVIELGQTTVKGS-KTSDYTAPPKEQKN
---------------*  *  *    *       *    **              ***    ***  **
```

FN

```
TYTITQEKIQERNYKNVEDVLRDAPGIVVQNTAFGPRIDMRGSGEKSLSRVKVLVDGISI
TYTITQEKIQERNYKNVEDVLRDAPGIVVQNTAFGPRIDMRGSGEKSLSRVKVLVDGISI
TYTITQEKIRERNYKNVEDVLRDAPGVVVQNTAFGPRIDMRGSGEKSLSRVKVLVDGISI
TYTITQEKIRERNYKNVEDVLRDAPGVVVQNTAFGPRIDMRGSGEKSLSRVKVLVDGISI
TYTITQEKIQERNYKNVEDVLRDAPGVVIQNTAFGPRIDMRGSGEKSLSRVKVLVDGVSI
TYTITQETIRERNYKNVEDVLRDAPGVIIQNTAFGPRVDMRGSGEKSLARVKVLVDGISI
TYVITQEKIRERNYKNVEDVLRDAPGVTIQNTAFGPRVDMRGSGEKSLSRVKVLIDGVSI
TYVITQEKIRERNYKNVEDVLRDAPGVTIQNTAFGPRVDMRGSGEKSLSRVKVLIDGVSI
TFVITQERIREKNYKNVEDILRDAPGVVVQNTAFGPRIDMRGSGEKSLSRVKVLVDGVSI
*  ****  *  *  *******  ******    *******  ***********  *****  **  **
```

FN

```
NPTEETMASLPINSIPIESVKKIEIIPGGGATLYGSGSVGGVVSISTNSNVTKNNFFMDL
NPTEETMASLPINSIPIESVKKIEIIPGGGATLYGSGSVGGVVSISTNSNVTKNNFFMDL
NPTEETMASLPINSIPIESVKKIEIIPGGGATLYGSGSVGGVVSISTNSNVTKNNFFMDL
NPTEETMASLPINSIPIESVKKIEIIPGGGATLYGSGSVGGVVSISTNSNVTKNNFFMDL
NPTEETMASLPINSIPIETVKKIEIIPGGGATLYGSGSVGGVVSITTNSNATKNNFFMDL
NPTEETMASLPINSIPIESVKKIEIIPGGGATLYGSGSVGGVVSISTNSNVTKNNFFMDL
NPTEETMASLPINSIPIESVKKIEIIPGGGATLYGSGSVGGVISITTNSNVTKNNFFADL
NPTEETMASLPINSIPIESVKKIEIIPGGGATLYGSGSVGGVISITTNSNVTKNNFFADL
NPTEETMASLPINAIPVESIKKIEIIPGGGATLYGSGSVGGVVNISTNSNVTKDNFFMDL
************  **  *  ********************    *  ****  **  ***  **
```

FN

```
NYGSFDNRNFGFAGGYNVSDKLYVNYGFNYLNSEDYREHEEKENKIYLLGFDYKINPKNR
NYGSFDNRNFGFAGGYNVSDKLYVNYGFNYLNSEDYREHEEKENKIYLLGFDYKINPKNR
NYGSFDNRNFGFAGGYNVSDKLYVNYGFNYLNSEDYREHEEKENKIYLLGFDYKINPKNR
NYGSFDNRNFGFAGGYNVSDKLYVNYGFNYLNSEDYREHEEKENKIYLLGFDYKINPKNR
NYGSFDNRNFGFAGGYNVTDKLYVNYGFNYLNSEDYREHEEKENKIYLLGFDYKINAKNR
NYGSFDNRNFGFAGGYNVNKKLYVNYGFNYLNSESYRKHEEKENKIYLVGFDYKFNGKNR
NYGSFDNRNFGFAGGYNVTKNLYVNYGFNYLNSEGYRREEEKENKIYLLGFDYKINSKNR
NYGSFDNRNFGFAGGYNVTKNLYVNYGFNYLNSEGYRREEEKENKIYLLGFDYKINAKNR
NYGSFDNRNFGFAGGYNFNKHLYVNYGFSYLNSEDYREHEEKENKIYLLGFDYKINAKHR
****************      *******  *****  **    ********  *****  *  *  *
```

FRVQTRYSKMKHDGSNWLSQEELKISRKKAGLNLDLDTTDKSYTFDYEYRSSQNLTLAAT
FRVQTRYSKMKHDGSNWLSQEELKISRKKAGLNLDLDTTDKSYTFDYEYRPSQNLTLAAT
FRVQTRYSKMKHDGSNWLSQEELKISRKKAGLNLDLDTTDKSYTFDYEYRPSQNLTLAAT
FRVQTRYSKMKHDGSNWLSQEELKISRKKAGLNLDLDTTDKSYTFDYEYRPSQNLTLAAT
FRVQTRYSKMKHDGSNWLSQDELKTSRKKAGLNLDLDTTDKSYTFDYEYRPTENLTLAAT
VRFQTRQSDIMDHGSNQLRKTELEGDRRAPGLALNLDTKDQSYTMDYEYRPTEKLTLGAT
FRFQTRYSKFKDDGSNQVTREVLEYDRRAIGLNLDMITKDKSYTFDYEYRPKNNLTLAAT
FRFQTRYSKFKDDGSNQVAREVLEYDRRAVGLNLDMITKDKSYTFDYEYRPKNNLTLAAT
FRFQTRFSDIKQDSSNQIPVEELKNDRRKAGLNMDINTKDRSYTFDYEYRPTQNATLSTT
* ***  *        **       *    *     **      * * * **       *

FN

AYKQQQDRDITTDDIRDIEIIASNRNYTDLKEYMTFYDVKSTLKAKFKEKKYGLKLKG
AYKQQQDRDITTDDIRDIEIIASNRNYT--DLKEYMTFYDVKSTLKAKFKEKKYGLKLKG
AYKQQQDRDITTDDIRDIEIIASNRNYT--DLKEYMTFYDVKSTLKAKFKEKKYGLKLKG
AYKQQQDRDITTDDIRDIEIIASNRNYT--DLKEYMTFYDVKSTLKAKFKEKKYGLKLKG
AYKQQQDRDITTDDIRDIEIVASNRNYT--DLKEYMTFYDVKSTLKAKFKEEKHGIKLKG
AYQQQQDRDIYTEDIRDIEIVASDRNYT--DIKEYMIFHDVKSTMKAKFKEKKHGIKLKG
IYKQEQDRDIQTESIDDIRIVSSPAGYTYGSYKEEMNFYGVTSKMNAKFEEDKKGLKLKS
IYKQEQDRDIQTESIDDIRIVSSPAGYTYGSYKEEMNFYGVTSKMNAKFEEDKKGLKLKS
FYKQKQERDIDTESIDDIKIIASDRTHTW--HKEEMNFYDIKSKMHADFKEDKDGAKLKA
 * *  ***    *    **  *     *        **  *     *  * * * *  ***

FN

KYEYG------RGEVIFGYDYQDSNNKRNSLVQSETLKTYNDKISDLNLSPEDRKPIINRV
KYEYG------RGEVIFGYDYQDSNNKRNSLVQSETLKTYNDKISDLNLSPEDRKPIINRV
KYEYG------RGEVIFGYDYQDSNNKRNSLVQSETLKTYNDKISDLNLSPEDRKPIINRV
KYEYG------RGEVIFGYDYQDSNNKRNSLVQSETLKTYNDKISDLNLSPEDRKPIINRV
KYEYG------NGEVIFGYDYQDSNNKRNSLVQSETLKTYNDRISDLNLDPTDRKPIVNRV
KYDYG------KGEIIFGYDYYDSNNRRDSHVRSETLKTYNTKYTDSVLSPEERLPIINNV
KYDYS------NGQIIFGYDYQKAVNKRDSFVQSETLKSYNNGYSNKTLEGEDIQPVINRV
KYDYS------NGQIIFGYDYQKAVNKRDSFVQSETLKSYNNGYSNKTLEGEDIQPVINRV
KFDYNLVENLPSETIIGYDYQSATNKRNSLVQSETLKTYNNGYMDINLSQSERLPVINRV
 *  *          * ****    * *  *  ***               *     * *

FN

NIDLTKKSHGFYVFNKLELTDKWDFTTGFRTEITKYNGYRKNGPNTMPIVSPKVNEIRTD
NIDLTKKSHGFYVFNKLELTDKWDFTTGFRTEITKYNGYRKNGPNTMPIVSPKVNEIRTD
NIDLTKKSHGFYVFNKLELTDKWDFTTGFRTEITKYNGYRKNGPNTMPIVSPKVNEIRTD
NIDLTKKSHGFYVFNKLELTDKWDFTTGFRTEITKYNGYRKNGPNTMPIVSPKVNEIRTD
DIDLTKKSHGFYAFNKLELGKKFDFTTGFRTEITEYNGYRKNGPNTMPIISPKTNEIKTN
KIDLTKKSHGFYAFNKWNVNKNFDFTTGFRIEKTKYNGYRKNGKNTMPIAVAKTDVIRTD
KVNMEKESHGFYVFNKFDVTDKLDITTGFRTEITKYNGKRVNGPNTMPFVAAKTAEINTD
KVNMEKESHGFYVFNKFDATDKLDITTGFRTEITKYNGKRVNGPNTMPFVAAKTAEINTD
DMEMKRKSQGIYVFNKWGLANWLDVTLGGRMEKTKYNGYRENGPNVMPYVEPEVKRIETN
 *   *   **         * * *  *  *   * *** *  **  * ***     * *

EKMTNYAGEAGMLYKYSDTGRAFVRYERGFVTPFANQLTDKIHDTKLKSPAGFFTPPIV
EKMTNYAGEAGMLYKYSDTGRAFVRYERGFVTPFANQLTDKIHDTKLKSP-AGFFTPPIV
EKMTNYAGEAGMLYKYSDTGRAFVRYERGFVTPFANQLTDKIHDTKLKSP-AGFFTPPIV
EKMTNYAGEAGMLYKYSDTGRAFVRYERGFVTPFANQLTDKIHDTKLKSP-AGFFTPPIV
EKMTNYAGEAGMLYKYSDTGRAFVRYERGFVTPFANQLTDKIHDTELKNP-GGFFTPPIV
ERHTNFAGEVGGLWKYSDTGRFFTRYERGFVTPFSTQLTDKIHDTELKNP-NGFFIPPIV
RKLENYAGEFGALYEYRDTGRVFLRYEKGFVTPFANQLTDKVRDTTLPKK-VGFFDPPQV
RKLENYAGEFGALYKYRDTGRVFLRYEKGFVTPFANQLTDKVRDTTLPKK-VGFFDPPQV
RKLDNYAEELGFLFKYNDTGRFYTRYERGFVTPFGNQLTDKIHDTTLKNPNSGFIIPPTV
*   *   *   *   *   **      *   ****   *      *              *

FN

NVSSLYVANNLKSEITDTIEVGFRDYIFNSLISASFFATDTTDEITLISSGITNPAVNRW
NVSSLYVANNLKSEVTDTIEVGFRDYIFNSLISASFFATDTTDEITLISSGITNPAVNRW
NVSSLYVANNLKSEITDTIEVGFRDYIFNSLISASFFATDTTDEITLISSGITNPAVNRW
NVSSLYVANNLKSEITDTIEVGFRDYIFNSLISASFFATDTTDEITLISSGITNPAVNRW
NVASLYVANNLKSEITDTIEVGFRDYIFDSLVSASFFATDTTDEITLISSGITNPAVNRW
NSASKYVANHLQPEITDTVEIGFRDYFYNSLFSASFFVTDTKDEITLISSGITNPAVNRW
NVASKYVDNNLKSEKTDTVELGVRDYFFGSLFSASVFLTDTKDEITLISSGVTNPAVNRW
NVASKYVDNNLKSEKTDTVELGVRDYFFGSLFSASVFLTDTKDEITLISSGVTNPAVNRW
NVASKYVDNNLNAEKTDTFEIGFRDYILGSTLSTSFFLTNTKDEITLISSGVTNPAVNRW
*   *   **   *   *   *   ***   *   *   ***       *    *    *    *    *   *******   *****

FN

KFRNIGKTRRLGIELEAEQKWGKFDFSQSLTFVDTKVLKTDAESRIFRGDKVPMVPRIKA
KFRNIGKTRRLGIELEAEQKWGKFDFSQSLTFVDTKVLKTDAESRIFRGDKVPMVPRIKA
KFRNIGKTRRLGIELEAEQKWGKFDFSQSLTFVDTKVLKTDAESRIFRGDKVPMVPRIKA
KFRNIGKTRRLGIELEAEQKWGKFDFSQSLTFVDTKVLKTDAESRIFRGDKVPMVPRIKA
KFRNIGKTRRLGIELEAEQKWGDFEFSQSLTFVDTKVLKTDKESNIYRGDKVPMVPNIKA
RYRNIGKTRRFGIELEAEQKFGKFGLTESLTFVDSKVLKTDANSNIFRGDRVPMVPRLKA
KYRNIGKTRRMGLELEAEQNFGNWSLSQSLTLLNTKVLKANEEARLEKGDKVPLVPRVKA
KYRNIGKTRRMGLELEAEQNFGNWSLSQSLTLLNTKVLKANEEARLEKGDQVPLVPRVKA
KYRNIGKTRRFGLEFEAEQNFGKFRFNQSLTLVRTKVLVANEEAKLERGDQVPMVPRLKA
********   *   *   ****       *          *       *

```
TLGLKYNVTDNLALIGTYTYLSKRETRE------LDEKDKVYKHTIKGYGTADLGILYKV
TLGLKYNVTDNLALIGTYTYLSKRETRE------LDEKDKVYKHTIKGYGTADLGILYKV
TLGLKYNVTDNLALIGTYTYLSKRETRE------LDEKDKVYKHTIKGYGTADLGILYKV
TLGLKYNVTDNLALIGTYTYLSKRETRE------LDEKDKVYKHTIKGYGTADLGILYKV
TLGLKYNVTDNLSLIGTYTYLSKRETRE------LDEKDKVYKHTIKGYGTADLGVLYKV
TLGIKYRMTDDLTLLANYTYLSKREARE------LDEKDKIYRHTIKGHGVLDVGALYRI
TLGVKYNFTDKIALIGTYTYFSKRETREIRESEDLNKDDNIIKHTIGGYGITDLGVLYKA
TLGVKYNFTDKIALVGTYTYFSKRDTREIRESEDLNKDDDIIKHTIGGYGVTDLGVLYKA
TLGLRYNFTDRLAGFVNYTYLAKQESRELRENEDLNKDDIVVKHTIGGHGVVDAGFSYKP
***  *  **         ***   *   **       *    *    *** * *    * *    *
```

FN

```
DKYSNFKVGAKNIFGKKYNLRETKLEALPAPERNYYLEFNVKFN  (SEQ ID NO:6)
DKYSNFKVGAKNIFGKKYNLRETKLEALPAPERNYYLEFNVKFN  F. necrophorum (SEQ ID NO:79)
DKYSNFKVGAKNIFGKKYNLRETKLEALPAPERNYYLEFNVKFN  F. necrophorum (SEQ ID NO:80)
DKYSNFKVGAKNIFGKKYNLRETKLEALPAPERNYYLEFNVKFN  F. necrophorum (SEQ ID NO:81)
DKYSNFKVGAKNLFGKKYNLRETKLEALPAPERNYYLEFNVKF-  F. gonidiaformans (SEQ ID NO:82)
DKYSNVKVGAKNLFSKKYNLRETKVEALPAPERNYYLEFNVKFD  F. necrophorum (SEQ ID NO:83)
DAYSNIKVGAKNIFNKKYNLRETSLEALPAPEKTYYLEMNVRF-  F. nucleatum (SEQ ID NO:84)
DAYSNIKVGAKNIFNKKYNLRETSLEALPAPEKTYYLEMNVRF-  F. nucleatum (SEQ ID NO:85)
DAYSDIKIGAKNLFSKKYNLRETSLEALPAPERNYYLELNVRF-  F. periodonticum (SEQ ID NO:86)
* **   * ****  * ********  *******   **** ** *
```

POLYPEPTIDES OF FUSOBACTERIUM AND METHODS OF USE

CROSS-REFERENCE TO RELATED APPLICATIONS

This application is a continuation application of U.S. patent application Ser. No. 17/888,916, filed Aug. 16, 2022, which is a continuation application of U.S. patent application Ser. No. 16/921,243, filed Jul. 6, 2020, which is a continuation application of U.S. patent application Ser. No. 15/774,168, filed May 7, 2018, which is the § 371 U.S. National Stage of International Application No. PCT/US2016/061108, filed Nov. 9, 2016, which claims the benefit of U.S. Provisional Application Ser. No. 62/252,951, filed Nov. 9, 2015, the disclosures of which are incorporated by reference herein in their entireties.

SEQUENCE LISTING

This application contains a Sequence Listing electronically submitted via Patent Center to the United States Patent and Trademark Office in XML format entitled "0293_000054US03_ST26" having a size of 149,000 bytes and created Feb. 19, 2023. The information contained in the Sequence Listing is incorporated by reference herein.

BACKGROUND

*Fusobacterium* spp. are gram-negative, obligately anaerobic and pleomorphically rod shaped bacterium responsible for a variety of necrotic infections in animals and in humans (Langworth, Bacteriol. Rev., 41, 373-390 (1977)). Pathogenic species in the Genus *Fusobacterium* include *F. necrophorum*, *F. nucleatum*, *F. canifelinum*, *F. gonidiaformans*, *F. mortiferum*, *F. naviforme*, *F. necrogenes*, *F. russii*, *F. ulcerans*, and *F. varium*. *Fusobacterium necrophorum* is the most pathogenic and is classified into two subspecies: *F. necrophorum* subsp. *necrophorum* and *F. necrophorum* subsp. *funduliforme* and are responsible for a number of clinical manifestations in various species of animals, such as cattle, horses, goats, sheep, fowl, and swine, including hepatic abscesses, foot rot, laminitis, purulent and interdigital dermatitis, contagious ecthyma, necrotic rhinitis, and necrotic laryngitis. Taxa formally in the genus *Fusobacterium* include *Filifactor alocis*, commonly found in the periodontal pockets of patients having periodontitis (Kumar et al., 2003, J Dent Res., 82(5):338-44); *Faecalibacterium prausnitzii*, and *Eubacterium sulci*, also associated with odontogenic infections (Munson et al., 2002, J. Dent Res., 81:761, Paster et al., 2006, Periodontology 2000, 42:80). Although the primary etiologic agent of liver abscesses has been shown to be *Fusobacterium necrophorum* abscessation has been associated with other bacteriological agents such as *Arcanobacterium pyogenes*. *Bacteroides* spp., *Salmonella* spp., *Clostridium* spp., *Pasteurella* spp., *E. coli* spp., and *Peptostreptococcus* spp.

In humans, *F. necrophorum* and *F. nucleatum* are considered to be the most pathogenic and is the causative agent of skin ulcers, peritonsillar abscesses, septic arthritis, Lemierre's syndrome, periodontal diseases, endocarditis and metastatic abscesses in the lungs, liver, joints, and pleural spaces. On a population-based perspective *Fusobacterium* bacteremia is relatively uncommon in humans with an overall annual incidence of 0.55 per 100,000 population. The incidence of *F. nucleatum* was found to be 0.34/100,000 and *F. necrophorum* was 0.14/100,000 with a median age of 53.5 years while *F. necrophorum* cases had a median age of 21 years. Overall mortality due to bacteremia was 11 percent. *F. necrophorum* affects mostly young health adults. In contrast, *F. nucleatum* affects older individuals with seemingly compromised healthy conditions (*Afra*, Infectious Diseases, 13: 264 (2013)). A number of other species of fusobacteria have been implicated as the etiological agent in a variety of diseases, for example, *F. ulcerans* (skin ulcers), *F. russii* (animal bite infections), and *F. varium* (eye infections) (Smith et al., Epidemiol Infect., 110, 499-506 (1993)).

In beef-breed and Holstein steers, the incidence of liver abscesses average from 12 to 32% in most feedlots, and has been shown to be influenced by a number of dietary and management factors. Liver abscesses are categorized as mild, moderate or severe. Severe liver lesions are most often associated with high economic losses to producers, packers, and ultimately consumers. Besides liver condemnation, economic impacts include reduced feed intake, reduced weight gain, decreased feed efficiency, and decreased carcass yield.

*F. necrophorum* possesses a number of virulence factors that participate in the penetration and colonization of the ruminal epithelium and subsequent entry and establishment of infection in the liver, including a potent secreted leukotoxin which has been shown to be specifically toxic to ruminant polymorphonuclear leukocytes (Tan et al., Vet. Res. Commun. 20, 113-140 (1996)). The role of leukotoxin as a virulence factor has been documented. For instance, experiments have indicated a correlation between toxin production and the ability of *F. necrophorum* to induce abscesses in laboratory animals (Coyle et al., Am. J. Vet. Res., 40, 274-276. (1979), and Tan et al., Am. J. Vet. Res., 55, 515. (1994)). Experiments have also shown that non-leukotoxin producing strains are unable to induce foot abscesses in cattle following challenge. It has also been shown that neutralizing antibody produced by an inactivated toxoid derived from leukotoxin reduced infection and liver abscesses in vaccinated cattle.

Control of liver abscesses in feedlot cattle generally has depended on the use of antimicrobial compounds. Five antibiotics (i.e., bacitracin methylene disalicylate, chlortetracycline, oxytetracycline, tylosin, and virginiamycin) are approved for prevention of liver abscesses in feedlot cattle. Tylosin is the most effective and the most commonly used feed additive.

A number of commercial killed whole cell bacterins have been used to control necrotic infection in farm animals incorporating multiple strains including the most prevalent serotypes such as biotype A (*F. necrophorum* subsp. *necrophorum*). Another approach to vaccine development has been the incorporation of leukotoxin as a toxoid to prevent the pathological effect of the secreted toxin (Saginala et al., J. Anim. Sci., 75, 11601166 (1997)).

Divalent metal ions such as iron, cobalt, copper, magnesium, manganese, molybdenum, nickel, selenium, and zinc and are trace elements often required for the survival of bacteria infecting both animal and human hosts. These trace metal elements are used by bacteria as cofactors for enzymes that catalyze biochemical reactions for various metabolic pathways required by the organism. The impact of iron on the pathogenesis of bacteria has been studied extensively. Iron is essential for nearly all life and is required for enzymatic and metabolic pathways of cells at all phylogenic levels. It has been well-documented that during bacterial sepsis there is an alteration in the concentration of a number of metal ions in serum such as, iron, copper, and zinc. For instance, serum levels of zinc decrease from 10 percent to 60 percent with the onset of infection. Following the onset of infection, zinc is then redistributed from plasma to liver where it is bound to metallothionein. Decreases in serum iron of up to 50 percent have been described during infectious illness, whereas serum copper has been shown to increase in response to inflammatory stimuli. The alteration of these trace metal ions in serum may directly affect the severity or progression of any bacterial infection.

The ability of *Fusobacterium* to evade the natural defense mechanisms of the vertebrate host depends in part on its ability to obtain host iron, which in turn, directly influences the host-pathogen interaction. Because of iron's essential nature, vertebrate hosts have developed elaborate mechanisms to bind iron in body fluids (e.g., transferrin in blood and lymph fluids and lactoferrin in external secretions). These high affinity iron binding proteins create an iron restricted environment within the host, reducing the level of iron to approximately $10^{-18}$ molar, a concentration too low to support the growth of nearly all bacteria. These iron sequestering mechanisms of the host act as a natural defense mechanism to combat bacterial invasion. To circumvent these iron-restrictive conditions many bacterial species have evolved mechanisms for obtaining iron. The most common mechanisms include the diffusion of soluble iron through porins and specialized transport systems that mediate the uptake of iron by siderophores. This latter system is one of the most common and well-studied mechanisms for iron acquisition and involves the specific chelation of ferric iron by siderophores and the synthesis of their cognate transport systems, which permits the bacteria to continue to replicate and overcome the non-specific defense mechanisms of the host. Continued replication, and thus each step in the infectious process, is ultimately dependent on the ability of the organism to obtain iron from its host.

With so many basic functions relying on the availability of iron, bacteria have evolved a complex regulatory network for acquiring iron under varying physiological conditions. Under anaerobic conditions, iron is present in the soluble ferrous form (Fe II) and can freely diffuse through outer membrane porins into the periplasm. For instance, in *E. coli* the FeoAB transport system present in the cytoplasmic membrane will transport the ferrous iron molecules into the cell cytoplasm. Under aerobic conditions and neutral pH, iron is primarily present in the insoluble ferric form (Fe III) and cannot pass through the outer membrane porins by passive diffusion. Instead, molecules called siderophores are secreted by bacteria, which have a high affinity for ferric iron. The ferric-siderophore complexes are recognized by receptors in the outer membrane collectively referred to as the TonB-dependent receptors. These receptors, once bound to loaded siderophores, are believed to interact with TonB and its associated proteins localized in the periplasm and cytoplasmic membrane. These protein-protein interactions, though poorly understood, serve to provide the energy necessary to transport the ferri-siderophore complexes across the outer membrane and through the periplasmic space. ABC transport systems present in the cytoplasmic membrane serve to transport the iron-siderophore complexes across the cytoplasmic membrane. Reductase enzymes reduce the ferric iron to its ferrous form, which dissociates it from the siderophore and releases iron into the cell.

Several species of pathogenic bacteria use additional mechanisms to obtain iron from mammalian hosts, including the direct binding of transferrin, heme, and other heme-containing compounds. The receptor proteins that bind these iron-containing molecules most likely rely on the TonB complex for the energy required to transport heme across the outer membrane, similar to the iron-siderophore complexes. Specialized ABC transporters are then used to transport the heme across the cytoplasmic membrane. In addition, some bacteria secrete hemophores, small molecules that can bind heme and present it to receptors on the bacterial cell surface. Several pathogenic species also produce hemolysins, which are toxins that lyse red blood cells, releasing heme and hemoglobin for uptake by the bacteria.

The outer membrane proteins of gram-negative bacteria control the selective permeability of many essential nutrients critical to the survival of bacteria, including all pathogenic bacteria that cause disease in animals and man. This selective permeability of nutrients is controlled by a class of membrane proteins called porins. It now appears that the majority of the outer membrane proteins on the surface of gram-negative bacteria are porins, identified as the general porins (e.g., OmpF), monomeric porins (e.g., OmpA), the specific porins (e.g., the maltose-specific porin LamB) and the TonB-dependent, gated porins (e.g., the siderophore receptor FepA). The porin class of proteins generally share structural features, including the presence of beta-barrels that span the outer membrane.

Little is known regarding the iron-acquisition by *Fusobacterium* spp, and genomic comparisons are difficult since the genome of only five strains of *Fusobacterium nucleatum* have been completely sequenced and made publicly available: *F. nucleatum* subspecies *nucleatum*, strain ATCC 25586 (Kapatral et al., J. Bacteriol., 184, 2005-2018 (2002)); *Fusobacterium nucleatum* subsp. *vincentii* 3_1_36A2; *Fusobacterium nucleatum* subsp. *vincentii* 3_1_36A2; *Fusobacterium nucleatum* subsp. *animalis* 7_1; and *Fusobacterium nucleatum* subsp. *animalis* 48 (Tatusova T, et al. Nucleic Acids Res 42, D553-D559 (2014). No complete sequence of *Fusobacterium necrophorum* strains have been published, although there are a number of partial sequences in the NCBI database The genomic sequence of ATCC 25586 was used in a comparison with a partially sequenced genome of *F. nucleatum* subspp. *vincentii* (Kapatral et al., Genome Res., 13, 1180-1189 (2003)) to investigate differences among these two subspecies. The results suggested that there were differences between the two genomes with respect to the iron uptake systems. Although iron transport systems were discovered in both genomes, the genome of strain ATCC 25586 contains three additional iron-specific ABC transport systems. In addition, hemin receptor proteins appear to be encoded by both genomes, but while the subspp. *vincentii* isolate encodes three receptors, the genome of strain ATCC 25586 apparently encodes five such proteins. Furthermore, the feoAB genes, encoding a putative ferrous iron transport system, are only found in the genome of the subspp. *vincentii* isolate. Since both organisms are obligate anaerobes and ferrous iron is the predominant form of the metal under anaerobic conditions, strain ATCC 25586 may have a second mechanism for uptake of ferrous iron. Given the differences among these two subspecies of *F. nucleatum*, it is likely that there will be many differences among the iron uptake systems between other *Fusobacterium* species. Therefore, the *F. nucleatum* genomic data may not be useful for predicting the presence or absence of iron acquisition systems in other species of *Fusobacterium*.

*Fusobacterium necrophorum* is ubiquitous in the environment of cattle and is considered a normal inhabitant of the intestine and rumen, and is present in feces. The organism is the causative agent of both liver abscesses and footrot. The disease is rarely fatal but can result in substantial economic losses to both the producer and packer due to cost in treatment and performance losses. It is thought that liver abscessation follows a condition of ruminal acidosis which impairs the integrity of the rumen wall allowing *Fusobacterium* to transverse to the blood stream to the liver and cause abscessation.

Beyond the role of iron as an essential nutrient for microbial survival, there are now many other well-defined transitional metals that play critical roles in bacterial survival, homeostasis and pathogenesis such as iron, manganese, copper, zinc, magnesium, cobalt, and nickel (Waldron and Robinson, 2009, Nature Reviews Microbiology, 7:25-35; Porcheron, 2013, Frontiers in Cellular and Infection Microbiology 3:172-194). Iron, zinc and copper are the three most abundant divalent metal ions in mammals in descending order of concentration. The ability of a bacterium to use these transitional metals by finely regulated uptake or acquisition systems significantly contributes to the virulence of pathogenic bacteria. It is well known that bacteria within the same genus/species do not have the same uptake systems for the acquisition of transitional metals owing to the difference in pathogenicity from one strain of bacteria to another. These differences in the ability of bacteria to use different transitional metals based on expressed uptake systems may specifically direct what organ or tissue an organism can invade.

Copper is the third most prevalent transitional metal behind iron and zinc and plays a major role in many enzymatic pathways. Copper is present in every tissue of the body but is stored in its highest concentration in the liver. What role copper plays in the virulence of *Fusobacterium* is unknown. With the concentration of copper being the highest in the liver it would make sense that *Fusobacterium* has adapted some mechanism to utilize this divalent metal ion once in the liver.

In the following examples we show the expression of unique proteins that are expressed in *Fusobacterium* when grown under iron, zinc and copper chelation.

SUMMARY OF THE INVENTION

Provided herein are compositions. In one embodiment, a composition includes at least one isolated polypeptide having a molecular weight of 92 kDa to 79 kDa, 73 kDa to 63 kDa, 62 kDa to 58 kDa, or 57 kDa to 47 kDa, wherein the at least one polypeptide is isolatable from a *Fusobacterium necrophorum* when incubated in media including an iron chelator and not isolatable when grown in the media without the iron chelator; at least one isolated polypeptide having a molecular weight of 108 kDa to 98 kDa or 79 kDa to 69 kDa, wherein the at least one polypeptide is isolatable from a *Fusobacterium necrophorum* when incubated in media including an iron chelator, is expressed by the *Fusobacterium necrophorum* when incubated in media without the iron chelator and expressed at an enhanced level during growth in media including an iron chelator; and at least one protein selected from the group consisting of a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, and a polypeptide having at least 85% similarity to SEQ ID NO:53 or a fragment thereof.

In one embodiment, a composition includes isolated polypeptides having molecular weights of 92 kDa to 79 kDa, 73 kDa to 63 kDa, 62 kDa to 58 kDa, and 57 kDa to 47 kDa, wherein the polypeptides are isolatable from a *Fusobacterium necrophorum* when incubated in media including an iron chelator and not isolatable when grown in the media without the iron chelator; isolated polypeptides having molecular weights of 155 kDa to 145 kDa or 89 kDa to 79 kDa, wherein the at least one polypeptide is isolatable from a *Fusobacterium necrophorum* when incubated in media including an iron chelator and an iron-containing porphyrin and not isolatable when grown in the media without the iron chelator and iron-containing porphyrin, and not isolatable when grown in the media with the iron chelator and in the absence of the iron-containing porphyrin; and isolated polypeptides having molecular weights of 108 kDa to 98 kDa and 79 kDa to 69 kDa, wherein the polypeptides are isolatable from a *Fusobacterium necrophorum* when incubated in media including an iron chelator, are expressed by the *Fusobacterium necrophorum* when incubated in media without the iron chelator and expressed at an enhanced level during growth in media including an iron chelator.

In one embodiment, a composition includes at least one isolated polypeptide having a molecular weight of 131 kDa to 121 kDa, 79 kDa to 69 kDa, or 33 kDa to 23 kDa, wherein the at least one polypeptide is isolatable from a *Fusobacterium necrophorum* when incubated in media including a copper chelator and not isolatable when grown in the media without the copper chelator; and at least one isolated polypeptide having a molecular weight of 93 kDa to 83 kDa, 65 kDa to 55 kDa, or 52 kDa to 42 kDa, wherein the at least one polypeptide is isolatable from the *Fusobacterium necrophorum* when incubated in media including a copper chelator, is expressed by the *Fusobacterium necrophorum* when incubated in media without the copper chelator and expressed at an enhanced level during growth in media including an copper chelator.

In one embodiment, a composition includes at least one isolated polypeptide having a molecular weight of 131 kDa to 121 kDa, 108 kDa to 98 kDa, 92 kDa to 64 kDa, 53 kDa to 43 kDa, or 33 kDa to 19 kDa, wherein the polypeptide is isolatable from a *Fusobacterium necrophorum* when incubated in media including a zinc chelator and not isolatable when grown in the media without the zinc chelator; and at least one isolated polypeptide having a molecular weight of 79 kDa to 69 kDa or 65 kDa to 55 kDa, wherein the at least one polypeptide is isolatable from the *Fusobacterium necrophorum* when incubated in media including a zinc chelator, is expressed by the *Fusobacterium necrophorum* when incubated in media without the zinc chelator and expressed at an enhanced level during growth in media including the zinc chelator.

In one embodiment, a composition includes isolated polypeptides having molecular weights of 131 kDa to 121 kDa, 79 kDa to 69 kDa, and 33 kDa to 23 kDa, wherein the polypeptides are isolatable from a *Fusobacterium necrophorum* when incubated in media including a copper chelator and not isolatable when grown in the media without the copper chelator; and isolated polypeptides having molecular weights of 93 kDa to 83 kDa, 65 kDa to 55 kDa, and 52 kDa to 42 kDa, wherein the polypeptides are isolatable from the *Fusobacterium necrophorum* when incubated in media including a copper chelator, are expressed by the *Fusobacterium necrophorum* when incubated in media without the copper chelator and expressed at an enhanced level during growth in media including an copper chelator.

In one embodiment, a composition includes isolated polypeptides having molecular weights of 131 kDa to 121 kDa, 108 kDa to 98 kDa, 92 kDa to 64 kDa, 53 kDa to 43 kDa, and 33 kDa to 19 kDa, wherein the polypeptides are isolatable from a *Fusobacterium necrophorum* when incubated in media including a zinc chelator and not isolatable when grown in the media without the zinc chelator; and isolated polypeptides having molecular weights of 79 kDa to 69 kDa and 65 kDa to 55 kDa, wherein the polypeptides are isolatable from the *Fusobacterium necrophorum* when incubated in media including a zinc chelator, are expressed by the *Fusobacterium necrophorum* when incubated in media without the zinc chelator and expressed at an enhanced level during growth in media including the zinc chelator.

In one embodiment, a composition can further include a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, a polypeptide having at least 85% similarity to SEQ ID NO:53 or a fragment thereof, or a combination thereof.

In one embodiment, a composition includes an isolated polypeptide having at least 85% similarity to SEQ ID NO:2, 4, 6, 8, 10, 12, 14, 16, 18, 20, 22, 24, 26, 28, 30, 32, 34, 35, 36, 37, 38, 39, 40, 41, 43, 44, 45, 46, 47, 48, 49, 50, 51, 52, 53, or 54, or a fragment thereof.

In one embodiment, a composition can further include isolated polypeptides having molecular weights of 340 kDa to 330 kDa, 247 kDa to 237 kDa, 247 kDa to 237 kDa, 235 kDa to 215 kDa, 120 kDa to 110 kDa, 51 kDa to 25 kDa, and 21 kDa to 11 kDa.

A composition can further include a pharmaceutically acceptable carrier, such as an adjuvant. In one embodiment, a composition protects an animal against challenge with *Fusobacterium necrophorum*.

Also provided herein are methods. In one embodiment, a method includes administering to a subject an amount of a composition described herein effective to induce the subject to produce antibody that specifically binds to at least one polypeptide of the composition.

In one embodiment, a method is for treating an infection in a subject, and the method includes administering an effective amount of a composition described herein to a subject having or at risk of having an infection caused by a *Fusobacterium* spp.

In one embodiment, a method is for treating a symptom in a subject, and the method includes administering an effective amount of a composition described herein to a subject having or at risk of having an infection caused by a *Fusobacterium* spp.

In one embodiment, a method is for decreasing colonization in a subject, and the method includes administering an effective amount of a composition described herein to a subject colonized by a *Fusobacterium* spp.

In one embodiment, a method is for treating an infection in a subject, and the method includes administering an effective amount of a composition to a subject having or at risk of having an infection caused by a *Fusobacterium* spp., wherein the composition includes antibody that specifically binds to a polypeptide described herein. In one embodiment, a method is for treating a symptom in a subject, and the method includes administering an effective amount of a composition to a subject having or at risk of having an infection caused by a *Fusobacterium* spp., wherein the composition includes antibody that specifically binds to a polypeptide described herein. In one embodiment, an infection causes a condition selected from metritis, hepatic abscesses, and foot rot.

In one embodiment, a method is for decreasing colonization in a subject, and the method includes administering an effective amount of a composition to a subject colonized by a *Fusobacterium* spp., wherein the composition includes antibody that specifically binds to a polypeptide described herein.

Also provided are kits. In one embodiment, a kit is for detecting antibody that specifically binds a polypeptide, including in separate containers an isolated polypeptide described herein, and a reagent that detects an antibody that specifically binds the polypeptide. In one embodiment, a kit is for detecting a polypeptide, including in separate containers an antibody that specifically binds an isolated polypeptide described herein, and a second reagent that specifically binds the polypeptide.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2. FIG. 2A shows SDS-PAGE gel with the banding profile of *Fusobacterium necrophorum* grown in mTSB containing Naringenin and Catechin. Lane 1, Molecular Weight Marker; Lane 2, 100 µM Naringenin in mTSB. Lane 3, 200 µM Catechin in mTSB. Brackets surround unique 60 kDa protein in lane 3 resulting from growth in the presence of the metal chelator Catechin. FIG. 2B shows the corresponding Western Blot probed with the convalescent bovine sera of Example 7. Lane 1, 100 µM Naringenin; Lane 2, 200 µM Catechin. Note the intense sero-reactive 60 kDa protein of lane 2 of FIG. 2B in contrast to lane 1 of FIG. B.

FIG. 4A shows an SDS-PAGE gel with the banding profile of *Fusobacterium necrophorum* grown in mTSB containing Quercetin and TPEN. Lane 1, Molecular Weight Marker; Lane 2, 100 µM Quercetin in mTSB, Lane 3, 50 µM TPEN in mTSB, Lane 4, 15 µg/ml 2,2-dipyridyl in mTSB. Brackets surround unique 81 kDa protein up-regulated during grown in the presence of the zinc chelator TPEN (Lane 3) compared to Lanes 2 and 4 grown with Quercetin and 2,2-dipyridyl, respectively. FIG. 4B shows the corresponding Western Blot probed with the convalescent bovine sera of Example 7. Lane 1,100 µM Quercetin in mTSB; Lane 2, 50 µM TPEN in mTSB, Lane 3, 15 µg/ml 2,2-dipyridyl in mTSB. Note the intense sero-reactive 81 kDa protein of lane 2 grown in the presence TPEN in contrast to Lanes 1 and 3 grown in Quercetin and 2,2-dipyridyl.

FIG. 7A shows a Western Blot of the serological response to the rZinc protein. Lane 1, Molecular Weight Marker; Lane 2, Fuso-SRP Extract probed with sera derived from the 250 µg rZinc vaccine of Group C; Lane 3, rZinc protein probed with sera derived from the 100 µg rZinc vaccine of Group B; Lane 4, rZinc protein probed with sera derived from the 250 µg rZinc vaccine of Group C; Lane 5, rHemin protein probed sera derived from the 250 µg rZinc vaccine of Group C. FIG. 7B shows a Fuso-SRP Extract probed with sera derived from the combination vaccine of Group D at 10 µg Fuso-SRP Extract plus 50 µg rZinc protein. Lane 1, Fuso SRP extract probed with the sera derived from the combination vaccine of group D. Lane 2, rZinc protein probed with sera derived from the combination vaccine of Group D.

FIGS. 14-23, 24A, 24B, 48, 49A, 49B, and 50. Amino acid sequences and examples of nucleotide sequences encoding the amino acid sequences.

FIG. 51A-51J. CLUSTL Alignment of polypeptides using Clustl Omega. * (asterisk), indicates positions which have a single, fully conserved residue.

DETAILED DESCRIPTION OF EXEMPLARY EMBODIMENTS

Polypeptides

Figure 1:
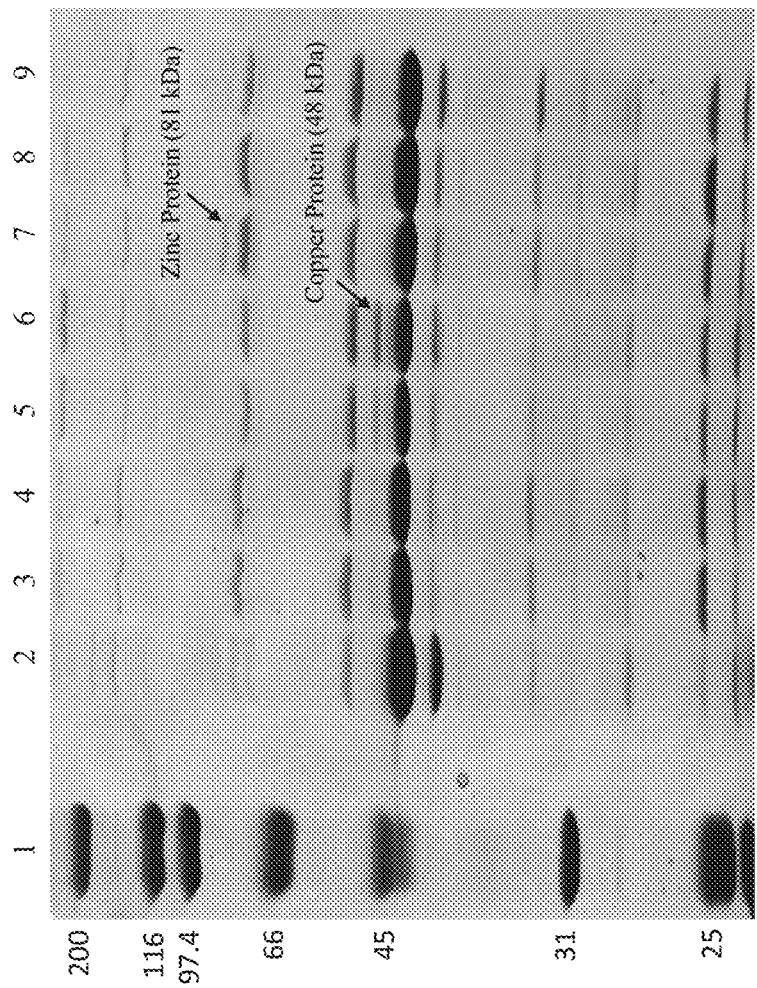
FIG. 1. SDS-PAGE of Gel image of extracted proteins derived from *Fusobacterium necrophorum* grown under metal-depleted growth conditions using different chelators. Lane 1-Molecular Weight Marker; Lane 2-15 µg/ml 2,2-dipyridyl in mTSB; Lane 3-100 µM Naringenin in mTSB; Lane 4-200 µM Catechin in mTSB; Lane 5-50 µM Quercetin in mTSB; Lane 6-100 µM Quercetin in mTSB; Lane 7-50 µM TPEN in mTSB; Lane 8-50 µM ammonium tetrathiomolybdate in mTSB and Lane 9-15 µg/ml 2,2-dipyridyl in pBHI. Lane 6 shows the expression of a novel copper protein expressed when *Fusobacterium necrophorum* when grown under copper chelation and lane 7 shows a novel zinc protein when *Fusobacterium necrophorum* was grown under zinc chelation.
Figure 3:
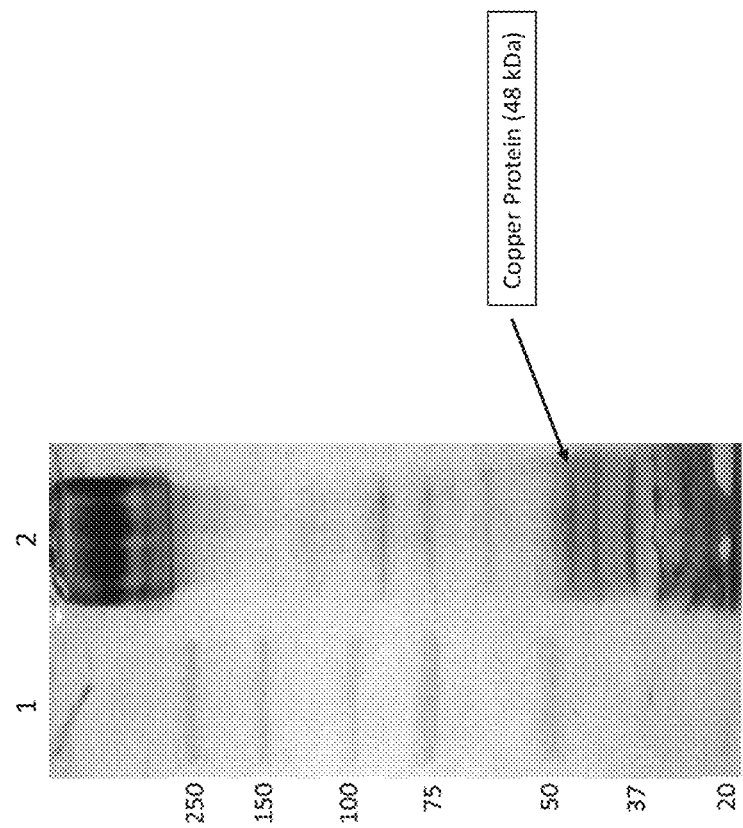
FIG. 3. Western Blot showing the sero-reactivity of the *Fusobacterium necrophorum* 48 kDa protein grown under copper deplete growth conditions. Lane 1, Molecular Weight Marker (MWM); Lane 2-Sero-reactivity of the 48 kDa copper protein. Arrow shows the up-regulation of a novel protein at 48 kDa that reacted with sera of Example 7.
Figure 4:
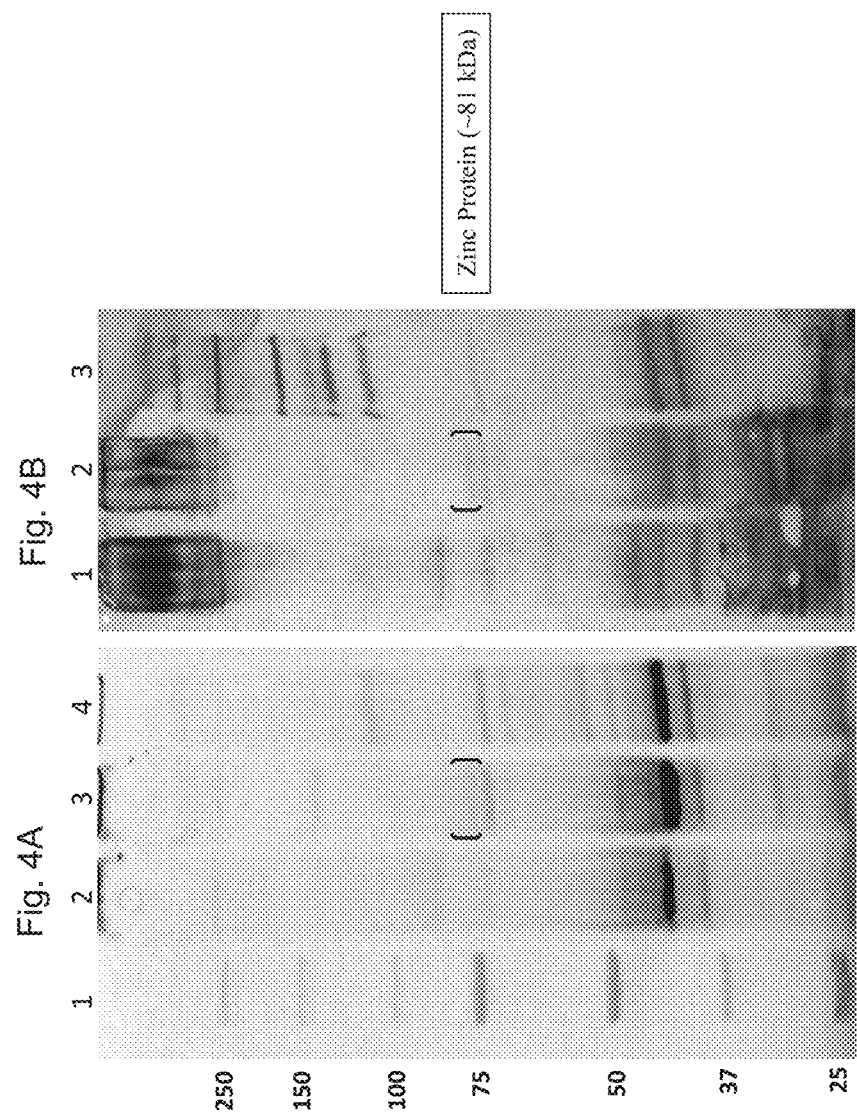
FIG. 4.

In one aspect, this disclosure provides polypeptides and compositions including polypeptides. As used herein, "polypeptide" refers to a polymer of amino acids linked by peptide bonds. Thus, for example, the terms peptide, oligopeptide, protein, and enzyme are included within the definition of polypeptide. This term also includes polypeptides that may include one or more post-expression modifications of the polypeptide such as, for example, a glycosylation, an acetylation, a phosphorylation, and the like. The term polypeptide does not connote a specific length of a polymer of amino acids. A polypeptide may be isolatable directly from a natural source or can be prepared with the aid of recombinant, enzymatic, or chemical techniques. In the case of a polypeptide that is naturally occurring, such a polypeptide is typically isolated.

An "isolated" polypeptide is one that has been removed from its natural environment. For instance, an isolated polypeptide is a polypeptide that has been removed from the cytoplasm or from the membrane of a cell, and many of the polypeptides, nucleic acids, and other cellular material of its natural environment are no longer present.

A polypeptide characterized as "isolatable" from a particular source is a polypeptide that, under appropriate conditions, is produced by the identified source, although the polypeptide may be obtained from alternate sources using, for example, conventional recombinant, chemical, or enzymatic techniques. Thus, characterizing a polypeptide as "isolatable" from a particular source does not imply any specific source from which the polypeptide must be obtained or any particular conditions or processes under which the polypeptide must be obtained.

A "purified" polypeptide is one that is at least 60% free, preferably at least 75% free, and most preferably at least 90% free from other components with which they are naturally associated. Polypeptides that are produced outside the organism in which they naturally occur, e.g., through chemical or recombinant means, are considered to be isolated and purified by definition, since they were never present in a natural environment.

Generally, a polypeptide may be characterized by molecular weight, amino acid sequence, nucleic acid that encodes the polypeptide, immunological activity, or any combination of two or more such characteristics. The molecular weight of a polypeptide, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, liquid chromatography (including HPLC), and calculating the molecular weight from an observed or predicted amino acid sequence. Unless indicated otherwise, reference to molecular weight refers to molecular weight as determined by resolving a polypeptide using an SDS polyacrylamide gel having a stacking gel of about 4% and a resolving gel of about 10% under reducing and denaturing conditions. A molecular weight of a protein determined by SDS-PAGE is also referred to herein as an apparent molecular weight. In one embodiment, the molecular weight of a protein identified by SDS-PAGE includes molecular weights of 1, 2, 3, 4, or 5 kDa above and below the stated value.

The polypeptides described herein may be metal-regulated. As used herein, a "metal-regulated polypeptide" is a polypeptide that is expressed by a microbe at a greater level when the microbe is grown in low metal conditions compared to when the same microbe is grown in high metal conditions. Low metal and high metal conditions are described herein. For instance, certain metal-regulated polypeptides produced by *Fusobacterium* spp. are not expressed at detectable levels during growth of the microbe in high metal conditions but are expressed at detectable levels during growth in low metal conditions. In one embodiment, certain metal-regulated polypeptides produced by *Fusobacterium* spp. are not expressed at detectable levels during growth of the microbe in high metal conditions but are expressed at detectable levels during growth in low metal conditions that also include hemin as a supplement. Table 1 summarizes the expression of proteins in the absence of different metals.

TABLE 1

The Comparison of MW in kDA of the vaccine compositions of Fusobacterium necrophorum 1694 as examined by SDS-PAGE and MALDI-TOF-MS under various conditions of metal ion restriction

| Protein Analysis of Isolate 1694 | Molecular Weights in Kilodaltons (kDa) | | | | | | | | |
|---|---|---|---|---|---|---|---|---|---|
| SDS-PAGE | | | | | | | | | |
| Iron-deplete | | | | | | 103* | 88 | | 74* |
| Iron-deplete, hemin supplemented | | | | 150 | | 103* | 88 | 84 | 74* |
| copper-deplete | | | 126 | | | | 88* | | 74 |
| zinc-deplete | | | 126 | | | 103 | 88 | 81 | 74* |
| MALDI-TOF-MS | | | | | | | | | |
| Iron-deplete | | | | | | | | | |
| iron deplete, hemin supplemented | | | | | | | 84,309 | | |
| copper-deplete | | | | | | | | | |
| zinc-deplete | | | | | | | | 81,723 | |
| Proteins Present in All Conditions | 335 | 243 | 230 | 220 | | 115 | | | |

The Comparison of MW in kDA of the vaccine compositions of Fusobacterium necrophorum 1694 as examined by SDS-PAGE and MALDI-TOF-MS under various conditions of metal ion restriction

| Protein Analysis of Isolate 1694 | Molecular Weights in Kilodaltons (kDa) | | | | | | |
|---|---|---|---|---|---|---|---|
| SDS-PAGE | | | | | | | |
| Iron-deplete | 68 | 60 | 52 | | | | |
| Iron-deplete, hemin supplemented | 68 | 60 | 52 | | | | |
| copper-deplete | | 60* | | 48* | | 28 | |
| zinc-deplete | 68 | 60* | | 48 | | 28 | 24 |

TABLE 1-continued

| MALDI-TOF-MS | | | | | | |
|---|---|---|---|---|---|---|
| Iron-deplete | | | | | | |
| iron deplete, hemin supplemented | | | | | | |
| copper-deplete | 48,413 | | | | | |
| zinc-deplete | | | | | | |
| Proteins Present in All Conditions | | 45 | 42 | 38 | 35 | 30 | 16 |

Protein Analysis: The molecular weights of the metal regulated proteins and porins of Fusobacterium Necrophorum were analyzed by single dimension SDS-PAGE and MALDI-TOF-MS.
Note:
The organism was grow under conditions of metal ion restriction i.e., iron-restriction; iron restriction with he min supplementation, zinc restriction and copper restriction.
*protein is additionally enhanced under these conditions.

Examples of metal-regulated polypeptides isolatable from a *Fusobacterium* spp., such as *F. necrophorum*, after growth in low iron conditions include metal-regulated polypeptides having molecular weights of 92 kDa to 79 kDa, 73 kDa to 63 kDa, 62 kDa to 58 kDa, and 57 kDa to 47 kDa. Specific examples of metal-regulated polypeptides isolatable from a *Fusobacterium* spp., such as *F. necrophorum*, after growth in low iron conditions include polypeptides of 88 kDa, 68 kDa, 60 kDa, and 52 kDa. In one embodiment, the low iron condition is growth in the presence of 2,2'-dipyridyl.

Examples of metal-regulated polypeptides isolatable from a *Fusobacterium* spp., such as *F. necrophorum*, after growth in low iron conditions supplemented with an iron-containing porphyrin, such as hemin, include metal-regulated polypeptides having molecular weights of 155 kDa to 145 kDa and 89 kDa to 79 kDa. Specific examples of this type of metal-regulated polypeptide isolatable from a *Fusobacterium* spp. after growth in low iron conditions in the presence of an iron-containing porphyrin include polypeptides of 150 kDa and 84 kDa. In one embodiment, the low iron condition is growth in the presence of 2,2'-dipyridyl and hemin.

Examples of metal-regulated polypeptides isolatable from a *Fusobacterium* spp., such as *F. necrophorum*, after growth in low copper conditions include metal-regulated polypeptides having molecular weights of 131 kDa to 121 kDa, 79 kDa to 69 kDa, and 33 kDa to 23 kDa. Specific examples of metal-regulated polypeptides isolatable from a *Fusobacterium* spp., such as *F. necrophorum*, after growth in low copper conditions include polypeptides of 126 kDa, 74 kDa, and 28 kDa. In one embodiment, the low copper condition is growth in the presence of catechin. In one embodiment, the low copper condition is growth in the presence of quercetin.

Examples of metal-regulated polypeptides isolatable from a *Fusobacterium* spp., such as *F. necrophorum*, after growth in low zinc conditions include metal-regulated polypeptides having molecular weights of 131 kDa to 121 kDa, 108 kDa to 98 kDa, 92 kDa to 64 kDa, 53 kDa to 43 kDa, and 33 kDa to 19 kDa. Specific examples of metal-regulated polypeptides isolatable from a *Fusobacterium* spp., such as *F. necrophorum*, after growth in low zinc conditions include polypeptides of 126 kDa, 103 kDa, 88 kDa, 81 kDa, 68 kDa, 48 kDa, 28 kDa, and 24 kDa. In one embodiment, the low zinc condition is growth in the presence of TPEN.

In one embodiment, polypeptides described herein are expressed at detectable levels during growth of the microbe in high metal conditions but more of the polypeptide is expressed during growth in low metal conditions. The expression of such polypeptides is referred to herein as "enhanced" during growth in low metal conditions. Typically, the increase in expression of a polypeptide during growth in low metal conditions is between 20% and 500% compared to the expression of the polypeptide during growth in high metal conditions.

Examples of metal-regulated polypeptides having enhanced expression and isolatable from *F. necrophorum* after growth in low iron conditions include metal-regulated polypeptides having molecular weights of 108 kDa to 98 kDa and 79 kDa to 69 kDa. Specific examples of metal-regulated polypeptides isolatable from a *Fusobacterium* spp., such as *F. necrophorum*, after growth in low iron conditions include polypeptides of 103 kDa and 74 kDa.

Examples of metal-regulated polypeptides having enhanced expression and isolatable from *F. necrophorum* after growth in low copper conditions include metal-regulated polypeptides having molecular weights of 93 kDa to 83 kDa, 65 kDa to 55 kDa, and 52 kDa to 42 kDa. Specific examples of metal-regulated polypeptides isolatable from a *Fusobacterium* spp., such as *F. necrophorum*, after growth in low copper conditions include polypeptides of 88 kDa, 60 kDa, and 48 kDa.

Examples of metal-regulated polypeptides having enhanced expression and isolatable from *F. necrophorum* after growth in low zinc conditions include metal-regulated polypeptides having molecular weights of 79 kDa to 69 kDa, and 65 kDa to 55 kDa. Specific examples of metal-regulated polypeptides isolatable from a *Fusobacterium* spp., such as *F. necrophorum*, after growth in low zinc conditions include polypeptides of 73 kDa and 60 kDa.

This disclosure also describes certain polypeptides that are not metal-regulated. Such polypeptides are expressed in the presence of a metal ion such as, for example, in the presence of ferric chloride, and also expressed when grown in low iron conditions. Examples of this type of polypeptide isolatable from *Fusobacterium* spp., such as *F. necrophorum*, have molecular weights 340 kDa to 330 kDa, 247 kDa to 237 kDa, 235 kDa to 215 kDa, 120 kDa to 110 kDa, 51 kDa to 25 kDa, and 21 kDa to 11 kDa. Examples of molecular weights of this type of polypeptide include 335 kDa, 243 kDa, 230 kDa, 220 kDa, 115 kDa, 45 kDa, 42 kDa, 38 kDa, 35 kDa, 30 kDa, and 16 kDa.

Other proteins provided herein include a protein at SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54 (FIGS. 14-48, 49A, 49B, and 50).

In one embodiment, a polypeptide disclosed herein, for instance at SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54 lacks one or more amino acids from the amino terminus, e.g., the polypeptide lacks a signal sequence. Thus, a fragment can lack at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, or at least 63 amino acids from the amino terminus of the polypeptide.

For instance, in one embodiment a polypeptide includes the following amino acids of SEQ ID NO:2; amino acids 2 through 423, amino acids 3 through 423, amino acids 4 through 423, amino acids 5 through 423, amino acids 6 through 423, amino acids 7 through 423, amino acids 8 through 423, amino acids 9 through 423, amino acids 10 through 423, amino acids 11 through 423, amino acids 12 through 423, amino acids 13 through 423, amino acids 14 through 423, amino acids 15 through 423, amino acids 16 through 423, amino acids 17 through 423, amino acids 18 through 423, amino acids 19 through 423, amino acids 20 through 423, amino acids 21 through 423, amino acids 22 through 423, amino acids 23 through 423, amino acids 24 through 423, amino acids 25 through 423, amino acids 26 through 423, amino acids 27 through 423, amino acids 28 through 423, amino acids 29 through 423, amino acids 30 through 423, amino acids 31 through 423, amino acids 32 through 423, amino acids 33 through 423, amino acids 34 through 423, amino acids 35 through 423, amino acids 36 through 423, amino acids 37 through 423, amino acids 38 through 423, amino acids 39 through 423, amino acids 40 through 423, amino acids 41 through 423, amino acids 42 through 423, amino acids 43 through 423, amino acids 44 through 423, amino acids 45 through 423, amino acids 46 through 423, amino acids 47 through 423, amino acids 48 through 423, amino acids 49 through 423, amino acids 50 through 423, amino acids 51 through 423, amino acids 52 through 423, amino acids 53 through 423, amino acids 54 through 423, amino acids 55 through 423, amino acids 56 through 423, amino acids 57 through 423, amino acids 58 through 423, amino acids 59 through 423, amino acids 60 through 423, amino acids 61 through 423, amino acids 62 through 423, or amino acids 63 through 423.

In one embodiment, a polypeptide includes the following amino acids of SEQ ID NO:4; amino acids 2 through 714, amino acids 3 through 714, amino acids 4 through 714, amino acids 5 through 714, amino acids 6 through 714, amino acids 7 through 714, amino acids 8 through 714, amino acids 9 through 714, amino acids 10 through 714, amino acids 11 through 714, amino acids 12 through 714, amino acids 13 through 714, amino acids 14 through 714, amino acids 15 through 714, amino acids 16 through 714, amino acids 17 through 714, amino acids 18 through 714, amino acids 19 through 714, amino acids 20 through 714, amino acids 21 through 714, amino acids 22 through 714, amino acids 23 through 714, amino acids 24 through 714, amino acids 25 through 714, amino acids 26 through 714, amino acids 27 through 714, amino acids 28 through 714, amino acids 29 through 714, amino acids 30 through 714, amino acids 31 through 714, amino acids 32 through 714, amino acids 33 through 714, amino acids 34 through 714, amino acids 35 through 714, amino acids 36 through 714, amino acids 37 through 714, amino acids 38 through 714, amino acids 39 through 714, amino acids 40 through 714, amino acids 41 through 714, amino acids 42 through 714, amino acids 43 through 714, amino acids 44 through 714, amino acids 45 through 714, amino acids 46 through 714, amino acids 47 through 714, amino acids 48 through 714, amino acids 49 through 714, amino acids 50 through 714, amino acids 51 through 714, amino acids 52 through 714, amino acids 53 through 714, amino acids 54 through 714, amino acids 55 through 714, amino acids 56 through 714, amino acids 57 through 714, amino acids 58 through 714, amino acids 59 through 714, amino acids 60 through 714, amino acids 61 through 714, amino acids 62 through 714, or amino acids 63 through 714.

In one embodiment, a polypeptide includes the following amino acids of SEQ ID NO:6; amino acids 2 through 736, amino acids 3 through 736, amino acids 4 through 736, amino acids 5 through 736, amino acids 6 through 736, amino acids 7 through 736, amino acids 8 through 736, amino acids 9 through 736, amino acids 10 through 736, amino acids 11 through 736, amino acids 12 through 736, amino acids 13 through 736, amino acids 14 through 736, amino acids 15 through 736, amino acids 16 through 736, amino acids 17 through 736, amino acids 18 through 736, amino acids 19 through 736, amino acids 20 through 736, amino acids 21 through 736, amino acids 22 through 736, amino acids 23 through 736, amino acids 24 through 736, amino acids 25 through 736, amino acids 26 through 736, amino acids 27 through 736, amino acids 28 through 736, amino acids 29 through 736, amino acids 30 through 736, amino acids 31 through 736, amino acids 32 through 736, amino acids 33 through 736, amino acids 34 through 736, amino acids 35 through 736, amino acids 36 through 736, amino acids 37 through 736, amino acids 38 through 736, amino acids 39 through 736, amino acids 40 through 736, amino acids 41 through 736, amino acids 42 through 736, amino acids 43 through 736, amino acids 44 through 736, amino acids 45 through 736, amino acids 46 through 736, amino acids 47 through 736, amino acids 48 through 736, amino acids 49 through 736, amino acids 50 through 736, amino acids 51 through 736, amino acids 52 through 736, amino acids 53 through 736, amino acids 54 through 736, amino acids 55 through 736, amino acids 56 through 736, amino acids 57 through 736, amino acids 58 through 736, amino acids 59 through 736, amino acids 60 through 736, amino acids 61 through 736, amino acids 62 through 736, or amino acids 63 through 736.

In one embodiment, a polypeptide includes the following amino acids of SEQ ID NO:34; amino acids 2 through 638, amino acids 3 through 638, amino acids 4 through 638, amino acids 5 through 638, amino acids 6 through 638, amino acids 7 through 638, amino acids 8 through 638, amino acids 9 through 638, amino acids 10 through 638, amino acids 11 through 638, amino acids 12 through 638, amino acids 13 through 638, amino acids 14 through 638, amino acids 15 through 638, amino acids 16 through 638, amino acids 17 through 638, amino acids 18 through 638, amino acids 19 through 638, amino acids 20 through 638, amino acids 21 through 638, amino acids 22 through 638, amino acids 23 through 638, amino acids 24 through 638, amino acids 25 through 638, amino acids 26 through 638, amino acids 27 through 638, amino acids 28 through 638, amino acids 29 through 638, amino acids 30 through 638, amino acids 31 through 638, amino acids 32 through 638, amino acids 33 through 638, amino acids 34 through 638, amino acids 35 through 638, amino acids 36 through 638, amino acids 37 through 638, amino acids 38 through 638, amino acids 39 through 638, amino acids 40 through 638, amino acids 41 through 638, amino acids 42 through 638, amino acids 43 through 638, amino acids 44 through 638, amino acids 45 through 638, amino acids 46 through 638, amino acids 47 through 638, amino acids 48 through 638, amino acids 49 through 638, amino acids 50 through 638, amino acids 51 through 638, amino acids 52 through 638, amino acids 53 through 638, amino acids 54 through 638, amino acids 55 through 638, amino acids 56 through 638, amino acids 57 through 638, amino acids 58 through 638, amino acids 59 through 638, amino acids 60 through 638, amino acids 61 through 638, amino acids 62 through 638, or amino acids 63 through 638.

In one embodiment, a polypeptide includes the following amino acids of SEQ ID NO:53; amino acids 2 through 1420, amino acids 3 through 1420, amino acids 4 through 1420, amino acids 5 through 1420, amino acids 6 through 1420, amino acids 7 through 1420, amino acids 8 through 1420, amino acids 9 through 1420, amino acids 10 through 1420, amino acids 11 through 1420, amino acids 12 through 1420, amino acids 13 through 1420, amino acids 14 through 1420, amino acids 15 through 1420, amino acids 16 through 1420, amino acids 17 through 1420, amino acids 18 through 1420, amino acids 19 through 1420, amino acids 20 through 1420, amino acids 21 through 1420, amino acids 22 through 1420, amino acids 23 through 1420, amino acids 24 through 1420, amino acids 25 through 1420, amino acids 26 through 1420, amino acids 27 through 1420, amino acids 28 through 1420, amino acids 29 through 1420, amino acids 30 through 1420, amino acids 31 through 1420, amino acids 32 through 1420, amino acids 33 through 1420, amino acids 34 through 1420, amino acids 35 through 1420, amino acids 36 through 1420, amino acids 37 through 1420, amino acids 38 through 1420, amino acids 39 through 1420, amino acids 40 through 1420, amino acids 41 through 1420, amino acids 42 through 1420, amino acids 43 through 1420, amino acids 44 through 1420, amino acids 45 through 1420, amino acids 46 through 1420, amino acids 47 through 1420, amino acids 48 through 1420, amino acids 49 through 1420, amino acids 50 through 1420, amino acids 51 through 1420, amino acids 52 through 1420, amino acids 53 through 1420, amino acids 54 through 1420, amino acids 55 through 1420, amino acids 56 through 1420, amino acids 57 through 1420, amino acids 58 through 1420, amino acids 59 through 1420, amino acids 60 through 1420, amino acids 61 through 1420, amino acids 62 through 1420, or amino acids 63 through 1420.

Additional examples of polypeptides include recombinantly-produced versions of polypeptides described herein. A recombinantly-produced polypeptide may include the entire amino acid sequence translatable from an mRNA transcript. Alternatively, a recombinantly-produced metal-regulated polypeptide can include a fragment of the entire translatable amino acid sequence. For example, a recombinantly-produced metal-regulated polypeptide may lack a cleavable sequence at either terminal of the polypeptide—e.g., a cleavable signal sequence at the amino terminus of the polypeptide.

Whether a polypeptide is a metal-regulated polypeptide or a non-metal-regulated polypeptide can be determined by methods useful for comparing the presence of polypeptides, including, for example, gel filtration, gel electrophoresis including sodium dodecyl sulfate-polyacrylamide gel electrophoresis (SDS-PAGE), capillary electrophoresis, mass spectrometry, isobaric tags for relative and absolute quantification (iTRAQ), and liquid chromatography including HPLC. Separate cultures of a microbe can be grown under high metal conditions and under low metal conditions, polypeptides may be isolated as described herein, and the polypeptides present in each culture can be resolved and compared. Typically, an equal amount of polypeptides from each culture is used. Preferably, the polypeptides can be resolved using an SDS polyacrylamide gel having a stacking gel of about 4% and a resolving gel of about 10% under reducing and denaturing conditions. For instance, 30 micrograms (µg) of total polypeptide from each culture may be used and loaded into wells of a gel. After running the gel and staining the polypeptides with Coomassie Brilliant Blue, the two lanes can be compared. When determining whether a polypeptide is or is not expressed at a detectable level, 30 µg of total polypeptide from a culture is resolved on an SDS-PAGE gel and stained with Coomassie Brilliant Blue using methods known in the art. A polypeptide that can be visualized by eye is considered to be expressed at a detectable level, while a polypeptide that cannot be visualized by eye is considered to not be expressed at a detectable level.

Alternatively, whether a polypeptide is a metal-regulated polypeptide or a non-metal-regulated polypeptide can be determined using microarray-based gene expression analysis. Separate cultures of a microbe can be grown under high metal conditions and under low metal conditions, RNA can be extracted from cells of each culture, and differences in RNA expression in cells grown in high metal conditions versus RNA expression in cells grown in low metal conditions can be detected and compared. For example, labeled cDNA can be prepared from 8-10 µg of bacterial RNA using established protocols. The labeled cDNA can be applied to a microarray of the *Fusobacterium* spp. genome. Such microarrays are commercially available and evaluating gene expression using such arrays is routine.

The polypeptides described herein may have immunological activity. "Immunological activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody is produced. The immunological activity may be protective. "Protective immunological activity" refers to the ability of a polypeptide to elicit an immunological response in an animal that inhibits or limits infection by *Fusobacterium* spp. Whether a polypeptide has protective immunological activity can be determined by methods known in the art such as, for example, methods described in Examples 2 and 7-11. A polypeptide may have seroactive activity. As used herein, "seroactive activity" refers to the ability of a candidate polypeptide to react with antibody present in convalescent serum from an animal infected with a *Fusobacterium* spp.

A polypeptide as described herein may have the characteristics of a polypeptide expressed by a reference microbe—i.e., a reference polypeptide. The characteristics can include, for example, molecular weight, mass fingerprint, amino acid sequence, or any combination thereof. The reference microbe can be a gram negative, preferably a member of the family Bacteroidaceae, such as the genus *Fusobacterium*. A member of the genus *Fusobacterium* is also referred to herein as *Fusobacterium* spp. Examples of *Fusobacterium* spp. include *F. necrophorum* (including *F. necrophorum* subsp. *necrophorum* and *F. necrophorum* subsp. *funduliforme*), *F. nucleatum*, *F. ulcerans*, *F. russii*, *F. varium*, *F. mortiferum*, *F. gonidiaformans*, *F. canifelinum*; *F. necrogenes*; and *F. naviforme*. An example of a representative strain is *F. necrophorum* 1694.

In one embodiment, a candidate polypeptide can be considered to be a polypeptide as described herein if it has an amino acid sequence that is structurally similar, as described in detail below, to a reference amino acid sequence disclosed herein, for instance, SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54, or a fragment thereof, such as a fragment that lacks one or more amino acids from the amino terminus. In one embodiment, such a polypeptide is metal-regulated when expressed by a *Fusobacterium* spp., such as *F. necrophorum* 1694.

As used herein, a polypeptide may be "structurally similar" to a reference polypeptide if the amino acid sequence of the polypeptide possesses a specified amount of sequence similarity and/or sequence identity compared to the reference polypeptide. A polypeptide also may be "structurally similar" to a reference polypeptide if the polypeptide exhibits a mass fingerprint possessing a specified amount of identity compared to a comparable mass fingerprint of the reference polypeptide. Thus, a polypeptide may be "structurally similar" to a reference polypeptide if, compared to the reference polypeptide, it possesses a sufficient level of amino acid sequence identity, amino acid sequence similarity, or a combination thereof.

Polypeptide Sequence Similarity and Polypeptide Sequence Identity

Structural similarity of two polypeptides can be determined by aligning the residues of the two polypeptides (for example, a candidate polypeptide and any appropriate reference polypeptide described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference polypeptide may be a polypeptide described herein or any known metal-regulated polypeptide, as appropriate. A candidate polypeptide is the polypeptide being compared to the reference polypeptide. A candidate polypeptide can be isolated, for example, from a microbe, or can be produced using recombinant techniques, or chemically or enzymatically synthesized.

Unless modified as otherwise described herein, a pairwise comparison analysis of amino acid sequences can be carried out using the BESTFIT algorithm in the GCG package (version 10.2, Madison WI). Alternatively, polypeptides may be compared using the Blastp program of the BLAST 2 search algorithm, as described by Tatiana et al. (*FEMS Microbiol Lett,* 174:247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a polypeptide may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a polypeptide containing deletions or additions of one or more contiguous or noncontiguous amino acids that do not eliminate a functional activity—such as, for example, immunological activity—of the polypeptide are also contemplated.

Thus, as used herein, reference to a polypeptide as described herein and/or reference to the amino acid sequence of one or more SEQ ID NOs can include a polypeptide with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to a polypeptide as described herein and/or reference to the amino acid sequence of one or more SEQ ID NOs can include a polypeptide with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

FIG. 51A-51J shows cross-species sequence alignment for polypeptides having the amino acid sequences shown in SEQ ID NO:2, 4 and 6 (also referred to herein as proteins FT, FQ, and FN, respectively). The alignment indicates amino acids that are conserved in the variants of each polypeptide across different *Fusobacterium* species. The alignment also shows regions of variability in the variants of each polypeptide across the different *Fusobacterium* species. A person of ordinary skill in the art can deduce from such data regions of the polypeptide in which substitutions, particularly conservative substitutions, may be permitted without unduly affecting biological activity of the modified polypeptide. Further, the skilled person can use readily available algorithms, such as Clustl Omega, to produce alignments with related proteins and identify regions of conservation and variability.

Consequently, a polypeptide as described herein can include certain variants including, for example, homologous polypeptides that originate-biologically and/or recombinantly—from microbial species or strains other than the microbial species or strain from which the polypeptide was originally isolated and/or identified.

A polypeptide as described herein also can be designed to provide one or more additional sequences such as, for example, the addition of coding sequences for added C-terminal and/or N-terminal amino acids that may facilitate purification by trapping on columns or use of antibodies. Such tags include, for example, histidine-rich tags that allow purification of polypeptides on nickel columns. Such gene modification techniques and suitable additional sequences are well known in the molecular biology arts. A polypeptide as described herein also may be designed so that certain amino acids at the C-terminal and/or N-terminal are deleted.

A "modification" of a polypeptide as described herein includes a polypeptide (or an analog thereof such as, e.g., a fragment thereof) that is chemically or enzymatically derivatized at one or more constituent amino acids. Such a modification can include, for example, a side chain modification, a backbone modification, an N-terminal modification, and/or a C-terminal modification such as, for example, acetylation, hydroxylation, methylation, amidation, and the attachment of a carbohydrate and/or lipid moiety, a cofactor, and the like, and combinations thereof. Modified polypeptides as described herein may retain the biological activity—such as, for example, immunological activity—of the unmodified polypeptide or may exhibit a reduced or increased biological activity compared to the unmodified polypeptide.

A polypeptide as described herein (including a biologically active analog thereof and/or a modification thereof) can include a native (naturally occurring), a recombinant, a chemically synthesized, or an enzymatically synthesized polypeptide. For example, a polypeptide as described herein may be prepared by isolating the polypeptide from a natural source or may be prepared recombinantly by conventional methods including, for example, preparation as fusion proteins in bacteria or other host cells.

A polypeptide expressed by a reference microbe can be obtained by growing the reference microbe under low metal conditions as described herein and the subsequent isolation of a polypeptide by the processes disclosed herein. Alternatively, a polypeptide expressed by a reference microbe can be obtained by identifying coding regions expressed at higher levels when the microbe is grown in low metal conditions—i.e., metal-regulated. A metal-regulated coding region can be cloned and expressed, and the expressed metal-regulated polypeptide may be identified by the processes described herein. A candidate polypeptide can be isolatable from a microbe or identified from a microbe, preferably a gram negative microbe, more preferably, a member of the family Bacteroidaceae, such as the genus *Fusobacterium*, including *F. necrophorum* (e.g., *F. necrophorum* subsp. *necrophorum* and *F. necrophorum* subsp. *funduliforme*), *F. nucleatum, F. ulcerans, F. russii, F. varium, F. mortiferum, F. gonidiaformans, F. canifelinum; F. necrogenes*; and *F. naviforme*.

Polynucleotide Sequence Similarity and Polynucleotide Sequence Identity

Polypeptides as described herein also may be identified in terms of the polynucleotide that encodes the polypeptide. Thus, this disclosure provides polynucleotides that encode a polypeptide as described herein or hybridize, under standard hybridization conditions, to a polynucleotide that encodes a polypeptide as described herein, and the complements of such polynucleotide sequences.

As used herein, reference to a polynucleotide as described herein and/or reference to the nucleic acid sequence of one or more SEQ ID NOs can include polynucleotides having a sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides (for example, aligning the nucleotide sequence of the candidate sequence and a nucleotide sequence that includes, for example, a nucleotide sequence disclosed herein, such as SEQ ID NO: 1, 3, 5, 7, 9, 11, 13, 15, 17, 19, 21, 23, 25, 27, 29, 31, 33, 78, or a fragment thereof) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence—e.g., a nucleotide sequence that includes a nucleotide sequence described herein, for example, SEQ ID NO: 1, 3, 5, 7, 9, 11, 13, 15, 17, 19, 21, 23, 25, 27, 29, 31, 33, 78, or a fragment thereof. For example, two polynucleotide sequences can be compared using the Blastn program of the BLAST 2 search algorithm, as described by Tatusova et al., (*FEMS Microbiol Lett.*, 174:247-250 (1999)), and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x_dropoff=50, expect=10, wordsize=11, and filter on.

Finally, a polynucleotide as described herein can include any polynucleotide that encodes a polypeptide as described herein. Thus, the nucleotide sequence of the polynucleotide may be deduced from the amino acid sequence that is to be encoded by the polynucleotide.

This disclosure also provides whole cell preparations of a microbe, where the microbe expresses one or more of the polypeptides described herein. The cells present in a whole cell preparation may be inactivated such that the cells cannot replicate but the immunological activity of the polypeptides as described herein expressed by the microbe is maintained. Typically, the cells may be killed by exposure to agents such as glutaraldehyde, formalin, or formaldehyde. In one embodiment, the whole cell is a member of the family Bacteroidaceae, such as the genus *Fusobacterium*, including *F. necrophorum* (e.g., *F. necrophorum* subsp. *necrophorum* and *F. necrophorum* subsp. *funduliforme*), *F. nucleatum, F. ulcerans, F. russii, F. varium, F. mortiferum, F. gonidiaformans, F. canifelinum; F. necrogenes*; and *F. naviforme*.

In one embodiment, a fusobacteria is engineered to express a recombinantly produced protein that has structural similarity (sequence similarity or sequence identity) with SEQ ID NO:2 or a fragment thereof, structural similarity (sequence similarity or sequence identity) with SEQ ID NO:4 or a fragment thereof, structural similarity (sequence similarity or sequence identity) with SEQ ID NO:6 or a fragment thereof, structural similarity (sequence similarity or sequence identity) with SEQ ID NO:34 or a fragment thereof, structural similarity (sequence similarity or sequence identity) with SEQ ID NO:53 or a fragment thereof, or a combination thereof.

In one embodiment, a microbe, such as fusobacteria or *E. coli*, is engineered to express one or more recombinantly produced proteins that have structural similarity (sequence similarity or sequence identity) with SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54, or a fragment thereof.

Compositions

A composition as described herein may include at least one isolated polypeptide described herein, or a number of polypeptides that is an integer greater than one (e.g., at least two, at least three, at least four, at least five, at least six, at least seven, at least eight, at least nine, at least 10, at least 11, at least 12, at least 13, at least 14, at least 15, and so on), in any combination. Unless a specific level of sequence similarity and/or identity is expressly indicated herein (e.g., at least 80% sequence similarity, at least 85% sequence similarity, at least 90% sequence identity, etc.), reference to the amino acid sequence of an identified SEQ ID NO includes variants having the levels of sequence similarity and/or the levels of sequence identity described herein in the section headed "Polypeptide sequence similarity and polypeptide sequence identity."

A recombinantly-produced polypeptide may be expressed from a vector that permits expression of the polypeptide when the vector is introduced into an appropriate host cell. A host cell may be constructed to produce one or more recombinantly-produced polypeptides as described herein and, therefore, can include one or more vectors that include at least one polynucleotide encoding a polypeptide described herein. Thus, each vector can include one or more polynucleotides as described herein—i.e., a polynucleotide that encodes a polypeptide as described herein. Examples of host cells include, but are not limited to, *E. coli* and Fusobacteria. Methods for the genetic manipulation of Fusobacteria are known and routine in to art (see, for instance, Attarian et al., U.S. Pat. No. 6,962,990).

Certain compositions such as, for example, those including recombinantly-produced polypeptides, can include a maximum number of different types of polypeptides. In some embodiments, the maximum number of different types of polypeptides can refer to the maximum total number of polypeptides. Certain compositions can include, for example, no more than 50 polypeptides such as, for example, no more than 40 polypeptides, no more than 30 polypeptides, no more than 25 polypeptides, no more than 20 polypeptides, no more than 17 polypeptides, no more than 16 polypeptides, no more than 15 polypeptides, no more than 14 polypeptides, no more than 13 polypeptides, no more than 10 polypeptides, no more than eight polypeptides, no more than seven polypeptides, no more than six polypeptides, no more than five polypeptides, no more than four polypeptides, no more than three polypeptides, no more than two polypeptides, or no more than one polypeptide. A non-limiting example of a composition having no more than two polypeptides is one having the polypeptide SEQ ID NO:2 and the polypeptide SEQ ID NO:4. In other embodiments, a maximum number of recombinantly-produced polypeptides may be specified in a similar manner. In still other embodiments, a maximum number of nonrecombinantly-produced polypeptides may be specified in a similar manner.

A composition can include polypeptides isolatable from one microbe, or can be isolatable from a combination of two or more microbes. For instance, a composition can include polypeptides isolatable from two or more *Fusobacterium* spp., or from a *Fusobacterium* spp. and a different microbe that is not a member of the genus *Fusobacterium*. In certain embodiments, a composition can include a whole cell preparation in which the whole cell expresses one or more of the polypeptides as described herein. In some of these embodiments, the whole cell can be a *Fusobacterium* spp. In some embodiments, a composition can include whole cell preparations from two, three, four, five, or six strains.

In one embodiment, a composition includes at least one, at least two, at least three, at least four, or at least five recombinantly produced proteins, for instance SEQ ID NO:2, SEQ ID NO:4, SEQ ID NO:6, SEQ ID NO:34, and SEQ ID NO:53, or a fragment thereof. In one embodiment, a composition includes polypeptides expressed by a *Fusobacterium* spp. during growth in low iron and SEQ ID NO:2 (which is not expressed at a detectable level in low iron), SEQ ID NO:4 (which is not expressed at a detectable level in low iron), SEQ ID NO:6 (which is not expressed at a detectable level in low iron when a chelator such as 2,2-dipyridyl is used to reduce the amount of available iron and is expressed at a detectable level when 2,2-dipyridyl and hemin are present), SEQ ID NO:34, SEQ ID NO:53 (which is not expressed at a detectable level in low iron when a chelator such as 2,2-dipyridyl is used to reduce the amount of available iron and is expressed at a detectable level when 2,2-dipyridyl and hemin are present), or a combination thereof. Such compositions are not naturally occurring. A specific example of such a composition is one including proteins that are not detectable during growth of a *Fusobacterium* spp., such as *F. necrophorum*, after growth in low iron conditions (proteins having molecular weights of 88 kDa, 68 kDa, 60 kDa, and 52 kDa), proteins having enhanced expression by a *Fusobacterium* spp., such as *F. necrophorum*, after growth in low iron conditions (proteins having molecular weights of 103 kDa and 74 kDa), non-metal-regulated proteins expressed by a *Fusobacterium* spp., such as *F. necrophorum*, (335 kDa, 243 kDa, 230 kDa, 220 kDa, 115 kDa, 45 kDa, 42 kDa, 38 kDa, 35 kDa, 30 kDa, and 16 kDa), and one or more recombinantly produced proteins selected from SEQ ID NO:2, SEQ ID NO:4, SEQ ID NO:6, SEQ ID NO:34, SEQ ID NO:53, or a fragment thereof. Optionally, such a composition also includes metal-regulated proteins that are expressed after growth in low metal conditions supplemented with hemin (150 kDa and 84 kDa).

In one embodiment, a composition includes one or more polypeptides, for instance SEQ ID NO: 2, 4, 6, 8, 10, 12, 14, 16, 18, 20, 22, 24, 26, 28, 30, 32, 34, 35, 36, 37, 38, 39, 40, 41, 42, 43, 44, 45, 46, 47, 48, 49, 50, 51, 52, 53, or 54, or a fragment thereof.

Optionally, a polypeptide of the present invention can be covalently bound to a carrier polypeptide to improve the immunological properties of the polypeptide. Useful carrier polypeptides are known in the art, and include, for instance, leukotoxin derived from *Fusobacterium* spp. The chemical coupling of a polypeptide of the present invention can be carried out using known and routine methods. For instance, various homobifunctional and/or heterobifunctional cross-linker reagents such as bis(sulfosuccinimidyl) suberate, bis (diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl)cyclohexane-1-carboxylate, sulfosuccinimidyl 4-(p-maleimido-phenyl) butyrate and (1-ethyl-3-(dimethyl-aminopropyl) carbodiimide can be used (Harlow and Lane, Antibodies, A Laboratory Manual, generally and Chapter 5, Cold Spring Harbor Laboratory, Cold Spring Harbor, New York, NY (1988)). In one embodiment, a protein described herein covalently bound to a carrier protein (such as a leukotoxin) has structural similarity (sequence similarity or sequence identity) with SEQ ID NO:2 or a fragment thereof, has structural similarity (sequence similarity or sequence identity) with SEQ ID NO:4 or a fragment thereof, has structural similarity (sequence similarity or sequence identity) with SEQ ID NO:6 or a fragment thereof, has structural similarity (sequence similarity or sequence identity) with SEQ ID NO:34 or a fragment thereof, or has structural similarity (sequence similarity or sequence identity) with SEQ ID NO:53 or a fragment thereof.

Preferably, such compositions of the present invention include low concentrations of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (O-specific chain, the outer and inner core) and the lipid A region. The lipid A component of LPS is the most biologically active component of the LPS structure and together induces a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scarring or blemishes of the tissue at the injection site (see, for instance, Rae, Injection Site Reactions, available at www.animal.ufl.edu/extension/beef/documents/SHORT94/RAE.HTM, which is available through the website maintained by the Department of Animal Sciences of the University of Florida, Gainesville, FL).

The concentration of LPS can be determined using routine methods known in the art. Such methods typically include measurement of dye binding by LPS (see, for instance, Keler and Nowotny, *Analyt. Biochem.*, 156, 189 (1986)) or the use of a *Limulus* amebocyte lysate (LAL) test (see, for instance, Endotoxins and Their Detection With the *Limulus* Amebocyte Lystate Test, Alan R. Liss, Inc., 150 Fifth Avenue, New York, NY (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOX-ATE (Sigma Chemical Co., St. Louis, MO; see Sigma Technical Bulletin No. 210), and PYROTELL (Associates of Cape Cod, Inc., East Falmouth, MA). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for 1 hour undisturbed at 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, MD, Catalog No. 235503), and Associates of Cape Cod, Inc., (Catalog No. E0005). In general, when a composition of the present invention is prepared by isolating polypeptides from a *Fusobacterium* spp. by a method as described herein (e.g., a method that includes disrupting and solubilizing the cells, and collecting the insoluble polypeptides), the amount of LPS in a composition of the present invention is less than the amount of LPS present in a mixture of same amount of the *Fusobacterium* spp. that has been disrupted under the same conditions but not solubilized. Typically, the level of LPS in a composition of the present invention is decreased by, in increasing order of preference, at least 50%, at least 60%, at least 70%, at least 80%, or at least 90% relative to the level of LPS in a composition prepared by disrupting, but not solubilizing, the same *Fusobacterium* spp.

In some aspects, a composition of the present invention does not include a leukotoxin isolatable from a *Fusobacterium* spp. Leukotoxins that are optionally not present in a composition of the present invention include polypeptides having a molecular weight of 335 kDa based on analysis with an 10% SDS-PAGE gel under reducing and denaturing conditions, and having an activity that is toxic to bovine leukocytes (Narayanan et al., Infect. Imun., 69, 5447-5455 (2001), and Narayanan et al., Infect. Immun., 70, 4609-4620 (2002)). Whether a polypeptide has leukotoxin activity can be determined using the monoclonal antibody F7B10 which is reactive against a *F. necrophorum* leukotoxin (Tan et al., Vet. Microbiol., 42, 121-133 (1994), or by determining whether the polypeptide is toxic to ruminant leukocytes. Methods for measuring the toxicity of a polypeptide for ruminant leukocytes are known in the art (Narayanan et al., Infect. Imun., 69, 5447-5455 (2001), and Narayanan et al., Infect. Immun., 70, 4609-4620 (2002).

The compositions as described herein optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. Exemplary pharmaceutically acceptable carriers include buffer solutions and generally exclude blood products such as, for example, whole blood and/or plasma. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, oral; parenteral including intradermal, transcutaneous and subcutaneous, intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition as described herein can also be administered via a sustained or delayed release implant. Implants suitable for use according to the invention are known and include, for example, those disclosed in International Publication No. WO 2001/037810 and/or International Publication No. WO 1996/001620. Implants can be produced at sizes small enough to be administered by aerosol or spray. Implants also can include nanospheres and microspheres.

A composition of the present invention is administered in an amount sufficient to provide an immunological response to polypeptides or whole cells described herein. The amount of polypeptide present in a composition can vary. For instance, the dosage of polypeptide can be between 0.01 micrograms (μg) and 3000 milligrams (mg), typically between 10 μg and 2000 ug. When the composition is a whole cell preparation, the cells can be present at a concentration of $10^6$ bacteria/ml, $10^7$ bacteria/ml, $10^8$ bacteria/ml, or $10^9$ bacteria/ml. For an injectable composition (e.g. subcutaneous, intramuscular, etc.) the polypeptide is preferably present in the composition in an amount such that the total volume of the composition administered is 0.5 ml to 5.0 ml, typically 1.0-3.0 ml. When the composition is a whole cell preparation, the cells are preferably present in the composition in an amount that the total volume of the composition administered is 0.5 ml to 5.0 ml, typically 1.0-2.0 ml. The amount administered will vary depending on various factors including, but not limited to, the specific polypeptides or cells chosen, the weight, physical condition and age of the animal, and the route of administration. Thus, the absolute weight of the polypeptide or number of cells included in a given unit dosage form can vary, and depends upon factors such as the species, age, weight and physical condition of the animal, as well as the method of administration. Such factors can be determined by one skilled in the art. Other examples of dosages suitable for the invention are disclosed in Emery et al. (U.S. Pat. No. 6,027,736).

The formulations may be conveniently presented in unit dosage form and may be prepared by methods well known in the art of pharmacy. All methods of preparing a composition including a pharmaceutically acceptable carrier include the step of bringing the active compound (e.g., a polypeptide or whole cell of the present invention) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyldioctadecylammonium bromide (DDA), avirdine, aluminum hydroxide, oils, saponins, alpha-tocopherol, polysaccharides, emulsified paraffins (available from under the tradename EMULSIGEN from MVP Laboratories, Ralston, Nebraska), ISA-70, RIBI and other substances known in the art.

In another embodiment, a composition of the invention including a pharmaceutically acceptable carrier can include a biological response modifier, such as, for example, IL-2, IL-4 and/or IL-6, TNF, IFN-alpha, IFN-gamma, and other cytokines that effect immune cells. A composition can also include an antibiotic, preservative, anti-oxidant, chelating agent, etc. Such components are known in the art.

Methods of Making

This disclosure also provides methods for obtaining the polypeptides and whole cells described herein. Polypeptides and whole cell preparations described herein may be obtained by incubating a member of the genus *Fusobacterium* under conditions that promote expression of one or more of the polypeptides described herein. The polypeptides and whole cells as described herein may be isolatable from a member of the family Bacteroidaceae, such as the genus *Fusobacterium*, including *F. necrophorum* (such as *F. necrophorum* subsp. *necrophorum* and *F. necrophorum* sub sp. *funduliforme*), *F. nucleatum*, *F. ulcerans*, *F. russii*, *F. varium*, *F. mortiferum*, *F. gonidiaformans*, *F. canifelinum*; *F. necrogenes*; and *F. naviforme*. An example of a representative strain is *F. necrophorum* 1694. Microbes useful for obtaining polypeptides described herein and making whole cell preparations are commercially available from a depository such as American Type Culture Collection (ATCC). In addition, such microbes are readily obtainable by techniques routine and known in the art. The microbes may be derived from an infected animal as a field isolate, and used to obtain the polypeptides and/or the whole cell preparations as described herein, or stored for future use, for example, in a frozen repository at from −20° C. to −95° C., or from −40° C. to −50° C., in bacteriological media containing 20% glycerol, and other like media.

The present invention also includes compositions prepared by the processes disclosed herein. Typically, such conditions are low metal conditions. As used herein, the phrase "low metal conditions" refers to an environment, typically bacteriological media that contains amounts of a free metal that cause a microbe to express a metal regulated polypeptide at a detectable level. As used herein, the phrase "high metal conditions" refers to an environment that contains an amount of a free metal that causes a microbe to express a metal-regulated polypeptide at a decreased level compared to expression of the metal-regulated polypeptide under low metal conditions. In some cases, "high metal conditions" can refer to an environment that causes a cell to fail to express one or more of the metal-regulated polypeptides described herein at a detectable level.

In some cases, "high metal conditions" can include a metal-rich natural environment and/or culture in a metal-rich medium without a metal chelator. In contrast, in some cases, "low metal conditions" can include culture in a medium that includes a metal chelator, as described in more detail below. Metals are those present in the periodic table under Groups 1 through 17 (IUPAC notation; also referred to as Groups I-A, II-A, III-B, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron, copper, or zinc.

Low metal conditions are generally the result of the addition of a metal chelating compound to a bacteriological medium, the use of a bacteriological medium that contains low amounts of a metal, or a combination thereof. High metal conditions are generally present when a chelator is not present in the medium, when a metal is added to the medium, or a combination thereof. Examples of metal chelators include natural and synthetic compounds. Examples of natural compounds include plant phenolic compounds, such as flavonoids. Examples of flavonoids include the copper chelators catechin, naringenin, and quercetin, and the iron chelator myricetin. Examples of synthetic copper chelators include, for instance, ammonium tetrathiomolybdate, and examples of synthetic zinc chelators include, for instance, N,N,N',N'-Tetrakis (2-pyridylmethyl)-ethylene diamine (also referred to as TPEN). Examples of synthetic iron chelators include 2,2'-dipyridyl (also referred to in the art as α,α'-bipyridyl), 8-hydroxyquinoline, ethylenediamine-di-O-hydroxyphenylacetic acid (EDDHA), desferrioxamine methanesulfonate (desferal), transferrin, lactoferrin, ovotransferrin, biological siderophores, such as the catecholates and hydroxamates, and citrate.

In one embodiment, 2,2'-dipyridyl is used for the chelation of iron. Typically, 2,2'-dipyridyl is added to the media at a concentration of at least 0.0025 micrograms/milliliter (μg/ml), at least 0.025 μg/ml, or at least 0.25 μg/ml. High levels of 2,2'-dipyridyl can be 10 μg/ml, 20 μg/ml, or 30 μg/ml.

In one embodiment, a medium is supplemented with an iron-containing porphyrin, such as hemin. Typically, hemin is added to the medium at a concentration of 20 ug/ml, and other concentrations can be used.

In one embodiment, quercetin is used for the chelation of copper. Typically, quercetin is added to the media at a concentration of 50 μM, and concentrations between 25 μM and 100 μM can be used.

In one embodiment, TPEN is used for the chelation of zinc. Typically, TPEN is added to the media at a concentration of 50 μM is used, and it is expected that higher concentrations can be used.

It is expected that a *Fusobacterium* spp. with a mutation in a fur gene will result in the constitutive expression of many, if not all, of the metal regulated polypeptides of the present invention. A potential fur gene has been identified in a *F. nucleatum* (Kapatral et al., J. Bacteriol. 184 (7), 2005-2018 (2002)). The production of a fur mutation in a *Fusobacterium* spp. can be produced using routine methods including, for instance, electroporation and genetic constructs useful for gene knock-out in gram negative bacteria.

In one embodiment, the fusobacteria used to make a composition described herein, e.g., a composition including isolated polypeptides or a composition including whole cells, may be produced using a fusobacteria that has been engineered to recombinantly express a protein that has structural similarity (sequence similarity or sequence identity) with SEQ ID NO:2 or a fragment thereof, structural similarity (sequence similarity or sequence identity) with SEQ ID NO:4 or a fragment thereof, structural similarity (sequence similarity or sequence identity) with SEQ ID NO:6 or a fragment thereof, a portion thereof, structural similarity (sequence similarity or sequence identity) with SEQ ID NO:34 or a fragment thereof, structural similarity (sequence similarity or sequence identity) with SEQ ID NO:53 or a fragment thereof, or a combination thereof. In one embodiment, such a fusobacteria is incubated in the presence of low iron conditions, and the one of more recombinant polypeptides are expressed during the incubation in the low iron conditions. The result is a fusobacteria that expresses iron-regulated proteins and the one of more recombinant polypeptides.

Many *Fusobacterium* spp. are able to grow in low metal conditions in vitro in artificial media only after adaptation. For instance, a *Fusobacterium* spp., such as the isolate given the identification number MS 040525 and *F. necrophorum* 1694 can be adapted to low iron conditions in vitro by growth in the presence of low concentrations of an iron chelator after growth in a medium containing the chelator, gradually increasing the concentration of the chelator. For instance, a *Fusobacterium* spp. can be adapted to growth in low iron conditions by adding 0.0025 μg/ml of 2,2'-dipyridyl to a medium, and exposing the culture to gradually increasing concentrations of the chelator to a greater concentration, for instance 20 μg/ml as previously reported Straub et al. (U.S. Pat. No. 8,329,192). Adaptation of *Fusobacterium* spp. to reduced zinc and copper is also possible. Repeat passage of at least five consecutive passes in 50 μM TPEN adapted *Fusobacterium* spp. to reduced zinc. Repeat passage of at least five consecutive passes in 50 or in 100 μM quercetin, repeat passage of at least five consecutive passes in 100 μM catechin, or repeat passage of at least five consecutive passes in 100 μM Naringenin adapted *Fusobacterium* spp. to reduced copper. Culture of adapted *Fusobacterium* spp. in the presence of any of these chelators resulted in increased expression of unique proteins. Adaptation of other *Fusobacterium* spp. strains to low metal conditions can be accomplished in this way.

The medium used to incubate the microbe is not critical, and conditions useful for the culture of fusobacteria are known to the skilled person. In one embodiment, supplements may be added to a culture medium, such as, but not limited to, hemin. The volume of medium used to incubate the microbe can vary. When a *Fusobacterium* spp. microbe is being evaluated for the ability to produce the polypeptides described herein, the microbe can be grown in a suitable volume, for instance, 10 milliliters to 1 liter of medium. When a microbe is being grown to obtain polypeptides for use in, for instance, administration to animals, the microbe may be grown in a fermenter to allow the isolation of larger amounts of polypeptides. Methods for growing microbes in a fermenter are routine and known in the art. The conditions used for growing a microbe preferably include a metal chelator, more preferably an iron chelator, for instance 2,2'-dipyridyl, TPEN, or quercetin, a pH of between 6.5 and 7.5, preferably between 6.9 and 7.1, and a temperature of 37° C. When a fermenter is used, the culture may be purged with an appropriate gas, for instance, nitrogen, to maintain anaerobic conditions. Members of the genus *Fusobacterium* are obligate anaerobes, thus growth conditions do not include levels of oxygen that will prevent growth.

In some aspects of the invention, a *Fusobacterium* spp. may be harvested after growth. Harvesting includes concentrating the microbe into a smaller volume and suspending in a media different than the growth media. Methods for concentrating a microbe are routine and known in the art, and include, for example, filtration and/or centrifugation. Typically, the concentrated microbe is suspended in decreasing amounts of buffer. Preferably, the final buffer includes a metal chelator, preferably, ethylenediaminetetraacetic acid (EDTA). An example of a buffer that can be used contains Tris-base (7.3 grams/liter) and EDTA (0.9 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at −20° C. or below until disrupted. In one embodiment, bacterial cells may be concentrated into a pellet by, for instance, centrifugation, and the concentrated cells suspended in osmotic shock buffer (OMS; 7.26 grams/liter Tris-base and 0.93 grams/liter EDTA adjusted to a pH of 8.5). The ratio of cells to OMS may be 50 grams cell pellet, 60 grams cell pellet, or 70 grams cell pellet to 1 liter of OMS. The suspension of cells in OMS can be incubated at 2-8° C. for at least 24 hours, at least 48 hours, or at least 60 hours to remove excess endotoxin from the cells. In one embodiment, the incubation is for no greater than 72 hours. After the incubation the suspension is centrifuged again and the supernatant discarded to remove free endotoxin and any extracellular material, e.g., secreted proteins.

When the *Fusobacterium* spp. is to be used as a whole cell preparation, the harvested cells may be processed using routine and known methods to inactivate the cells. Alternatively, when a *Fusobacterium* spp. is to be used to prepare polypeptides of the present invention, the *Fusobacterium* spp. may be disrupted using chemical, physical, or mechanical methods routine and known in the art, including, for example, french press, sonication, or homogenization. Preferably, homogenization is used. As used herein, "disruption" refers to the breaking up of the cell. Disruption of a microbe can be measured by methods that are routine and known in the art, including, for instance, changes in optical density. Typically, a microbe is subjected to disruption until the percent transmittance is increased by 20% when a 1:100 dilution is measured. The temperature during disruption is typically kept at 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., polypeptides, nucleic acids, carbohydrates) into the aqueous phase of the buffer in which the microbe was disrupted, and the formation of aggregates of insoluble cellular materials. The conditions for solubilization preferably result in the aggregation of polypeptides of the present invention into insoluble aggregates that are large enough to allow easy isolation by, for instance, centrifugation.

Preferably, the sarcosine is added such that the final ratio of sarcosine to gram weight of disrupted microbe is between 1.0 gram sarcosine per 4.5 grams pellet mass and 6.0 grams sarcosine per 4.5 grams pellet mass, preferably, 4.5 gram sarcosine per 4.5 grams pellet mass. The solubilization of the microbe may be measured by methods that are routine and known in the art, including, for instance, changes in optical density. Typically, the solubilization is allowed to occur for at least 24 hours, more preferably, at least 48 hours, most preferably, at least 60 hours. The temperature during disruption is typically kept low, preferably at 4° C.

The insoluble aggregates that include the polypeptides described herein may be isolated by methods that are routine and known in the art, such as centrifugation, filtration, or a combination thereof. In one embodiment, the insoluble aggregates are isolated by filtration, such as tangential or crossflow filtration. Examples of a molecular weight cutoff to use with tangential filtration are 40 kDa, 50 kDa, or 60 kDa. In one embodiment, a tangential filtration system has a molecular weight cutoff of 50 kDa. Tangential filtration may aid in removal of residual sarcosine from the protein suspension. Tangential filtration results in concentration of the protein suspension. Thus, the insoluble aggregates can be isolated at a significantly lower cost.

In one embodiment, the sarcosine is removed from the isolated polypeptides. Methods for removing sarcosine from the isolated polypeptides are known in the art, and include, for instance, diafiltration, precipitation, hydrophobic chromatography, ion-exchange chromatography, and/or affinity chromatography, and ultrafiltration and washing the polypeptides in alcohol, such as isopropyl alcohol, by diafiltration. After isolation, the polypeptides suspended in buffer and stored at low temperature, for instance, −20° C. or below.

Polypeptides of the present invention may also be isolated from *Fusobacterium* spp. using methods that are known in the art. The isolation of the polypeptides may be accomplished as described in, for instance, Hussain, et al. *Infect. Immun.*, 67, 6688-6690 (1999); Trivier, et al., *FEMS Microbiol. Lett.*, 127, 195-199 (1995); Heinrichs, et al., *J. Bacteriol.*, 181, 1436-1443 (1999).

In those aspects of the present invention where a whole cell preparation is to be made, after growth of a *Fusobacterium* spp. the microbe can be killed with the addition of an agent such as glutaraldehyde, formalin, or formaldehyde, at a concentration sufficient to inactivate the cells in the culture. For instance, formalin can be added at a concentration of 0.3% (vol:vol). After a period of time sufficient to inactivate the cells, the cells can be harvested by, for instance, diafiltration and/or centrifugation, and washed.

In other aspects, an isolated polypeptide of the invention may be prepared recombinantly. When prepared recombinantly, a polynucleotide encoding the polypeptide may be identified and cloned into an appropriate expression host. The recombinant expression host may be grown in an appropriate medium, disrupted, and the polypeptides isolated as described above.

Methods of Use

Also provided are methods of using the polypeptides described herein. The methods include administering to an animal an effective amount of a composition that includes at least one polypeptide described herein. The composition may further include a pharmaceutically acceptable carrier. As used herein, an "effective amount" of a composition of the present invention is the amount able to elicit the desired response in the recipient. The composition can be administered at a time that maternal antibody may be present, for instance, as early as one day of age, or at a later time during the life of the animal. The animal can be, for instance, an ungulate, a companion animal, or a human. Examples of ungulates include animals that are bovine (including, for instance, cattle), caprine (including, for instance, goats), ovine (including, for instance, sheep), porcine (including, for instance, swine), equine (including, for instance, horses), avian (including, for instance, turkeys and chickens), members of the family Cervidae (including, for instance, deer, elk, moose, caribou and reindeer), and Bison (including, for instance, buffalo). Examples of companion animals include dogs and cats. In one embodiment, an animal is a mouse. In one embodiment, an animal is a hooved animal. In some aspects, the methods may further include additional administrations (e.g., one or more booster administrations) of the composition to the animal to enhance or stimulate a secondary immune response. A booster can be administered at a time after the first administration, for instance, 1 to 8 weeks, preferably 2 to 4 weeks, after the first administration of the composition. Subsequent boosters can be administered one, two, three, four, or more times annually. Without intending to be limited by theory, it is expected that annual boosters will not be necessary, as an animal will be challenged in the field by exposure to members of the genus *Fusobacterium* expressing polypeptides having epitopes that are identical to or structurally related to epitopes present on the polypeptides present in the composition administered to the animal.

In one aspect, the invention is directed to methods for making antibody to a polypeptide described herein, for instance, by inducing the production of antibody in an animal, or by recombinant techniques. The antibody produced includes antibody that specifically binds at least one polypeptide present in the composition. In this aspect of the invention, an "effective amount" is an amount effective to result in the production of antibody in the animal. Methods for determining whether an animal has produced antibodies that specifically bind polypeptides present in a composition of the present invention can be determined as described herein.

As used herein, an antibody that can "specifically bind" a polypeptide is an antibody that interacts only with the epitope of the antigen that induced the synthesis of the antibody, or interacts with a structurally related epitope. An antibody that "specifically binds" to an epitope will, under the appropriate conditions, interact with the epitope even in the presence of a diversity of potential binding targets.

In one aspect the invention is also directed to treating an infection in an animal caused by a member of the genus *Fusobacterium*. The infection may be caused exclusively by *Fusobacterium* spp., or may be a mixed infection of *Fusobacterium* spp. and, for instance, *Bacteroides nodosus*. The method includes administering an effective amount of the composition to an animal having an infection caused by a member of the genus *Fusobacterium*, and determining whether the *Fusobacterium* spp. causing the infection has decreased. Methods for determining whether an infection is caused by a member of the genus *Fusobacterium* are routine and known in the art. It is expected that compositions made with polypeptides isolatable from one species of *Fusobacterium* will be useful in the methods described herein against other species of *Fusobacterium*.

In another aspect, the present invention is directed to methods for treating one or more symptoms of certain conditions in animals that may be caused by infection by a member of the genus *Fusobacterium*. Examples of conditions caused by *Fusobacterium* spp. infections include hepatic abscesses, foot rot, laminitis, purulent dermatitis, interdigital dermatitis, contagious ecthyma, necrotic rhinitis, skin ulcers, peritonsillar abscesses, septic arthritis, Lemierre's syndrome, endocarditis, metritis, and shipping fever. Treatment of these conditions can be prophylactic or, alternatively, can be initiated after the development of a condition described herein. Treatment that is prophylactic, for instance, initiated before a subject manifests symptoms of a condition caused by *Fusobacterium* spp., is referred to herein as treatment of a subject that is "at risk" of developing the condition. Typically, an animal "at risk" of developing a condition is an animal likely to be exposed to a *Fusobacterium* spp. causing the condition. For instance, the animal is present in an area where the condition has been diagnosed in at least one other animal, or is being transported to an area where a *Fusobacterium* spp. is endemic, and/or where conditions caused by *Fusobacterium* spp. are prevalent. Accordingly, administration of a composition can be performed before, during, or after the occurrence of the conditions described herein. Treatment initiated after the development of a condition may result in decreasing the severity of the symptoms of one of the conditions, including completely removing the symptoms. In this aspect of the invention, an "effective amount" is an amount effective to prevent the manifestation of symptoms of a condition, decrease the severity of the symptoms of a condition, and/or completely remove the symptoms.

The potency of a composition described herein can be tested according to standard methods. For instance, the use of mice as an experimental model for *Fusobacterium* spp. infection in humans and large animals such as cattle is well established (Conion et al, Infect. Immun, 15, 510-517 (1977), Garcia and McKay, Can. J. Comp. Med, 42, 121-127 (1978), Abe et al, Infect. Immun, 13, 1473-1478 (1976), Emery and Vaughan, Vet. Microbiol, 12, 255-268 (1986), Smith et al, Epidemiol. Infect, 110, 499-506 (1993), and Narayanan et al., Vet. Micro. 93, 335-347 (2003)). A mouse model of *Fusobacterium* infection is available, and is recognized as correlating to with abscess formation and useful for evaluating the in vivo efficacy of antimicrobial agents (Nagaoka et al., 2013, J. Med. Microbiol., 62(11):1755-1759). This model has proven to be a valuable model to evaluate the immunogenicity and identification of various target antigens provided by various fusobacteria species. Alternatively, when the condition is present in an animal such as, for instance, a sheep or cow, a controlled experimental trial can be run by vaccinating animals with varying levels of the composition and challenging vaccinated and unvaccinated animals with a *Fusobacterium* spp. Methods for determining whether an animal has the conditions disclosed herein and symptoms associated with the conditions are routine and known in the art. Symptoms often associated with hepatic abscesses can be a range of pathologies, from small foci of lymphocyte inflammation surrounded by low numbers of degenerating hepatcytes, to pronounced foci with necrosis and hemorrhage, loss of hepatocytes, fibrin and mixed inflammatory cells at the margin of the necrotic area.

A composition of the invention can be used to provide for passive immunization against infection by *Fusobacterium* spp. For instance, the composition can be administered to an animal to induce the production of immune products, such as antibodies, which can be collected from the producing animal and administered to another animal to provide passive immunity. Immune components, such as antibodies, can be collected to prepare antibody compositions from serum, plasma, blood, colostrum, etc. for passive immunization therapies. Antibody compositions including monoclonal antibodies, anti-idiotypes, and/or recombinant antibodies can also be prepared using known methods. Passive antibody compositions and fragments thereof, e.g., scFv, Fab, $F(ab')_2$ or Fv or other modified forms thereof, may be administered to a recipient in the form of serum, plasma, blood, colostrum, and the like. However, the antibodies may also be isolated from serum, plasma, blood, colostrum, and the like, using known methods and spray dried or lyophilized for later use in a concentrated or reconstituted form. Passive immunizing preparations may be particularly advantageous for treatment of acute systemic illness, or passive immunization of young animals that failed to receive adequate levels of passive immunity through maternal colostrum.

Another aspect of the present invention provides methods for detecting antibody that specifically binds polypeptides of the present invention. These methods are useful in, for instance, detecting whether an animal has antibody that specifically binds polypeptides of the present invention, and diagnosing whether an animal may have an infection caused by *Fusobacterium* spp. Preferably, such diagnostic systems are in kit form. The methods include contacting an antibody with a preparation that includes at least one polypeptide of the present invention to result in a mixture. Preferably, the antibody is present in a biological sample, more preferably blood, milk, or colostrum. The method further includes incubating the mixture under conditions to allow the antibody to specifically bind a polypeptide to form a polypeptide:antibody complex. As used herein, the term "polypeptide:antibody complex" refers to the complex that results when an antibody specifically binds to a polypeptide. The preparation that includes the polypeptides present in a composition of the present invention may also include reagents, for instance a buffer, that provide conditions appropriate for the formation of the polypeptide:antibody complex. The polypeptide:antibody complex is then detected. The detection of antibodies is known in the art and can include, for instance, immunofluorescence and peroxidase.

The methods for detecting the presence of antibodies that specifically bind to polypeptides of the present invention can be used in various formats that have been used to detect antibody, including radioimmunoassay and enzyme-linked immunosorbent assay.

The present invention also provides a kit for detecting antibody that specifically binds polypeptides of the present invention. The kit includes at least one polypeptide of the present invention in a suitable packaging material in an amount sufficient for at least one assay. Optionally, other reagents such as buffers and solutions needed to practice the invention are also included. Instructions for use of the packaged polypeptides are also typically included.

As used herein, the phrase "packaging material" refers to one or more physical structures used to house the contents of the kit. The packaging material is constructed by known methods, preferably to provide a sterile, contaminant-free environment. The packaging material has a label which indicates that the polypeptides can be used for detecting antibodies induced by infection with *Fusobacterium* spp. In addition, the packaging material contains instructions indicating how the materials within the kit are employed to detect such antibodies. As used herein, the term "package" refers to a solid matrix or material such as glass, plastic, paper, foil, and the like, capable of holding within fixed limits the polypeptides. Thus, for example, a package can be a microtiter plate well to which microgram quantities of polypeptides have been affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

ILLUSTRATIVE EMBODIMENTS

Embodiment 1. A composition comprising:
at least one isolated polypeptide having a molecular weight of 92 kDa to 79 kDa, 73 kDa to 63 kDa, 62 kDa to 58 kDa, or 57 kDa to 47 kDa, wherein the at least one polypeptide is isolatable from a *Fusobacterium necrophorum* when incubated in media comprising an iron chelator and not isolatable when grown in the media without the iron chelator,
at least one isolated polypeptide having a molecular weight of 108 kDa to 98 kDa or 79 kDa to 69 kDa, wherein the at least one polypeptide is isolatable from a *Fusobacterium necrophorum* when incubated in media comprising an iron chelator, is expressed by the *Fusobacterium necrophorum* when incubated in media without the iron chelator and expressed at an enhanced level during growth in media comprising an iron chelator, and
at least one protein selected from the group consisting of a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, and a polypeptide having at least 85% similarity to SEQ ID NO:53 or a fragment thereof, wherein the composition protects an animal against challenge with *Fusobacterium necrophorum*.

Embodiment 2. A composition comprising:
isolated polypeptides having molecular weights of 92 kDa to 79 kDa, 73 kDa to 63 kDa, 62 kDa to 58 kDa, and 57 kDa to 47 kDa, wherein the polypeptides are isolatable from a *Fusobacterium necrophorum* when incubated in media comprising an iron chelator and not isolatable when grown in the media without the iron chelator,
isolated polypeptides having molecular weights of 108 kDa to 98 kDa and 79 kDa to 69 kDa, wherein the polypeptides are isolatable from a *Fusobacterium necrophorum* when incubated in media comprising an iron chelator, are expressed by the *Fusobacterium necrophorum* when incubated in media without the iron chelator and expressed at an enhanced level during growth in media comprising an iron chelator, and
at least one protein selected from the group consisting of a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, a polypeptide having at least 85% similarity to SEQ ID NO:53 or a fragment thereof,
wherein the composition protects an animal against challenge with *Fusobacterium necrophorum*.

Embodiment 3. A composition comprising:
isolated polypeptides having molecular weights of 92 kDa to 79 kDa, 73 kDa to 63 kDa, 62 kDa to 58 kDa, and 57 kDa to 47 kDa, wherein the polypeptides are isolatable from a *Fusobacterium necrophorum* when incubated in media comprising an iron chelator and not isolatable when grown in the media without the iron chelator,
isolated polypeptide having molecular weights of 155 kDa to 145 kDa and 89 kDa to 79 kDa, wherein the at least one polypeptide is isolatable from a *Fusobacterium necrophorum* when incubated in media comprising an iron chelator and an iron-containing porphyrin and not isolatable when grown in the media without the iron chelator and iron-containing porphyrin, and not isolatable when grown in the media with the iron chelator and in the absence of the iron-containing porphyrin, and
isolated polypeptides having molecular weights of 108 kDa to 98 kDa and 79 kDa to 69 kDa, wherein the polypeptides are isolatable from a *Fusobacterium necrophorum* when incubated in media comprising an iron chelator, are expressed by the *Fusobacterium necrophorum* when incubated in media without the iron chelator and expressed at an enhanced level during growth in media comprising an iron chelator, and
wherein the composition protects an animal against challenge with *Fusobacterium necrophorum*.

Embodiment 4. A composition comprising:
at least one isolated polypeptide having a molecular weight of 131 kDa to 121 kDa, 79 kDa to 69 kDa, or 33 kDa to 23 kDa, wherein the at least one polypeptide is isolatable from a *Fusobacterium necrophorum* when incubated in media comprising a copper chelator and not isolatable when grown in the media without the copper chelator, and
at least one isolated polypeptide having a molecular weight of 93 kDa to 83 kDa, 65 kDa to 55 kDa, or 52 kDa to 42 kDa, wherein the at least one polypeptide is isolatable from the *Fusobacterium necrophorum* when incubated in media comprising a copper chelator, is expressed by the *Fusobacterium necrophorum* when incubated in media without the copper chelator and expressed at an enhanced level during growth in media comprising an copper chelator, wherein the composition protects an animal against challenge with *Fusobacterium necrophorum*.

Embodiment 5. A composition comprising:

at least one isolated polypeptide having a molecular weight of 131 kDa to 121 kDa, 108 kDa to 98 kDa, 92 kDa to 64 kDa, 53 kDa to 43 kDa, or 33 kDa to 19 kDa, wherein the polypeptide is isolatable from a *Fusobacterium necrophorum* when incubated in media comprising a zinc chelator and not isolatable when grown in the media without the zinc chelator, at least one isolated polypeptide having a molecular weight of 79 kDa to 69 kDa or 65 kDa to 55 kDa, wherein the at least one polypeptide is isolatable from the *Fusobacterium necrophorum* when incubated in media comprising a zinc chelator, is expressed by the *Fusobacterium necrophorum* when incubated in media without the zinc chelator and expressed at an enhanced level during growth in media comprising the zinc chelator, wherein the composition protects an animal against challenge with *Fusobacterium necrophorum*.

Embodiment 6. A composition comprising:

isolated polypeptides having molecular weights of 131 kDa to 121 kDa, 79 kDa to 69 kDa, and 33 kDa to 23 kDa, wherein the polypeptides are isolatable from a *Fusobacterium necrophorum* when incubated in media comprising a copper chelator and not isolatable when grown in the media without the copper chelator, and isolated polypeptides having molecular weights of 93 kDa to 83 kDa, 65 kDa to 55 kDa, and 52 kDa to 42 kDa, wherein the polypeptides are isolatable from the *Fusobacterium necrophorum* when incubated in media comprising a copper chelator, are expressed by the *Fusobacterium necrophorum* when incubated in media without the copper chelator and expressed at an enhanced level during growth in media comprising an copper chelator, wherein the composition protects an animal against challenge with *Fusobacterium necrophorum*.

Embodiment 7. A composition comprising:

isolated polypeptides having molecular weights of 131 kDa to 121 kDa, 108 kDa to 98 kDa, 92 kDa to 64 kDa, 53 kDa to 43 kDa, and 33 kDa to 19 kDa, wherein the polypeptides are isolatable from a *Fusobacterium necrophorum* when incubated in media comprising a zinc chelator and not isolatable when grown in the media without the zinc chelator, and isolated polypeptides having molecular weights of 79 kDa to 69 kDa and 65 kDa to 55 kDa, wherein the polypeptides are isolatable from the *Fusobacterium necrophorum* when incubated in media comprising a zinc chelator, are expressed by the *Fusobacterium necrophorum* when incubated in media without the zinc chelator and expressed at an enhanced level during growth in media comprising the zinc chelator, wherein the composition protects an animal against challenge with *Fusobacterium necrophorum*.

Embodiment 8. The composition of any one of embodiments 1-7 further comprising:

a polypeptide having at least 85% similarity to SEQ ID NO:4 or a fragment thereof, a polypeptide having at least 85% similarity to SEQ ID NO:2 or a fragment thereof, a polypeptide having at least 85% similarity to SEQ ID NO:6 or a fragment thereof, a polypeptide having at least 85% similarity to SEQ ID NO:34 or a fragment thereof, a polypeptide having at least 85% similarity to SEQ ID NO:53 or a fragment thereof, or a combination thereof, wherein the composition protects an animal against challenge with *Fusobacterium necrophorum*.

Embodiment 9. A composition comprising:

an isolated polypeptide having at least 85% similarity to SEQ ID NO:2, 4, 6, 8, 10, 12, 14, 16, 18, 20, 22, 24, 26, 28, 30, 32, 34, 35, 36, 37, 38, 39, 40, 41, 43, 44, 45, 46, 47, 48, 49, 50, 51, 52, 53, or 54, or a fragment thereof, wherein the composition protects an animal against challenge with *Fusobacterium necrophorum*.

Embodiment 10. The composition of any one of embodiments 1-9 further comprising:

isolated polypeptides having molecular weights of 340 kDa to 330 kDa, 247 kDa to 237 kDa, 247 kDa to 237 kDa, 235 kDa to 215 kDa, 120 kDa to 110 kDa, 51 kDa to 25 kDa, and 21 kDa to 11 kDa, wherein the polypeptides are isolatable from a *Fusobacterium necrophorum*.

Embodiment 11. The composition of any one of embodiments 1-10 further comprising a pharmaceutically acceptable carrier.

Embodiment 12. The composition of any one of embodiments 1-11 further comprising an adjuvant.

Embodiment 13. A method comprising:

administering to a subject an amount of the composition of any one of embodiments 1-12 effective to induce the subject to produce antibody that specifically binds to at least one polypeptide of the composition.

Embodiment 14. A method for treating an infection in a subject, the method comprising:

administering an effective amount of the composition of any one of embodiments 1-12 to a subject having or at risk of having an infection caused by a *Fusobacterium* spp.

Embodiment 15. A method for treating a symptom in a subject, the method comprising:

administering an effective amount of the composition of any one of embodiments 1-12 to a subject having or at risk of having an infection caused by a *Fusobacterium* spp.

Embodiment 16. A method for decreasing colonization in a subject, the method comprising:

administering an effective amount of the composition of any one of embodiments 1-12 to a subject colonized by or at risk of being colonized by a *Fusobacterium* spp.

Embodiment 17. A method for treating an infection in a subject, the method comprising:

administering an effective amount of a composition to a subject having or at risk of having an infection caused by a *Fusobacterium* spp., wherein the composition comprises antibody that specifically binds to a polypeptide of the composition of any one of embodiments 1-12.

Embodiment 18. A method for treating a symptom in a subject comprising:

administering an effective amount of a composition to a subject having or at risk of having an infection caused by a *Fusobacterium* spp., wherein the composition comprises antibody that specifically binds to a polypeptide of the composition of any one of embodiments 1-12.

Embodiment 19. A method for decreasing colonization in a subject, the method comprising:

administering an effective amount of a composition to a subject colonized by a *Fusobacterium* spp., wherein the composition comprises antibody that specifically binds to a polypeptide of the composition of embodiment any one of embodiments 1-12.

Embodiment 20. The method of any one of embodiments 13-19 wherein the subject is a mammal.

Embodiment 21. The method of any one of embodiments 13-20 wherein the mammal is a human, a bovine, or an ovine.

Embodiment 22. The method of any one of embodiments 13-21 wherein the *Fusobacterium* spp. is *F. necrophorum*.

Embodiment 23. The method of any one of embodiments 13-22 wherein at least 10 micrograms (µg) and no greater than 2000 µg of polypeptide is administered.

Embodiment 24. The method of any one of embodiments 13-23 wherein the infection causes a condition selected from metritis, hepatic abscesses, and foot rot.

Embodiment 25. A kit for detecting antibody that specifically binds a polypeptide, comprising in separate containers:
an isolated polypeptide of the composition of any one of embodiments 1-12; and
a reagent that detects an antibody that specifically binds the polypeptide.

Embodiment 26. A kit for detecting a polypeptide, comprising in separate containers:
an antibody that specifically binds an isolated polypeptide of the composition of any one of embodiments 1-12; and
a second reagent that specifically binds the polypeptide.

Embodiment 27. A composition comprising:
isolated antibody that specifically binds to a polypeptide of the composition of any one of embodiments 1-12.

Embodiment 28. A composition comprising:
an isolated whole cell that comprises a polypeptide of the composition of any one of embodiments 1-12.

Embodiment 29. The composition of embodiment 28 wherein the isolated whole cell comprises the polypeptides of the composition of any one of embodiments 1-12.

Embodiment 30. A composition comprising:
isolated antibody that specifically binds to a whole cell of any one of embodiments 28-29.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

The present invention is illustrated by the following examples. It is to be understood that the particular examples, materials, amounts, and procedures are to be interpreted broadly in accordance with the scope and spirit of the invention as set forth herein.

In the following studies we examined the expression of proteins of *Fusobacterium necrophorum* subsp. *necrophorum* under various conditions of metal ion restriction in order to mimic the expression of novel proteins that may be expressed during systemic invasion and colonization of the liver.

Example 1

Selection of *Fusobacterium necrophorum* Isolates

More than a dozen clinical isolates of *Fusobacterium necrophorum* were isolated from infected livers of beef cattle obtained from multiple processing plants. To preserve the original isolates a master seed stock of each isolate was prepared under anaerobic conditions. Briefly, single colonies were selected off blood agar plates grown under anaerobic conditions at 37° C. for approximately 48 hours. Colonies were transferred to 10 mL modified Trypticase Soy Broth (mTSB) (Becton Dickenson and Company, Franklin Lakes, NJ) containing 0.05% cysteine HCL and 5 g/L yeast extract. A frozen master seed of each isolate was prepared by inoculating the isolate into 10 ml mTSB. The cultures were incubated anaerobically for 16 hours at 37° C. Five ml of each culture was transferred into 100 ml bottles of mTSB with either 15 μg/ml 2,2'-dipyridyl (DP) (Sigma Chemicals, St Louis, MO) or 20 μg/mL $FeCl_3$ (Sigma) and allowed to grow anaerobically for 6 hours at 37° C. Fifty ml of the resulting cultures was combined with 50 ml of fresh mTSB containing 15 ug/ml DP and 20% glycerol, and the bacterial suspensions were sterilely dispensed into 2 ml cryogenic vials (1.5 ml per vial) and stored at −80° C. until use. Master seed stocks of each isolate were expanded into a working seeds. Briefly, one vial of the previously prepared master seed was grown as previously described, sterilely dispensed into 1.5 ml per vials and stored at −80° C. until use.

One isolate was selected based on its ability to grow well in metal ion chelators and showed good outer membrane protein expression. The isolate selected as the Master for the production of the Fuso-SRP Extract was designated as Master Seed 1694.

Example 2

Test for Novel Protein Expression

To test for novel protein expression under conditions of iron, zinc and copper chelation, frozen working seeds of *Fusobacterium necrophorum* as described above were transferred into 100 ml deplete modified Tryptic Soy Broth (TSB) containing 0.05% cysteine HCL and 5 g/L yeast extract and one of four metal ion chelators, 2,2'-dipyridyl (Dp), 2-pyridylmethyl-ethylene diamine (TPEN), catechin, and naringenin (all obtained from Sigma, St. Louis, Mo.). The metal ion chelators were used at the following concentration; 50 μM N,N,N',N'-tetrakis(2-pyridylmethyl)ethylenediamine (TPEN); 50 and 100 μM quercetin; 100 μM catechin; or 100 μM Naringenin respectively. Cultures were grown with each chelator for 12 hours, at which point the culture was subcultured a second time for an additional 12 hours. Each culture was subcultured for five consecutive passes at 12-hour intervals. At the end of the fifth pass, each culture was harvested by centrifugation at 10,000×g for 20 minutes. Each culture was washed twice by centrifugation at 10,000×g and resuspended in 20 ml Tris-buffered saline, pH 7.2 at 4° C.

The bacterial cell suspensions were disrupted by sonication for 1.5 minutes at 4° C. using a Branson 450 equipped with a half inch disruption horn (Branson, Danbury Conn.). The disrupted bacterial suspensions were clarified by centrifugation at 32,000×g for 12 minutes. The supernatants were collected and solubilized by the addition of sodium lauroyl sarcosinate (4% vol/vol) at 4° C. for 24 hours. The detergent-insoluble protein-enriched fractions were collected by centrifugation at 32,000×g for 2.5 hours at 4° C. The protein pellets were resuspended in 200 μl Tris-buffer (pH 7.2) and stored at −90° C.

Cell extracts, derived from each metal chelation, were size-fractionated on SDS-PAGE gels using a 4% stacking gel and 10% resolving gel. Samples for electrophoresis were prepared by combining 30 μg of sample with 30 μl of SDS reducing sample buffer (62.5 mM Tris-HCL pH 6.8, 20% glycerol, 2% SDS, 5% beta-mercaptoethanol) boiled for 4 minutes. A sample of each extract was resolved on a 10% SDS-PAGE gel per standard methods and visualized by Coomassie Blue staining.

The SDS-PAGE patterns of *Fusobacterium necrophorum* 1694 grown under iron, zinc, and/or copper chelation showed unique banding patterns that were different when compared to the same isolate when grown under iron-restriction in the presence of 2,2'-dipyridyl. For example, when the *Fusobacterium necrophorum* 1694 isolate was grown under iron-restriction or in the presence of the chelator 2,2'-dipyridyl, unique iron-regulated proteins were expressed at the 88, 84, 68, 60, and 52 kDa regions (Table 1). These proteins were not detected when the isolate was grown in the presence of ferric chloride. Growth of *Fusobacterium necrophorum* 1694 in iron restriction also resulted in the increased expression of proteins having molecular weights of 103 and 74 kDa (Table 1). These proteins were detected when the isolate was grown in the presence of ferric chloride, but expressed at higher levels during growth under iron restriction.

When *Fusobacterium necrophorum* 1694 isolate was grown under copper-restriction, unique copper-regulated proteins were expressed at the 126, 74, and 28 kDa regions (Table 1). These proteins were not detected when the isolate was grown in the presence of free copper. Growth of *Fusobacterium necrophorum* 1694 in copper restriction also resulted in the increased expression of proteins having molecular weights of 88, 60, and 48 kDa (Table 1). These proteins were detected when the isolate was grown in the presence of free copper, but expressed at higher levels during growth under copper restriction.

When *Fusobacterium necrophorum* 1694 isolate was grown under zinc-restriction, unique zinc-regulated proteins were expressed at the 126, 103, 88, 81, 68, 48, 28, and 24 kDa regions (Table 1). These proteins were not detected when the isolate was grown in the presence of free zinc. Growth of *Fusobacterium necrophorum* 1694 in zinc restriction also resulted in the increased expression of proteins having molecular weights of 73 and 60 kDa (Table 1). These proteins were detected when the isolate was grown in the presence of free zinc, but expressed at higher levels during growth under zinc restriction.

We show for the first time a novel subset of proteins expressed by *Fusobacterium necrophorum* when the organism is grown under Iron, copper and zinc-restriction that are not expressed when the same isolate is grown under non-restricted conditions. Since transitional metals are used by organisms to build enzymes that catalyze various biochemical reactions, the metal ions may play a vital role in microbial survival during a systemic infection and/or the tissues they infect. It is perhaps for this reason that during sepsis there is a transient decrease in the availability of these transitional metals, making them unavailable for growth of the organism. These novel proteins could very well enhance the protective efficacy of the existing composition grown under iron-restriction because they may also be expressed by the bacteria under the metal ion restriction.

Example 3

Analysis of Proteins

The electrophoretic banding profiles of the proteins isolated from the *Fusobacterium necrophorum* isolate grown in the following five conditions as described above were compared: iron-deplete media (400 ml mTSB containing 15 μg 2,2-dipyridyl), and controlled fermentation conditions (the iron-deplete fermentation conditions of Example 4); mTSB containing 100 μM naringenin; mTSB containing 100 μM catechin; mTSB containing 50 or 100 μM Quercetin; and mTSB containing 100 μM of N,N,N,N Tetrakis. The results revealed different banding profiles between each sample grown under different metal-depleting conditions.

In the presence of catechin (Quinde-Axtell et al., 2006, J. Agric. Food Chem., 54(26):9978-9984), a unique protein of ~60 kDa by SDS-PAGE was visibly upregulated that was not enhanced in the presence of the other flavonoids and chelators (FIG. 2; Lane 3A). This protein was further shown to be immuno-reactive in a western blot against convalescent sera of a calf exposed to experimental challenge of Example 7 with *Fusobacterium necrophorum* (FIG. 2; Lane 2B).

In the presence of Quercetin (copper restriction) a protein of ~48 kDa by SDS-PAGE, was shown to be preferentially upregulated, as compared to the other flavonoids and chelators (FIG. 1; Lane 6). This protein was also shown to be immuno-reactive when exposed to the convalescent serum above (FIG. 3; Lane 2). The band from FIG. 1; Lane 6 was identified via matrix assisted laser desorption/ionization time-of-flight spectrometry (MALDI-TOF). The closest match found via Scaffold is the outer membrane protein of *Fusobacterium necrophorum* strain DAB KDE68083. The function of this protein is unknown. The identified protein sequence was used to search the nucleotide sequence of *F. necrophorum* 1694. The nucleotide sequence and amino acid sequence identified is shown in FIG. 14 (SEQ ID NOs: 1 and 2, respectively).

A protein of ~81 kDa by SDS-PAGE was shown to be upregulated in the presence of N,N,N,N tetrakis, a mostly zinc chelator (FIG. 1; Lane 7 and FIG. 4 Lane A3). This protein was shown to be immuno-reactive in a western blot against convalescent sera from an experimentally challenged calf of Example 7 as illustrated in FIG. 4; Lane B2. The closest match found via Scaffold was an outer membrane protein of *Fusobacterium necrophorum*. The function of this protein is listed as TonB-dependent receptor. The identified protein sequence was used to search the nucleotide sequence of *F. necrophorum* 1694. The nucleotide sequence and amino acid sequence identified is shown in FIG. 15 (SEQ ID NOs: 3 and 4, respectively).

Example 4

Production of Metal Regulated Proteins

Fermentation

A cryogenic vial of the working seed of *Fusobacterium necrophorum* 1694 (1 ml at $10^9$ CFU/ml) was used to inoculate 250 ml of 37° C. modified TSB (mTSB) containing 5 g/L yeast extract and 0.05% cysteine (Sigma) and incubated in an anaerobic chamber. The culture was incubated at 37° C. for 20 hours at which point was sterilely transferred into 1.25 liters of the above media plus 25 micrograms (μg) 2,2-dipyridyl. This second culture was allowed to grow for an additional 3 hours at 37° C. This culture was used to inoculate a 15-liter Bioflo IV bench-top fermentor, (New Brunswick Scientific Co, Edison NJ) charged with 9.5 liters of the above-described media. The pH was held constant between 6.9 and 7.1 by automatic titration with 50% NaOH and 20% $H_3PO_4$. The stirring speed was adjusted to 250 revolutions per minute (rpm), and the culture purged with pure nitrogen to maintain an anaerobic condition. The culture was allowed to grow continuously at these conditions for 24 hours at which point the fermentation was terminated by raising the pH to 8.5.

Harvest

The bacterial cells were concentrated by centrifugation (Beckman Coultier, Brea, CA) at 7,000 rpm for 20 minutes. The bacterial pellet was then resuspended at a ratio of 60 g cell pellet to 1 liter sterile Osmotic Shock Buffer (OMS) containing 7.26 grams/liter Tris-base and 0.93 grams/liter EDTA adjusted to a pH of 8.5. The cell suspension was then incubated at 2-8° C. for 24 hours to remove excess endotoxin from the cells. The resulting suspension was then centrifuged again and the supernate discarded to remove free endotoxin and any extracellular material, e.g., secreted proteins. The cell pellet was resuspended in 3 liters of OMS. The cell suspension was mixed thoroughly and dispensed into a sterile four liter Nalgene containers and placed into a −20° C. freezer for storage. The pellet mass was calculated by centrifuging 30 ml samples of the fermented culture and final harvest. Briefly, pre-weighted 50 ml Nalgene conical tubes were centrifuged at 39,000×g for 90 minutes in a Beckman J2-21 centrifuge using a JA-21 rotor (Beckman Coulter, Brea, CA). At the end of the run, the supernate was poured off and the tubes were weighed again. The pellet mass was calculated for each stage.

Disruption (Homogenization)

One liter of the harvested three liter frozen bacterial cell slurry in OMS was thawed at 4° C. (60 gram pellet mass). The liquid culture suspension was disrupted by homogenization. Briefly, the tank containing the bacterial suspension was connected to a model Emulsiflex C500B Homogenizer, (Avisten Inc, Ottowa, Canada). A second process tank (empty) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of each pass, fluid was circulated at 40-65 psi through the homogenizer and back to the tank of origin, while the homogenizer pressure was adjusted to ≥20,000 psi. Prior to the first pass, two pre-homogenizing samples were withdrawn from the homogenizer to establish a baseline for determining the degree of disruption and monitoring of pH. The degree of disruption was monitored by transmittance (% T at 540 nanometers (nm) at 1:100 dilution) compared to the non-homogenized sample. The bacterial suspension was passed three times through the homogenizer to give a final percent transmittance >80% T at a 1:100 dilution.

After homogenization, Sodium Lauroyl Sarcosinate (Hamptosyl L-30, Chem/Serv, Minneapolis, MN) was aseptically added to the homogenized bacterial suspension for solubilization. The amount of Sarcosine (30%) added equaled 0.5% of the solubilizing volume, in liters. The process tank was removed from the homogenizer and kept at 4° C. while shaking at 120 rpm for 16-24 hours.

Protein Harvest and Diafiltration

The protein suspension (1 Liter) was adjusted to 5 liters using sterile Tris-buffer, pH 8.5. The suspension was washed and dialyzed using a Optisep 1000 SmartFlow Tangential Flow Filter device (NCSRT Inc, Apex, NC), equipped with a 0.8 ft² screen-channel series Alpha 50 kDa Centrasette filter (Pall Filtron) to remove residual sarcosine. The protein solution was concentrated by filtration to a target volume of 1 liter at which point 10 liters of Tris-buffer pH 7.2 containing 10% isopropyl alcohol was slowly added to the concentrate from a second process tank. Isopropyl alcohol is thought to cause a slight unfolding of the protein structure allowing for the removal of bound sarcosine without compromising the immunogenicity of the proteins. Diafiltration continued until the pH stabilized to 7.2 at which point 5 liters Tris-buffer pH 7.2 was slowly added by diafiltration to remove residual alcohol. The Fuso-SRP Extract suspension was then concentrated to approximately 325 ml. The protein concentrate was stored at −20° C. until use.

Alternative methods for bacterial harvest can be used. Bacterial harvest may be performed by the use of hollow fiber filter methods. Bacterial culture is harvested using filter cartridges ranging in size from 0.2 µM to 5 kDa; preferably with a 750 kDa cartridge. Culture is reduced in volume from 2-20× and subsequently washed 1-5× by diafiltration with buffer prior to storage at 4° C. or freezing at −20° C. In this manner, undesired media proteins, bacterial proteins and LPS are removed from the culture. In another alternative, bacterial harvest may be performed by the use of industrial scale centrifugation, for example, by use of a disc-stack centrifuge.

Example 5

*Fusobacterium* Recombinant Zinc Protein (rZinc) Construction

The full nucleotide sequence of the rZinc protein, including signal peptide, was submitted to GenScript USA Inc. (Piscataway, NJ) for gene synthesis. The amino acid sequence was optimized for expression in *Escherichia coli*. Synthesized DNA was cloned in to plasmid pET-20b+ (Novagen) by GenScript using the NdeI-XhoI cloning sites allowing for a C-terminal 6×Histidine tag. The resulting plasmid is named rZinc_pET-20b+.

Plasmid pTHV (Epitopix, LLC) was amplified using primers 3 and 4 (Table 2) to exclude the existing gene insert and only amplify the plasmid backbone. Fragment rZinc, excluding the signal peptide, was amplified from plasmid FT_pET-20b+ using oligonucleotide primers 1 and 2 (Table 2). The primers include nucleotides that overlap with the destination plasmid, pTHV. The vector and fragment PCR products were assembled using the NEBuilder® HiFi DNA assembly protocol (New England Biolabs) and transformed into NEB 10-beta competent *E. coli* for expression.

TABLE 2

Fusobacterium rZinc Oligonucleotide Primers

| Primer No. | Name | Sequence (5'-3') |
|---|---|---|
| 1 | FT.Fragment. FOR | TCAATTTGCTAGGGGATCTG CCGAAATCGATCTGGGCAC |
| 2 | FT.Fragment. REV | CCATGGCTAGCTAGCTAGTG GTGGTGGTGGTGGTGC |
| 3 | pTHV.Vector. FOR | TAGCTAGCTAGCCATGGCAT CAC |
| 4 | pTHV.Vector. REV | AGATCCCCTAGCAAATTGAA GAGAAAGATCT |

Example 6

*Fusobacterium* Recombinant Hemin Protein (rHemin) Construction

The full nucleotide sequence of the rHemin protein, including signal peptide, was submitted to GenScript USA Inc. (Piscataway, NJ) for gene synthesis. The amino acid sequence was optimized for expression in *Escherichia coli*. Synthesized DNA was cloned in to plasmid pET-20b+ (Novagen) by GenScript using the NdeI-XhoI cloning sites allowing for a C-terminal 6×Histidine tag. The resulting plasmid is named rHemin_pET-20b+.

Plasmid pTHV (Epitopix, LLC) was amplified using primers 7 and 8 (Table 3) to exclude the existing gene insert and only amplify the plasmid backbone. Fragment rHemin, excluding the signal peptide, was amplified from plasmid rHemin_pET-20b+ using oligonucleotide primers 5 and 6 (Table 3). The primers include nucleotides that overlap with the destination plasmid, pTHV. The vector and fragment PCR products were assembled using the NEBuilder® HiFi DNA assembly protocol (New England Biolabs) and transformed into NEB 10-beta competent *E. coli* for expression.

TABLE 3

Fusobacterium rHemin Oligonucleotide Primers

| Primer No. | Name | Sequence (5'-3') |
|---|---|---|
| 5 | FH.Fragment.FOR | TACTGTTATAGATCTTTCTAACAAACGATTGAACTGGGG |
| 6 | FH.Fragment.REV | TCCCTGCCTCTGTCACTTCCTTTCGGGCTTTGTTAG |
| 7 | pTHV.201601.FOR | TGACAGAGGCAGGGAGTG |
| 8 | pTHV.201601.REV | AGAAAGATCTATAACAGTAGCCATATTTAAAC |

Example 7

Preparation of Convalescent Sera in Holstein Calves

Convalescent serum was collected as part of a vaccination and challenge study in which steers with an average weight of approximately 350 pounds were used for generation of sera. Calf number 72 was an unvaccinated control animal challenged via the portal vein according to the method of K. Lechtenberg et al (Am J Vet Res. 1991 June; 52(6) 803-9) with approximately $6\times10^8$ cfu of a virulent *Fusobacterium necrophorum* strain.

Example 8

Blood Sample Collection

Blood samples were collected from all steers on day 66 (10 days post-challenge). All blood was collected in sterile 13×75 millimeter vacutainer collection tubes (SST No. 369783, Becton Dickinson, Franklin Lakes, NJ). After clotting the blood tubes were centrifuged at 800×g for thirty minutes and frozen at −20° C.

Example 9

Identification of Sero-Reactive Membrane Proteins of *Fusobacterium necrophorum* Using Western Blot Analysis The proteins in the vaccine composition as described in Example 2 were subjected to electrophoresis followed by western blot analysis with convalescent serum as described in Example 7. Briefly, the membrane proteins derived from *Fusobacterium necrophorum* grown under iron-limiting conditions were size-fractionated on an SDS-PAGE gel using a 4% stacking gel and 7.5% resolving gel. A 10 μl sample was combined with 10 μl of SDS reducing sample buffer (62.5 mM Tris-HCL ph 6.8, 20% glycerol, 2% SDS, 5% β-mercaptoethanol) and boiled for 4 minutes. Samples were electrophoresed at 18 mA constant current for 5 hour at 4° C. using a Protein II xi cell and model 1000/500 power supply (BioRad Laboratories, Richmond, CA). Band migration was visualized using broad range kaleidoscope standards (BioRad) to aid in the electro-blot transfer while biotinylated broad range standards were used as molecular weight references on the blot, see FIG. 7. For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BioRad Trans-Blot transfer cell and a Pac 300 power supply (BioRad). The nitrocellulose membrane was blocked using 3% fish gelatin (Sigma Chemical, St. Louis, Mo) in Tris buffered saline (TBS-20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the polyclonal convalescent sera collected from the challenged steer as described in example 7. The primary antibody was diluted 1/500 in TBS containing 1% fish gelatin, 0.05% Tween 20 and 0.2% sodium azide (Antibody Buffer). The membrane was incubated with the primary antibody solution overnight on a shaker at room temperature. The membrane was then washed two times in TBS containing 0.05% Tween 20 (TTBS) and transferred to antibody buffer containing a 1/10,000 dilution of Alkaline phosphatase-conjugated mouse anti-bovine IgG clone BG-18 (Sigma) and a 1/3000 dilution of avidin conjugated to alkaline phosphatase (BioRad). The membrane was incubated at 37° C. for 2 hours on a shaker, then washed in TTBS four times to remove unbound conjugate. The blot was resolved in substrate solution containing alkaline phosphate color reagent A and B in 1×AP color development Buffer (BioRad) for 30 min. at 37° C. on a shaker. The resulting Western immunoblot was documented using a BioRad GS-800 Densitometer (see FIGS. 2-4, 7 and 8).

The purpose of this analysis was to determine which of the proteins present in the immunizing composition induced antibody responses following challenge of steers. The results revealed unique immunological reactivity with proteins at 48 kDa in the presence of the copper chelator Quercetin, catechin, or naringenin (FIGS. 2, 3 and 4); at ~60 kDa in the presence of the copper chelator catechin (FIG. 2); and an ~82 kDa protein in the presence of the zinc chelator Tetrakis (TPEN) (FIG. 4); and an ~90 kDa protein in the presence of quercetin. In addition, the results revealed unique immunological reactivity proteins at 131 kDa, 85 kDa, 60 kDa, and in the area of 40-43 kDa in the presence of the copper chelator Quercetin; at 107 kDa, 75 kDa, 60 kDa, and in the area of 40-43 kDa in the presence of the copper chelator catechin; at 73 kDa and in the area of 40-43 kDa in the presence of the copper chelator naringenin; and at 82 kDa, 75 kDa, 73 kDa, 60 kDa, 48 kDa, and in the area of 40-43 kDa in the presence of the zinc chelator Tetrakis (TPEN). The molecular weights of the immunologically reactive proteins are not identical with the molecular weights of the metal regulated proteins described herein identified by SDS-PAGE; however, the molecular weights of the immunologically reactive were determined using the results of western immunoblot assays, and the skilled person will recognize that the ability to accurately determine molecular weights from a western immunoblot is reduced.

These results demonstrated that the membrane proteins of the composition described in Example 2 reacted strongly with the convalescent sera described in Example 7, suggesting that these components of the vaccine may provide protection against disease. However, the sensitivity limits of the assay may have prevented the detection of weaker interactions, that, although less evident, may still contribute to the vaccine's effectiveness by augmenting the immune response to the composition. In addition, the proteins that were not sero-reactive in this assay may elicit responses other than antibody production, such as stimulation of cytokines, interferon, interleukins, T-cells, or colony-stimulating factors. Such responses could enhance, direct, or restore the ability of the host's immune system to fight disease.

Example 10

Preparation of the Immunizing Compositions Derived from *Fusobacterium necrophorum*

The composition made from *Fusobacterium necrophorum* strain 1694 of Example 4 was used as the vaccine in this experimental study. The vaccine was prepared from the composition by diluting the antigen into phosphate buffered saline (PBS) containing 8.0 g/l NaCl, 0.2 g/l KCl, 1.44 g/l $Na_2HPO_4$ and 0.24 g/l $KH_2PO_4$ pH 7.4 The suspension (500 µg total protein/ml) was then emulsified into the commercial adjuvant, EMULSIGEN, (MVP Laboratories, Ralston, Nebraska) using the syringe method of emulsification. The process can be summarized as follows: (1) force an amount of adjuvant from syringe B by pushing it into syringe A filled with antigen solution to mingle with the latter; (2) push the same volume of the mix from syringe A back to syringe B slowly; (3) repeat the above mixing process until the mixed portion becomes milky white. A mouse dose was administered to give a final dose of 100 µg total protein in a 0.1 ml injectable volume with an adjuvant concentration of 22.5% vol/vol. A placebo was prepared by replacing the antigen with physiological saline in the above formulation and emulsifying the suspension into EMULSIGEN to give an adjuvant concentration of 22.5%.

Example 11

Mouse Vaccination

The efficacy of the Fuso-SRP Extract derived from *Fusobacterium necrophorum* 1694 was carried out against a live virulent challenge in mice. Eighty (N=80) female CF-1 mice obtained from Charles River Laboratories (Wilmington DE) weighing 16-22 grams were equally distributed into two groups (40 mice/group). Mice were housed in polycarbonate cages in a self-contained HEPA filtered Mobile Housing System (Thoren Caging systems; Hazleton; PA). Treatment groups were designated as Group-A (Placebo) and Group-B (Fuso-SRP Extract Vaccinated). Food and water was supplied ad libitum to all mice. Mice were vaccinated subcutaneously twice at 21 day intervals. The volume administered was 0.1 ml/mouse see Table 4.

TABLE 4

Experimental Design

| Groups | Mice | Vaccine | Total Antigen | Adjuvant | Vaccine Volume (ml) | # Vaccines | Vaccine Route |
|---|---|---|---|---|---|---|---|
| A | 40 | Placebo | N/A | 22.5% Emulsigen | 0.1 | 2 | SQ |
| B | 40 | Fuso-SRP Extract | 100 µg | 22.5% Emulsigen | 0.1 | 2 | SQ |

Example 12

Preparation of Challenge Organism

Twenty eight days after the second vaccination, mice in groups A and B were intravenously challenged. The *Fusobacterium necrophorum* isolate 1694 as previously described in Example 1 was used as the challenge strain. Briefly, a cryogenic vial of the frozen working seed of *Fusobacterium necrophorum* 1694 of Example 1 was used for challenge. Briefly, the frozen stock was thawed at 4° C. then diluted 1:10 in cold mTSB and the resulting dilution was used for challenge. All mice in groups A and B were intravenously challenged via the caudal vein with 0.1 ml of *Fusobacterium necrophorum* (~$1\times10^8$ colony forming units per ml) as previously enumerated as described in Example 7 Just prior to challenge, 100 µl of the above bacterial suspension was serially diluted tenfold to enumerate the number of CFU/dose. Mortality was recorded daily for 10 days post challenge at which point the experimental trial was terminated. All surviving mice from Groups A- and B were euthanized by carbon dioxide. The liver from all dead and surviving mice was aseptically removed and gross examination was performed to determine differences in liver abscessation.

Example 13

Challenge Results

The results showed a strong protective index against a caudal vein challenge as seen in Table 5. Ten out of 40 (25%) of the placebo-vaccinated mice (Group A) died within 10 days after challenge. In contrast, no mortality (0 out of 40) was seen in the vaccinated mice of Group B (degree of significance of P=0.001).

TABLE 5

Comparison of Mortality; Liver Abscess and Percent Survivability between Vaccinated and Placebo Controls Following Intravenous Challenge with *Fusobacterium necrophorum*

| Groups | Mice | [a]Mortality (%) | [b]Liver Lesions (%) | [c]Percent Survivability |
|---|---|---|---|---|
| A) Placebo | 40 | 10 (25) | 9 (22.5) | 75 |
| B) Fuso-SRP Extract | 40 | 0 | 1 (2.5) | 100 |

[a]The mortality of mice that died within 10 days after IV challenge with $3.0 \times 10^8$ CFU of *Fusobacterium necrophorum*.
[b]The percent of mice that had visible liver abscess upon death or at 10 days post challenge (two-sided P value) was P = 0.0143.
[c]Percent Survivability; 100 percent of the vaccinated mice survived challenge compared to the non-vaccinated controls where only 75 percent survived (two-sided P value) was P = 0.0010.

Gross examination of each liver revealed a dramatic difference in the number of abscesses between the Placebo and Vaccinated mice. It was clearly evident that mice given the vaccine rapidly reduced the number of bacteria able to proliferate successfully in the liver as indicated by the reduction in visible abscesses as compared to the placebo vaccinated mice (Table 5). The difference in the number of abscessed livers of Placebo vaccinated controls and the vaccinated group was statistically significant (degree of significance of P=0.0143), indicating a direct correlation in the reduction of lesions through vaccination by preventing the proliferation and colonization of *Fusobacterium necrophorum* in the liver The number of mice with abscesses was 9 out of 40 (22.5%) in the placebo vaccinated group as compared to only 1 out of 40 (2.5%) in the vaccinated group (Table 5).

The Fuso-SRP Extract vaccine of Group B showed a high degree of systemic protection as compared to non-vaccinated mice of Group A; (Placebo vaccinated). The vaccine prepared from *Fusobacterium necrophorum* was highly efficacious in preventing mortality associated with an intravenous challenge with *Fusobacterium necrophorum* in a standardized mouse model as well as reducing the formation of liver abscesses.

Example 14

Vaccine-Mediated Protection of Novel Recombinant Zinc and Hemin Proteins of *Fusobacterium necrophorum* in a Mouse Sepsis Model The purpose of the following experimental study was to evaluate the vaccine efficacy of two recombinant proteins, rZinc and rHemin of *Fusobacterium necrophorum*. In addition, a vaccine formulation consisting of the rZinc protein in combination with the Fuso-SRP extract and the Fuso-SRP extract as a stand-alone vaccine formulation was evaluated as illustrated in Table 6. The bovine strain of *Fusobacterium necrophorum* 1694 was used as the challenge strain as previously described in Example 1. The outcome parameters used to evaluate vaccine efficacy in this experiment were 1) serological response to vaccination 1) the reduction in the incidence of lesions between vaccinates and placebo control mice 2) the difference in the size of lesions based on a lesion score, where a lesion ≤0.5 cm=1 and a lesion ≥0.5=2) the difference in the Prevented Fraction which is defined as the percentage of animals in each treatment group that is protected against liver lesions calculated as:

$1-p_2/p_1$ $p_2$=affected fraction in vaccine group
$p_1$=affected fraction in control group where, the prevented fraction is the complement of the risk ratio $1-p_2/p_1$; where $p_2$ is the affected fraction in the experimental product and $p_1$ is the affected fraction in the placebo group. The precision of the estimate is evaluated by determining the 95% confidence interval.

Briefly, three hundred twenty (N=320) female Harlan CF-1 mice obtained from Charles River Laboratory (Wilmington, MA) weighing 16-22 grams were equally divided into 8 treatment groups (40 mice/group) designated as groups A-H (Table 6). Mice were housed in polycarbonate cages in a self-contained HEPA filtered Mobile Housing System (Thoren Caging systems; Hazleton; PA) at 5 mice per cage with food and water supplied ad libitum. All mice were allowed to acclimate one week prior to the first vaccination.

Example 15

Vaccine Preparation and Vaccination

Vaccines of the recombinant Zinc and Hemin proteins as well as the *Fusobacterium necrophorum* SRP extract was prepared at their appropriate dosage levels in phosphate buffered saline (PBS) containing 8.0 g/l NaCl, 0.2 g/l KCl, 1.44 g/l $Na_2HPO_4$ and 0.24 g/l $KH_2PO_4$ pH 7.4 formulated with 10 percent Rehydragel HPA; (General Chemical; Berkeley Heights; New Jersey). The antigen/aluminum hydroxide suspensions was stirred for 24 hours at 4° C. to allow maximum adsorption of the protein to the adjuvant. The antigen/aluminum hydroxide suspension was then emulsified into the commercial adjuvant, EMULSIGEN, (MVP Laboratories, Ralston, Nebraska) to give and adjuvant concentration of 22.5% vol/vol. The rZinc vaccine of groups B and C was formulated at 100 μg and 250 μg respectively. The combination vaccine of Group D was formulated containing 10 μg of the Fuso-SRP extract as previously described in Example 4 and 50 μg of the rZinc protein to give a mouse dose of 60 μg total protein. The rHemin protein of Groups E and F was formulated at 25 μg and 100 μg dose levels respectively, while the Fuso-SRP extract of Groups G and H was formulated at 10 and 100 μg total protein respectively. All vaccines of Groups A-H were formulated to be delivered at 0.1 ml injectable volume. A placebo vaccine was prepared by substituting physiological saline for the aqueous protein suspension as described above. Mice were vaccinated subcutaneously two times at 21 day intervals and then challenged 14 days following the last vaccination. Blood was taken randomly from five mice from each group three times during the course of the study 1) first vaccination (pre-immune); 2) second vaccination and 3) 24 hours pre-challenge. Individual blood samples were equally pooled and stored at −80° C. until analyzed by western blot and ELISA to determine the serological response to vaccination.

TABLE 6

Experimental Design

| Group | Mice | Vaccine | Total Antigen | Adjuvant | Vaccine Volume (ul) | # Vaccines | Vaccine Route |
|---|---|---|---|---|---|---|---|
| A | 40 | Placebo | N/A | 10% ALOH + 22.5% Emulsigen | N/A | 2 | SQ |
| *B | 40 | rZinc | 100 µg | 10% ALOH + 22.5% Emulsigen | 100 | 1 | SQ |
| C | 40 | rZinc | 250 µg | 10% ALOH + 22.5% Emulsigen | 100 | 2 | SQ |
| D | 40 | rZinc + Fuso-SRP Extract | 10 µg SRP + 50 µg rZinc | 10% ALOH + 22.5% Emulsigen | 100 | 2 | SQ |
| E | 40 | rHemin | 25 µg | 10% ALOH + 22.5% Emulsigen | 100 | 2 | SQ |
| F | 40 | rHemin | 100 µg | 10% ALOH + 22.5% Emulsigen | 100 | 2 | SQ |
| G | 40 | Fuso-SRP Extract | 10 µg | 10% ALOH + 22.5% Emulsigen | 100 | 2 | SQ |
| H | 40 | Fuso-SRP Extract | 100 µg | 10% ALOH + 22.5% Emulsigen | 100 | 2 | SQ |

Please note;
the recombinant zinc protein (*B) in the above experimental design was inadvertently vaccinated only one time rather than the proposed two time vaccination regimen.

Example 16

Preparation of Challenge Organism

The *Fusobacterium necrophorum* isolate 1694 as previously described in Example 1 was used as the challenge strain. Briefly, a cryogenic vial of the frozen working seed of *Fusobacterium necrophorum* 1694 of Example 1 was used for challenge. The frozen stock was thawed at 4° C. then diluted 1:10 in cold mTSB and the resulting dilution was used for challenge. All mice in groups A through H were intravenously challenged via the caudal vein with 0.1 ml of *Fusobacterium necrophorum* ($\sim 1 \times 10^8$ colony forming units per ml) as previously enumerated as described in Example 7. Just prior to challenge, 100 µl of the above bacterial suspension was serially diluted tenfold to enumerate the number of CFU/dose. Mortality was recorded daily for 7 days post challenge at which point the experimental trial was terminated. All surviving mice from Groups A-H were euthanized by carbon dioxide. The liver from all dead and surviving mice was aseptically removed and gross examination was done to determine differences in liver abscessation.

Example 17

Challenge Results

Figure 5:
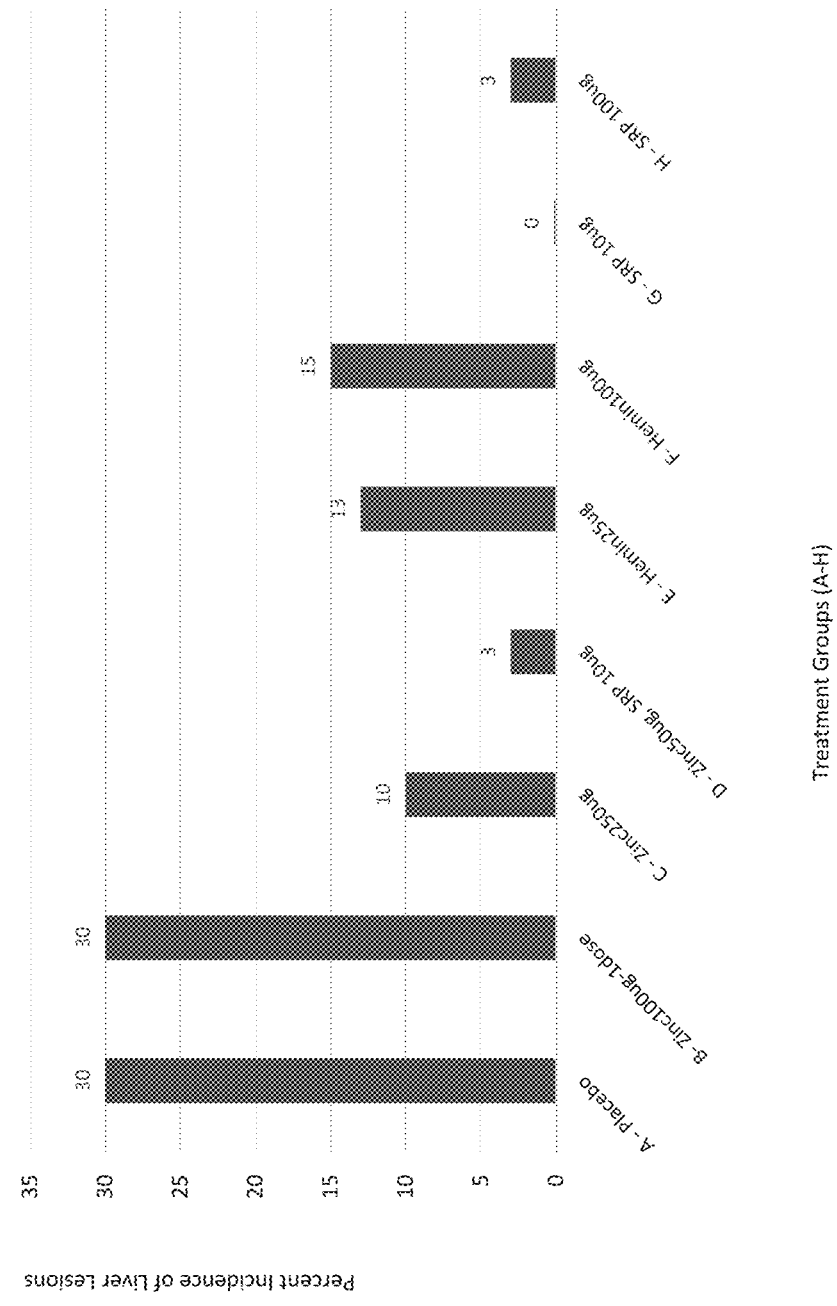
FIG. 5. The incidence of liver lesions between groups seven days post challenge with *Fusobacterium necrophorum*. All treatment groups were vaccinated two times except for Group B which received only one vaccination. There was a decrease in liver lesions between all treatment groups compared to controls. The only treatment group that did not show a significant difference compared to the non-vaccinated control was Group B.

Seven days post challenge the livers of all dead and surviving mice were aseptically removed and the difference in incidence and size of lesions was determined between vaccinates and placebo controls. Gross examination of each liver revealed a dramatic difference in both the size and incidence of lesions between the Placebo and Vaccinated mice. For example; thirty percent of the Placebo control mice had well defined foci in the livers in contrast to vaccinates; (Table 7; FIG. 5). Both the rZinc and rHemin proteins showed a reduction in the incidence of lesions to 10 and 15 percent respectively at the 250 µg (rZinc) and 25 µg (rHemin) dose level compared to controls which showed an incidence rate of 30 percent, see Table 7; FIG. 5). It is interesting note the difference in the vaccine dose between the two recombinant proteins that induced efficacy i.e., 250 µg for the rZinc protein and 25 µg for the rHemin protein of Groups C and E (Table 7; FIG. 5). Both vaccine formulations of the Fuso-SRP Extracts of Groups G and H at the 10 µg and 100 µg dose level were highly effective at reducing the incidence of lesions compared to the Placebo control of Group A. In fact; the vaccine at 10 µg dose level completely protected mice from abscessation and only 1 out of 40 mice in the 100 µg dose level of Group H showed lesions in the liver. In comparison; the combo vaccine of Group D containing 10 µg of the Fuso-SRP extract and 50 µg of the rZinc protein was also highly effective in reducing the incidence of lesions; only 3 percent or 1 out of 40 mice were found to have lesions.

TABLE 7

The percent difference of lesions in the liver and the calculated Prevented Fraction between vaccinates compared to the placebo control

| Treatment Groups (A-H) | Total Antigen | Mortality | [a]Liver Lesions (%) | [b]Prevented Fraction (%) |
|---|---|---|---|---|
| A) Placebo (N = 40) | N/A | 4 | 30 | 0 |
| B) rZinc | 100 µg | 2 | 30 | 0 |
| C) rZinc | 250 µg | 1 | 10 | 73 |
| D) rZinc + Fuso-SRP Extract | 10 µg SRP + 50 µg rZinc | 0 | 3 | 92 |

TABLE 7-continued

The percent difference of lesions in the liver and the calculated Prevented Fraction between vaccinates compared to the placebo control

| Treatment Groups (A-H) | Total Antigen | Mortality | $^a$Liver Lesions (%) | $^b$Prevented Fraction (%) |
|---|---|---|---|---|
| E) rHemin | 25 µg | 3 | 13 | 58 |
| F) rHemin | 100 µg | 0 | 15 | 50 |
| G) Fuso-SRP Extract | 10 µg | 1 | 0 | 100 |
| H) Fuso-SRP Extract | 100 µg | 0 | 3 | 92 |

$^a$Liver lesions - The difference in the number of mice having lesions calculated as a percent between treatment groups compared to controls.
$^b$Prevented fraction is the percentage of mice in each treatment group that was protected against liver lesions.

Figure 6:
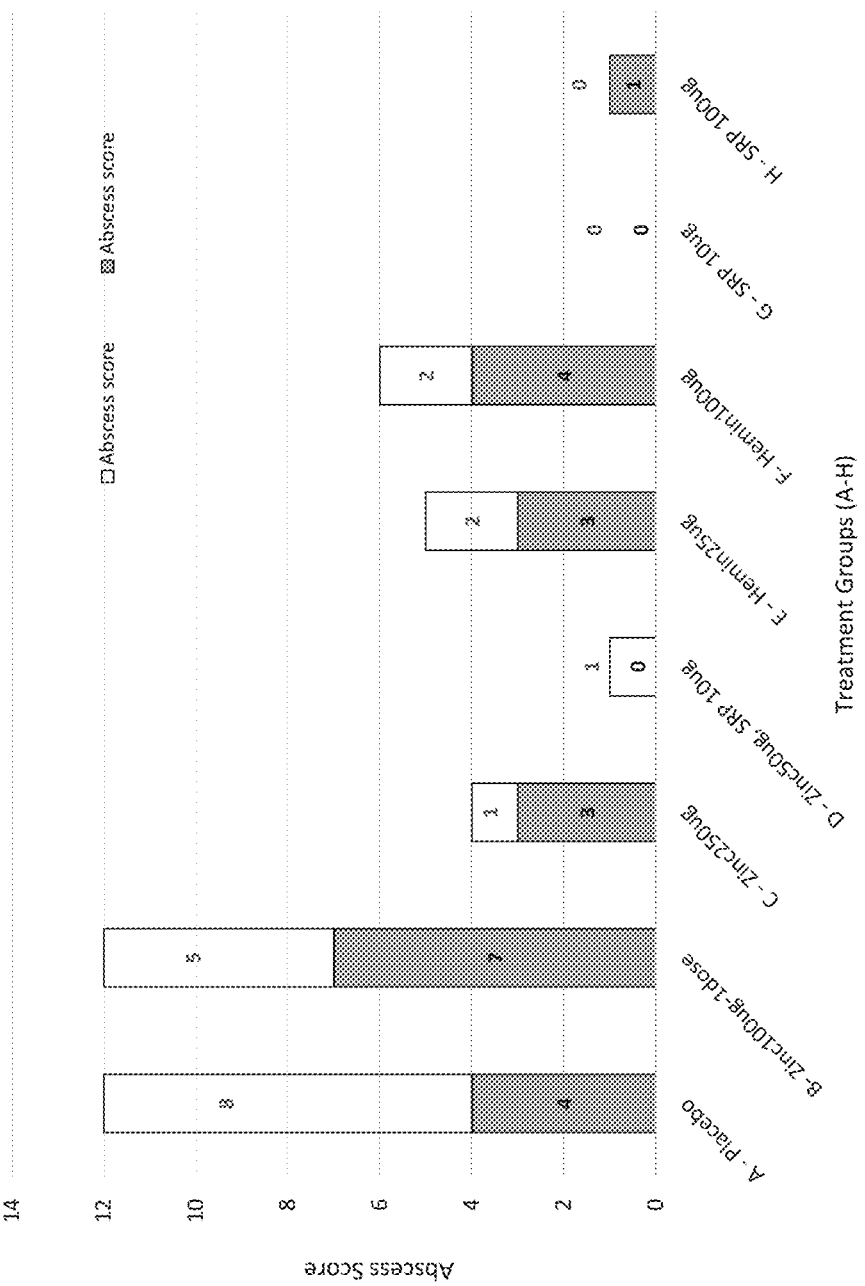
FIG. 6. The difference in the size of lesions between vaccinates and placebo controls. The lesion score was enumerated where a lesion ≤0.5 cm=1 (shaded boxes) and a lesion ≥0.5=2 (unshaded boxes). Each bar represents the number of challenged mice showing the total number of lesion per group that had a lesion size of ≤0.5 cm or ≥0.5.

FIG. 6 shows the difference in the size of lesions between vaccinates and controls. Please note; the significant reduction in the size of the lesions in all vaccinated groups (C—H) with the greatest reduction being in the Fuso-SRP Extract formulations at both the 10 and 100 µg dose levels. As illustrated; it is clearly evident that each vaccine formulation including the recombinant rZinc; rHemin and Extracted Fuso-SRP proteins reduced the number of bacteria able to proliferate successfully in the liver as indicated by the reduction in visible abscesses as well as the size of lesions compared to the placebo vaccinated mice; see FIGS. 5 and 6.

The only vaccinated group that was not significantly different than the placebo controls was the rZinc protein at the 100 µg dose level of Group B. This vaccine was inadvertently administered only one time rather than the proposed two time vaccine regimen (Table 6). These results clearly show that a single dose of the rZinc protein at a 100 µg is not sufficient to induce a proper protective response. The rZinc protein administered at the 250 µg dose level of Group C was highly effective in reducing both the incidence and the size of lesions, clearly demonstrating a dose response; as the dose increased the incidence and size of lesions decreased. It's interesting to speculate that if the dose of the rZinc protein was increased beyond the 250 µg dose level if one could have obtained a greater degree of protection that would have been equivalent to the Fuso-SRP Extract. These results clearly demonstrate that a single recombinant protein at an optimal dose can protect against a systemic challenge of *Fusobacterium*. The rZinc protein reduced the incidence and the size of lesions.

Not unlike the rZinc protein, the rHemin protein was also effective as a vaccine candidate in reducing both the incidence and the size of lesions compared to the non-vaccinated controls. Both the 25 µg and 100 µg dose levels of the rHemin protein reduced the incidence and overall size of lesions in the liver (FIGS. 5 and 6). Due to the lack of availability of final antigen of this protein the experiment did not allow for dose matching of the two recombinant proteins; i.e., it would have been more appropriate to compare the recombinant proteins at the same dose levels rather than at different protein amounts. Nevertheless, results clearly demonstrate that the rHemin protein is an excellent target antigen for controlling both the size and incident of liver lesions.

TABLE 8

The percentage of animals in each treatment group that is protected against liver lesions

| TREATMENT GROUPS | *PREVENTED FRACTION | P VALUE BY FISHER'S |
|---|---|---|
| ZINC 100 UG SINGLE DOSE | 0% | |
| ZINC 250 UG | 73% | 0.048 |
| ZINC 50 UG/SRP 10 UG | 92% | 0.0015 |
| HEMIN 25 UG | 58% | 0.099 |
| HEMIN 100 UG | 50% | 0.18 |
| SRP 10 UG | 100% | 0.0002 |
| SRP 100 UG | 92% | 0.0015 |

*Prevented Fraction is defined as the percentage of animals in each treatment group that is protected against liver lesions calculated as $(1 - p_2/p_1)$ where $p_2$ is the affected fraction in the vaccine groups and $p_1$ is the affected fraction in placebo control group.

In addition, the results show the calculated Prevented Fraction as described in Example 14 for each treatment group compared to the non-vaccinated placebo controls. For example, the Fuso-SRP Extracts at both the 10 µg and 100 µg dose levels had calculated Prevented Fractions of 100 and 92 percent with p-values of 0.0002 and 0.0015 respectively (Table 8). In fact the only other group that equaled these values was the combo vaccine of Group D consisting of 50 µg of the rZinc protein plus 10 µg of the Fuso-SRP Extract having a Prevented Fraction of 92 percent. These results showed a high degree of statistical significance having a p-value of 0.0015. The rZinc at the 250 µg dose level had a Prevented Fraction of 73 percent with a degree of significance of p=0.048. The rHemin protein at the 25 µg and 100 µg dose levels had Prevented Fractions of 58 and 50 percent with degrees of significance of p=0.099 and p=0.180 respectively. The rHemin protein showed a reduction in the incidence and the size of lesions when compared to the non-vaccinated controls but was not statistically significant. Results may have been different if a more rigorous dose finding regiment would have been performed. Nevertheless, all vaccine formulations tested except for Group B showed a reduction in the incidence and the overall size of liver lesions.

Example 18

Western Blot

First the rZinc; rHemin and Fuso-SRP Extract were subjected to electrophoresis followed by western blot analysis with the sera taken 24 hours pre-challenge as described in Example 15. Briefly, rZinc; rHemin and Fuso-SRP Extract were size-fractionated on an SDS-PAGE gel using a 4% stacking gel and 7.5% resolving gel. A 10 µl sample was combined with 10 µl of SDS reducing sample buffer (62.5 mM Tris-HCL ph 6.8, 20% glycerol, 2% SDS, 5% 0-mercaptoethanol) and boiled for 4 minutes. Samples were electrophoresed at 18 mA constant current for 5 hour at 4° C. using a Protein II xi cell and model 1000/500 power supply (BioRad Laboratories, Richmond, CA). Band migration was visualized using broad range kaleidoscope standards (Bio-Rad) to aid in the electro-blot transfer while biotinylated broad range standards were used as molecular weight references on the blot, see FIGS. 7 and 8. For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BioRad Trans-Blot transfer cell and a Pac 300 power supply (BioRad). The nitrocellulose membrane was blocked using 3% fish gelatin (Sigma Chemical, St. Louis, Mo) in Tris buffered saline (TBS-20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the mouse sera as described above. The primary antibody was diluted ⅟50 in TBS containing 1% fish gelatin, 0.05% Tween 20 and 0.2% sodium azide (Antibody Buffer). The membrane was incubated with the primary antibody solution overnight on a shaker at room temperature. The membrane was then washed two times in TBS containing 0.05% Tween 20 (TTBS) and transferred to antibody buffer containing a ⅟10,000 dilution of Alkaline phosphatase-conjugated mouse anti-bovine IgG clone BG-18 (Sigma) and a ⅟3000 dilution of avidin conjugated to alkaline phosphatase (BioRad). The membrane was incubated at 37° C. for 2 hours on a shaker, then washed in TTBS four times to remove unbound conjugate. The blot was resolved in substrate solution containing alkaline phosphate color reagent A and B in 1×AP color development Buffer (BioRad) for 30 min. at 37° C. on a shaker. The resulting Western immunoblots was documented using a BioRad GS-800 Densitometer (see FIGS. 7 and 8).

Figure 7:
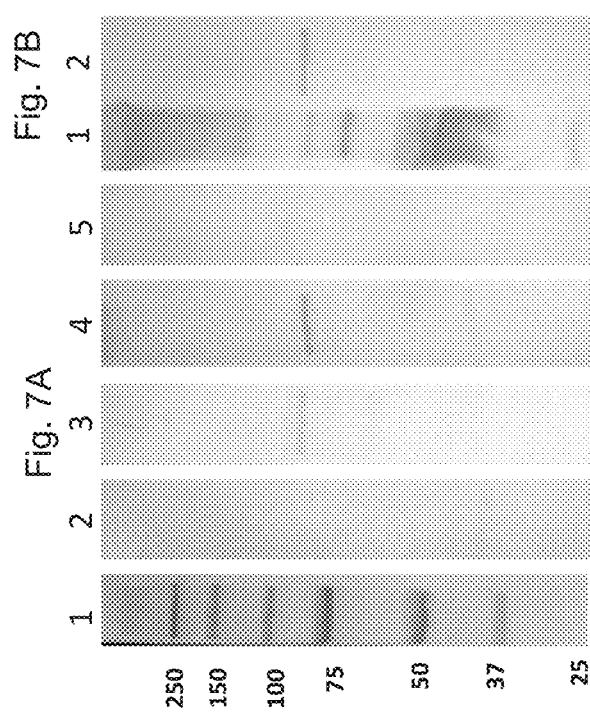
FIG. 7.

FIG. 7 shows the serological response to vaccination using the rZinc protein as examined by Western blot (A). Lane A1 shows the molecular weight marker from 250 kDa-25 kDa; Lane A2 shows the Fuso-SRP Extract of Example 4 probed with sera derived from mice vaccinated with the 250 µg rZinc vaccine of Group C. Note; the lack of reactivity in this lane (A2) clearly showing that this protein is not expressed under conditions of iron restriction in contrast to lanes A3 and A4. These lanes were run with the purified rZinc protein and probed with sera derived from mice vaccinated with the 100 µg rZinc vaccine dose and the 250 µg dose respectively. Both lanes show a single reactive band at the ~81 kDa region; clearly showing a serological response to vaccination using the rZinc protein. The results of this study clearly demonstrate a dose response to protection. For example; when the rZinc vaccine was administered a single time at the 100 µg dose level; no difference was seen in reducing the incidence and/or the size of lesions compared to the placebo controls even with a measurable serological response to the vaccine as demonstrated by Western blot. Nevertheless; when the rZinc vaccine was administered two times at the 250 µg dose level there was a clear difference in the efficacy of the vaccine in reducing both the incidence and the size of lesions; clearly demonstrating a dose response; as the dose increased the incidence and size of lesions decreased. These results clearly demonstrate that the zinc receptor protein of *Fusobacterium* is an excellent immunogenic target protein that can offer a high degree of protection against abscessation of the liver.

When the rHemin protein of Lane A5 was probed with sera derived from mice given the 250 µg rZinc vaccine of Group C no reactivity was seen; as expected.

The western blot (B) of the Fuso-SRP Extract grown under iron deplete conditions was probed with sera derived from the combo vaccine of Group D (10 µg Fuso-SRP Extract plus 50 µg rZinc protein). Note; multiple bands reacted in Lane B1 probed with sera derived from mice vaccinated with the combo vaccine. In contrast; the rZinc protein of Lane B2 was probed with sera derived from the combo vaccine of Group D consisting of 10 µg Fuso-SRP Extract plus 50 µg rZinc protein. Please note; the single rZinc band at the ~81 kDa region (Lane-B2) showing immunological reactivity and a band in Lane B1 but with a slightly lower molecular weight than the rZinc protein of Lane-B2 with an approximate molecular weight between the 76 kDa-79 kDa region. Results clearly have shown that the zinc protein is not expressed under iron-deplete conditions; please refer to Lane-A2; (Fuso-SRP Extract probed with sera derived from the 250 µg rZinc vaccine of Group C) showing no reactivity.

Figure 8:
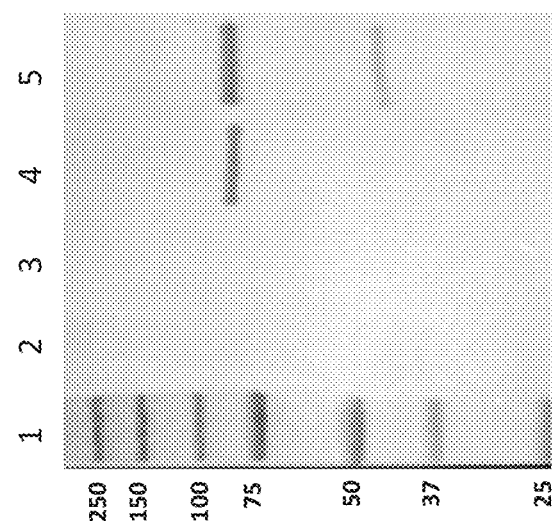
FIG. 8. Western Blot showing the serological response to the rHemin protein. Lane 1, Molecular Weight Marker; Lane 2, Fuso-SRP Extract probed with sera derived from the 100 µg rHemin vaccine of Group F; Lane 3, rZinc protein probed with sera derived from the 100 µg rHemin vaccine of Group E; Lane 4, rHemin protein probed with sera derived from the 25 µg rHemin vaccine of Group E, and Lane 5, rHemin protein probed with sera derived from the 100 µg rHemin vaccine of Group F.

The Western Blot showing the serological response to the rHemin protein is illustrated in FIG. 8. Lane 1 shows the molecular weight marker from 250 kDa-25 kDa range. Lane 2 shows the Fuso-SRP Extract of Example 4 probed with sera derived from mice vaccinated with the rHemin vaccine of Group E. Note; the lack of reactivity in this lane (2). If conditions were absolute the Hemin protein should have reacted with the same protein in the Fuso-SRP Extract since this protein is expressed under iron-restricted growth conditions; please refer to FIG. 1; lane 2 showing the Hemin protein expressed under iron-restricted conditions. This lack of reactivity to the sera derived from mice vaccinated with the 100 µg rHemin vaccine of Group F could simply be due to not enough protein of the Fuso-SRP Extract loaded in this lane.

Lane 3 shows the rZinc protein probed with sera derived from the 100 µg rHemin vaccine of Group F. Note the lack of reactivity in this lane (3) clearly showing that the rZinc protein has no homology to rHemin protein. In contrast; the rHemin protein run in lanes Lanes A4 and A5 probed with sera derived from the 25 µg and 100 µg rHemin vaccinated mice reacted strongly with the purified recombinant protein in lanes A4 and A5 respectively.

Example 19

Enzyme-Linked Immunosorbent Assay (ELISA)

The immunological response to the Fuso-SRP Extract and individual recombinant proteins after vaccination was determined by measuring the IgG titers by ELISA. In brief, the two recombinant proteins were coated in 5M urea, 100 mM NaCl, 20 mM Sodium Phosphate Buffer and the Fuso-SRP Extract was coated in the Carbonate Coating Buffer (Sigma S8875 Capsules). 100 µl of each antigen was added at 250 ng/well of a 96-well Immulon 2HB plate and incubated overnight at 4° C. with gentle agitation. The plate was washed three times with PBS wash buffer (PBS containing 0.05% Tween 20) followed by the addition of 200 µl/well 1% PVA/PBS and incubated at 37 degrees Celsius, gentle agitation. After one hour, the plate was washed three times with PBS wash buffer. 100 µl of PVA/PBS was placed into columns 2-11, all rows. Serial 4 fold dilutions of the primary antisera were performed in the plate by the addition of 133 µl of a 1:100 dilution to rows 1 and 12, mixing 3-4 times, with transfer of 33 µl to the next row, towards the center of the plate for a total of 6 dilutions for each sample. The plate was incubated for 1 hour at 37 degrees Celsius followed by three washes and addition of 100 µl/well of an HRP conjugated goat anti-mouse IgG, (H+L) chain antibody (KPL #074-1806) at a 1:10,000 dilution. After 1 hour incubation, the plate was washed three times followed by the addition of 100 µl 2 component ABTS Peroxidase Substrate System (KPL 50-62-01). Color was allowed to develop for 15 minutes. The absorbance was measured at a wavelength of 405-490 nm.

Example 20

ELISA Results

Figure 9:
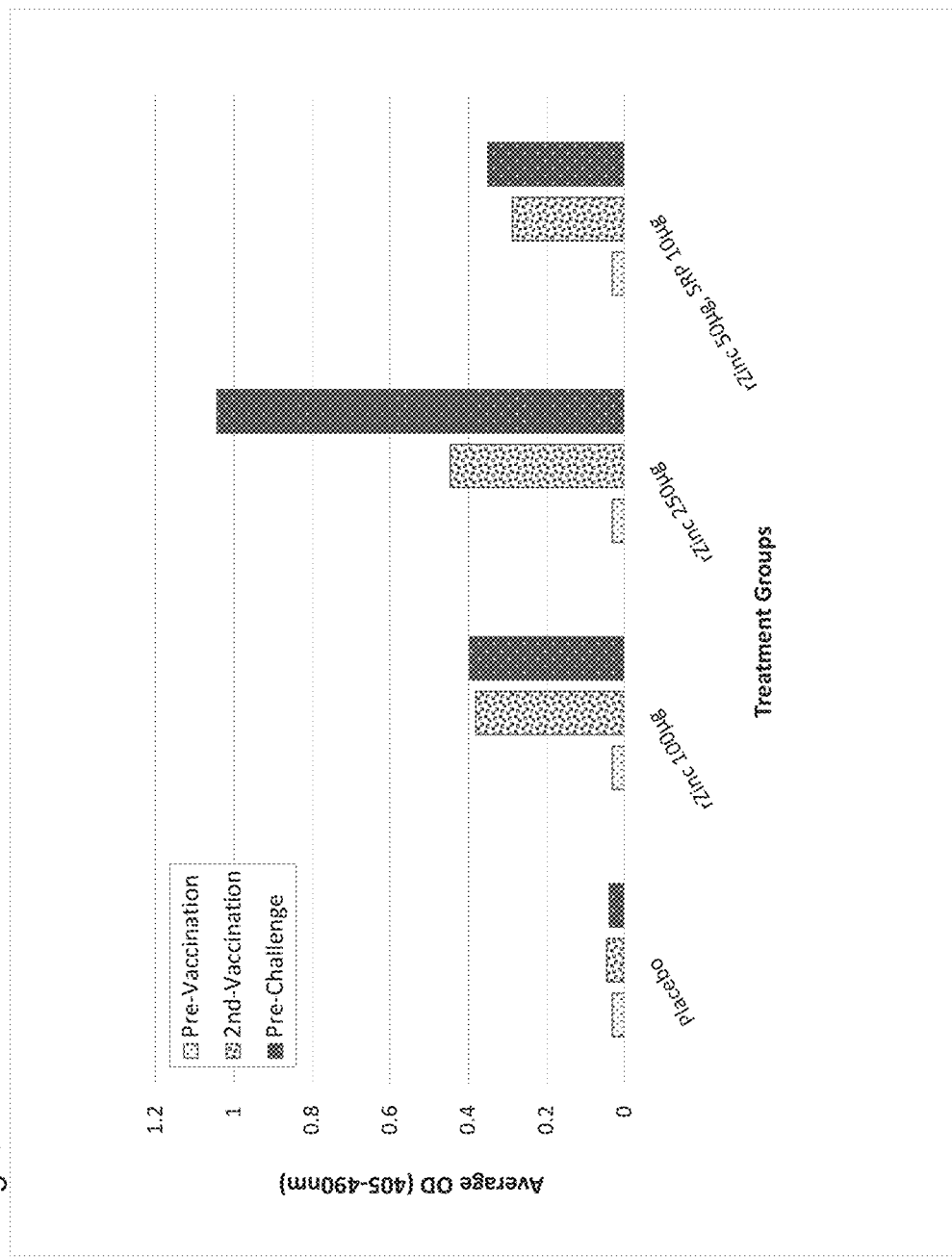
FIG. 9. The serological response to vaccination using the recombinant Zinc (rZinc) Protein of *Fusobacterium necrophorum* as analyzed by ELISA FIG. 10. The serological response to vaccination using the recombinant Hemin (rHemin) protein of *Fusobacterium necrophorum* as analyzed by ELISA FIG. 11. The serological response to vaccination using the Fuso-SRP Extract and the combo vaccine consisting of the rZinc protein plus the Fuso SRP-Extract of *Fusobacterium necrophorum* as analyzed by ELISA FIG. 12. SDS-PAGE gel showing the expression of the rHemin protein at approximately 84 kDa and a hemagglutinin protein at approximately 150 kDa. Lane 1, Molecular Weight Marker; Lane 2, Fuso iron-restricted and hemin supplemented SRP Extract; Lane 3, Fuso iron restricted SRP extract; Lane 4, Iron replete SRP Extract; Lane 5, Molecular weight marker. Note that the two proteins are expressed when iron is restricted and hemin is supplemented to the fermentation (in brackets), and not in the presence of ferric iron or iron-restriction alone.
Figure 11:
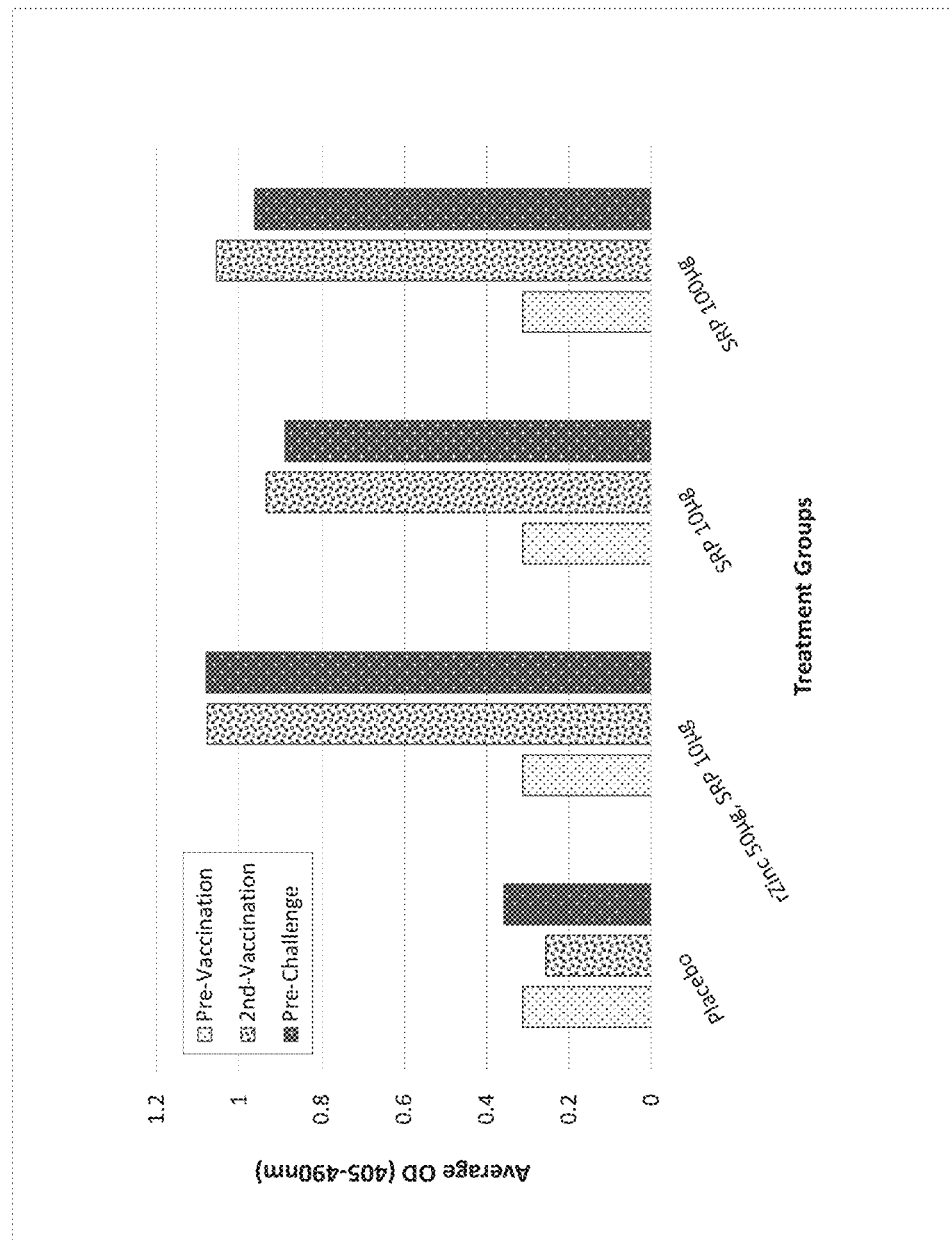

The serological response to vaccination was monitored by ELISA as described in Example 19. Blood samples were taken at the time first vaccination (pre-immune); second vaccination and 24 hours pre-challenge. Individual blood samples were equally pooled and analyzed by ELISA to determine the serological response to vaccination. FIG. 9 shows the serological response to the rZinc protein and FIG. 11 illustrates the response to the rZinc protein in combination with the addition of the Fuso-SRP Extract. First; note the amnestic response of the 250 µg rZinc vaccinated group. The results show an increasing titer from first vaccination to second vaccination in contrast to the placebo controls and the 100 µg rZinc vaccinated group. The lack of antibody response in the placebo controls shows that there was no pre-exposure to this protein. Now; in this study mice in the rZinc protein at the 100 µg dose level inadvertently received only one vaccination; resulting in a lack of any secondary immune response as seen in FIG. 9. This lack of secondary immunity clearly effected the overall efficacy of this group; since there was no difference in the reduction in the incidence and size of lesions compared to the non-vaccinated controls. In comparison; mice vaccinated with the combo vaccine consisting of 10 µg of the Fuso-SRP Extract plus 50 µg of the rZinc protein showed an immune response to vaccination with a very slight secondary response as shown in FIG. 9; yet this group showed the highest degree of efficacy in reducing the incidence and size of lesions. These results suggest that efficacy is not completely antibody mediated and that protection from infection may be also influenced by a non-defined cell-mediated immune response. It is interesting to speculate that the addition of the rZinc protein to the Fuso-SRP Extract may induce some type of immune-modulative effect on the immune response.

Figure 10:
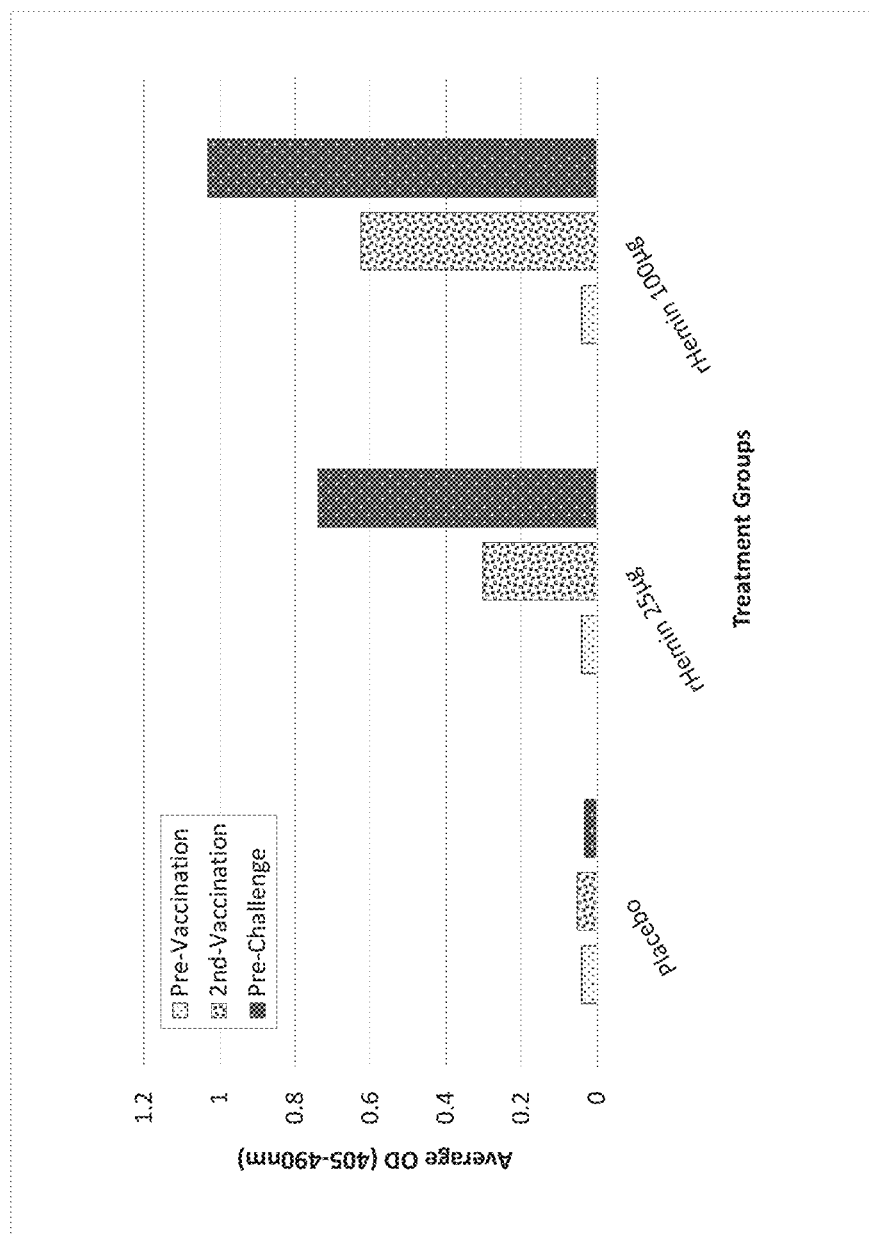

FIG. 10 shows the serological response in mice vaccinated with the rHemin at the 25 µg and 100 µg vaccine dose levels compared to non-vaccinated controls. Please note; the antibody response to vaccination with an increase in antibody titer from first vaccination followed by an amnestic response following second vaccination FIG. 10. The results showed a reduction in the incidence and size of lesions in mice vaccinated with the rHemin protein at both the 25 µg and 100 µg vaccine dose levels compared to controls. Numerically there was a significant reduction but was not statistically significant by Fisher Exact. Results may have been different if a more rigorous dose finding regiment would have been done; for example by increasing the dose to 250 µg as done in the rZinc protein of Group-C as defined in Table 6.

FIG. 11 shows the antibody response of the Fuso-SRP Extract at the 10 µg and 100 µg vaccine dose levels along with the combo vaccine consisting of 50 µg rZinc protein plus 10 µg of the Fuso-SRP Extract. All vaccine formulations showed both a primary and secondary antibody response following vaccination. This antibody response seemed to correlate well with high achievement of efficacy in all vaccinated groups; see summary Table 7. All of the Fuso-SRP Extract groups had the highest percentage in the Protected Fraction.

Example 22

Expression of Novel Hemin Proteins with the Addition of Hemin to Iron Restricted Fermentation Media The 1694 culture of example 1 was inoculated into 20 ml mTSB and incubated overnight at 37° C. in an anaerobic chamber. A 2.5 mg/ml solution of hemin was prepared by adding 0.05 g of hemin (Sigma, St Louis, Mo) to 20 ml of 0.1 Normal Sodium Hydroxide solution and vortexed to mix. The solubilized hemin was then sterilized through a 0.2 micron filter into a sterile 50 ml conical tube. Three sets of mTSB were prepared according to Table 9.

TABLE 9

| Media Formulation | Base medium | Hemin concentration | 2,2' bipyridyl concentration | FeCl3 |
| --- | --- | --- | --- | --- |
| A | mTSB | 20 ug/mL | 15 ug/mL | |
| B | mTSB | 0 | 20 ug/mL | |
| C | mTSB | 0 | 0 | 20 ug/mL |

2,2' bipyridyl was added to medium A at 15 ug/ml and autoclaved for 30 minutes at 121° C. The sterile hemin solution was added to media A at 800 uL per 100 mL for a final concentration of 20 ug/ml. Media B contained no hemin and 20 ug/ml 2,2' bipyridyl. Medium C contained no hemin or bipyridyl, but contained $FeCl_3$ at 20 ug/ml.

Five mL of the overnight culture was transferred to 100 mL of each medium A, B and C and incubated anaerobically for 7 hours at 37° C. After 7 hours, 25 ml of the cultures were transferred to fresh 500 ml volumes of their respective media and allowed to incubate overnight at 37° C. The following morning, strong growth was observed as measured by visual turbidity. All cultures were then centrifuged for 20 minutes at 7,500×G. The supernatant was decanted and discarded. The cell pellet was resuspended in 35 ml sterile Tris buffered water with 0.93 g/l EDTA salt. The cell suspension was then frozen at −80° C. for a minimum of 2 hours. The bacterial cell suspensions were disrupted by sonication for 90 seconds at 4° C. using a Branson 450 equipped with a half inch disruption horn (Branson, Danbury Conn.). The disrupted bacterial suspensions were clarified by centrifugation at 39,000×g for 20 minutes. The supernatants were collected and solubilized by the addition of sodium lauroyl sarcosinate (1% vol/vol) at 4° C. for 18 hours. The detergent-insoluble protein-enriched fractions were collected by centrifugation at 39,000×g for 2.5 hours at 4° C. The protein pellets were resuspended in 200 µl Tris-buffer (pH 7.2) and stored at −90° C.

The iron-restricted hemin-supplemented SRP extract, the iron-restricted SRP extract and the iron-supplemented SRP Extract were subjected to electrophoresis followed by western blot analysis with the mouse sera taken 24 hours pre-challenge as described in Example 16, and with the calf convalescent sera described in Example 7. Briefly, the SRP Extracts were size-fractionated on a Criterion TGX stain free pre-cast SDS-PAGE gel (BioRad Laboratories, Richmond CA) with a 4% stacking gel and 7.5% resolving gel. A 10 µl sample was combined with 10 µl of SDS reducing sample buffer (62.5 mM Tris-HCL ph 6.8, 20% glycerol, 2% SDS, 5% β-mercaptoethanol) and boiled for 4 minutes. Samples were electrophoresed at 200 volt constant current for 44 minutes at 4° C. using a Criterion cell and model 1000/500 power supply (BioRad). Band migration was visualized using broad range kaleidoscope standards (Bio-Rad) to aid in the electro-blot transfer while biotinylated Precision Plus standards (BioRad) were used as molecular weight references on the blot, see FIGS. 12 and 13. The gel was documented by Gel Doc EZ (BioRad). For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BioRad Trans-Blot transfer cell and a Pac 300 power supply (BioRad). The nitrocellulose membrane was blocked using 3% fish gelatin (Sigma Chemical, St. Louis, Mo) in Tris buffered saline (TBS-20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the mouse or calf sera as described above. The primary antibody was diluted 1/50 in TBS containing 1% fish gelatin, 0.05% Tween 20 and 0.2% sodium azide (Antibody Buffer). The membrane was incubated with the primary antibody solution overnight on a shaker at room temperature. The membrane was then washed two times in TBS containing 0.05% Tween 20 (TTBS) and transferred to antibody buffer containing a 1/10,000 dilution of Alkaline phosphatase-conjugated mouse anti-bovine IgG clone BG-18 (Sigma) and a 1/3000 dilution of avidin conjugated to alkaline phosphatase (BioRad). The membrane was incubated at 37° C. for 2 hours on a shaker, then washed in TTBS four times to remove unbound conjugate. The blot was resolved in substrate solution containing alkaline phosphate color reagent A and B in 1×AP color development Buffer (BioRad) for 30 min. at 37° C. on a shaker. The resulting Western immunoblots were documented using a BioRad GS-800 Densitometer (see FIGS. 12 and 13).

Figure 12:
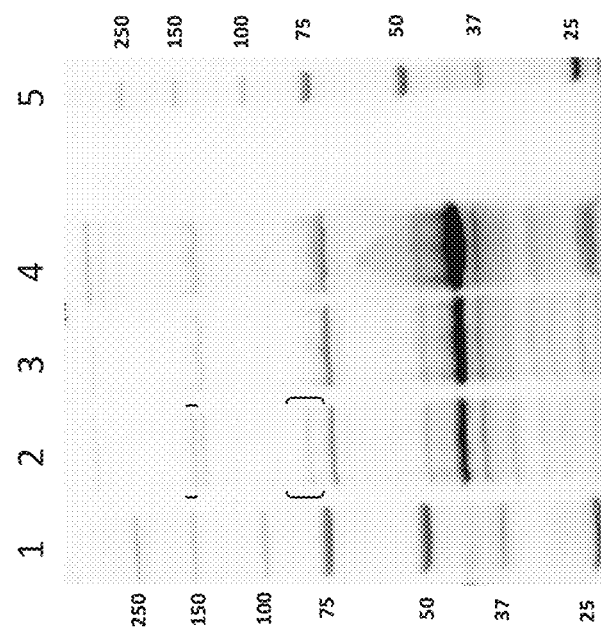

The SDS-PAGE showing the upregulation of the rHemin protein and the hemagglutinin protein is illustrated in FIG. 12. Lanes 1 and 5 show the molecular weight markers from 250 kDa-25 kDa range. Lane 2 shows the iron-restricted and hemin supplemented Fuso-SRP Extract from formulation (A) described in table 9. Note the upregulation of the rHemin protein at approximately 84 kDa, and a second protein, hemagglutinin, at approximately 150 kDa.

Lane 3 shows the iron restricted formulation B of table 9. Note the lack of expression of these two proteins in the presence of iron restriction alone without hemin supplementation. Lane 4 shows the iron replete formulation C of table 9. Note the lack of expression of the rHemin and hemagglutinin proteins in the presence of ferric iron. This demonstrates that iron restriction alone is not enough to upregulate these proteins; only by limiting iron and adding back hemin as an iron source are these proteins expressed.

Figure 13:
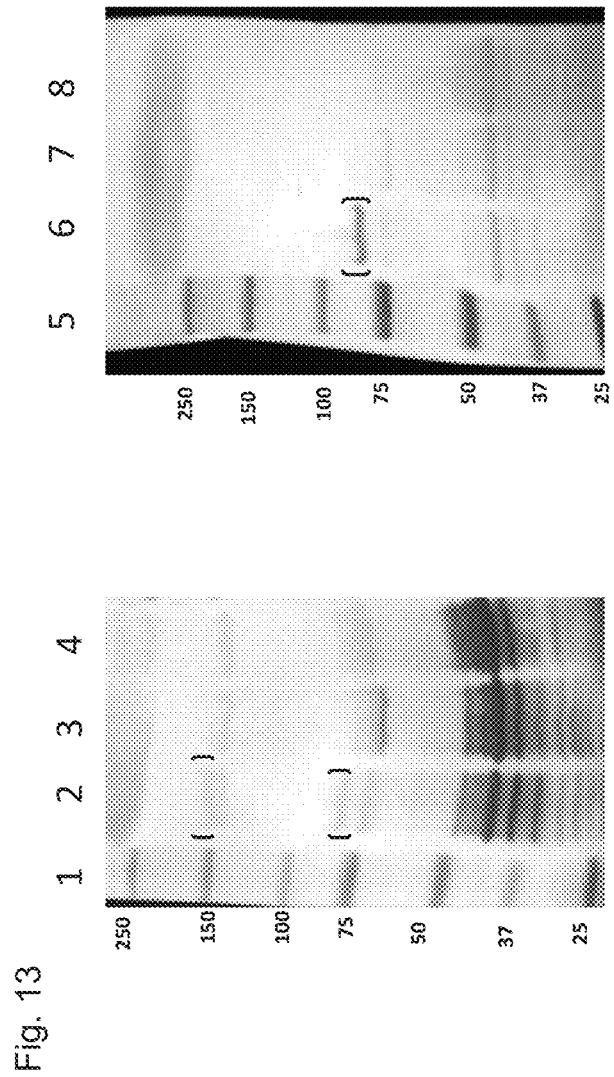
FIG. 13. Western Blots showing the sero-reactivity of the *Fusobacterium necrophorum* rHemin proteins and filamentous hemagglutinin 150 kDa protein grown under iron deplete growth conditions and probed with the convalescent calf serum of example 7 (lanes 1-4) and the rHemin mouse sera as described in example 16 taken 24 hours prior to challenge (lanes 5-8). Lane 1, Molecular Weight Marker; Lane 2, Fuso iron-restricted and hemin supplemented SRP Extract; Lane 3, Fuso iron restricted SRP extract; Lane 4, Iron replete SRP Extract; Lane 5, Molecular Weight Marker; Lane 6, Fuso iron-restricted and hemin supplemented SRP Extract; Lane 7, Fuso iron restricted SRP extract; Lane 8, Iron replete SRP Extract. Note the strong serologic response of the 84 kDa and 150 kDa proteins (shown in brackets in lane 2) to convalescent calf sera when grown in iron restriction plus hemin, and the lack of serologic response when the SRP extract is grown in iron limiting conditions alone, or in iron replete conditions. Also note in the brackets in lane 6 the very strong serologic response at 84 kDa (shown in brackets) to sera from mice vaccinated with the rHemin protein. This is also not present in Fuso SRP grown in iron deplete media or iron replete media as shown in lanes 7 and 8 respectively.

In addition to the upregulation of the rHemin protein, a protein of ~150 kDa by SDS-PAGE was shown to be upregulated in the presence of hemin in an otherwise iron deplete media (FIG. 12, Lane 2). This protein was shown to be immuno-reactive in a western blot against convalescent sera from an experimentally challenged calf of Example 7 as illustrated in FIG. 13 at Lane 2. The closest outer membrane protein found in the annotated genome of 1694 was a hypothetical protein of 154 kDa. This sequence was used to BLAST known sequences, and was a 100% match to filamentous hemagglutinin. The nucleotide sequence and amino acid sequence identified is shown in FIG. 47 (SEQ ID NOs: 78 and 53, respectively).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising an isolated polypeptide having at least 85% similarity to amino acids 63-736 of SEQ ID NO:6; and
a pharmaceutically acceptable adjuvant.

2. The composition of claim 1, further comprising:
at least one isolated polypeptide having a molecular weight of 92 kDa to 79 kDa, 73 kDa to 63 kDa, 62 kDa to 58 kDa, or 57 kDa to 47 kDa, wherein the at least one polypeptide is isolatable from a *Fusobacterium necrophorum* subsp. *necrophorum* when incubated in media comprising an iron chelator and not isolatable when grown in the media without the iron chelator; and
at least one isolated polypeptide having a molecular weight of 108 kDa to 98 kDa or 79 kDa to 69 kDa, wherein the at least one polypeptide is isolatable from a *Fusobacterium necrophorum* subsp. *necrophorum* when incubated in media comprising an iron chelator, is expressed by the *Fusobacterium necrophorum* subsp. *necrophorum* when incubated in media without the iron chelator and expressed at an enhanced level during growth in media comprising an iron chelator.

3. The composition of claim 2, further comprising a polypeptide having at least 85% similarity to amino acids 63-423 of SEQ ID NO:2.

4. The composition of claim 2, further comprising a polypeptide having at least 85% similarity to amino acids 63-714 of SEQ ID NO:4.

5. The composition of claim 2, further comprising a polypeptide having at least 85% similarity to amino acids 63-423 of SEQ ID NO:2 and a protein having at least 85% similarity to amino acids 63-714 of SEQ ID NO:4.

6. The composition of claim 2, wherein the iron chelator is 2,2-dipyridyl.

7. A method comprising:
administering to a subject an amount of the composition of claim 1 effective to induce the subject to produce antibody that specifically binds to at least one polypeptide of the composition.

8. A method for treating an infection in a subject, the method comprising:
administering an effective amount of the composition of claim 1 to a subject having or at risk of having an infection caused by a *Fusobacterium* spp.

9. A method for treating a symptom in a subject, the method comprising:
administering an effective amount of the composition of claim 1 to a subject having or at risk of having an infection caused by a *Fusobacterium* spp.

10. A method for decreasing colonization in a subject, the method comprising:
administering an effective amount of the composition of claim 1 to a subject colonized by or at risk of being colonized by a *Fusobacterium* spp.

11. The method of claim 7 wherein the subject is a mammal.

12. The method of claim 11 wherein the mammal is a human, bovine, or ovine.

13. The method of claim 8 wherein the *Fusobacterium* spp. is *F. necrophorum*.

14. The method of claim 7 wherein at least 10 micrograms (µg) and no greater than 2000 µg of polypeptide is administered.

15. The method of claim 8 wherein the infection causes a condition selected from metritis, hepatic abscesses, and foot rot.

16. A kit for detecting antibody that specifically binds a polypeptide, comprising in separate containers:
the isolated polypeptide of claim 1; and
a reagent that detects an antibody that specifically binds the polypeptide.

* * * * *

SEQUENCE LISTING

```
Sequence total quantity: 85
SEQ ID NO: 1            moltype = DNA  length = 1272
FEATURE                 Location/Qualifiers
source                  1..1272
                        mol_type = genomic DNA
                        organism = Fusobacterium necrophorum
SEQUENCE: 1
atgaaaaagc tatggatatt attttcctg ctggggagtg ttgcttttgg aagagaagtt    60
actttggaag aagcgattca agcgtcaatg gagaatagca aggcggtcaa aatttcagat   120
aagcagttag aaatttcaaa actaaaaatg aatcaggcaa ttaaaaaagc actgccaagc   180
gtagtgtaca gtgccaacta tcaacgtgga gaatatgaga gaaatattta taagaataaa   240
tcttctatgg aatcggaaaa aggcggttac aaacaatcga ttacaatcag ccaacctatt   300
tttcaaggag gagccattct tgccggaatt caaggggcaa aagcctataa aaccatagca   360
gatttgtcct atgttcaaga gacactaaat actcgtttga agacgattcg aactttttcg   420
aatattgtca acagcaaaag aaatttacaa gctttggaat attccgagaa acaattgcaa   480
aatcgatata aaaagcagga agctcaattg gagttgcgac tgattacgaa gacggattta   540
```

```
ttgaaaacgg aatactcttt attggaagta caatctttaa tttccaaagc gaaaagtaat    600
attgaagtac agacggaaga tttaaaattt caaatgggag tggacaaaaa agaagcattg    660
gaagtcaagg aatttatcgt tcccaatcat tgacagaaac gtattacatt tgaaaaagat    720
aaagagaggg cattggaatc cagtattcag gctttgattg caaatctcca agtgaagata    780
gcaaaggcac aggaaacggc agcactggga aatatgcttc ctaaggtaaa tgcctttgtg    840
agttatggag tggcttcgga gagaacacat tggaaacaaa cgaaagaaga tgcggaatgg    900
atgggaggtt tgtctgtttc ttggaatgtc ttttctttg ggagtgacta tgatgcttat     960
caaattgcaa aattggaaaa agagtccaaa gagttatcag aaacgacagc tcaggacaat    1020
atagctttga gccttaagac agcttatttg gaattgcaaa gattgaaat tttaagagag     1080
tccagaaaga gaggattgga agcggcagaa ttgaatttta caatggatca agaaaaattt    1140
gatgcaggct tgcttccac agtggattat ttatcatcgg aaacacaatt gcgggaagca     1200
agagtgaatt attccaagc agaattagat tattactatg cttttgaata ttatagatcg     1260
ttgttagtat aa                                                         1272

SEQ ID NO: 2            moltype = AA   length = 423
FEATURE                 Location/Qualifiers
source                  1..423
                        mol_type = protein
                        organism = Fusobacterium necrophorum
SEQUENCE: 2
MKKLWILFFL LGSVAFGREV TLEEAIQASM ENSKAVKISD KQLEISKLKM NQAIKKALPS     60
VVYSANYQRG EYERNIYKNK SSMESEKGGY KQSITISQPI FQGGAILAGI QGAKAYKTIA   120
DLSYVQETLN TRLKTIRTFS NIVNSKRNLQ ALEYSEKQLQ NRYKKQEAQL ELRLITKTDL   180
LKTEYSLLEV QSLISKAKSN IEVQTEDLKF QMGVDKKEAL EVKEFIVPNH LTERITFEKD   240
KERALESSIQ ALIAKSQVKI AKAQETAALG NMLPKVNAFV SYGVASERTH WKQTKEDAEW   300
MGGLSVSWNV FSFGSDYDAY QIAKLEKESK ELSETTAQDN IALSLKTAYL ELQRLEILRE   360
SRKRGLEAAE LNFTMDQEKF DAGLLSTVDY LSSETQLREA RVNYYQAELD YYYAFEYYRS   420
LLV                                                                   423

SEQ ID NO: 3            moltype = DNA   length = 2145
FEATURE                 Location/Qualifiers
source                  1..2145
                        mol_type = genomic DNA
                        organism = Fusobacterium necrophorum
SEQUENCE: 3
atgaaaaaag tggtatttgg gatttacagt atcttaatgt cctctgctat gcttggagca     60
gaaattgatc ttggaacaca gaatatctat tcggaaaccg gatttgaaac gagtcttcga   120
agctctgttt cttctcctta tatcgttact tcaaaagaaa tcaaagaaaa acattatacc   180
cgtgttttctg aaattttgag agatattccg catatctaca tcggtccgg tggcagtgta   240
gatatgcgtg gtcagggaag tgctcatgcc agaacaacag ttcaactgtt aattgatgga   300
gttcctgcca attttttgga tacttccac atcaatcttc ctatcgatac tttaaatcca    360
gaagatatta agagaattga agtcatccct ggaggaggag ctgtttata tggaagtgga    420
acttccggag gagtgatcaa catcattacc aaaaaatca tgcaaaggca                480
agctatcaaa taggaagcta tcacaatcat aaatatgacg tagctgccgg aacttctttg   540
ggaaattttg acattaacct aagttattca aaaaataata gggatggata tcgtaaaaaa   600
gccttttccg attccgattt cttctccgga aaattacgtt atcacttcaa tcccacagac   660
agtcttgaat tcaaatatag ctatttgat aataagttca gtggtgttaa atccctaacc    720
agagaacaag tcgagaaaga tcgaggcaa agtggtcttt ctcctgaaga caatttgaaa   780
aataccatcc gaaagaaga atggaattta acttacgatg caaatggac aagctggctg     840
gaacacaaat ccaatctttt ctatcagtcc acagaaataa aatctagtga atatgaagat   900
gctcttcctt tctatcaata tcaaatttct tcttatcgaa aaatgcttac tatgccaagt   960
attcctccta tgatgcaagc acaattgaaa aagcagataa aagccctaca aaatttgata   1020
acgagtaatc caaggatgga attacatcaa ggaagtcgtt tcaaagatca aaaattcggt   1080
tttaaaatga gaataaaatt taagtatgga gaaaatagtg atttattt aggtttggga    1140
tacattcaca acaaaatgtc tcgagattct tgggcttata cgaaaaatac gcaaacgaat   1200
caaacaatag caactcttac aaatactaaa attcctttaa ataagaaaac attcgaaatt   1260
ttcggattaa atacctatcg tcataatat tgggaatttg ttcagggctt acgctttgaa     1320
aaagcgaaat ataatggaaa aagacaatat aaaaatctgg aatatccttt aaaagatcgt   1380
agcatgaata atgttgcggc aaatctggct tcaattatc tctattccga tacaggaaat   1440
gtctatgtaa aatatgaaag aggatttact tctcctgctc ctgcacagtt aatggataaa   1500
atcagaaaag gaggagtgaa cgattatgtc aataatgatt taaaatctga aaatcaaac   1560
tccttttgaag ttggatggaa tgactatctc ttccattctt agtcagtgc tgatgttttt    1620
ttcagtgaaa cgaaagatga aatttctacc atattctcgg gagggcatgg gacaacattc   1680
agcaatttga accttggtca aacgaaacga tatggttttg atctaaaagc cagtcaagtt   1740
tttgaaaagt ggacattctc ggaagcttac agttatatcc atgcaaaaat catgaaagat   1800
aaaacaaagg cttatgaagg aaaatatatc agttatgttc caaggcataa attttctttg   1860
aatgctgatt atgcaatcac tccaaaatgg actcttgggg gagaatatca atacagttct   1920
tccgtatatc tggacaatgc aaataaaaat ggaaaagatg gagcgagatc tgttttaat   1980
cttcaaacct cttatgtct caattcacat tttctatct atgcaggaat taaaatgtg    2040
ttaaatcata gtattatga atctgtcagt gcaggttcca gtcaaaagta ttatagtccg   2100
gctccggaaa gaaattacta tgccggattc cgttatcaat tttaa                  2145

SEQ ID NO: 4            moltype = AA   length = 714
FEATURE                 Location/Qualifiers
source                  1..714
                        mol_type = protein
                        organism = Fusobacterium necrophorum
SEQUENCE: 4
MKKVVFGIYS ILMSSAMLGA EIDLGTQNIY SETGFETSLR SSVSSPYIVT SKEIKEKHYT     60
```

```
RVSEILRDIP HIYIGPGGSV DMRGQGSAHA RTTVQLLIDG VPANFLDTSH INLPIDTLNP    120
EDIKRIEVIP GGGAVLYGSG TSGGVINIIT KKYTGNYAKA SYQIGSYHNH KYDVAAGTSL    180
GNFDINLSYS KNNRDGYRKK AFSDSDFFSG KLRYHFNPTD SLEFKYSYFD NKFRGVKSLT    240
REQVEKDRRQ SGLSPEDNLK NTIRKEEWNL TYDAKWTSWL EHKSNLFYQS TEIKSSEYED    300
ALPFYQYQIS SYQKMLTMPG IPPMMQAQLK KQIKALQNLI TSNPRMELHQ GSRFKDQKFG    360
FKMKNKFKYG ENSDFILGLG YIHNKMDRDS WAYTKNTQTN QTIATLTNTK IPLNKKTFEI    420
FGLNTYRHNN WEFVQGLRFE KAKYNGKRQY KNLEYPLKDR SMNNVAANLA VNYLYSDTGN    480
VYVKYERGFT SPAPAQLMDK IRKGGVNDYV NNDLKSEKSN SFEVGWNDYL FHSLVSADVF    540
FSETKDEIST IFSGGHGTTF SNLNLGQTKR YGFDLKASQV FEKWTFSEAY SYIHAKIMKD    600
KTKAYEGKYI SYVPRHKFSL NADYAITPKW TLGGEYQYSS SVYLDNANKN GKDGARSVFN    660
LQTSYEFNSH FSIYAGIKNV LNHKYYESVS AGSSQKYYSP APERNYYAGF RYQF         714

SEQ ID NO: 5           moltype = DNA  length = 2211
FEATURE                Location/Qualifiers
source                 1..2211
                       mol_type = genomic DNA
                       organism = Fusobacterium necrophorum
SEQUENCE: 5
atgaaaaaaa ttttgttttt agttggggct tgttttcta tttctgcttt tgcggagcag      60
actatagaat taggaagtac ttccataaaa ggaaatagaa agacagatta tactttaaca    120
ccaaaagagt ataaaaatac atataccatt acgcaagaaa aaattcaaga cgaaactat    180
aaaaatgtag aagatgtttt acgagatgct cctggtattg ttgttcaaaa tacagcattt    240
ggacctcgaa ttgatatgag agggagtggg gagaaatctt tgtcaagagt aaaggttctt    300
gtggatggaa ttagtatcaa tcctacagag gaaacgatgg cgagtttacc aattaattcg    360
attcccattg aaagtgttaa aaagattgaa attattccag gaggaggagc tactttatat    420
ggaagtggct ctgtaggagg agttgtcagt atttctacga attccaatgt aacgaagaat    480
aatttcttta tggatttgaa ctatggttct tttgataata gaaactttgg atttgcagga    540
ggatataatg taagtgacaa attatatgtg aactatggtt ttaattattt gaacagtgaa    600
gattatagag aacatgagga gaaggaaaat aaaaatttat tgttgggttt tgactataaa    660
atcaacccaa agaatcgttt cagagtacaa acaagatata taaaatgaa gcatgatgga    720
agtaactggc taagtcagga ggaattaaag atttcgcgaa agaaagctgg attgaatttg    780
gacctagata acacagataa aagttacact ttcgattatg agtatagatc tagtcaaaat    840
ttaacgctag ccgctactgc ctataaacaa caacaagata gagacattac aaccgatgat    900
attcgagata ttgaaattat agcttctaac cgaaactaca ctgatttaaa agaatatatg    960
acttttatg atgtaaaatc tacttttaag gcaagtttaa aagaaaaaaa atatggacta   1020
aaattaaaag gaaaatacga gtatggaaga ggggaagtta ttttcgggta tgattatcaa   1080
gattctaaca ataaaagaaa ctctcttgta caatcagaga ctttaaaaac ttataatgac   1140
aaaatcagtg acttaaattt atctcctgaa gatagaaagc caatcatcaa tagagtcaac   1200
attgatttaa caaagaaatc tcacggtttt tatgtgttta ataagttaga attaacagat   1260
aaatgggatt ttacgacagg atttagaacc gaaattacaa aatataatgg atatcgaaaa   1320
aatgggccaa ataccatgcc aatcgtctct ccgaaagtaa atgaaatcag aacagacgag   1380
aagatgacaa actatgcggg agaagcagga atgttgtaca gtatagtga cacaggaaga   1440
gcctttgttc gatatgaaag aggatttgta acaccgttg caaaccagtt gacagataaa   1500
attcatgata caaaattaaa aagtccagct ggattttta ccccaccaat tgtgaacgtt   1560
tcttctttgt atgtagcaaa taacttgaaa tcagaaatca cagatactat agaagtggga   1620
ttccgagatt atatttttaa ttccttaatc agtgcttcct tctttgcaac ggacactacc   1680
gatgaaatta cacttatcag ttccggaatt acgaatccgg cagtcaatg atggaaattt   1740
cgaaatatag gaaaacaag aagattagga attgaattgg aagcggaaca aaaatgggga   1800
aaatttgatt tcagtcaatc gctaactttt gtagatacaa aagtattaaa aacagatgca   1860
gaatccagaa ttttagagg agataaggtt ccaatggttc ctagaatcaa agcaacatta   1920
ggattaaaat ataatgtgac agataacttg gctttgattg gaacttatac gtatttgagt   1980
aaacgggaaa ccagagaatt ggatgaaaaa gataaggtat ataaacatac tatcaaagga   2040
tatgaaacag cggatttggg aatattgtat aaggtggaca agtattcaaa ctttaaagtg   2100
ggggcaaaga atattttttgg aaagaaatat aatttacgag acaaaatt agaagcattg   2160
ccagcaccgg aaagaaatta ctatttagaa tttaatgtca aatttaacta a            2211

SEQ ID NO: 6           moltype = AA  length = 736
FEATURE                Location/Qualifiers
source                 1..736
                       mol_type = protein
                       organism = Fusobacterium necrophorum
SEQUENCE: 6
MKKILFLVGA LFSISAFAEQ TIELGSTSIK GNRKTDYTLT PKEYKNTYTI TQEKIQERNY     60
KNVEDVLRDA PGIVVQNTAF GPRIDMRGSG EKSLSRVKVL VDGISINPTE ETMASLPINS    120
IPIESVKKIE IIPGGATLY GSGSVGGVVS ISTNSNVTKN NFFMDLNYGS FDNRNFGFAG     180
GYNVSDKLYV NYGFNYLNSE DYREHEEKEN KIYLLGFDYK INPKNRFRVQ TRYSKMKHDG    240
SNWLSQEELK ISRKKAGLNL DLDTTDKSYT FDYEYRSSQN LTLAATAYKQ QQDRDITTDD    300
IRDIEIIASN RNYTDLKEYM TFYDVKSTLK AKFKEKKYGL KLKGKYEYGR GEVIFGYDYQ    360
DSNNKRNSLV QSETLKTYND KISDLNLSPE DRKPIINRVN IDLTKKSHGF YVFNKLELTD    420
KWDFTTGFRT EITKYNGYRK NGPNTMPIVS PKVNEIRTDE KMTNYAGEAG MLYKYSDTGR    480
AFVRYERGFV TPFANQLTDK IHDTKLKSPA GFFTPPIVNV SSLYVANNLK SEITDTIEVG    540
FRDYIFNSLI SASFFATDTT DEITLISSGI TNPAVNRWKF RNIGKTRRLG IELEAEQKWG    600
KFDFSQSLTF VDTKVLKTDA ESRIFRGDKV PMVPRIKATL GLKYNVTDNL ALIGTYTYLS    660
KRETRELDEK DKVYKHTIKG YGTADLGILY KVDKYSNFKV GAKNIFGKKY NLRETKLEAL    720
PAPERNYYLE FNVKFN                                                    736

SEQ ID NO: 7           moltype = DNA  length = 2097
FEATURE                Location/Qualifiers
source                 1..2097
```

```
                        mol_type = genomic DNA
                        organism = Fusobacterium necrophorum
SEQUENCE: 7
atgaaaacaa acattttatt ttaactttt ttattttgta atactgtttc ttttgcagaa      60
acaaccattc atctaccaga aagcaatatt caatccgatt atgtggaaat caataagatg    120
aaaaatctca aaaatataat tgtgattgaa aaaaaagaaa ttcaggagaa agggtataca    180
aatttatccg ccgtattgca agatatccca aatattcatg tcggaacaac cggttgggga    240
gaaattgata ttcgaggtca gggagaagga atgcagcaa aaaatttgca ggtgttaatc      300
gatggagctc cgattaccac tttggtaaac catcctttgc aaacgaatta cgacgtagtt    360
ccggtagaaa atattgaaag aattgaaatt attcccggga gaggttccat catttatggt    420
tccgggacag ctgaggagt tatcaatatt actaccaatc taagtcgttt acacagacca      480
ataaacattg tagaagtttc cgccggaacc ggtggagaaa aatataatct tgccttggt      540
catagagtta ctaagaaact aaacgtacaa ttatcatcc ttcgaaataa tcagaatcta      600
tatttcaaag ataccatcg acatagcaac tatttcacgg caggattaca ttatcaaatc      660
tccgacagac aaaatttgtc tctgcgatat agtactctca cagaagacgg aaaatttgtt    720
cgaaatattt tatataaaaa attgaatcag gatggaaaaa attatcgacc ggaaaagaaa    780
aaagtaaccg ccggtttgga caagacgga cataaaattg aaaatggat ggacggatat      840
tccaatgcca agagaaatat ggacagcttc aatctaagtt atcgttttcg acttgggga      900
aactcaactt atcttatgga tgccttttac aataagggac attttttcaa tatggctttg    960
agtgatcaga ccatgtatca tcatacctac ggagttaaaa ataaattgga cttttttctat   1020
gcaaagaata gtgcttttga cggaagtagc ttgttgattg gattggattc ttaccaacag    1080
gatgcaaaat tggaatacaa tgattacaaa ttttttagat tacaaaaagaa aacttattac    1140
atcagaccgc tttcctttaa atataaaaag aaaaccaatg cttttttatct attgaatact    1200
ctaaaatatg gaaattggga gtcttcacaa ggaattcgaa gagattatac ctattggcat    1260
tttgacaagg ttacttccaa aaatgaagga aaagaaacca gccatcgtca ataccaat      1320
tacgaattca gtcttgccta taaatatcgt gataccgaga ggatctatgc tcgttacgaa    1380
agaggcttta cttcccctga tggtctagaa attacagatg acttttccaa acaagacatt    1440
aagcctacaa aaggaaaaga tgaaatctat gacttatatg aaatcggttg gagagaatac    1500
ttcggattta ctaccataaa cttaactgca ttctattctt ttacagacaa tgaaatgagc    1560
cgaaattatg ttttcaatga actaggattc ggaaggaaa ccatcaacat tctaaaaacc    1620
aaaagaaaag gaatagaatt aagtctattc caaaaattag gaaatttgga attaaaagaa    1680
agttacgctt atttaaaagg aaaaagaact tacaacggaa aagaatctca attcttagat    1740
ccggatgact atgtagattg gtccaatacg ggacttccca agtcccaaa acagtctcta    1800
accttggaag caaaaatatca ttttagccca aaaatttcac tcggtttacg atataaatac    1860
aatgaaaaat atagtaattt cagtgattta agacaaaaag aagaagg atacatcaaa      1920
tctcattctg taacggactt atctttcat tatcaaaatg aaaaaggatt tcatctgtat    1980
ggaggaatca ataatgtatt caatgaaaaa tattttgaat ataccggttc taaaatgtat    2040
accatcatcc ctgcggaaga aagaacattc tttgtgggaa cgaaatatca atttttaa      2097

SEQ ID NO: 8          moltype = AA  length = 698
FEATURE               Location/Qualifiers
source                1..698
                      mol_type = protein
                      organism = Fusobacterium necrophorum
SEQUENCE: 8
MKTNILFLTF LFCNTVSFAE TTIHLPESNI QSDYVEINKM KNLKNIIVIE KKEIQEKGYT     60
NLSAVLQDIP NIHVGTTGWG EIDIRGQGEG NAAKNLQVLI DGAPITTLVN HPLQTNYDVV    120
PVENIERIEI IPGGGSIIYG SGTAGGVINI TTNLSRLHRP INIVEVSAGT GGEKYNLAFG    180
HRVTKKLNVQ LSYLRNNQNL YFKDTYRHSN YFTAGLHYQI SDRQNLSLRY STLTEDGKFV    240
RNILYKKLNQ DGKNYRPEKK KVTAGLDKDG HKIEKWMDGY SNAKRNMDSF NLSYRFRLGE    300
NSTYLMDAFY NKGHFSNMAL SDQTMYHHTY GVKNKLDFFY AKNSAFDGSS LLIGLDSYQQ    360
DAKLEYNDYK FLDYKKKTYY IRPLSFKYKK KTNAFYLLNT LKYGNWESSQ GIRRDYTYWH    420
FDKVTSKNEG KETSHRHNTN YEFSLAYKYR DTGRIYARYE RGFTSPDGLE ITDDFSKQDI    480
KPTKGKDEIY DLYEIGWREY FGFTTINLTA FYSFTDNEMS RNYVFNELGF GRKTINILKT    540
KRKGIELSLF QKLGNLELKE SYAYLKGKRT YNGKESQFDL PDDYVDWSNT GLPKVPKQSL    600
TLEAKYHFSP KISVGLRYKY NGKYSNFSDL RQKEEEGYIK SHSVTDLSLH YQNEKGFHLY    660
GGINNVFNEK YFEYTGSKMY TIIPAEERTF FVGAKYQF                            698

SEQ ID NO: 9          moltype = DNA  length = 1965
FEATURE               Location/Qualifiers
source                1..1965
                      mol_type = genomic DNA
                      organism = Fusobacterium necrophorum
SEQUENCE: 9
atgaaaaagt actttgttgc agtgtcgatt tccttagcac tttcgtatca gatttttgca     60
gaggaaaatc ctgttatcaa attaaatgaa actgttataa cttctgaaag ttttggaaca    120
aatattttga gaactccaaa gaatattaca gtaattactg caagaaatat taaaattcaa    180
ggagcaaaga atatagaaga tgctttaaga ggggttgcag gcttaactgc ttataataat    240
atgggcggct ctgatcccaa aatttctctt cgaggaatgg ctcccggaaa agaagaacaa    300
agtattctgt ttattagat ggaatcccc tataacagta cagtagaatac tggagccggta    360
aatctgaatt tgattcctat tgacatcgta gagaaattg aaattattcc taatggggga    420
aacgtagttt atggagaagg agctgtcgga ggagttatca atattatcac taaaaaagga    480
aaaaatataa aatattacgg ttcttttttca atagatggag gatcttatga tttaaaggag    540
tataaggtaa atttggggag caacctgacg gagcagcttt ctctagattt gaaatataat    600
aatagaaggc aaaaaaatta ccgggatcac cacacaagag acattgaata tatcaatttg    660
ggaatggaat ataagaaaa tgagcacagt atttatttcg attttcagaa ttcagaaaca    720
gaatatcgtt ttcctggtta tctgacaaag aaacaaatag aagagggtaa gattaaaaaa    780
tcaacaggaa atataaaggg aaaagaaaaa ttaagaaattt accgtgcaaa atacgaggga    840
aaatgggcta aaaattatt tttttaatatt gcaggagatt ttaaagataa attatataag    900
```

```
tccattgatg aaaaaacaaa taccgtcagt accataagag atacggaatc ttttttacatc    960
agtccacaaa tcaaatatca atatatgccg aattcttact ttatactagg aggagatttc   1020
ctgaaaggga aatcaaaata tagatataaa aaagacatta aaacagaaac aagcagaaaa   1080
tctgtcggag tgtttcttac caataatata aaatgggaaa attttatatt tacacaggga   1140
tatcgacatc aaaaaatcaa gtatgatgta aaggataagt tgtatccttc cccaaaccat   1200
aaacaaaaaa ttctattgga taaaactttc caacaggatt cctatgaact gacagcaaat   1260
tatcttttgt cggatacagg tagtatatac gcttcttaca caaaagcttt cagagcccct   1320
actgcagatg aagcaggtag atggcgaaaa ggatacgatg taaaaataca agaagcggat   1380
acttttgaag ttggaggaaa gcttgcttgg aagaactggt atatatctgg ttctatcttt   1440
cataccagaa ccgaaaatga gattctatat attgcctatg aagatggaaa gctgggtaaa   1500
aattataact tgcccggaaa gaatataaga cagggaattg agctttctct ggaacaatac   1560
ttagaaaaat taacgttacg ggaaagtttc cattatttaa aacataaaat caaaaaagga   1620
actttcgccg gaaataagat tccaggagtc cctcagtaca tttatagttt aggtatggat   1680
tatagaatat tagatcatgt tatctggagt aattcttttc atttattatg aagtgcctat   1740
ggaaattatg attatcataa taaatttgga aaacagaaag ggcatacgga attaaacacc   1800
agtcttcgct atgaaatgaa aaacggcttg agttttatg gagggattca caatcttctg   1860
gataaggaat attttactcc aaaattaaat gcggccggaa cagggatgaa ttattattat   1920
ggcagcagaa gaaattacta tattggattc cagtatacct tctaa                   1965

SEQ ID NO: 10          moltype = AA   length = 651
FEATURE                Location/Qualifiers
source                 1..651
                       mol_type = protein
                       organism = Fusobacterium necrophorum
SEQUENCE: 10
MKKYFVAVSI SLALSYQIFA EENPVIKLNE TVITSESFGT NILRTPKNIT VITARNIKIQ    60
GAKNIEDALR GVAGLTAYNN MGGSDPKISL RGMAPGKEEQ SILFLLDGIP YNSTVDTGAV   120
NLNLIPIDIV ERIEIIPNGG NVVYGEGAVG GVINIITKKG KNKKYYGSFS IDGGSYDLKE   180
YKVNLGSNLT EQLSLDLKYN NRRQKNYRDH HTRDIEYINL GMEYKENEHS IYFDFQNSET   240
EYRFPGYLTK KQIEEGKIKK STGNIKGKEK LRIYRAKYEG KWAKNLFFNI AGDFKDKLYK   300
SIDEKTNTVS TIRDTESFYI SPQIKYQYMP NSYFILGGDF LKGKSKYRYK KDIKTETSRK   360
SVGVFLTNNI KWENFIFTQG YRHQKIKYDV KDKLYPSPNH KQKILLDKTF QQDSYELTAN   420
YLLSDTGSIY ASYTKAFRAP TADEAGRWRK GYDVKIQEAD TFEVGGKLAW KNWYISGSIF   480
HTRTENEILY IAYEDGKLGK NYNLPGKNIR QGIELSLEQY LEKLTLRESF HYLKHKIKKG   540
TFAGNKIPGV PQYIYSLGMD YRILDHVIWS NSFHYYGSAY GNYDYHNKFG KQKGHTELNT   600
SLRYEMKNGL SFYGGIHNLL DKEYFTPKLN AAGTGMNYYY GSRRNYYIGF Q            651

SEQ ID NO: 11          moltype = DNA   length = 2001
FEATURE                Location/Qualifiers
source                 1..2001
                       mol_type = genomic DNA
                       organism = Fusobacterium necrophorum
SEQUENCE: 11
atgaaaaaaa tttttatggt aacagcaatt ttagcaacag cttccggtct tggttttgca    60
aaggagattt ctcctattga actggagcaa acagtcgtaa cttctgaatc tttcggaaca   120
tcaactcata ggacagccaa aaatatacag gtaattacag caaaggaaat ggaagaaaaa   180
ggggcattaa cagtagatga agcattaaag ggagtaccgg gagttatggt aagaaaaatg   240
gatgcaggaa ctcctgttat tgatttacgg gggtcaggag cggcatccag tttcagttcc   300
agcatactct tgttgatgg agttccgtta aacggtttgg tgaaattgga catcaattcc   360
attcctctaa gtgaaatcag tcgtatcgaa attattcaag gaggaggagc tgttatgtat   420
ggggatggct ccacaggagg ggttgttaat attattacga agagtccgaa atacaaaaaa   480
cattatggaa gtgcaggctt ggaatacggt tctggaaaaa caagtcgggc aagcttacat   540
tacgaacgg ctttaacaga taaattatcc gtcagtgctt cctattccgg atatgcttct   600
atggaatacc gagatcgagg acatggaaaa acttggagcg agaaagtttt cgattacaga   660
aataaaaaag ataagaaata ttcccctttt gg ttacaagga aatatcaatt ggaagacgtta   720
agtatcggct tcaagtataa tcataacgaa agaaaggatt attacaccgg atatttggaa   780
aagaaacagt atgaagaaaa tcctaaacaa ataggaagtt attcaggtaa atacaggat   840
gtgacggata tttataatct ttcttatcaa acaaagttga cagataccct tggaattttta   900
gtttacggag gatattatcg aggaaagagc atcgaccaaa atcagcttac cagtgaatat   960
tttataaaac ctcaattcaa atatacttac ggagaaaaca gctatgttat ttttaggtgg   1020
gattaccgag atgaaagcg ggaattcaaa gaaaaagttc tggtaaacgg aaggatgcaa   1080
aaagctccca acgatgaaag agaatccaaa gcaatctatg ttatgaataa acttctttg   1140
ggaaactggg aattttctca aggatatcgt tatgaaaagg tggattataa atacagttcc   1200
aaaattttatg gaccaggctg gtcattatcc gaaattaacc gtgaattc aaaatattct   1260
cataatgaca gctttgaatt gggagtgaat tatctctatt ccgatacggg aaatgtatat   1320
tcaattata ccaaagcgat gagaactccg acaattggag aggcaggagc ttggtacgga   1380
gatgtaaaga cacagaaaaa tgatattttt gaaataggat taaggattaa tttcaaaaat   1440
acacaaatct cttcttctat tttctatatt acttccaaaa atgaagtctac ctatgataaa   1500
acgaatccga ataattcaaa taacagaaac tttgacggaa gggtaagaag aacgggggca   1560
caattgtctt tgaccccatta tttgataaa ttaagtgtaa gagaaagaat ttcttacatc   1620
catccaaaag tatccagtgg aatttatagc ggaaaaactt tgcaggagtc caaaatggg   1680
actttaaatc taggggcaac ttatcatgtt acggataagt ttttagtaaa tacagattta   1740
tattatcaat ccaaagctta tgcagaagat gattttgaca actatttaa gaaggataat   1800
tcttatgcaa ctttggatat caatacttct gtcgtttag aaaatggaat ggagatgaa   1860
ggaggagtca aaaatgtatt tgataaaaaa tatgccaata cgataacttc tagcagaagc   1920
acatggtctc cggacctag aactgtgttc tatcctgcag atggaaagag tgtttatgta   1980
ggattcaaat atcatttta a                                              2001

SEQ ID NO: 12          moltype = AA   length = 666
```

```
FEATURE                 Location/Qualifiers
source                  1..666
                        mol_type = protein
                        organism = Fusobacterium necrophorum
SEQUENCE: 12
MKKIFMVTAI LATASGLGFA KEISPIELEQ TVVTSESFGT STHRTAKNIQ VITAKEMEEK   60
GALTVDEALK GVPGVMVRKM DGGTPVIDLR GSGAASSFSS SILLLDGVPL NGLVKLDINS  120
IPLSEISRIE IIQGGGAVMY GDGSTGGVVN IITKSPKYKK HYGSAGLEYG SWKTSRASLH  180
YGTALTDKLS VSASYSGYAS MEYRDRGHGK TWSGESFDYR NKKDKKYSLW LQGKYQLEDG  240
SIGFKYNHNE RKDYYTGYLE KKQYEENPKQ IGSYSGKIQD VTDIYNLSYQ TKLTDTLEFL  300
VYGGYYRGKS IDQNQLTSEY FIKPQFKYTY GENSYVILGG DYRDGKREFK EKVLVNGRMQ  360
KAPNDERESK AIYVMNKTSL GNWEFSQGYR YEKVDYKYSS KIYGPGWSLS EIKPMNSKYS  420
HNDSFELGVN YLYSDTGNVY FNYTKAMRTP TIGEAGAWYG DVKTQKNDIF EIGLRDYFKN  480
TQISSSIFYI TSKNEVYYDK TNPNNSNNRN FDGRVRRTGA QLSLTHYLDK LSVRERISYI  540
HPKVSSGIYS GKTFAGVPKW TLNLGATYHV TDKFLVNTDL YYQSKAYAED DFDNYFKKDN  600
SYATLDINTS YAFENGMEVY GGVKNVFDKK YANTITSSRS TWSPGPRTVF YPADGKSVYV  660
GFKYHF                                                             666

SEQ ID NO: 13           moltype = DNA  length = 2382
FEATURE                 Location/Qualifiers
source                  1..2382
                        mol_type = genomic DNA
                        organism = Fusobacterium necrophorum
SEQUENCE: 13
atggaagaaa acaatggaac gattgtcatc acggaagaaa tgatacaaaa gaagcattat    60
gacagcgttg ccaaaatttt tgaagattct ccggtttccg tcgtaagaca tacggcattc   120
ggaccgattg tcgatttgcg aggaagcgga gagagaacca tcagtcgagt gaaagtgatg   180
attgatggca caccgatcaa ccccttagaa gaaactcacg gaaccatccc ttttgatacc   240
attccggtgg aatccattgc caagataaaa attgttccgg gaacaggaac gacaaaatat   300
ggaggaggaa ccacaggagg gtatatcaac attcatacga aaaaacagaa acagaataat   360
tacattacga tcaatgcgca caatgcctct tataatgcca agagtattgg aattgctgcg   420
ggaatgaatg taaccaagaa attatttgtt tatgcgggag aagcctatca agaaaagac    480
ggctatcgaa agaaagacca ttcggacaga acaatttttt taggaggctt tgattatcaa   540
atcaatgcaa aacataggat caaaggacaa ggaaatctct accgagagga tttaaaatcc   600
acaacggaag taactcatga agaattgaaa gaagatagaa gaaaagcggg agaagataca   660
aagatagaaa tggatcgaga ttttgcttct tggactatg  aatacacacc tactteccat    720
tttaaattaa gaaccaatgt caatcgagct cattttacaa gagatgtatc tatgaatgcg   780
aagcaggatc aacttgttct tgcttttatg ccaagagatg aacaaggata ttttttgcat   840
tttgatgcag gattattggc agatcctaag ttatctgatg taaggccgat tcttcctggat  900
tttgaatcta ctatggaagg aaaattcaag gaaaaaatc  aggagggaaa gctggacgga   960
gaatggaaat acaatcaagg aaagggcat  ttacaatttg gatatagtta aatgagaag  1020
aaattgaatc aagatttaaa atcaatttcc aaacctttta cttaaaaaa tcaattggga  1080
tatttgattc aagtgaccc  ggctccgaaa ggatatggaa attacaccgg aaaaattatt  1140
gccccggaag aaatgtttaa aatcaaattt aaagattttc ctcaaatact ggaaactttt  1200
ttaggactta ggagagaagg cgtcgaaag  gaaaaaattg attttcaaaa ttataataaa  1260
attgatgctt taaggatac  tcatgccttg tatttgttaa atgattacaa attaactcca  1320
aaatttaatt ttagagcagg tttaagatgg gaacattcaa aatatggttc tgatagaaaa  1380
aatagaatga ttttgggagt tcataatgca caatcatcag gaatggcaaa tagaatggca  1440
attgcgggtc ttcttaatga gtatcaaatg gaggcttatg tacaaggaaa attatcctac  1500
ttggatgttg atttatcttt gaaagaaact catgtcaaag ataggagtga aatttcgga   1560
ggagagcttg gatttactta tcaatatcat cgaaaaggaa gtgtattttt ccgatatga   1620
agaggatttt tatctccatt gccttcccaa cttaccaata aggatttctt aacaggaatt  1680
tattatccaa gtcatgtcaa atcggaaaaa gtagacacta ttgaaatggg aatcaaacat  1740
tctctatgga caatactca  tatcgaagcc actactttct tttctttgac aaaagatgaa  1800
attacaaata tgcgatacaa tgcgaacaac catatgaata tgcgttgtga atatgccaat  1860
atttctaaaa caagaagatt gggattggaa ttgaatgcgg aacatatttt cgacaaatta  1920
aagattcgag agtccttcag ttatgtggat gctaagatag caaaagatac cggattcaaa  1980
gattactatc attccgatta caagtgaaa  tcggaaaaag aatttaaaga cgcccccta   2040
tattataaaa aaggacaaca agtacctctt gtttctaagg tcaaagtgac ggtaggagca  2100
gaatatcaat ttacagataa attgagttta ggaggaaact ataactatgt cagtggctat  2160
gatacccgag aacgggcga  aggcttccaa gcaaagacct ataaagtaaa aggccatgga  2220
actttggacc tgtttggaag atattctttc acagactatg cctatgtacg atttggagtg  2280
aataatgtgt aggagaaaa  atacaattta cgagaagact ctcactatgc agtaccggct  2340
ccaaaacaaa attattatgc aggattagt  tataagttct aa                     2382

SEQ ID NO: 14           moltype = AA  length = 793
FEATURE                 Location/Qualifiers
source                  1..793
                        mol_type = protein
                        organism = Fusobacterium necrophorum
SEQUENCE: 14
MEENNGTIVI TEEMIQKKHY DSVAKIFEDS PVSVVRHTAF GPIVDLRGSG ERTISRVKVM   60
IDGTPINPLE ETHGTIPFDT IPVESIAKIE IVPGTGTTKY GGGTTGGYIN IHTKKQKQNN  120
YITINADNAS YNAKSIGIAA GMNVTKKLFV YAGEAYQRKD GYRKKDHSDR NNFLGGEDYQ  180
INAKHRIKGQ GNLYREDLKS TTEVTHEELK EDRRKAGEDT KIEMDRDFAS LDYEYTPTSH  240
FKLRTNVNRA HFTRDVSMNA KQDQLVLAFM PRDEQGYFLH FDAGLLADPK LSDVRPVLLD  300
FESTMEGKFK EKNQEGKLDG EWKYNQGKGH LQFGYSYNEK KLNQDLKSIS KPFTLKNQLG  360
YLIQGDPAPK GYEDYTGKII APEEMFKIKF KDFPQILETF LGLRREGVEK EKIDFQNYNK  420
IDAFKDTHAL YLLNDYKLTP KFNFRAGLRW EHSEYGSDRK NRMILGVHNA QSSGMANRMA  480
```

```
IAGLLNEYQM EAYVQGKLSY LDVDLSLKET HVKDRSDNFG GELGFTYQYH RKGSVFFRYE        540
RGFLSPLPSQ LTNKDFLTGI YYPSHVKSEK VDTIEMGIKH SLWNNTHIEA TTFFSLTKDE        600
ITNMRYNANN HMNMRWAYAN ISKTRRLGLE LNAEHIFDKL KIRESFSYVD AKIAKDTGFK        660
DYYHSDYKVK SEKEFKDAPL YYKKGQQVPL VSKVKVTVGA EYQFTDKLSL GGNYNYVSGY        720
DTREPGEGFQ AKTYKVKGHG TLDLFGRYSF TDYAYVRFGV NNVLGEKYNL REDSHYAVPA        780
PKQNYYAGFS YKF                                                          793

SEQ ID NO: 15          moltype = DNA  length = 2934
FEATURE                Location/Qualifiers
source                 1..2934
                       mol_type = genomic DNA
                       organism = Fusobacterium necrophorum
SEQUENCE: 15
atgaaaaaag aaaatacggg tatgtggcaa aggattttga aaatcggtat gttaagtata          60
atactcttat actggacaga ctctctatat gcaatagaga ctagcgagaa tatgcagtcg         120
acaacgatgt cggtttccgg agaaacggta aacttcaaaa tggaaggaat taccgtggag         180
gcaaaaagac cggattggga atcgaaatta tcaccgggaa cagtgacggt cattcgtccg         240
gatgattata aaggagagca aaaagattta cctgattttt tgaaaatggt tccccggagtt        300
catgtgcggg aaatcaatgg aaaagggcag tacaccacag tcagtgttcg tggttccact         360
gcggctcagg tcggagtgtt tgtagacgga gttcttttta atctcggagg agatgcggca         420
gctgatattt caacaattcc cgtgcataat gtggaaagaa ttgaagtgta tcgtggatat         480
attcctgcac gtttcggtgg aacttttatg ggaggagtta tcaatatcgt taccaaaaaa        540
ccgaatcgag gaaatgtgag cgcaagcgtc ggacgaagtt cttttggcgg taaaaaagca         600
aatttgcagt ttgatcttcc cttgggaagc ggaactttaa tggtcggaat caatcatgat         660
gaaagcaaag gaaatttcaa atataaaaac ttctcctatg atagagataa agagtatcaa         720
aaggaagtgg aaaatgcaaa aagttcggaa cgaggagcaa tagtaatta taaaggcga          780
tttaaagaat taaaaaaata cgattttaca gatgatagcg gaaatatatt taaggttgat         840
actctggaag aagcaactca gattgtcaaa aataatcagg atcgttggga aaagtctttg         900
caggaagcta aaaatgacat tgataataat tttttaaaaa agaaacatat tatagcaaga         960
ttcccgggaa ttcccaaaga agagattctt cctcttctta gaagtactca tattgatgca        1020
gagcaagctc tttatgaatc tgctttaaaa gaatactctg taaatcaagg caataatttt        1080
attccaaaat ggaagattc agtggtaac tgggttgtcc ctgatagagt ggaagattat        1140
gttgaagctt ataataagag tcatgaaata ggatatcaac attttcaaca gattatagca        1200
aagggtgtgc agggagatat agaaagatgg atagcaaaat atggaaaaag ctatgctgtt        1260
aattatgcac aacaggcgga gtatagtgtc aaagaaatgg aaaaacataa aaaacgggcg        1320
gaagcggtga aagaccacta tagacgaaga aaagccaatg attataaaaa tatggatatt        1380
attttaaaat ggcaggatga acattggatg gcgaaggcaa cttggaaaag aatcaaaaga        1440
catctgccgt ttcctattga tgagaactat ggtaatgcac catatataga taccgacctt        1500
atggcaaata tccgctctc tatctttat catcgaaatc agaaattgac cgttcaggaa         1560
tttcttttcg gaagacggga tactttcagg aatcttgaat ggggctggag tgttaattat        1620
ctaaaacaag agaagattac ctatgttgat gattgggaat ggttgaaaa aaatacggga        1680
agtctcttaa acagctatcg tccaaacact ctgtggagta aatatgacag tcatcgctgg        1740
ggtgcaaaat tggatggaag ctacaaagcg ggagaacgtc atattatega gttcatggtc        1800
aacgcttcca agaaaaaat ggatattgac ggctggcgta tgaaggattt cagttctcac        1860
agttcagata cacttgccag atggagaaat tattatgagc aggatatttt caatgcacag        1920
cttcaggata ccatcacttt aaatcggaaa ggagatctgt ggttaacccc gagcattcgt        1980
tataatcgtt ctacaatact cggacgcagt gaacgctaca ataaaaagaa agatccgcaa        2040
aagtggaaat ttttcagccg gaagacaaaa caaccgatg ataaagtgac ttggcaagtc        2100
gcaatcaaaa aacaattcaa tgagcatttc accttgcgtg ctaccggagg aagctattat        2160
cgtctgttga atatgtatga aattgccgga gacggagcag gaattatccc tatgcccaat        2220
atcaaagggg atgaagtat cgaagaagga gggaaaactc atgttttttcc tatgccgaat        2280
gaaggaaaac aatgggatgt cagtgctatc tgggacggga ctgcattggg agcaaaggcg        2340
gccaagcttc aactgacata tttcggacga gattccaaaa gaattttgga actgggttcc        2400
tggaatcgtt ttttctttgt ttataccaat gccatcagtg ccaaggttca cggagcggaa        2460
atacaggga atttatcttg gaaaaaatgg gatctcaacc tacaggcaac ttataccaga        2520
cccagaaatg tagttgtatga caatagtgct ctgccggaag ctatattctg gaatggagga        2580
gtctttaagg gctttctgac atatcagccg aaatgggaag ggacggcaag aattacctat        2640
cgtccgaatc cacgttggag tatctttttct caatttcgtt atgtcggaga aatgattacg        2700
agcagaattc ctttggcaac gggagatttt atgcatcagt cttcactgac agcttgggat        2760
tgggaatcaa agtgtaaact aacgaacat tttcaaatcg ctcttggagt gatgatcta        2820
ttcaataaag caaacgatat gtatcataaa tataaaagca tcaattatca gaccaacatt        2880
caatatccta ttcagggaag aagctactat gcaagctttc aatacaaatt ttaa             2934

SEQ ID NO: 16          moltype = AA  length = 977
FEATURE                Location/Qualifiers
source                 1..977
                       mol_type = protein
                       organism = Fusobacterium necrophorum
SEQUENCE: 16
MKKENTGMWQ RILKIGMLSI ILLYWTDSLY AIETSENMQS TTMSVSGETV NFKMEGITVE         60
AKRPDWESKL SPGTVTVIRP DDYKGEQKDL PDFLKMVPGV HVREINGKGQ YTTVSVRGST        120
AAQVGVFVDG VLFNLGGDAA ADISTIPVHN VERIEVYRGY IPARFGGTFM GGVINIVTKK        180
PNRGNVSASV GRSSFGGKKA NLQFDLPLGS GTLMVGINHD ESKGNFKYKN FSYDRDKEYQ        240
KEVENAKSSE RGAIDNYNKA FKELKKYDFT DDSGNIFKVD TLEEATQIVK NNQDRWEKSL        300
QEAKNDIDNN FLKKKHIIAR FPGIPKEEIL PLLRSTHIDA EQALYESAFK EYSVNQGNNF        360
IPKWKDSSGN WVVPDRVEDY VEAYNKSHEI GYQHFQQIIA KGVQGDIERW IAKYGKSYAV        420
NYAQQAEYSV KEMEKHKKQA EAVKDHYRRR KANDYKNMDI ILKWQDEHWM AKATWKRIKR        480
HLPFPIDENY GNAPYIDTDL MANNPLSIFY HRNQKLTVQE FLFGRRDTFR NLEWGWSVNY        540
LKQEKDYYVD DWEWLEKNTG SLLNSYRPNT LWSKYDSHRW GAKLDGSYKA GERHIIEFMV        600
```

-continued

```
NASKEKMDID GWRMKDFSSH SSDTLARWRN YYEQDIFNAQ LQDTITLNRK GDLWLTPSIR    660
YNRSTILGRS ERYDKKKDPQ KWKFFSREDK QTDDKVTWQV AIKKQFNEHF TLRATGGSYY    720
RLLNMYEIAG DGAGIIPMPN IKGDGSIEEG GKTHVFPMPE EGKQWDVSAI WDGAALGAKA    780
AKLQLTYFGR DSKRILELGS WNRFFFVYTN AISAKVHGAE IQADLSWKKW DLNLQATYTR    840
PRNVVYDNSA LPEAIFWNGG VFKGFLTYQP KWEGTARITY RPNPRWSIFS QFRYVGEMIT    900
SRIPLATGDF MHQSSLTAWD LGIKCKLTEH FQIALGVNDL FNKANDMYHK YKSINYQTNI    960
QYPIQGRSYY ASFQYKF                                                  977

SEQ ID NO: 17            moltype = DNA  length = 1986
FEATURE                  Location/Qualifiers
source                   1..1986
                         mol_type = genomic DNA
                         organism = Fusobacterium necrophorum
SEQUENCE: 17
atgagaaaaa attttttatt ggcaagtttt ttggtatttg gagtaaatat agcttttgcg      60
gaagaaaacc cggtgttgac attgaacaa acgattgtga gtacggaatc ctttggaaca    120
tctgctcgaa agacaccaag aaatgtaaga gtgatgacag agaaagaaat taagagaaa    180
ggagccttga ccatagagga agctctcaaa ggacttccgg gagtgatagt cagaagaata    240
gatggctctg ctcctattat tgacttaaga ggaacaggta tggcttccag tatcagttcc    300
agtcttcttc ttttaaacgg agttccttta aatggactta ttgtatttga tattaattcc    360
attcctatca acgaagtgga aagaattgaa attattcaag aggaggagc tctgatgtat    420
ggggatggtg ccgttggtgg aatgataaat atcatcacaa aatctcctaa gaataagaaa    480
tattttggaa gtgtcaatct ggaacttggt tcttggaaga ctaaacgagc caatatcaat    540
tatgaatga aagtgggaga aaattatcg gtgaatgctt cctattctgg atattcctct    600
atggattatc gggacaggta tcatggaatg gattggacag acagtacct tgattaccga    660
aatcgagcgg ataagaaata ttctgttttg tttagcggaa agtatgactt acaagatgga    720
aatatagaat tacgctacaa tcatactgaa aatagagaca tctttgccgg ttcttttggat    780
aaaaaacaat ttcaagacaa tccaaaacaa accggcggtt ttggaaggga agtgaaaat    840
atatctgatg tttggaatct atcttatcag aaagcattga agaaaatttt agaattttca    900
cttattggag gacatcacca agacaagagt atccttttga atcaaatttc ttccgagtat    960
tttatcaaac cacaattaaa atatcgctat ggaaaaaata gttatcttat ttttggagga   1020
gattataaaa atggaaaacg tgtcttaag cacccctta ttacaaatca taaaaaagcc   1080
ccagatgata agagaaaagc tatggcattc tattttatga taaattttc caatggaaaa   1140
tggaattttt cacaaggata cagaagagaa agtagtagaa atgattatac ttccaaagcc   1200
tatagaaatc tttactattt atcagaagca aatccagttt cttcgcgttc ttctaataac   1260
aatagttttg aattgggagt aaattattta tattctgata caggaaatat gtatttcaat   1320
tacacaaggc tgttagaac tccaacaata gaagatgcta aaatttggta tggagaggta   1380
aagagtaaaa aaagtgatat tttgagata ggaatgagag actattcaa aaataccta   1440
atctcctcct ctatttttta tatgaatgca aaaatgaaa tttattatga tacgagagat   1500
atgttgcgta tcaaaagtag aaattttgat ggaacagtaa gacggattgg ggcacagtta   1560
gcattaagcc attacttgg gaaattcgtt ttgaaagaaa atatttctta tgttaatccc   1620
aaaattgtga gtggaccta aaaggaaaa agctttgtta cggtgccaaa ttggattttg   1680
aatctgggg cagcttatcg tttttcagaa caattttat taaatgcaga cttatatatt   1740
caatccaaaa tgtatgcaga agatgatttc gagaatattc ttggaaaaga taattcctat   1800
gtaactttga atatgaacgc atcctataag tttgataatg gaattgagat ttatgggagga   1860
attaaaaatc tgttgaatga agatatgcg gatacgatag cgataaatcc ttatccaagc   1920
cctaaaaatag catattatcc gggagatggg agaaatttt atatgggatt tcgatatcag   1980
ttttag                                                              1986

SEQ ID NO: 18            moltype = AA  length = 661
FEATURE                  Location/Qualifiers
source                   1..661
                         mol_type = protein
                         organism = Fusobacterium necrophorum
SEQUENCE: 18
MRKNFLLASF LVFGVNIAFA EENPVLTLEQ TIVSTESFGT SARKTPRNVR VMTEKEIKEK     60
GALTIEEALK GLPGVIVRRI DGSAPIIDLR GTGMASSISS SLLLLNGVPL NGLIVFDINS   120
IPINEVERIE IIQGGGALMY GDGAVGGMIN IITKSPKNKK YFGSVNLELG SWKTKRANIN   180
YGMKVGEKLS VNASYSGYSS MDYRDRYHGM DWTGQYLDYR NRADKKYSVW FSGKYDLQDG   240
NIELRYNHTE NRDIFAGSLD KKQFQDNPKQ TGGFGREVKN ISDVWNLSYQ KALKENLEFS   300
LIGGHHQDKS ILLNQISSEY FIKPQLKYRY GKNSYLIFGG DYKNGKRVFK TPLITNHKKA   360
PDDKRKAMAF YFMNKFSNGK WEFSQGYRRE RVEYDYTSKA YRNLYYLSEA NPVSSRSSNN   420
NSFELGVNYL YSDTGNMYFN YTRAVRTPTI EDAKIWYGEV KSKKKSDIFEI GMRDYFKNTL   480
ISSSIFYMNA KNEVYYDTRD MLRIKSRNFD GTVRRIGAQL ALSHYLGKFV LKENISYVNP   540
KIVSGPYKGK SFVTVPNWIL NLGAAYRFSE QFLINADLYY QSKMYAEDDF ENILGKDNSY   600
VTLNMNASYK FDNGIEIYGG IKNLLNERYA DTIAINPYPS PKIAYYPGDG RNFYMGFRYQ   660
F                                                                   661

SEQ ID NO: 19            moltype = DNA  length = 2907
FEATURE                  Location/Qualifiers
source                   1..2907
                         mol_type = genomic DNA
                         organism = Fusobacterium necrophorum
SEQUENCE: 19
atgagagtga agtattggt agacggaaac tcgatgactt cgattgatga agtatggga      60
gtgattcctt tcaattccat tcccgcagga agcattaaga gaattgaaat cattccgggg   120
ggaggaatca ctttatacgg aagcggaagt tccagtggag tcatcaatat tgtgaccaaa   180
atgggagaac ttaaaaatta tggaagcgta agcgtttcca caggttcctt tgacacctac   240
aaggcggaaa tcacaaaagg gatccgtatc aatcgatatt tgtttagtaa tctttcttta   300
```

```
gaggcgaaaa aaggaaaagg ataccgggac cgggagcaag ataaaagaat caatgcactt    360
ctcggactta acatcaattt tcatcccaaa catcgaatga aaattcaagg aagccatttt    420
caagaggacg cggaagggac caatgaattg tatttgacag aattacaaaa aaatcgtagg    480
ggagcgggag attctttttc taccatagat tcaaaacgaa ctgcccttc tattgattat     540
gaatacagtc cgacagaaaa ttggactcta actgccaatg tcaatcaatc gaaatttaca    600
cgggacattc gccaagattc tcacccttat ttgacttttt tgccttccat tgatttgagt    660
ttttatggag tgcctcaagg atatacagcg gaaatggttt ctgtgaatac tcccatggaa    720
ttaaaaggaa acatggaaga gaagattaag ggagcaagaa tcaaatcgga atatcgttat    780
gcggaacaaa aaggaaaatt tacatttgga gcggaacata gtgacatag cctacaccga     840
gatatgaata tggaagtgaa accttttcat cctttaaca gtatggcttt tttgattcat     900
aaagaagacg ataaaatttt tacggaagaa agattgaaaa atagtcatga acttatggat    960
attaattcag tttttttacc ttttattatt gagaaaaata atacacctac tttaaaggaa   1020
gagaaaataa ataatggaaa agaaaatttt ttatatcaaa aagctagtga agaagaaaaa   1080
aaagcttatg atgcgggggg aggaatagca gctttggcta attcttgta tgaaaaccaa    1140
ggaattatga attatgaatt ttcacatttc aagataaaaa attattttga tttggtggaa   1200
aaagatggga aaaaaggaat ttattatatt tttagagaga aaaaaaaggt agaaataact   1260
ttgccaaatg ggaaaaaaag aaaaaagaca gttactgtgg aaagacctga atttatgaa    1320
gtgaatgatg aaagtcgatt aaaagatatt cttaatttta tacaaaagga taaagtagat   1380
ccctctttaa cagtaaatac tttgataaca tcaaaaatag atgtaaaaaa gaaaacagat   1440
tctttctatt tacataacag ctatccgcta accgagaaat taactgtcaa tgcaggactt   1500
cgttatgaaa aggcaaagta tcatggaaat cgggaaacac agacaataca acgaattaca   1560
ggaaatgcgg ataagaaaga aacacaggat gctgtaaatt tatatatttc cgtttcggat   1620
gtggaatatt tgaaaaaaga tccaagaatc aattggaatg ctaatatcaa tgcagaaaca   1680
caggcaaagt taaagaatt gaaagaaaca ggaagcacac agattgtcat gtcacaatta   1740
ttccgaaaag aaaagagaga gaggaaaat ttgggtggag aaattggctt tgattataaa    1800
atcaatgata gtgatttggc atatgtgaaa tatgaaagac ttcaattc tccttacca     1860
aatcaactaa ccaataaaac ctatgacccg attcataaag tgaagacata tgggaaagt    1920
gatttgaaaa cggagaaaat ggataatttt gaaattggaa ttcgtggggc ttggaatgag   1980
catattacct acgattggc aggatttttg agtacaacct atgatgaaat tgtttctgtg    2040
gtaaaagatg gaaattccca tatgtcaaga gaatggaat ttatcaattt ggacaaaacg    2100
agaagaatgg gaatagaatt gcaatccgga caagtctttg ataaatggag attacgccaa   2160
tctttgactt atgtggatcc gaaagtgttg tccaatgatt ataaaaaaca agtggcaaga   2220
atcgcacagg agcagtccga tgcgatgata gacagtcatg agaaaattat gagaaacaat   2280
gtatatccaa ttcgtttaga cattgctgca tggaagggaa agatatcgga agctgagttt   2340
caaaaattga aacctcaaat tatggcatta acagatcatg gtttagaggg aaagatttca   2400
caagtggaaa tgaacgcaca gttggaaaaa ttattggaaa gtctttctaa tatggcgaag   2460
aaggaaatca aggaaacggt caaggcaaga tttacagacc gagatattta caagagcga    2520
gtggaaaagc aatttagaga acagtatcaa actgagggag aagctttat taaaaaagga    2580
gatagaatc cttggcacc gaaaatcaaa gcgacttttg gacggatta ccaatttaca     2640
aatcatttaa aaatgggaac aaatgtcact tatgtaggaa attatatgac agcggaacca   2700
agtaagggct atgaaattgt acaagtgaaa gttccttctc acttgctaac ggatttttat   2760
ggaagttatg agtttgacag cggcttttct ataaaattcg gaattaacaa tgtcttcaat   2820
cataagtact atttaagaca gattccagaa acggcaacac ctgcaccggg aagaacttac   2880
agtgcaggat ttagttatcg tttttaa                                       2907
SEQ ID NO: 20            moltype = AA   length = 968
FEATURE                  Location/Qualifiers
source                   1..968
                         mol_type = protein
                         organism = Fusobacterium necrophorum
SEQUENCE: 20
MRVKVLVDGN SMTSIDESMG VIPFNSIPAG SIKRIEIIPG GGITLYGSGS SSGVINIVTK     60
MGELKNYGSV SVSTGSFDTY KAEITKGIRI NRYLFSNLSL EAKKGKGYRD REQDKRINAL   120
LGLNINFHPK HRMKIQGSHF QEDAEGTNEL YLTELQKNRR GAGDSFSTID SKRTALSIDY   180
EYSPTENWTL TANVNQSKFT RDIRQDSHPY LTFLPSIDLS IFVVPQGYTA EMVSVNTPME   240
LKGNMEEKIK GARIKSEYRY AEQKGKFTFG AEHSEHSLHR DMNMEVKPFH PFNSMAFLIH   300
KEDDKIFTEE RLKNSHELMD INSVFLPFII EKNNTPTLKE EKINKWKENF LYQKASEEEK   360
KAYDAGGGIA ALANSWYENQ GIMNYEFSHF KIKDYFDLVE KDGKKGIYYI FREKKKVEIT   420
LPNGKKRKKT VTVERPEFME VNDESRLKDI LNFIQKDKVD PSLTVNTLIQ SKIDVKKKTD   480
SFYLHNSYPL TEKLTVNAGL RYEKAKYHGN RETQTIQRIT GNADKKETQD AVNLYISVSD   540
VEYLKKDPRI NWNANINAET QAKLKELKET GSTQIVMSQL FREKREEEN LGGEIGFDYK    600
INDSDLAYVK YERAFNSPLP NQLTNKTYDP IHKVKTYWES DLKTEKMDNF EIGIRGAWNE   660
HITYGLAGFL STTYDEIVSV VKDGNSHMSR EWRFINLDKT RRMGIELQSE QVFDKWRLRQ   720
SLTYVDPKVL SNDYKKQVAR IAQEQSDAMI DSHEKIMRNN VYPIRLDIAA WKGKISEAEF   780
QKLKPQIMAL TDHGLEGKIS QVEMNAQLEK LLESLSNMAK KEIKETVKAR FTDRDIYKER   840
VEKQFREQYQ TEGGSFIKKG DRIPLAPKIK ATFGADYQFT NHLKMGTNVT YVGNYMTAEP   900
SKGYEIVQVK VPSHLLTDFY GSYEFDSGFS IKFGINNVFN HKYYLRQDSR TATPAPGRTY   960
SAGFSYRF                                                            968

SEQ ID NO: 21            moltype = DNA   length = 3315
FEATURE                  Location/Qualifiers
source                   1..3315
                         mol_type = genomic DNA
                         organism = Fusobacterium necrophorum
SEQUENCE: 21
atgagaaaag aaatgctttt gacattgttg tgttttgttt ctttgcatgc tatggcagca     60
acacaggaag tggagttgaa cccgacaaaa attcgaggag gggggcgac ctataatggc    120
tcggttctct ccaatgaaaa gaaaaatgta atcatcatta cgaaagcaga tattgaaaag   180
aaaaattata gagatttgga atctattttt aaggattctc cggttacttc tgtcgttat    240
```

```
                                                      -continued
acggaggcgg gtcctttggt caccttaaga ggaagtggac aaaagacggc aatgagagtt    300
aaagtactct tagatggcgt ttccatcaat accgtggatg attctatggg agtgattcct    360
ttcaacgcca ttccggttgc cagtattgaa aaaattgaaa ttattccggg aggagggatt    420
actcttcacg gttccggaac ttccagcgga gtcatcaaca tcgtgacggg aaaatcgagt    480
aagaaagatt atggagagct tggttttact gtaagttctt tcaatactta caatacaacc    540
ttcaataagg gaatttcctt tggagataag ctgtattgga atattggagt ggaagcggaa    600
aaaggaaagg catatcgaga gaagaggat agtaaaaaga taaatctgct gtccggaatc    660
aactataaaa tcaatgaaaa acatcaaatt aaattacatg gaagtaaata ttggtcggat    720
tttaacggaa caaatgaatt ggatcttatc agtttgcaaa aaaatcgaag aggggcagga    780
aaatcagatg ccgaagtaaa gtcaaatcga tattcccttt ctttcgatta tgaatataaa    840
cctacagaag atttgaccgt tacttccgga tacaatcaac aaaaatttcg aaggaatttt    900
acacagaaca caaaccttac tcttactttc ttatcgtcgg aatgggtgga agatatgttt    960
ggaattcccg acggaatgaa tgcagattca gtcattaaaa atgtaaataa ccattaacg   1020
ggacgtattg aagaaaaaat aaaaaatgga aaagtcaaag tggactggaa acacagtaa   1080
aatcgtggaa aattaacttt tggatatgat tattcttctc atgaattaaa acgaagaatg   1140
aatgtacaag ttgatgcttt taatccgatc gataataatt actttttttt gagaaaaaaa   1200
gaggagagaa ttatcaatga agaaatttta gaacaacatc cggatcagtt aatgcatttt   1260
ttcgataaca ctttagccgc aattctaata tttgatcctg attctatgga tagttatggg   1320
ctagattctg ttaaactaaa gaaaaaaata gacgaactct attatcattt gactacttcg   1380
gaaaaagata gaaaaaata tgaaatgga gaagaaaatc cttgggatta ttgggaaacc   1440
atcaaaccga atatgtggaa aatgatttat catttgacag aagaaaagat tcaagagtat   1500
gcaaaagacg gaaaaatat tcttaagaga gaagatgaaa tgattggga ttctgaacca   1560
agcgttcagg ttccgattga ggggaaaaaa ttttaagaat tttaagatt gattattcct   1620
agtatgtatg accccgattt tagtatgaca ccaatcacgc aaagtatggt agatgtgaag   1680
aagacaacga attcctttta tctatttgac agctataaac ttactgatcg tttagaaatc   1740
aatggaggtt tgcgatatga aaaagcaaaa tactccggaa atcgttatac aaaaacgaa   1800
caatttatca aggaaatgc ggagaataaa tctaccaact ctatgatagc gatgtataccg   1860
gaattgtcag aagcggaatc ggcaaagaaa aacataggag atactcatca ctggaatgga   1920
aatgatactt ccaaagaaaa aataaaagaa ctgaaagaaa aaggatata ccattta    1980
atgacggatt taactcgaaa agagaaaaga gaagagaaa atctgggagg agaaattggg   2040
attaattacc gtttcaatga tacagacaca gtatatttaa aatatgaaag aggcttaat   2100
actcctcttc ctacacaatt gaccaataaa acctttgatc cgaaaaccaa gataaaagca   2160
tattgggaaa gcaatataaa gacagaaaaa atagacaatg tagaactggg aattcgagga   2220
atgttacacc caaagtgac ctattctttg acaggattta tcagtgatac tcaaaatgaa   2280
attctatcca ttgtgaagaa tggaagttct catatgctcc gagaatggag atttatcaat   2340
attgataaaa cgagaagaat gggactgag ttccaatctc aacaaaattt tgataaattg   2400
actttaaaag aatctcttac ttatgtggat ccaagattc tatccaatga ttatgaaaaa   2460
caggttcata aaattggagt ggacagagcg gaggaaatgt accaaaacaa tcaaaaagta   2520
cgagattgga caattgaaaa tatcagattt catgaaaatg gctttacaat tccggcagga   2580
acttcggaag aagaaattgt aaaaatgaag gcgagtcca agcgattggg aaaagaagcg   2640
gttaaaatca ttcaaaaact aagagagaca ggagtaaaag tggactatag tgcacgagat   2700
gccaaactga aagaaattgt tccgggaatg tcttctgccg aacaatctaa gattagaatg   2760
gaagcttcaa aattagcaca agaagctgaa aatagagctg tggcagaacc tagaaagcc   2820
ttggaagatc ttcttgcaaa ctcagcttat cctgacattt ttaaagaaaa attgcgttca   2880
ttcaataacc ataccttaat tcaggaagga acgatgaaaa aaattattta tgaacatttt   2940
gaaaaagaga taaagtcttc ttatacgaaa ggaaccttag aaaagggaag cagaatcccg   3000
ctttctccaa aatggaaagg aactttcagt gcggactatc aattcacgga taggttaaaa   3060
ttaggaatga atactactta tataggaagc tatgattccg cggaaccggg aaaaggatat   3120
gaaattgtaa tgacaaaagt accgcatcat atggtagccg atttctatgg aagttatgat   3180
attcaggaag attttccat taaattcgga attaacaatg tatttaatca tcaatattat   3240
ttacgacaag attccagaac ggcaactccg gcacccggaa gaacctacag tgcgggattc   3300
agttatcgat tttaa                                                    3315

SEQ ID NO: 22       moltype = AA   length = 1104
FEATURE             Location/Qualifiers
source              1..1104
                    mol_type = protein
                    organism = Fusobacterium necrophorum
SEQUENCE: 22
MRKEMLLTLL CFVSLHAMAA TQEVELNPTK IRGGGATYNG SVLSNEKKNV IIITKADIEK      60
KNYRDLESIF KDSPVTSVVY TEAGPLVTLR GSGQKTAMRV KVLLDGVSIN TVDDSMGVIP    120
FNAIPVASIE KIEIIPGGGI TLHGSGTSSG VINIVTGKSS KKDYGELGFT VSSFNTYNTT    180
FNKGISFGDK LYWNIGVEAE KGKAYREKED SKKINLLSGI NYKINEKHQI KLHGSKYWSD    240
FNGTNELDLI SLQKNRRGAG KSDAEVKSNR YSLSFDYEYK PTEDLTVTSG YNQQKFRRNF    300
TQNNKPYLTF LSSEWVEDMF GIPDGMNADL VIKNVNNHLT GRIEEKIKNG KVKVDWKHSN    360
NRGKLTFGYD YSSHELKRRM NVQVDAFNPI DNNYFFLRKK EERIINEEIL EQHPDQLMHF    420
FDNTLAAILI FDPDSMDSYG LDSVKLKKKI DELYYHLTTS EKDKKKYENG EENPWDYWET    480
IKPNMWKMIY HLTEEKIQEY AKDGKNILKR EDENDWDSEP SVQVPIEGKK FKEFLRLIIP    540
SMYDPDFSMT PITQSMVDVK KTTNSFYLFD SYKLTDRLEI NGGLRYEKAK YSGNRYTKTE    600
QFIKGNAENK STNSMIAMYT ELSEAESAKK NIGDTHHWNG NDTSKEKIKE LKEKGYTTIL    660
MTDLTRKEKR EEENLGGEIG INYRFNDTDT VYLKYERGFN TPLPTQLTNK TFDPKTKIKA    720
YWESNIKTEK IDNVELGIRG MLHPKVTYSL TGFISDTQNE ILSIVKNGSS HMLREWRFIN    780
IDKTRRMGLE FQSQQNFDKL TLKESLTYVD PKILSNDYEK QVHKIGVDRA EEMYQNNQKV    840
RDWTIENIRF HENGFTIPAG TSEEEIVKMK AESKRLGKEA VKIIQKLRET GVKVDYSARD    900
AKLKEIVPGM SSAEQSKIRM EASKLAQEAE NRAVAEPRKA LEDLLANSAY PDIFKEKLRS    960
FNNHTLIQEG TMKEIIYEHF EKEIKSSYTK GTLEKGSRIP LSPKWKGTFS ADYQFTDRLK   1020
LGMNTTYIGS YDSAEPGKGY EIVMTKVPHH MVADFYGSYD IQEDFSIKFG INNVFNHQYY   1080
LRQDSRTATP APGRTYSAGF SYRF                                          1104
```

| SEQ ID NO: 23 | moltype = DNA length = 1941 |
| --- | --- |
| FEATURE | Location/Qualifiers |
| source | 1..1941 |
| | mol_type = genomic DNA |
| | organism = Fusobacterium necrophorum |

SEQUENCE: 23

```
atgaaaaaaa agttaatgat tttggcaatt ttaagtattt cagtttcagc atttgctatg    60
aaggaggaaa ttcctgtgca aagattaaat gaaacagtaa taacaactcc tgaaagattc   120
ggtacaaagg ttagaaatat atcaaaaaat atacaaataa ttacaaaaaa agatatgaag   180
gaaaagggg caaaaaacct ttttgaggca ttgagaggac tcccaggagt agttatacgt   240
agagatggag gaggacatat agatcttcgt ggttctggag aaaatgataa aaaaaatatg   300
atatttttaa tagatggaat acctatagt ggattaagta tatttgacat taattctatc   360
tcaatggaag aaattgaaag aattgaaatt atccaaagtg gtggtgtttt atatggagat   420
ggagctatag gaggagttat aaatttagtt actaagcgta ttactactgg aaaatacgt   480
aatagcattg gtttggaata cggctcttgg gaaacggcta aattaaatgt aaatgtcgga   540
actaaattaa cagataattt tgttgtaagt gtttcttact ctggtgaaca aactgaagaa   600
tataaaaata gaagcatga tttcaaagat aaaaaagata gccgggaatc tatttggtta   660
aaaactaaat ataatttaaa tgatggggaa attgagttaa aatataatca tttgaaaaac   720
aatgactaca tcacaggact tctatcagca aaagacttta agaaaatcc taaaaaagca   780
ggtacaacaa atgcttcttt taagctgaa tcagatttat ggaacctatc ttttaataaa   840
aaattaaata gtaagtttga agttttctta caaggtggat attatactga tgaaacaaaa   900
tactatgaaa taggtccagg atatgcagat ttttcaaaaa atggaaataa aagtcatttt   960
ataagacctc aaataaaata taattatatg gaagatagtt gcatcatatt aggaggagat  1020
agaaaaaaag aaactgttac taataaatta tctccaaatt ctcctaaaac tataaggaaa  1080
aaagaatcta tttacttatt aaatagtaat aagataggaa actttgaaat tacagaagga  1140
tataagaatag aaaaaattga tttaaaaaga aagataggaa ctaaagactt taaagaagat  1200
ggaatggaat taggaataaa ctatctttat tcagatactg gaaatcttta ttttaattac  1260
acaaaaggat ttagagtacc tacattgggg gaaatgaata gttgggttgg tgatatgaaa  1320
tcacataaaa atcatacttt tgaattaggt ttaagagatg tatatgaaaa tacttctata  1380
aatacttcta ttttcacatt gtattccaaa gatgaaatct tttatgatag tttagttgca  1440
aacccttcac aaaaaatcc taatagaaaa gggagcaata gaaacttttga aggtaaggtt  1500
agaagaatag gtgcacagtt agcttttaga acacaatattg gtaaattatc attaagagaa  1560
aaaatttctt acatggatcc taaaataatt gatggatatt ataagagaa agttttcccg  1620
ggagttccta aattaacagc agcactaggt ttaacttata attttgaaaa ttcccttaaa  1680
ttaaatattg atgggtatta tcaagaaaaa atttatgccg aactgatttt ttaaataaa  1740
tatggtaaac acaatagtta tacagtagta gatgctaata tttcatatac ttttgaaaat  1800
ggtttggaac tttatggtgg agttaaaaac ttatttgata aaacatatgc tactgcctt  1860
ttcccaagag caacaggaga attaagatat gatccagata tggaagaag ttttacact  1920
gggtttaagt tactttttta a                                           1941
```

| SEQ ID NO: 24 | moltype = AA length = 646 |
| --- | --- |
| FEATURE | Location/Qualifiers |
| source | 1..646 |
| | mol_type = protein |
| | organism = Fusobacterium necrophorum |

SEQUENCE: 24

```
MKKKLMILAI LSISVSAFAM KEEIPVQRLN ETVITTPERF GTKVRNISKN IQIITKKDMK    60
EKGAKNLFEA LRGLPGVVIR RDGGHIDLR GSGENDKKNM IFLIDGIPYS GLSIFDINSI   120
SMEEIERIEI IQSGGVLYGD GAIGGVINLV TKPITTGKYS NSIGLEYGSW ETAKLNVNVG   180
TKLTDNFVVS VSYSGEQTEE YKNRSIDFKD KKDSRESIWL KTKYNLNDGE IELKYNHLKN   240
NDYITGLLSA KDFKENPKKA GTTNASFKAE SDLWNLSFNK KLNSKFEVFL QGGYYTDETK   300
YYEIGPGYAD FSKNGNKSHF IRPQIKYNYM EDSCIILGGD RKKETVTNKL SPNSPKTIRK   360
KESIYLLNSN KIGNFEITEG YRIEKIDLKR KNRAKDFKED GMELGINYLY SDTGNLYFNY   420
TKGFRVPTLG EMNSWVGDMK SHKNHTFELG LRDVYENTSI NTSIFTLYSK DEIFYDSLVA   480
NPSPKNPNRK GANRNFEGKV RRIGAQLALE HNIGKLSLRE KISYMDPKII DGYYKEKVFP   540
GVPKLTAALG LTYNFENSLK LNIDGYYQEK IYAGTDFLNK YGKHNSYTVV DANISYTFEN   600
GLELYGGVKN LFDKTYATAF FPRATGELRY DPDNGRSFYT GFKYTF                  646
```

| SEQ ID NO: 25 | moltype = DNA length = 1992 |
| --- | --- |
| FEATURE | Location/Qualifiers |
| source | 1..1992 |
| | mol_type = genomic DNA |
| | organism = Fusobacterium necrophorum |

SEQUENCE: 25

```
atgaaaaaaa attttactt actgtctatt ttcatgttgg caactgttca acagttttt    60
ggaaaagagg atcccactgt gacattggag caaacaattg tcagtatgga ttcttttgga  120
agttctcccc acaggactgc aaaaaatgtt cgtgtggtta ccaagaagaa aataaaagaa  180
aaaggagctt tgaatgtaga agatgctttg aaggggagcc cggggcttct catacggaac  240
ttggatggag ctcctccggt cattgattta aggggagccg gagcttc cagtttgact  300
tccactctgt tgcttctcaa tggagttccc ttaagtggag ttcgagtttt tgatgtcaat  360
tccattcctg tttctgaaat tgagagaatt gaaatcattc agggaggagg agcttttgatg  420
tatggagacg tgctgcggg aggagttgtc aacattatca cacagacgat gaagaatata  480
aaatatatgg aaatgtcga tttggaatat ggttcttgga aacgggaag aattcatttg  540
ggaataggga gtcaaatgga gaaaaacttt ctctccaaga cttcctattc aggatattct  600
tctatggatt ggagagatag agcacatggg attgacatga gcggaaagac tttcgactac  660
agacataaaa aagataggaa agacagtttt tggttgagtg gaaaaagga agggaaagac  720
caaagtattg aattacgtta cagtcatatg aaaagcaaag actattttac cactttttctg  780
aacaaaaaac agtatgaaga aaatccgaaa caagcggaa tgcaggtaa ctacatagag  840
gatgtcacgg atatctggaa tctatccat cgtaaaaaat ggaatgataa gcttgatttt  900
```

```
ttactttatg gaggctatca tcacggaaaa aatgaaaatc aacatttttct aatggaagaa   960
tattttgtga ctccgcagat aaagtatctc tacggaaaca atagctatgt catcgtcggt  1020
ggggacatta gaaacggaaa aagggaatgg aaggatacct tcctatcgaa tggaaaaaag  1080
gctccgaacg ataccagaaa atcgaaggct ctctatctca tgaataaaat taccgttaag  1140
aattgggaat ttacacaagg ctatcgaaga gaaagggtaa attatgatta cacttccaaa  1200
gtttacggtc ctgtttggaa tttgttggaa gcaaatcctg tatcctccac ttcttccaat  1260
aacaacagtt ttgaactggg agtcaattat ctttattccg acagcggaaa cttgtatttc  1320
aattacacaa attcgatgag aactccaagt atcggggata tggaggcatg gaccggagat  1380
gtgaaaacga aaaaagacag tatttatgaa ctgggatggc gagattatct tgcgaacact  1440
ctttttctcga cttctatttt ctggatggat actcgaaatg aagtatatta cgataaaacg  1500
ggattgtatc aagtcaaaac aagaaatttt gatgggaaaa caagaagaag gggagctcaa  1560
atctccttga ttcattattt ggataagctg tccctacgag aaaatatctc ctatatccat  1620
cccaagatag aaagtggaat ctatcaaggg aaaacgttcc cggaagttcc gaaatggatt  1680
gtgaatttgg gagccagcta tcatgttaca gaacaattac atatcaatac ggatgtatat  1740
tatcaatcga aggcttatgc tgacgacgat tttaaaaatg aatttttcaaa agaaaattct  1800
tacacaacat gggaccttca tctttcctac cgttttcaaa atggaatgga aatttatggg  1860
ggagctaaaa acctattcga taaaaaatat gctcacagtg tagcgattat gcgaagtcct  1920
tttgcttctc agaaggtata tcatccggca aatggaagaa atgtctatgt aggatttaaa  1980
tatcgttttt aa                                                      1992

SEQ ID NO: 26          moltype = AA  length = 663
FEATURE                Location/Qualifiers
source                 1..663
                       mol_type = protein
                       organism = Fusobacterium necrophorum
SEQUENCE: 26
MKKNFYLLSI FMLATVQTVF GKEDPTVTLE QTIVSMDSFG SSPHRTAKNV RVVTKEEIKE   60
KGALNVEDAL KGIPGLLIRN LDGAPPVIDL RGAGMASSLT STLLLLNGVP LSGVRVFDVN  120
SIPVSEIERI EIIQGGGALM YGDGAAGGVV NIITQTMKNK KYYGNVDLEY GSWKTGRIHL  180
GIGGQMEKNF SLQASYSGYS SMDWRDRAHG IDMSGKTFDY RHKKDRKDSF WLSGKKEGKD  240
QSIELRYSHM KSKDYFTTFL NKKQYEENPK QAGMTGNYIE DVTDIWNLSY RKKWNDKLDF  300
LLYGGYHHGK NENQHFPLMEE YFVTPQIKYL YGNNSYVIVG GDIRNGKREW KDTFLSNGKK  360
APNDTRKSKA LYLMNKITVK NWEFTQGYRR ERVNYDYTSK VYGPVWNLLE ANPVSSTSSN  420
NNSFELGVNY LYSDSGNLYF NYTNSMRTPS IGDMEAWTGD VKTKKDSIYE LGWRDYLANT  480
LFSTSIFWMD TRNEVYYDKT GLYQVKTRNF DGKTRRRGAQ ISLIHYLDKL SLRENISYIH  540
PKIESGIYQG KTFPEVPKWI VNLGASYHVT EQFHINTDVY YQSKAYADDD FKNEFSKENS  600
YTTWDLHLSY RFQNGMEIYG GAKNLFDKKY AHSVAIMRSP FASQKVYHPA NGRNVYVGFK  660
YRF                                                                663

SEQ ID NO: 27          moltype = DNA  length = 1980
FEATURE                Location/Qualifiers
source                 1..1980
                       mol_type = genomic DNA
                       organism = Fusobacterium necrophorum
SEQUENCE: 27
atgaaaaaat tattcttact attttctttg attgcctgtt ccaattcggt ttactccgaa    60
atcatccatt tgggggcaag tgacatttac tctgatactg gttatgcgac caatataaga   120
agtacgactt catctccttt tataataact gcaaaagaaa ttcaggaaaa aaggttttgca  180
agtctctctg aaattttggc aagtcttccg ggaatcacta cgagagggg atacgaacct   240
gaaattgatt tgagaggaca gggatactcg aaagcaaggg caaccattca ggtcatgata   300
gacggttgtgc ctgtcaatat gctgattctc tctcatagaa aagttcccttt aaatactgta  360
aatccgaatc aaatcgaacg aatcgaagtc attccgggtg gaggagctgt tttatatgg    420
aatgaacgg caggcggtgt catcaatatt cttactaaaa aacatcgagg aaatttttgga  480
aatataggct atcgttatgg aagttttgga gatcgtaaat acgatattgc cgcaggaacc   540
agtttaggaa acttttgactt tgctcttgat tattccataa aagataaaaa cggctacgaa   600
agaaattctc cttccgattc ggattatttt tctgccagaa ttgcttataa cttcaataaa   660
aatgatacaa ttgctctaaa atacagagga tatagaacag gtataaaaca gtacaacggt   720
ttaagcaaaa agcaagtaca ggaagacaga agacagaacg gaatggcccc cggacaaaaa   780
ggttccactg atagaaagtt ggatgaatac agttttcaatt ttcataaagg agtaggaaaa   840
aacaacgatc ttagtttcca tgcctataaa ctagaaagcg atataaaaac aagtacacaa   900
actccaaaat taacgagaat tgtaaaagcg aagataata gatcaggagt aaaaatcaaa   960
gataaattga attatggaaa tggtaacaac attattatcg gtgcaggtta taccaatcat  1020
accatgtttt taagcaacat aaaagtagag aaaaagactc tggaaagctt cgccttgaac  1080
acattgaaat tcggaaaact tgaattttca caaggattga gattgaaaa atccaaatat  1140
caaggagatg ccgccaaagc tttcggatta aaagtggaaa aacttctaaa acactggaag  1200
aactatggtc cttccctagc tcttaattat ttgtattctc atgcaggaaa tgtatatgtg  1260
aaatatgaga gagcttttaa tactcctgcc ccttttacaaa ccataaaaaaa tattaactgg  1320
caaacctata acagtgatgc aaaatcagaa aaagtaatac tctgatgaaa acggcttccga  1380
gactatattc taaattccat agtcagtgct tccgcttatt atagtgaaac cgcaaatgaa  1440
ttaaaaacag tttggttagg tagccatttc catgatcttt ccaattttaa taccatcaac  1500
tatgaaagaa caaagagata cggattcgat ttgaaggcgg aacagaaatt tgaaaaattc  1560
agaatttcag aatcctattc ctttgtaaat gctaaaatca taaaagtgg ggaaactgcc  1620
agtcaaaaag caacggaagg aaaaatatatt cctgatgttc cgaaacacaa gtttgtactt  1680
tcgactgatt atgatttttaa tgaaaaattc tctattggag caagctatca ataccaagct  1740
gctgcatata ttgactctcg aaacagcttg ggaaaagaag gaaaaaaatc aattgtgaat  1800
ttgagagcaa actataaatt caatgatcat ttccacatttt atgccggaat taaaaatcta  1860
tttaatgcaa aatactatga ttctgtgggt tatactactg ccaaaccaaa taggatatat  1920
aaggtttaca accctgcacc aagcagaaat tactatatgg gatttgatta taaattctaa  1980
```

```
SEQ ID NO: 28            moltype = AA  length = 659
FEATURE                  Location/Qualifiers
source                   1..659
                         mol_type = protein
                         organism = Fusobacterium necrophorum
SEQUENCE: 28
MKKLFLLFSL IACSNSVYSE IIHLGASDIY SDTGYATNIR STTSSPFIIT AKEIQEKRFA    60
SLSEILASLP GITIREGYEP EIDLRGQGYS KARATIQVMI DGVPVNMLDS SHRKVPLNTV   120
NPNQIERIEV IPGGGAVLYG NGTAGGVINI LTKKHRGNFG NIGYRYGSFG DRKYDIAAGT   180
SLGNFDFALD YSNEDKNGYR RNSPSDSDYF SARIAYNFNK NDTIALKYRG YRTEYKQYNG   240
LSKKQVQEDR RQNGMAPGQK GSTDRKLDEY SFNFHKRVGK NNDLSFHAYK LESDIKTRSQ   300
TPKLTRIVKA EDNRSGVKIK DKLNYGNGNN IIIGAGYTNH TMFLSNIKVE KKTLESFALN   360
TLKFGKLEFS QGLRFEKSKY QGDAAKAFGL KSGETSKTLE NYGASLALNY LYSHAGNVYV   420
KYERAFNTPA PLQTIKNINW QTYNSDAKSE KSNTYEIGFR DYILNSIVSA SAYYSETANE   480
LKTVWLGSHF HDLSNFNTIN YGKTKRYGFD LKAEQKFEKF RISESYSFVN AKIIKSGETA   540
SQKATEGKYI PDVPKHKFVL STDYDFNEKF SIGASYQYQA AAYIDSRNSL GKEGKKSIVN   600
LRANYKFNDH FHIYAGIKNL FNAKYDSVG YTTAKPNRIY KVYNPAPSRN YYMGFDYKF    659

SEQ ID NO: 29            moltype = DNA  length = 2145
FEATURE                  Location/Qualifiers
source                   1..2145
                         mol_type = genomic DNA
                         organism = Fusobacterium necrophorum
SEQUENCE: 29
atgaaaaaag tggtatttgg gatttacagt atccttaatgt cctctgctat gcttggagca    60
gaaattgatc ttgaacacac gaatatctat tcggaaatcg gatttgaaac gagtcttcga   120
agctctgttt cttctcctta tatcgttact tcaaaagaaa tcaaagaaaa acattatacc   180
cgtgtttctg aaattttgag agatattccg catatctaca tcggtcccgg tgcagtgta    240
gatatgcgtg gtcagggaag tgctcatgcc agaacaacga ttcaactgtt aattgatgga   300
gttcctgcca atttttgga tacttcccac atcaatcttc ctatcgatac tttaaatcca   360
gaagatatta agagaattga agtcatccct ggaggaggag ctgttttata tggaagtgga   420
acttccggag gagtgatcaa catcattacc aaaaaatca cgggaaacta tgcaaaggca   480
agctatcaaa taggaagcta tcacaatcat aaatatgacg tagctgccgg aacttctttg   540
ggaaattttg acattaacct aagttattca aaaaataata gggatggata tcgtaaaaaa   600
gccttttccg attccgattt cttctccgga aaattacgtt atcacttcaa tcccacagac   660
agtcttgaat tcaaatatag ctattttgat aataagttca gaggtgttaa atccctaacc   720
agagaacaag tcgagaaaga tcgaaggcaa agtggtcttt ctcctgaaga caatttgaaa   780
aataccatcc gaaaagaaga atggaattta acttacgatg caaaatggac aagctggctg   840
gaacacaaat ccaatctttt ctatcagtcc acagaaataa aatctagtga atatgaagat   900
gctcttcctt tctatcaata tcaaatttct tcttatcaaa aaatgcttac tatgccaggg   960
attcctccta tgatgcaagc acaattgaaa aagcagataa aagccctaca aaatttgata  1020
acgagtaatc caaggatgga attacatcaa ggaagtcgtt tcaaagatca aaaattcggt  1080
tttaaaatga agaataaatt taagtatgga gaaaatagta attttatttt aggtttggga  1140
tacattcaca acaaaatgga tcgagattct tgggcttata cgaaaaatac gcaaacgaat  1200
caaacaatag caactcttac aaatactaaa attccttta ataagaaaac attcgaaatt  1260
ttcgattaa ataccatcg tcataataat tgggaatttg ttcagggctt acgctttgaa  1320
aaagcgaaat ataatggaaa aagacaatat aaaaaatctg aatatcctt aaaaagatcgt  1380
agcatgaata atgttgcggc aaatctggct gtcaattatc tctattccga tacaggaaat  1440
gtctatgtaa aatatgaaag aggatttact tctcctgctc ctgcacagtt aatggataaa  1500
atcagaaaag gaggagtgaa cgattatgtc aataatgatt taaaatctga aaatcaaac  1560
tcctttgaag ttgatggaa tgactatctc ttccattctt tagtcagtgc tgatgttttt  1620
ttcagtgaaa cgaagatga aatttctacc atattctcgg gagggcatgg gacaacattc  1680
agcaatttga accttggtca acgaaacga tatggttttg atctaaaagc cagtcaagtt  1740
tttgaaaagt ggacattctc ggaagcttac agttatatcc atgcaaaaat catgaaagat  1800
aaaacaaagg cttatgaagg aaaatatatc agttatgttc caaggcataa attttcttg  1860
aatgctgatt atgcaatcac tccaaaatgg actcttgggg agaaatcca atacagttcc  1920
tccgtatatc tggacaatgc aaataaaaat ggaaaagatg gagcgagatc tgtttttaat  1980
cttcaaacct cttatgagtt caattcacat ttttctatct atgcaggaat taaaaatgtg  2040
ttaaatcata gtattatga atctgtcagt gcaggttcca gtcaaaagta ttatagtccg  2100
gctccggaaa gaaattacta tgccggatc cgttatcaat tttaa                   2145

SEQ ID NO: 30            moltype = AA  length = 714
FEATURE                  Location/Qualifiers
source                   1..714
                         mol_type = protein
                         organism = Fusobacterium necrophorum
SEQUENCE: 30
MKKVVFGIYS ILMSSAMLGA EIDLGTQNIY SETGFETSLR SSVSSPYIVT SKEIKEKHYT    60
RVSEILRDIP HIYIGPGGSV DMRGQGSAHA RTTVQLLIDG VPANFLDTSH INLPIDTLNP   120
EDIKRIEVIP GGGAVLYGSG TSGGVINIIT KKYTGNYAKA SYQIGSYHNH KYDVAAGTSL   180
GNFDINLSYS KNNRDGYRKK AFSDSDFFSG KLRYHFNPTD SLEFKYSYFD NKFRGVKSLT   240
REQVEKDRRQ SGLSPEDNLK NTIRKEEWNL TYDAKWTSWL EHKSNLFYQS TEIKSSEYED   300
ALPFYQYQIS SYQKMLTMPG IPPMMQAQLK KQIKALQNLI TSNPRMELHQ GSRFKDQKFG   360
FKMKNFKYG ENSDFILGLG YIHNKMDRDS WAYTKNTQTN QTIATLTNTK IPLNKKTFEI   420
FGLNTYRHNN WEFVQGLRFE KAKYNGKRQY KNLEYPLKDR SMNNVAANLA VNYLYSDTGN   480
VYVKYERGFT SPAPAQLMDK IRKGGVNDYV NNDLKSEKSN SFEVGWNDYL PHSLVSADVF   540
FSETKDEIST IFSGGHGTTF SNLNLGQTKR YGFDLKASQV FEKWTFSEAY SYIHAKIMKD   600
KTKAYEGKYI SYVPRHKFSL NADYAITPKW TLGGEYQYSS SVYLDNANKN GKDGARSVFN   660
LQTSYEFNSH FSIYAGIKNV LNHKYYESVS AGSSQKYYSP APERNYYAGF RYQF         714
```

```
SEQ ID NO: 31            moltype = DNA  length = 1410
FEATURE                  Location/Qualifiers
source                   1..1410
                         mol_type = genomic DNA
                         organism = Fusobacterium necrophorum
SEQUENCE: 31
atgaatttaa aattaaaatg tatattactt agtagtctac taagcatgac agcatatgga    60
gcatccatag accatattca aacgtatgca ccagaatatt taggaaatca agctcaaaat   120
ggagcaatta acggagtttc tccttattac aatcctgccg gaactactca gctagaagaa   180
ggattctata tcaatggtgg attacaaata gcagctggac atgagcaatc agaatacaaa   240
gagaaagaat ataaagctat ttttatacaa cctgttccaa gtattgcatt gacgaaagta   300
aacaaagata gttcgactta ttttactttt agtgctattg cggaggagga acattaaac    360
tataaacatg gagtagtagg aactgcaatt attcctgatt tagtggcaaa tttaaaagtc   420
ggatatttaa attcagctgc ttttggtatg ccaacaattc catctacatt agctggaaaa   480
aaagtggcag ttcaagtttt agatggaaca agagcaaaag gaagtaatct atacagtcaa   540
atgacattag gaaaagcatt tcaagtgaat gataaaattat ctctttctgc aggaattcga  600
tttgtacatg gaagaagaga tttagaggga aacattaaat taaaagcata ttccccagat   660
tctccaaatt tggatcctgt tttagcaaaa ttgcctttag aagcagaaat tgattctaaa   720
agaagagcaa aaggatttgg atttgtattg gagcgaact  acaaggtaaa tgataagtgg   780
aatgttgaa tgagatacga ttctagagta aaattaaatt tcaaagcttc tacaagcgaa    840
aaagaaatta gcattcctac agtaggggga ataaagcata tcggatttac ttctgattta   900
tattatcctc aatataaaga tggaaagaaa gtaagaaggg atttaccagc tattttagca   960
ttaggaacaa cttatcaggt atcagataca tggaaaactg gtctatcgt aaattattat   1020
ttcaataaaa atgctaaaat ggatggacaa aaatacaaaa atggctttga agtggctttc  1080
ggaaatgaaa taaattaaa tgaaaaatgg actttgctag cttctattaa ctatgcaaa   1140
acaggagcat aaaggaaag ttatagtgat gtgaatatga ctttggatc tatcatgtta   1200
ggaacaggag tgaaatatca atatagcccct acttagaat taacagcaac tgtaggacac  1260
tatttttata gatcggaaga gggagatatc aaaggaagag ttgctaaaaa gacggattcc  1320
atgataaaac aattgcaaaa tgtaaatgaa caacaaaat acagaaaag tattactgct   1380
tttgggcttg gctttaccaa aaaattctag                                    1410

SEQ ID NO: 32            moltype = AA  length = 469
FEATURE                  Location/Qualifiers
source                   1..469
                         mol_type = protein
                         organism = Fusobacterium necrophorum
SEQUENCE: 32
MNLKLKCILL SSLLSMTAYG ASIDHIQTYA PEYLGNQAQN GAINGVSPYY NPAGTTQLEE    60
GFYINGGLQI AAGHEQSEYK EKEYKAIFIQ PVPSIALTKV NKDSSTYFTF SAIAGGGTLN   120
YKHGVVGTAI IPDLVANLKV GYLNSAAFGM PTIPSTLAGK KVAVQVLDGT RAKGSNLYSQ   180
MTLGKAFQVN DKLSLSAGIR FVHGRRDLEG NIKLKAYSPD SPNLDPVLAK LPLEAEIDSK   240
RRAKGFGFVL GANYKVNDKW NVGMRYDSRV KLNFKASTSE KEISIPTVGG IKHIGFTSDL   300
YYPQYKDGKK VRRDLPAILA LGTTYQVSDT WKTGLSVNYY FNKNAKMDGQ KYKNGFEVAF   360
GNEYKLNEKW TLLASINYAK TGALKESYSD VEYALDSIML GTGVKYQYSP TLELTATVGH   420
YFYRSEEGDI KGRVAKKTDS MIKQLQNVNE QQKYRKSITA FGLGFTKKF               469

SEQ ID NO: 33            moltype = DNA  length = 1917
FEATURE                  Location/Qualifiers
source                   1..1917
                         mol_type = genomic DNA
                         organism = Fusobacterium necrophorum
SEQUENCE: 33
atggggaatt ttaatttaaa attttttacc atatctttat taattttatt ggtacaaaat    60
tcttttgcag aagatccggt aataaaaaga ggaaataacc aagatagtat agtagccggt   120
ctccataaca aagctgtaaa cggatattcc ttagcttatg gagatgctaa tgaggcact    180
ggagatgcag ccagtgtagc ttttggctta aaaaatgtgg caagtgggaa aagtgccaaca  240
gcctttggta atgccaataa ggcgggtgga gatacagcag cagcttttgg gaacaataac   300
acagcaggcg gtcgttttag cttagctttt ggtaataaaa atgaggtcag tggaacaagc   360
agtgcagctt ttggtttcca aaataaggct aaatctaaag aaagtgttgc tgtaggtcat   420
gagaatgagg tagaagcgga ctacggcatt gctttgggta tggaaatgaa agtaaaatca   480
caaaaggtg tagcagtagg atatcaaaat gaagcaaaag gttttcaaa ttctgttttc    540
ggtattgaaa gtagagtcag tgggacaagc agtacagttg taggaaattc ttatgaagtt   600
tcaggaacta aatcgggtgc ctttggagtg ggagaaggca acaaagtc ttcaggaata    660
agctacaaat ataaaaatga aggtaatgaa tcttacacta taggaaatag aaacagtata   720
gcaacaagga cgaataataa cttttatattg ggaaatgatg ttactatagg tgacggaata   780
aacggtgctg tagttttaag taaaagttct aaggtaacgg aaagcaatac agtttctgtc   840
ggttctgaaa acgaaagaag aagaatagta tttgtggcgg atggaactca ggatacagat   900
gcggctactg tagggcaagt caagaaacta atttcttcaa catcagttg gggagctgga   960
atgggaaatg tttatacaaa ggctgagagt gatgctaaat ttgctactaa agatgcaggt  1020
aatttgtcgg caagtgatgt tgatgcttgg agaagtaagt taggagttat tgctaacaca  1080
gcagcagatc caaaaagtac aagtatagga ataataata aagtgaccgg aacttattca   1140
acagcggttg gttacaaaaa tgaagttagc ggaaatatat ctgagctttt tggagatcca  1200
aatattagta caggggaatcg ttcctatgcc tttggcaata ataatatcat tgcagggat   1260
gataattttg ttaggggttc taatgtaaat ataggagtgg aatatcaaa ttctgttgcg   1320
cttggaaata actcaaagt aaaagcttct aatgaagttt ctgtaggttc ggtaggaaat   1380
gaaagaaaga taacgaatat ggcagatgga gaagtttcat ctacatcgac agatgcaatt  1440
acaggtagac aactatatca tgtaatgcaa aattcaggaa caacaggaat agaaaattta   1500
agaaatgaag taaatgaaaa gttctcagat gttaaaatat aagtgaacca tgtaggttcc  1560
```

```
ttgagcgcgg cactttctgc attaaatcct atgcagtatg atccgaaagc tcctaatcaa  1620
atcatggcag gcttgggaca ttatagaaat aaacaggctg ttgcagtagg actaagccat  1680
catttcaata atagtgcgat gatgacagca gggcttgcct tagggaatga gtcaaagata  1740
aaagctatgg caaatcttgg atttacaata agattgggaa gaggcggaga aacttcggct  1800
gaaattcctc aaagtgtaat tcaaaatgaa atggcaagat tagctagaga gaatcaagaa  1860
ctaaaaaaag agttatttat cataagagag cagttagaag aattaataaa caaataa     1917

SEQ ID NO: 34           moltype = AA   length = 638
FEATURE                 Location/Qualifiers
source                  1..638
                        mol_type = protein
                        organism = Fusobacterium necrophorum
SEQUENCE: 34
MGNFNLKFFT ISLLILLVQN SFAEDPVIKR GNNQDSIVAG LHNKAVNGYS LAYGDANEAT   60
GDAASVAFGL KNVASGKSAT AFGNANKAGG DTAAAFGNNN TAGGRFSLAF GNKNEVSGTS  120
SAAFGFQNKA KSKESVAVGH ENEVEADYGI ALGNGNEVKS QKGVAVGYQN EAKGFSNSVF  180
GIESRVSGTS STVVGNSYEV SGTKSGAFGV GEAGLKSSGI SYKYKNEGNE SYTIGNRNSI  240
ATRTNNNFIL GNDVTIGDGI NGAVVLGKSS KVTESNTVSV GSENERRRIV FVADGTQDTD  300
AATVGQVKKL ISSSTVLGAG MGNVYTKAES DAKFATKDAG NLSASDVDAW RSKLGVIANT  360
AADPKSTSIG NNNKVTGTYS TAVGYKNEVS GNKSGAFGDP NIVTGNRSYA FGNDNTIAGD  420
DNFVLGSNVN IGVGISNSVA LGNNSKVKAS NEVSVGVGN ERKITNMADG EVSSTSTDAI   480
TGRQLYHVMQ NSGTTGIENL RNEVNEKFSD VKNEVNHVGS LSAALSALNP MQYDPKAPNQ  540
IMAGLGHYRN KQAVAVGLSH HFNNSAMMTA GLALGNESKI KAMANLGFTI RLGRGGETSA  600
EIPQSVIQNE MARLARENQE LKKELFIIRE QLEELINK                          638

SEQ ID NO: 35           moltype = AA   length = 507
FEATURE                 Location/Qualifiers
source                  1..507
                        mol_type = protein
                        organism = Fusobacterium necrophorum
SEQUENCE: 35
LGIFSPLGII QFLIRNSSDQ KMLILGIFFL YLSSLLFVYS FQSILKEKDM GLFFFLGILF   60
PYYFQKHPYV FKDLMRESHN IRNINYVYIF IFSIFFLKYF FYNTKKNWKE YLEVENIRNY  120
LLYLMPFFIL RAKDIKMIGF FYGIVVFVFC YKKDWNILLE KRKKICLLFL VLLFLFFSYM  180
SNYVWGIPNQ FGEQLLGNYV YNYFLLLILL LIPISEEMMK KIKMSIAISL FYPILLIVLE  240
WMQNHYTLEI AMGTEEWTSI WAVRAGLVSL ISLFFYLSEK RKVYLFGVIF SLLSLFLGQG  300
RGPILSFIAS FCILFFFFYE KKTDRKKVFT SLGIVLLLLF VIYNTENYII KKFQLVFLGA  360
DSSTNTRIEL YHGAIEQWKS QKWIGYGLGS YKETVELLKQ EYLEKYDLIR IPHAHNNILE  420
LLRSLGILGT FIYIFLNGYL CFWLLGKYWK TREKLYILPF VLIVNFELSG ITDFSLMMYK  480
SQLLLFFICS LSLSYTVSMS TDVEYKI                                      507

SEQ ID NO: 36           moltype = AA   length = 225
FEATURE                 Location/Qualifiers
source                  1..225
                        mol_type = protein
                        organism = Fusobacterium necrophorum
SEQUENCE: 36
VEMFVLFGTS HMIMILIGVI SVLLLIILGF LIRPQLLAKW ISVSVLVIKL AEMYYRHRVL   60
GEEIYRMLPF HLCNLTIILS LFMMFFHSKF LFQLVYFWFV GAIFAILTPD IIFAYPNFWT  120
ISFFITHFYL VFSALFALIH FHFRPTKRGM LMAFLFINLW AVLMYFVNQE LGTNYLFVNR  180
IPETTTLLSY FGAWPYYLLP VEGIYIIESI LLYLPFRKSN IKFHF                  225

SEQ ID NO: 37           moltype = AA   length = 166
FEATURE                 Location/Qualifiers
source                  1..166
                        mol_type = protein
                        organism = Fusobacterium necrophorum
SEQUENCE: 37
MRANSIRINA LEINIIEALK EELPEEMTIV LDDRALNFDF DKSVVKPKYN EMLTNLKEFI   60
TKNNYEVTIE GHTDYIASNE YNMGLSKRRA EAVKAKLIEL GLEPSRIVAI LPKGEEEPIA  120
DNKTTEGRAK NRRVEFKLVK RDSVGEVNSE ESRIIDVKKG VVEAEN                 166

SEQ ID NO: 38           moltype = AA   length = 183
FEATURE                 Location/Qualifiers
source                  1..183
                        mol_type = protein
                        organism = Fusobacterium necrophorum
SEQUENCE: 38
MKKYLGMTVL LASFVLAACG KTSNTSVRDL STEGNQNFAI EDIDTAKKPL EDIIVFNQDG   60
VTIRREGNNL ILSMPELILF DFDKYEVKDG IKPSLRTLAN ALGANSDIKI KIDGYTDFIG  120
SEGYNLELSV NRAKAIKSYL VNHGAIENNI SIEGYGKQNP VASNATESGR ARNRRVEFII  180
SRS                                                                183

SEQ ID NO: 39           moltype = AA   length = 172
FEATURE                 Location/Qualifiers
source                  1..172
                        mol_type = protein
                        organism = Fusobacterium necrophorum
SEQUENCE: 39
```

```
VGRKSTKIGI LFFLFLFSLP SFAVQKLTTT QMRENSIRIN ALELKEMDIH LKKVTVVLDE    60
RALNFDFDKW NIKEQYYEVL ENLKEYILAN DYEVVIEGHT DSIGTNAYNI GLSFKRANST   120
KEKLIEFGLP ADRIVGISGK GEESPIATNE TPEGRSQNRR VEFHLEKIGD KE           172

SEQ ID NO: 40           moltype = AA   length = 789
FEATURE                 Location/Qualifiers
source                  1..789
                        mol_type = protein
                        organism = Fusobacterium necrophorum
SEQUENCE: 40
MEENNGTIVI TEEMIQKKHY DSVAKIFEDS PVSVVRHTAF GPIVDLRGSG ERTISRVKVM    60
IDGTPINPLE ETHGTIPFDT IPVESIAKIE IVPGTGTTKY GGGTTGGYIN IHTKKDKQKN   120
YITINADHAS YHANSIGIAA GMNASKKLFV YAGEAYQRKD GYRKKDHSDR NNFLGGFDYQ   180
INAKHRIKGQ GNLYREDLKS TTEVTHEELK QDRRKAGEDT KIEMDRDFAS LDYEYTPTSH   240
FTLRANVNRA HFTRDVSMDA KQEQLTLVNA FRFTHNMSMV DDEVKTLKPV LKDFQSTMEG   300
KFKEENQEGK VDGEWKYNQG KGHLQFGYAY NKKSLDQNLK IQSKPFNLGK SLYYLFPGDP   360
APHPFEDYAG KVLDQETMWR VIFNDLGYSQ EYIDTHAPSM AGDNSGEILD LQNYNQVDSF   420
RNTHSLYLLN DYKITPKLNF RSGLRWEYSK YGSKRKNYMA IGIHKAQHSD LAASAGLAGL   480
LDSYEKEALL LGKLDYVDIE LSIKDTDMKD SSHNFGGEVG FSYQYHKKGN LYFRYERGFL   540
SPLPSQLTNK DFLTGNYYPS GVKSEKVDTI EIGIKHSLWN NTHIEANTFF SLTKDEITNM   600
RYNANNHMNM RWAYANISKT RRLGFELNAE HIFDKLKIRE SFSYVDAKIA KDTGFKDYYH   660
SDYKEGTKNE FKDAPLYYKK GQTVPLVSKV KVTVGAEYQC TDKLSLGGNY NYVSGYDTRE   720
PGEGFQAKTY KVKGHGTLDL FGRYYFTDYA YVRFGVNNVL GEKYNLREDS HYAVPAPKQN   780
YYAGFSYKF                                                          789

SEQ ID NO: 41           moltype = AA   length = 159
FEATURE                 Location/Qualifiers
source                  1..159
                        mol_type = protein
                        organism = Fusobacterium necrophorum
SEQUENCE: 41
MKKMLLVLGL VSAFSMSAFA DKIAVVDSQE VIGRYSGTKG VEATLQKEVK RIENDVNQRQ    60
VALQKEEVAL QAKGDKLTDA EKKAFQAKVE GFYKYVNTSR ESLAKMEQTK MSAIFTKANK   120
AVQAVAAEGK YDYVLDRGAV LVGGEDITDK VIKKMETIK                          159

SEQ ID NO: 42           moltype = AA   length = 377
FEATURE                 Location/Qualifiers
source                  1..377
                        mol_type = protein
                        organism = Fusobacterium necrophorum
SEQUENCE: 42
MKKLALVLGS LLVIGSAASA KEVMPAPMPE PEVKIVEKPV EVIVYRDRVV QAPAKWKPNG    60
SVGVELRTQG KVENKGKKAT EENARKGWAG KEPNVRLETK ASVNFTENQN LEVRTRQTHV   120
LTKTDSDKEE SNHKDTQVRI RHTYNFGKLG SSKVGFKVAS QYLHDDHVDS LRTRAVFDFA   180
DYIYSNSLFK TTALEIGPSY KYVWGGNDDR YYNALGLYAN AEFELPYGFG FQAEFEDAFT   240
YTSTGKGDGK RDKAKLGHAD FVLSHSLDLY KEGKHSLAFL NELEYETFWA WDKKDASMEE   300
WPHVDGHGRV NSEGKNKKWG AYELTYTPKL QYNYQATEFV KLYAAIGGEY VNRENNKSTA   360
RYWRWNPTAW AGMKVTF                                                 377

SEQ ID NO: 43           moltype = AA   length = 246
FEATURE                 Location/Qualifiers
source                  1..246
                        mol_type = protein
                        organism = Fusobacterium necrophorum
SEQUENCE: 43
MKKNFIIAIF CSFAAFSYAE EKMSGVNLGI TASHAKEIYK VSAKEKYSVL PLISVNYKDF    60
YINQSELGYQ FQVHDNFLIS GYFDFLDGYP VKGKEMQKEY KSIQTRRSQI VGGGRITYFK   120
DNFQTSIFAQ GGKRGSSTGA DLSLSFPLTE KLFFTTGLNY TIYSKNFTNY YFGVHKEDFG   180
GKLTKVYSPK ASYSYGAEAS LEYQITEPFS IFTSVSATNY SKEITNSPLV KDKTNISTTI   240
GLQYSF                                                             246

SEQ ID NO: 44           moltype = AA   length = 476
FEATURE                 Location/Qualifiers
source                  1..476
                        mol_type = protein
                        organism = Fusobacterium necrophorum
SEQUENCE: 44
MKQKWSFFLC LLFLSSCSSV NKEISETSLL QELKRKETET QRILTEQRLS LEEAIQIAKE    60
RNLELKTKQL EREISKIDSK IAFGNFLPRI SAFYTRSFWE EALSGQVDLP ASLSQFPLIG   120
PMLPKEIQGR LLDKSYSVYG LQASMPIFAP ATWFLYSARR KGEEIQSLVL TLTEKMISIQ   180
VIQQYYWILA LEAEEIQLKA SLKSAEQLLH NMKIALDTQS ILEWQYQKAQ AYYKQKKLAL   240
AQNQRDLKLA KMGLLSTLNL SPLSSVRLQK TQNITKRKED NYEEVIYQAL VHNDALGIQE   300
KVLEVEKEKL KISFSRFLPV IGLQGFYGEH SLSLLSSSHY QKLQSSIEEE EIAEINEKAE   360
YQKAKIEQRK AMLKKESLIL QSIAETTNVY QKLSLALKAEY QSAVLQEILD TLVGRGRFVE   420
RKVGMIDELS YLQAVQSYEE AKSLALKAEY QSAVLQEILD TLVGRGRFVE EGENND       476

SEQ ID NO: 45           moltype = AA   length = 465
FEATURE                 Location/Qualifiers
source                  1..465
```

```
                        mol_type = protein
                        organism = Fusobacterium necrophorum
SEQUENCE: 45
MKKNVFMLGG   FILLTSSVLA   KEALVVPEQK   PEILVVEKPV   EVIVYRDRVL   ETPAKWRPNG    60
SIDIQYRVYG   KTENKVASPR   TVPPIPIEPP   RIPLVPLEPP   HIPLVPLEPP   HIPLVPLLPP   120
PTLEEDDGET   HWQAASLLEG   EGEVYDDEDV   DDLSETVEIP   PMQAAEEALEE  KEDEKTSKWA   180
RKKRYNTGRL   QVEAKLNFTE   KQSLEIRERV   YHALRTTKVD   ENERYGKAAA   DEDELRLRHF   240
YRFGNLGNSK   VNASSRLEYN   TLHNSEKMSG   SAYLAFDISS   YLFQNNFIKT   DYFRVGPTYT   300
YAMKNKTNYS   NQIGLLLESY   FSLPYNFGLE   LNVHPKYMAY   NKEFEIGEGK   TKKHEFYAEV   360
EAKLFHSLNL   YKNNKWRLDL   NTEGGYDPYQ   FHQYKVVKNR   EKKVEKRAYS   LYALPTFQVS   420
YQATEYVNVY   ATAGAEYRNW   VDTAESTASH   WRWQPTAWAG   MKVTF                    465

SEQ ID NO: 46           moltype = AA   length = 423
FEATURE                 Location/Qualifiers
source                  1..423
                        mol_type = protein
                        organism = Fusobacterium necrophorum
SEQUENCE: 46
MKKIAAIFFL   TGTVLFAGEI   TLEEAIARAL   KHSREVQIAE   KKFLSSKIKA   KQAIKKALPS    60
LVYSGSYQQS   EYERMQAKNR   TEKQGEKIGY   RQSVTLTQPL   FQGGSIVAEI   QGAKYYESLF   120
EIEYLQKKIE   TRLKTIQIYS   HIIRAKKELE   ALRYSKKQLE   QRYEKQKVQL   ELQLITRTDL   180
LKTEYHLLSV   ESQMEKAKNE   IEVQMENLKI   QMGLFKDEKI   EIQEFFVPKQ   CSAKIDFDKD   240
RKQAMETSMS   VLSAKYRLEI   AKAEQRGRAG   EMLPEINLFA   SYENVGERRT   FNQSRKDMEW   300
IGGVEVRWKL   FSFGREYDSY   KVATLEKETQ   ELSQEKIQDS   LRLKLREAYL   DLCRLEILRD   360
SKTKALETAE   LNFQMEQEKY   DAGLISVVDY   LDSEKQLREA   KVSYYQTELE   YYYAFEYYQS   420
LLV                                                                         423

SEQ ID NO: 47           moltype = AA   length = 172
FEATURE                 Location/Qualifiers
source                  1..172
                        mol_type = protein
                        organism = Fusobacterium necrophorum
SEQUENCE: 47
VGRKSTKIGI   LFFLFLFSLP   SFAVQKLTTT   QMRENSIRIN   ALELKEMDIH   LKKVTVVLDE    60
RALNPDFDKW   NIKEQYYEVL   ENLKEYYILAN  DYEVVIEGHT   DSIGTNAYNI   GLSFKRANST   120
KEKLIEFGLP   ADRIVGISGK   GEESPIATNE   TPEGRSQNRR   VEFHLEKIGD   KE           172

SEQ ID NO: 48           moltype = AA   length = 385
FEATURE                 Location/Qualifiers
source                  1..385
                        mol_type = protein
                        organism = Fusobacterium necrophorum
SEQUENCE: 48
MKKLALVLGS   LLVIGSAASA   KEVMPAPMPE   PEVKIVEKPV   EVIVYRDRVV   QAPAKWKPNG    60
SVDVQYRWYG   ETENKVDGQL   KQEGLAEGEH   DWANDENNYG   RLQTEAKINF   TENQRLEIRT   120
RNFHTWAQGK   NTKDYSKAKA   EDDKIRLRHF   YNFGKIANTK   VNATSRLEWD   QKSGDGAKKL   180
EASVGFNFAD   YLFNNDFVKT   TNFTVRPLYA   HKWTAHRGGS   RKGAEVLGLN   LESNFEFPYG   240
FELEFKLEPT   YTFYGTKQTI   SDKDGENQRE   KKRAFDMDVT   LILSNSVNLY   TQDKFALDFN   300
FEGGYDPYSF   HQYRIYDKEE   KEVGVKRSYS   LYALPTLEAN   YQATEFVKLY   AGAGAEYRNW   360
KIEDEDYATR   WRWQPTAYAG   MKVNF                                              385

SEQ ID NO: 49           moltype = AA   length = 338
FEATURE                 Location/Qualifiers
source                  1..338
                        mol_type = protein
                        organism = Fusobacterium necrophorum
SEQUENCE: 49
VKTKNFVLES   KQDTSERKDS   SYGGSFSIDL   GNPSNLSVTM   NGRKGNGEKE   WVEKQTSFIA    60
RNGGKIDTDS   LTNIGAVIGS   ESETEKLKVS   ANQVIVKDLE   DKNQYENMGG   GISIGTSIPN   120
ISIKHDKIEK   EQINRATAAN   TEFGISGKKT   SAEDLGFNTD   INKTQEVTKN   EEKHLDAELH   180
ADLIGEDKRN   EIKYAFKKLG   SLHEILDQKK   FKESMEGVLV   DKFKDEHQKE   PHLIKDENLS   240
LEDKQKLAQN   LVEKYLRENG   YQGIIPEVLL   TEEAHSFTVD   SKDKTTGAKR   GEKIYFSIHD   300
IANPDLAFSQ   LFGHEKAHMN   TYDEGKYGEE   TSFHCKLQ                               338

SEQ ID NO: 50           moltype = AA   length = 559
FEATURE                 Location/Qualifiers
source                  1..559
                        mol_type = protein
                        organism = Fusobacterium necrophorum
SEQUENCE: 50
VKGSVNNSKT   IEATNIDITG   ENLVNSSSIK   ADNILATVKT   TKNDGDILAL   KDITLNTKKL    60
DNTKKIAALQ   NITANNTALT   NSGEIVSNHK   IELNHSNISN   TNKILSNTID   MKNTSNFNNT   120
GTISGTDVTL   TSVNDIHLIA   NLHGENSLII   EGKNIVNENS   ISANDLHMNA   KNLTNHDLIA   180
AENNANINVK   NKVTNTENSS   IYAGNKLNIQ   ASELFNDSAE   ILGTDVKLEA   NQITNHIGTL   240
QALNTMHIKA   GKFENIGKVE   DLDRYESYYE   TWDGQRIEAN   QIEDKVHFS    KSSSKRSNGS   300
AGKTIRKRQR   EAYHEISEKM   KNDKYASLLF   PKYDKLMRGY   LGDRGEYTEK   TGSARIQTVP   360
LQEKLRSLGK   TTHAKVLAGN   NILIEKKSDS   NNEVMNKDGI   LSAGNTIKID   ANQVQNLVSV   420
GDEKIKVKTG   EESMYIKLER   TGKKPRKKVK   MEVSYDRDFA   NDYITKKIPK   LDEKGRQVYQ   480
KKFGGRKKPV   YEYVTEYVGR   YAYVTGQPSV   IEGKNVVIDN   ASLVRQGIEE   ANGYIKSGKD   540
```

```
VNIQNFTSKN FHTGLSNGN                                                     559

SEQ ID NO: 51           moltype = AA  length = 172
FEATURE                 Location/Qualifiers
source                  1..172
                        mol_type = protein
                        organism = Fusobacterium necrophorum
SEQUENCE: 51
VGRKSTKIGI LFFLFLFSLP SFAVQKLTTT QMRENSIRIN ALELKEMDIH LKKVTVVLDE   60
RALNFDFDKW NIKEQYYEVL ENLKEYILAN DYEVVIEGHT DSIGTNAYNI GLSFKRANST  120
KEKLIEFGLP ADRIVGISGK GEESPIATNE TPEGRSQNRR VEFHLEKIGD KE          172

SEQ ID NO: 52           moltype = AA  length = 261
FEATURE                 Location/Qualifiers
REGION                  229..232
                        note = misc_feature - Xaa can be any naturally occurring
                         amino acid
source                  1..261
                        mol_type = protein
                        organism = Fusobacterium necrophorum
SEQUENCE: 52
LEKKKKGLSL SISKNSFKVA YGKNQFNYDE KDKTNIKSNL VLGDGTVLNK GAEITATNFN   60
HGDITINNGD VIYGARKDER DVKTSTKKSS FGISANVSSP ALERIKQGAN ALEQIGNGDA  120
LGGGLVNVGNV VTGTVDGLAS NIKTKDGKQA TAKDVKDNKF TSNNSFYVQA GGSAGYSKSK  180
QKTKSHTEKA VVTNITGLDE NAKITYNDNK NVKYQGTQTQ NTTFVYNNXX XXDSYIDGKL  240
TTDSKAIYNK YILESIGIFF F                                           261

SEQ ID NO: 53           moltype = AA  length = 1420
FEATURE                 Location/Qualifiers
source                  1..1420
                        mol_type = protein
                        organism = Fusobacterium necrophorum
SEQUENCE: 53
MKKLKNFENV LKSHLKQRVR ITTAFIVAFL IHGMLSFDVE ARDLRVRNQI TPSNSNNGLR   60
ITSSQNGTDV INIVDPNNGI SHNKYVDFNV GDKNNVIFNN SQKNGTSVTG GEVSANPNLT  120
NSASVILNEI QGNSASELNG GLEVFGKRAD LVIANENGIN VNGARFINTS ALTLSTGKVS  180
VDNKKISFNT ATNNAKIAVK EKGIETDSDY LNILSRRAEL DGAINSEHNK NLNINVIAGA  240
NTVTAVNDTF ELNAENAKDG ITNVEAISAS KFGAMYGNNI FILSTNKGEG IKYEGSLKAK  300
DEVEIISEGK VVSSDINGKD IKISSKEEIN NIGKMKADKN VSLNAPIVKN MSRLEGSVRL  360
KSNEHNKKYQ NRERGIIYYD YYLNVKNMSE VENELKLVKS SIEAGNNIEI NNNLENGSFE  420
NLSGDLKAGN DIKVKGNFKT KHLSEGIKLE DLLKRIKVDL RWEHRSLVDN AYFNGNSSLT  480
DGSLLDALKI MTQKKNKEYY TALKQIDDPQ LNKVLSGLLG ADWRTRERIK DEKDWNKEAA  540
ISFTNGTYSI EAGNDLKASG KVIELGGSNV MTKKEIFEVA STKTESLQST ISDVKNANIK  600
AKNVYMEADN ITNVNADIAA EDSAILYSKN NIDVKGAKVS ADKILLEAGK DINLSSELGF  660
KSSGEHAIIK ETDVTANKAV GIKSKNLNIY GADVEAKDGL IKIDSDKLNV KDISTINANY  720
KAELIEGKKY ILRDHQYTKA LQAKVESTPS KIIANKIFIT AKDGAAIEGS LISGKNADSI  780
IQIISEGNVN IKNSNNIDYS NFYSDSRGKN KKGVYKLLKI DKASKENLDI VGSNLKSEGN  840
INIKSKNLTV VSSKIKAGKK VNLEAEEDIK LLASLNSKKE ELNKMEWGSG AINSYKKSLE  900
KKDVVSTMIE AGEKANVHAK RDLYKQSVFV KAGSVTMNGE ANNYSDALAS TEIKKETDVK  960
AGFGVEGKIA FAGMGAAGEA NTLDNTATGK TSGIKGLLEK ENEFKKAEAR AKVYAKMEVN 1020
KSIKESKNYV NNNITSESGD VTIGSNGVTD IGNTDINSQN DVNLRGKKVE TTTKENVTKE 1080
VNHKLDLSVK GDIAFSNENV NKLNDLANDV LKSKEMLEKK DILGLAQKAE ETIKDLKETI 1140
PNLTKKDILG IKSSQGVGVE YTNKTSTTTE TTASSLKAKG KLNIKADEGD ITLKNTYLKA 1200
QEFNTETPGK VNLLAGKKTI HKEENSLKVG VSVNENVGVN IADGANAKIG VGVQASYNGG 1260
TDLNKKSLNT TVEVGKVNHK AAAVNEDNKT DFYYKDKRGA GVDVDLKIGV SSNHIVAADG 1320
NVGGNVNYSF AAGKSTTDVV TNKTESTDVK AGVGLKASVG IDGKSPDFSI STDQIEYKKD 1380
GKVLVNIDAK DKMITKERIE QMRDKVKNWR TPTNSAEKLI                      1420

SEQ ID NO: 54           moltype = AA  length = 707
FEATURE                 Location/Qualifiers
source                  1..707
                        mol_type = protein
                        organism = Fusobacterium necrophorum
SEQUENCE: 54
MKRTLVAMLL FLVSMVSFAA GGSLIVKKVE VLNNQEVPAS IILNQMDLKE GKPFSTEIML   60
HDFQTLKKSK YLEDVLIQPQ AYEGGVNVVV NVIEKKDVQS LLREDGVISM SEQANVDKSL  120
ILSDIIISGN QFVSTADLKK VLSVKQGGYF SKTAIEDGQK ALLATGYFRE VTPNTQKNGN  180
GVKIIYTVVE NPVIQGINIH GNTLFSTPDI LKVLKTKIGE VLNINSLRED RDTIMNLYQD  240
QGYTLSEISD MGLNDRGELE VVISEGIIRN VSFQKMVTKQ KGNRRKPTDD ILKTQDYVIQ  300
REIELQEGKI YNAKDYDNTV QNLMRLGVFK NIKSEIRRVP GDPNGRDIVL LIDEDRTAIL  360
QGAISYGSET GLMGTLSLKD NNWKGRAQEF GVNFEKSNKD YTGFTIDFFD PWIRDTDRIS  420
WGWSLYKTSY GDSDSALFND IDTIGAKINV GKGFARNWRF SLGFKGEYVK EKANKGNFRQ  480
LPDGTWYYTG KNKNDASNTP LPKDAVNDKY MVFSIFPYLT VDTRNNPWNA TTGEYAKLQL  540
ETGYAGGYKS GSFSNVTLEL RKYHRGFWKK NTFAYKVVGG VMTQSTKEGQ RFWVGGGNTL  600
RGYDGGTFRG TQKLAATIEN RTQINDILGI VFFADAGRAW KQNGRDPEYG NDEKFSKGIA  660
TTAGVGLRLN TPMGPLRFDF GWPVGKSQDK YSNDRGMKFY FNMGQSF                707

SEQ ID NO: 55           moltype = DNA  length = 39
FEATURE                 Location/Qualifiers
```

```
misc_feature            1..39
                        note = primer
source                  1..39
                        mol_type = other DNA
                        organism = synthetic construct
SEQUENCE: 55
tcaatttgct aggggatctg ccgaaatcga tctgggcac                              39

SEQ ID NO: 56           moltype = DNA  length = 36
FEATURE                 Location/Qualifiers
misc_feature            1..36
                        note = primer
source                  1..36
                        mol_type = other DNA
                        organism = synthetic construct
SEQUENCE: 56
ccatggctag ctagctagtg gtggtggtgg tggtgc                                 36

SEQ ID NO: 57           moltype = DNA  length = 23
FEATURE                 Location/Qualifiers
misc_feature            1..23
                        note = primer
source                  1..23
                        mol_type = other DNA
                        organism = synthetic construct
SEQUENCE: 57
tagctagcta gccatggcat cac                                               23

SEQ ID NO: 58           moltype = DNA  length = 31
FEATURE                 Location/Qualifiers
misc_feature            1..31
                        note = primer
source                  1..31
                        mol_type = other DNA
                        organism = synthetic construct
SEQUENCE: 58
agatccccta gcaaattgaa gagaaagatc t                                      31

SEQ ID NO: 59           moltype = DNA  length = 39
FEATURE                 Location/Qualifiers
misc_feature            1..39
                        note = primer
source                  1..39
                        mol_type = other DNA
                        organism = synthetic construct
SEQUENCE: 59
tactgttata gatctttctg aacaaacgat tgaactggg                              39

SEQ ID NO: 60           moltype = DNA  length = 36
FEATURE                 Location/Qualifiers
misc_feature            1..36
                        note = primer
source                  1..36
                        mol_type = other DNA
                        organism = synthetic construct
SEQUENCE: 60
tccctgcctc tgtcacttcc tttcgggctt tgttag                                 36

SEQ ID NO: 61           moltype = DNA  length = 18
FEATURE                 Location/Qualifiers
misc_feature            1..18
                        note = primer
source                  1..18
                        mol_type = other DNA
                        organism = synthetic construct
SEQUENCE: 61
tgacagaggc agggagtg                                                     18

SEQ ID NO: 62           moltype = DNA  length = 32
FEATURE                 Location/Qualifiers
misc_feature            1..32
                        note = primer
source                  1..32
                        mol_type = other DNA
                        organism = synthetic construct
SEQUENCE: 62
agaaagatct ataacagtag ccatatttaa ac                                     32

SEQ ID NO: 63           moltype = AA  length = 423
```

```
FEATURE                 Location/Qualifiers
source                  1..423
                        mol_type = protein
                        organism = Fusobacterium necrophorum
SEQUENCE: 63
MKKLWILFFL LGSVAFGREV TLEEAIQASM ENSKAVKISD KQLEISKLKM NQAIKKALPS    60
VVYSANYQRG EYERNIYKNK SSMESEKGGY KQSITISQPI FQGGAILAGI QGAKAYKTIA   120
DLSYVQETLN TRLKTIRTFS NIVNSKRNLQ ALEYSEKQLQ NRYKKQEAQL ELRLITKTDL   180
LKTEYSLLEV QSLISKAKSN IEVQTEDLKF QMGVDKKEAL EVKEFIVPNH LTERITFEKD   240
KERALESSIQ ALIAKSQVKI AKAQETAALG NMLPKVNAFV SYGVASERTH WKQTREDAEW   300
MGGLSVSWNV FSFGSDYDAY QIAKLEKESK ELSETTAQDN IALSLKTAYL ELQRLEILRE   360
SRKRGLEAAE LNFTMDQEKF DAGLLSTVDY LSSETQLREA RVNYYQAELD YYYAFEYYRS   420
LLV                                                                 423

SEQ ID NO: 64           moltype = AA  length = 423
FEATURE                 Location/Qualifiers
source                  1..423
                        mol_type = protein
                        organism = Fusobacterium necrophorum
SEQUENCE: 64
MKKLWILFFL LGSVAFGREV TLEEAIQASM ENSKAVKISD KQLEISKLKM NQAIKKALPS    60
VVYSANYQRG EYERNIYKNK SSMESEKGGY KQSITISQPI FQGGAILAGI QGAKAYKTIA   120
DLSYVQETLN TRLKTIRTFS NIVNSKRNLQ ALEYSEKQLQ NRYKKQEAQL ELRLITKTDL   180
LKTEYSLLEV QSLISKAKSN IEVQTEDLKF QMGVNKKEAL EVKEFIVPNH LTERITFEKD   240
KERALESSIQ ALIAKSQVKI AKAQETAALG NMLPKVNAFV SYGVASERTH WKQTREDAEW   300
MGGLSVSWNV FSFGSDYDAY QIAKLEKESK ELSETTAQDN IALSLKTAYL ELQRLEILRE   360
SRKRGLEAAE LNFTMDQEKF DAGLLSTVDY LSSETQLREA RVNYYQAELD YYYAFEYYRS   420
LLV                                                                 423

SEQ ID NO: 65           moltype = AA  length = 423
FEATURE                 Location/Qualifiers
source                  1..423
                        mol_type = protein
                        organism = Fusobacterium necrophorum
SEQUENCE: 65
MKKLWILFFL LGNVAFGREV TLEEAIQASM ENSKAVKISD KQLEISKLKM NQAIKKALPS    60
VVYSTNYQRG EYERNIYKNK SSMESEKGGY KQSITISQPI FQGGAILAGI QGAKAYKTIA   120
DLSYVQETLN TRLKAIRTFS NIVNSKRNLQ ALEYSEKQLQ NRYKKQEAQL ELRLITKTDL   180
LKTEYSLLEV QSLISKAKSN IEVQTEDLKF QMGVDKKEVL EVKEFIVPNH LTERITFEKD   240
KEKALESSIQ ALIAKSQVKI AKAQETAALG NMLPKVNAFV SYGVASERTH WKQTREDAEW   300
MGGLSVSWNV FSFGSDYDAY QIAKLEKESK ELSMTAQDS IALSLKTAYL ELQRLEILRE    360
SRKRGLEAAE LNFTMDQEKF DAGLLSTVDY LSSETQLREA RVNYYQAELD YYYAFEYYRS   420
LLV                                                                 423

SEQ ID NO: 66           moltype = AA  length = 423
FEATURE                 Location/Qualifiers
source                  1..423
                        mol_type = protein
                        organism = Fusobacterium gonidiaformans
SEQUENCE: 66
MKKIWTMFFL VGSLAFAREI TLEEAIQESM NHSKTLKISE KKLQISKLNR SQAIKKALPS    60
VLYNTSYQRT EYERNISKNK SSMQLEKGGY KQSITISQPI FQGGAIIAGI QGAKAYETIA   120
DLSYVQEGLN TRLKTIRTFS NIVNSKRNLQ ALENSEKQLQ KRYQKQEAQL ELRLITKTDL   180
LKTKYNLLEI QSLIAKAKSN IEVQTEDLKF QMGIDKEEQL EVKEFNVPNH LTDTIDFQKD   240
KEKALESSIQ SLIAKSQVEI AKAQETAALG NMLPKINAFA SYGVATERTK WKQTREDAEW   300
MGGLSVSWNV FSFGSDYDNY QIAKLEKENK ELSEMTAQDT IELTLKTAYS ELQRLEILRE   360
SRKRGLEAAE LNFSMDQEKF DSGLISTIDY LLSETQLREA RVNYYQAELD YYYAFEYYRS   420
LLV                                                                 423

SEQ ID NO: 67           moltype = AA  length = 423
FEATURE                 Location/Qualifiers
source                  1..423
                        mol_type = protein
                        organism = Fusobacterium nulcerans
SEQUENCE: 67
MKKILGLLLI LSSSVFAREI TLDQAIQMSL ENSKEIKISE KDVEVSKLRV GMAFKDALPS    60
VVYSGTYTRG ESDRKMYRHG WEDQVERKGG YTQTISISQP LFQGGAVLGG IKGAKAYKTI   120
ANLLYLGERR DTRLKTIQNY SNIVKYEKDL EALESSKREL QARYNKQKAQ LDLRLITKTD   180
LLKTEYSLLE VESQIIGTKN GITIEKENLK IKTGIPKQED VTVVDFNVPM YLSRNINFKA   240
DLDQAMNESI NALVAKNYVE AADASKMVSR ADMLPKVNAF ASYGTSERTK YNPTIDEAEW   300
RGGVQVTWNV FEFGKNYDSY KVAAIGKEQE ILREKISKDS IDISVTDAYL ELIRMEKERD   360
SKERAMEAAI ENFRMDQERY DAGLISTVDY LLSESQEREA KVSYNQIVID YLYAFEKYRS   420
LLI                                                                 423

SEQ ID NO: 68           moltype = AA  length = 423
FEATURE                 Location/Qualifiers
source                  1..423
                        mol_type = protein
                        organism = Fusobacterium varium
```

```
SEQUENCE: 68
MKKILGLLLI  LSSSLFAREI  TLDQAIQMAL  ENSKEIKVSE  KDVEVSKLKV  GIAFKDALPS   60
VVYNGKYTRG  EYERKMYKHG  WEEQVDRKGG  YTQTISISQP  LFQGGAILGG  IKGAKAYKSI  120
ANLLYLGERR  DTRLRTIQNY  SNIVKYQKDL  EALEASKKEL  QARYNKQKAQ  LDLRLITKTD  180
LLKTEYSLLD  VESQIIGTKN  GITIEKENLK  IKTGIPKHED  VSVVEFEVPM  YLSRNINFKA  240
DLDQAMNESI  NALVAKNYVE  AADASRIVSR  ADMLPKVNAF  ASYGTSERTK  YNPTIDEAEW  300
RGGIEVTWNV  FEFGKNYDNY  RVAAIGKEQE  MLREKISKDS  IDINVTDAYL  ELIKMEKERD  360
SKERAMEAAI  ENFRMDQERY  DAGLISTVDY  LLSESQVREA  TVAYNQIVID  YLYAFEKYRS  420
LLI                                                                    423

SEQ ID NO: 69          moltype = AA  length = 423
FEATURE                Location/Qualifiers
source                 1..423
                       mol_type = protein
                       organism = Fusobacterium nucleatum
SEQUENCE: 69
MKKILTIFML  MASVALARDL  TLEQAIDLSL  NNSKEMRISE  KNLEISKLNV  SKAFKNALPS   60
VTYSGTYAVG  EHERQILTQS  ERNYASKKRG  YTQNLRLTQP  LFTGGTITAG  IKGAKAYENI  120
ASYSYLQSKI  QNRLDTIKIF  SDIINAERNL  EALEYSENIL  QKRYQKQEEQ  LNLRLITRTD  180
ILQTEYSIED  IRAQMINAKN  TIDTNMEKLY  IRTGINKSES  LNLIPFDIPN  NFSEKINLNN  240
DLKQAINESL  SAKVAEEQVK  VASATRMAAV  GDLLPQVNAY  ASYGTGERTS  FERSYKDGEW  300
TGGIEVSWKV  FSFGSDLDSY  RVAKLQEEQE  ELRETSTKED  IEVNVRSAYL  NVLSLEKQID  360
SQAKALEAAK  VNFELNQEKY  DAGLISTVDY  LDFENTYRQA  RIAYNKVLLD  YYYAFETYRS  420
LLI                                                                    423

SEQ ID NO: 70          moltype = AA  length = 433
FEATURE                Location/Qualifiers
source                 1..433
                       mol_type = protein
                       organism = Fusobacterium mortiferum
SEQUENCE: 70
MKKTLGLLLL  LSSSVFAREL  TLDQAIQMAL  DNSKEMQISQ  RDVETAKLNV  GIAFKNALPS   60
VVYTGSYTRS  EYDRKITAEE  RPNHRLEKNG  SREVEAKGGY  TQKITISQPI  FQGGAILGGI  120
QYAKAYKSVA  NLMYLSSQRD  VRLETIQIYS  DIVKSEKDLE  ALMSSKEELK  ATYDKQKAQL  180
DLRLITKADL  LKTEYSMLEV  DSQIIGTQNQ  ITVQKENLKL  KLGLPKTEDL  TVVEFDVPMY  240
LSRNIDFQAD  LNQALTESID  AMVANKYVDM  ADAQRKVARA  DMLPQVSAFA  SYGVDSDRRK  300
YNATMDDAEW  RGGVQVTWNV  FEFGKNYDTY  KTAAIAKEQE  ELREKISKDT  IDINVTDAYL  360
ELVRMEKDRD  SKGRALEAAM  ENYKIDKEKY  TAGLISTIDF  LASETQLREA  KVAYNQVVID  420
YLYAFEKYRS  MLI                                                        433

SEQ ID NO: 71          moltype = AA  length = 422
FEATURE                Location/Qualifiers
source                 1..422
                       mol_type = protein
                       organism = Fusobacterium russii
SEQUENCE: 71
MKKLLSIFFL  LTGSLFAREL  TLDEAINLSL  TNSKDIQISE  KNLEISEINL  QKAFKLALPT   60
VTYNGKYSRT  NYDRKIAIDD  HSSEKGRGSY  SQSITIAQPL  FAGGTIFAGI  KGAQAYENIA  120
NYNFLNSKIK  MRIETIAAYF  SLLNAEKDLN  ALKNSKSILQ  KRYDKQKVQL  ELRLIRKSDI  180
SQTEYSLLNV  ESNIIAIKSQ  IDTYREQLRI  KTGLAKNEFI  TVVDFNVPMN  LSKNINIDKD  240
LEQAINESLN  AKIAEEMYKI  SEAQTIAAAG  SILPKVSAFA  TYGTTERTKF  ENSYRDAKWV  300
GGIQVTWNVF  SFGSDIDEYR  IAKLEEEQQK  LKEISTKENI  EIAVKSAYFD  LLRLEKLRES  360
KSKALEVAKL  NFEMDQERYD  AGLISTIDYL  DTENTYRNAN  IDYNKTLMDY  YLAFEKYRSL  420
II                                                                     422

SEQ ID NO: 72          moltype = AA  length = 714
FEATURE                Location/Qualifiers
source                 1..714
                       mol_type = protein
                       organism = Fusobacterium necrophorum
SEQUENCE: 72
MKKVVFGICS  ILISSAMLGA  EIDLGTQNIY  SETGFETSLR  SSVSSPYIVT  SKEIKEKHYT   60
RVSEILRDIP  HIYIGPGGSV  DMRGQGSAHA  RTTVQLLIDG  VPANFLDTSH  INLPIDTLNP  120
EDIKRIEVIP  GGGAVLYGSG  TSGGVINIIT  KKYTGNYAKA  SYQIGSYHNH  KYDVAAGTSL  180
GNFDINLSYS  KNNRDGYRKK  AFSDSDFFSG  KLRYHFNPTD  SLEFKYSYFD  NKFRGVKSLT  240
REQVEKDRRQ  SGLSPEDNLK  NTIRKEEWNL  TYDAKWTSWL  EHKSNLFYQS  TEIKSSEYED  300
ALPFYQYQIS  SYQKMLTMPG  IPPMMQAQLK  KQIKALQNLI  TSNPRMELHQ  GSRFKDQKFG  360
FKMKNKPKYG  ENSDFILGLG  YIHNKMDRDS  WAYTKNTQTN  QTIATLTNTK  IPLNKKTFEI  420
FGLNTYRHNN  WEFVQGLRFE  KAKYNGKRQY  KNLEYPLKDR  SMNNVAANLA  VNYLYSDTGN  480
VYVKYERGFT  SPAPAQLMDK  IRKGGVNDYV  NNDLKSEKSN  SFEVGWNDYL  FHSLVSADVF  540
FSETKDEIST  IFSGGHGTTF  SNLNLGQTKR  YGFDLKASQV  FEKWTFSEAY  SYIHAKIMKD  600
KTKAYEGKYI  SYVPRHKFSL  NADYAITPKW  TLGGEYQYSS  SVYLDNANKN  GKDGARSVFN  660
LQTSYEFNSH  FSIYAGIKNV  LNHKYYESVS  AGSSQKYYSP  APERNYYAGF  RYQF        714

SEQ ID NO: 73          moltype = AA  length = 714
FEATURE                Location/Qualifiers
source                 1..714
                       mol_type = protein
                       organism = Fusobacterium necrophorum
```

```
SEQUENCE: 73
MKKVVFGICS ILISSAMLGA EIDLGTQNIY SETGFETSLR SSVSSPYIVT SKEIKEKHYT    60
RVSEILRDIP HIYIGPGGSV DMRGQGSAHA RTTVQLLIDG VPANFLDTSH INLPIDTLNP   120
EDIKRIEVIP GGGAVLYGSG TSGGVINIIT KKYTGNYAKA SYQIGSYHNH KYDVAAGTSL   180
GNFDINLSYS KNNRDGYRKK AFSDSDFFSG KLRYHFNPTD SLEFKYSYFD NKFRGVKSLT   240
REQVEKDRRQ SGLSPEDNLK NTIRKEEWNL TYDAKWTSWL EHKSNLFYQS TEIKSSEYED   300
ALPFYQYQIS SYQKMLTMPG IPPMMQAQLK KQIKALQNLI TSNPRMELHQ GSRFKDQKFG   360
FKMKNKFKYG ENSDFILGLG YIHNKMDRDS WAYTKNTQTN QTIATLTNTK IPLNKKTFEI   420
FGLNTYRHNN WEFVQGLRFE KAKYNGKRQY KNLEYPLKDR SMNNVAANLA VNYLYSDTGN   480
VYVKYERGFT SPAPAQLMDK IRKGGVNDYV NNDLKSEKSN SFEVGWNDYL FHSLVSADVF   540
FSETKDEIST IFSGGHGTAF SNLNLGQTKR YGFDLKASQV FQKWTFSEAY SYIHAKIVKD   600
KNKAYEGKYI SYVPRHKFSL NADYAITPKW TLGGEYQYSS SVYLDNANKN GKDGARAVFN   660
LQTSYEFNSH FSIYAGIKNV LNHKYYESVT AGSGQKYYSP APERNYYAGF RYQF         714

SEQ ID NO: 74           moltype = AA   length = 714
FEATURE                 Location/Qualifiers
source                  1..714
                        mol_type = protein
                        organism = Fusobacterium necrophorum
SEQUENCE: 74
MKKVVFGICS ILMSSAMLGA EIDLGTQNIY SETGFETSLR SSVSSPYIVT SKKIKEKHYT    60
RVSEILRDIP NIYIGSGGSV DMRGQGSIHS RTTVQLLIDG VPANFLDTSH INLPIDTLNP   120
EDIERIEVIP GGGAVLYGSG TSGGVINIIT KKYTGNYAKA GYQIGSYHNH KYDVAAGTSL   180
GKFDINLSYS KNNRDGYRKK AFSDSDFFSG KLRYHFNPTD SLEFKYSYFD NKFRGVKSLT   240
REQVEKDRRQ SDLSPEDNLK NTIRKEEWNL TYDAKWTSWL EHKSNLFYQS TEIKSSEYED   300
ALPFYQYQIS SYQKMLTMPG IPPMMQAQLK KQIKALQNLI MSNPRMELHQ GSRFKDQKFG   360
FKMKNKFKYG ENSDFILGLG YIHNKMDRDS WAYTKNTQTN QTIATLTNTK IPLNKKTFEI   420
FGLNTYRHNN WEFVQGLRFE KAKYNGKRQY KNLEYPLKDR SMNNVAANLA VNYLYSDTGN   480
VYVKYERGFT SPAPAQLMDK IRKGGVNDYV NNDLKSEKSN SFEVGWNDYL FHSLVSADVF   540
FSETKDEIST IFSGGHGTTF SNLNLGQTKR YGFDLKASQV FQKWTFSEAY SYIHAKIVKD   600
KTKAYEGKYI SYVPRHKFSL NADYAITPKW TLGGEYQYSS SVYLDNANKN GKDGARSVFN   660
LQTSYEFNSH FSIYAGIKNV LNHKYYESVS AGSSQKYYSP APERNYYAGF RYQF         714

SEQ ID NO: 75           moltype = AA   length = 714
FEATURE                 Location/Qualifiers
source                  1..714
                        mol_type = protein
                        organism = Fusobacterium necrophorum
SEQUENCE: 75
MKKVIFGIYS ILLSSAMLGA EIDLGTQNIY SETGFETSLR SSVSSPYIVT SKKIKEKHYT    60
RVSEILRDIP NIYIGSGGSV DMRGQGSIHS RTTVQLLIDG VPANFLDTSH INLPIDTLNP   120
EDIERIEVIP GGGAVLYGSG TSGGVINIIT KKYTGNYAKA GYQIGSYHNH KYDVAAGTSL   180
GKFDINLSYS KNNRDGYRKK AFSDSDFFSG KLRYHFNPTD SLEFKYSYFD NKFRGVKSLT   240
REQVEEDRRQ SGLSPEDNLK NTIRKEEWNL TYDAKWTNWL EHKSNLFYQS SEIKSSDYED   300
AIPFYQARIA MYQQMLATPG IPPMMLEKLK KQIQIWENII TNNPKMELRQ GSLFKDRKFG   360
FKMKNKFKYG ENSDFILGLG YIHNKMNRNS WAYTKNTQTN QTIETITDTK IPLNKKTFEI   420
FGLNTYRHNN WEFVQGLRFE KAKYSGKRQY KNLEYPLKDR SMNNVAANLA VNYLYSDTGN   480
VYVKYERGFT SPAPAQLMDK IKKGGVNDYV NNDLKSEKSN SFEVGWNDYL FHSLVSADVF   540
FSETKDEIST IFSGGHGTAF SNLNLGQTKR YGFDLKASQV FRKWTFSEAY SYIHAKIVKD   600
KNKAYEGKYI SYVPRHKFSL NADYAITPKW TLGGEYQYSS SVYLDNANKN GKDGARAVFN   660
LQTSYEFNSH FSIYAGIKNV LNHKYYESVT AGSGQKYYSP APERNYYAGF HYQF         714

SEQ ID NO: 76           moltype = AA   length = 714
FEATURE                 Location/Qualifiers
source                  1..714
                        mol_type = protein
                        organism = Fusobacterium necrophorum
SEQUENCE: 76
MKKVVFGIYS ILMSSAMLGA EIDLGTQNIY SETGFETSLR SSVSSPYIVT SKKIKEKHYT    60
RVSEILRDIP NIYIGSGGSV DMRGQGSIHS RTTVQLLIDG VPANFLDTSH INLPIDTLNP   120
EDIERIEVIP GGGAVLYGSG TSGGVINIIT KKYTGNYAKA GYQIGSYHNH KYDVAAGTSL   180
GKFDINLSYS KNNRDGYRKK AFSDSDFFSG KLRYHFNPTD SLEFKYSYFD NKFRGVKSLT   240
GEQVEEDRRQ SGLSPEDNLK NTIRKEEWNL TYDAKWTNWL EHKSNLFYQS SEIKSSDYED   300
AIPFYQARIA MYQQMLATPG IPPMMLEKLK KQIQIWENII TNNPKMELRQ GSLFKDRKFG   360
FKMKNKFKYG ENSDFILGLG YIHNKMNRNS WAYTKNTQTN QTIETITDTK IPLNKKTFEI   420
FGLNTYRHNN WEFVQGLRFE KAKYSGKRQY KNLEYPLKDR SMNNVAANLA VNYLYSDTGN   480
VYVKYERGFT SPAPAQLMDK VKKGGVNDYV NNDLKSEKSN SFEVGWNDYL FHSLVSADVF   540
FSETKDEIST IFSGGHGTAF SNLNLGQTKR YGFDLKASQV FQKWTFSEAY SYIHAKIVKD   600
KNKAYEGKYI SYVPRHKFSL NADYAITPKW TLGGEYQYSS SVYLDNANKN GKDGARAVFN   660
LQTSYEFNSH FSIYAGIKNV LNHKYYESVT AGSGQKYYSP APERNYYAGF RYQF         714

SEQ ID NO: 77           moltype = AA   length = 714
FEATURE                 Location/Qualifiers
source                  1..714
                        mol_type = protein
                        organism = Fusobacterium gonidiaformans
SEQUENCE: 77
MKKVVFGICS ILMSSAMLGA EIDLGTQNIY SETGFETSLR SSVSSPYIVT SKKIKEKHYT    60
RVSEILRDIP NIYIGSGGSV DMRGQGSIHS RTTVQLLIDG VPANFLDTSH INLPIDTLNP   120
```

```
EDIERIEVIP GGGAVLYGSG TSGGVINIIT KKYTGNYAKA GYQIGSYHNH KYDVAAGTSL    180
GKFDINLSYS KNNRDGYRKK AFSDSDFFSG KLRYHFNPTD SLEFKYSYFD NKFRDVKSLT    240
REQVEEDRRQ SGLSPKDNLK NTIRKEEWNL TYDAKWTNWL EHKSNLFYQS SEIKSSEYED    300
AIPFYQARIA MYQQMLATPG IPSMMLEKLK KQIQFWENII TNNPKMELRQ GSLFKDRKFG    360
FKMKNKFKYG ENSDFILGLG YIHNKMNRNS WAYTKNTQTN QTIETITDTK IPLNKKTFEI    420
FGLNTYRHNN WEFVQGLRFE KAKYSGKRQY KNLEYPLKDR SMNNVAANLA VNYLYSDTGN    480
VYVKYERGFT SPAPAQLMDK IKKGGVNDYV NNDLKSEKSN SFEVGWNDYL FHSLVSADVF    540
FSETKDEIST IFSGGHGTAF SNLNLGQTKR YGFDLKASQV FQKWTFSEAY SYIHAKIVKD    600
KNKAYEGKYI SYVPRHKFSL NADYAITPKW TLGGEYQYSS SVYLDNANKN GKDGARAVFN    660
LQTSYEFNSH FSIYAGIKNV LNHKYYESVT AGSGQKYYSP APERNYYAGF RYQF         714

SEQ ID NO: 78           moltype = DNA   length = 4263
FEATURE                 Location/Qualifiers
source                  1..4263
                        mol_type = genomic DNA
                        organism = Fusobacterium necrophorum
SEQUENCE: 78
atgaaaaaat taaaaaattt tgaaaatgtt ttaaaatcgc atttaaaaca aagagtaaga     60
attacgacag cattcattgt tgctttttta attcatggga tgctaagctt tgatgttgaa    120
gcaagagatt taagagttag gaatcaaata actccgtcaa attcaaataa tggcttaaga    180
ataacttcaa gccaaaatgg gaccgatgtt attaatattg ttgatcctaa taatggaata    240
tctcacaata agtatgtaga ttttaatgtt ggggacaaaa ataatgttat ttttaacaac    300
agtcaaaaaa atgggaacttc tgttacagga ggagaagtca gtgcaaaccc aaatttaaca    360
aactctgctt ctgttatctt gaatgaaatt caaggaaatt ctgctcaga attaaacgga    420
ggacttgaag ttttgggaa agagcagat cttgttattg ccaatgaaaa tggaataaat    480
gtaaatggag caagatttat aaacacttca gctctaacta tatcaacagg aaaagtctca    540
gtcgataata aaaaaattcc ttttaacaca gctacaaata atgcaaagat agcagtaaaa    600
gaaaaaggaa tagaaacaga ttctgattac ttgaatatcc tttcaagaag ggctgaacta    660
gatggagcaa tcaactctga acataataaa aatttaaata tcaatgttat agctggtgca    720
aatactgtta cagctgtaaa tgatacttc gaattaacatc tgaaaacgc caaagatgga    780
attaccaatg tagaagctat ttccgcttca aaatttggag ctatgtatgg aaataacatt    840
tttatcttga gtactaataa aggcgaagga atcaaatatg aaggaagcct aaaagcaaag    900
gatgaagtgg agataatctc tgaaggaaaa gttgtaagtt ctgacataaa tggaaaagat    960
atcaaaatat cgtctaaaga agaaattaac aatattggaa gataaaagc ggataaaaat   1020
gtcagtctta atgctcctat cgtaaaaaat atgtccagat tagaaggaag tgttagatta   1080
aaatcaaatg aacataataa aaagtatcaa aatagagaaa gaggaattat ctattatgac   1140
tattatttaa atgtgaaaaa tatgtcgaaa gtggaaaatg aattaaaatt agttaaatcg   1200
tctattgaag ccggaaataa tattgaaata aataataatc ttgaaaatgg aagtttttgaa   1260
aatttatctg gggatttaaa agcaggaaat gatatcaaag taaaggaaa ttttaaaaca   1320
aaacatttgt cagaaggaat aaagctagaa gatcttttaa aaagaataaa agtagatctt   1380
cgttgggagc acagaagtct agttgataac gcatatttta atggaaactc ttcttttaaca   1440
gatggaagct tgttggatgc tttaaaaata atgactcaaa agaaaaataa agaatattac   1500
acagccttaa aacaaattga tgaccctcaa ttaaataaag ttttaagtgg tttattaggg   1560
gctgattgga gaacaaggga acgaataaaa gatgaaaaag attggaataa agaagcagcc   1620
ataagtttta caaatggaac ttattcaata gaagcaggaa atgacttgaa agcttctgga   1680
aaagtgattg aacttggtgg ttctaatgtt atgactaaaa agaaatatt tgaagtagca   1740
tctacgaaaa cggaaaattt acaatcaacg atttcagatg ttaaaatgc taatataaaa   1800
gcgaaaaatg tttatatgga agccgataat ataacaaatg taaatgcaga tattgcagcg   1860
gaagacagtg cgattcttta ttctaaaaac aatattgatg tgaagggagc taaagttttct   1920
gctgataaaa ttcttcttga agctggtaaa gatataaatt tatcttcaga acttggtttc   1980
aaatcttctg gggaacatgc gattattaaa gaaacagatg ttactgcaaa taaggctgtt   2040
ggaatcaaat ccaagaactt aaatatttat ggtgcagatg tagaggcaaa agatggactt   2100
ataaaaaatag actctgataa gttaaatgta aaagatatca gtacaatcaa tgcaaattat   2160
aaggccgaat aatagaaggg aaaaaaatat attttaagag atcatcaata tacaaaagct   2220
ttacaagcta aagtggaatc tacaccttct aaaataaattg ctaataaaat tttttatcact   2280
gcaaagatgg tgctgctat tgagggttca ctgatttcag gaaaaaatgc tgacagcata   2340
atccaaatca tttctgaggg aaatgtcaat atcaaaaata gcaataatat tgattatagt   2400
aattttttat cagatagcag aggaaaaaat aaaaaggag tctacaaatt attaaaaata   2460
gataaggctt caaaagaaaa tcttgacata gtaggaagca acttaaaatc ggaaggaaat   2520
ataaatataa aatcaaaaaa tttaactgtt gtatcaagta aaataaaagc aggaaaaaaa   2580
gttaacttag aagccgaaga agatataaaa ttactagctt ctttgaattc taagaaagag   2640
gaattaaaata agatggaatg gggtagcggt gctatcaata gttataaaaa gtctttggag   2700
aaaaaagatg tagtgtctac tatgattgaa gctggagaaa aagcaaatgt acatgcaaaa   2760
agagatttgt ataaacaatc tgtttttgtg aaagctgaaa gcgtaactat gaatggtgag   2820
gcaaataatt acagtgatgc tttagcttca acagaaataa aaaagaaac agatgtgaaa   2880
gctggctttg tgtagaagg aaagattgct tttgctggaa tgggagcagc tggggaagca   2940
aacactttag ataatacagc aacaggaaaa acttccggga taaaaggtct tttagaaaaa   3000
gagaatgaat ttaaaaaagc ggaagccaga gcgaaagttt acgcaaaaat ggagttaat   3060
aagagcataa aagaaagtaa aaattatgta aataacaaca ttacctcgga aagtggtgat   3120
gtgactatag ttctaatgg ggtcactgat ataggaaata ccgatatcaa ttctcaaaat   3180
gatgttaact taagaggtaa aaaagtagaa accactacaa aggaaaaatgt aacgaaagag   3240
gttaatcata agcttgatct ttctgtaaaa ggtgacatcg ctttttctaa tgaaaatgtc   3300
aataaattga atgatttggc aaatgatgtt ctaaaagtaa aagagatgtt agaaaagaaa   3360
gatatactcg ggttagctca aaagcagaa gaaacaatta aaagaacttc g             3420
ccaaatctaa ctaaaaaaga catttttagga ataaaatcaa gtcagggagt aggggtagaa   3480
tacactaata aaacttctac tactacgaa acaacagctt cttcttttgaa agcgaaaggg   3540
aagtttaaata taaggcaga tgaaggaat attactttaa aaaacactta tttaaagtct  3600
caagagttta acacagaaac tcctggaaaa gttaatcttt tagcagggaa gaaacgatt  3660
cataaagaag aaaattcttt aaaggttggt gtatcagtta acgaaaatgt aggagtcaat   3720
```

```
atagcagatg gagccaatgc taaaattggt gtaggtgttc aagctagtta caatggcgga    3780
actgatttga ataaaaaaag tttaaataca actgtagagg taggaaaagt gaatcataaa    3840
gctgcagctg taaatgaaga taataaaaca gactttttatt acaaagataa aagaggtgca    3900
ggagttgatg ttgatttaaa aataggagtt tcttcgaatc atatagtagc ggcagatgga    3960
aatgtaggag gaaatgtgaa ttattctttt gcggctggaa aatcaacaac agatgttgta    4020
acaaataaga cagaaagtac tgatgtaaaa gcagggggttg gactgaaagc ttctgttgga    4080
atagatggaa aaagtccaga ttttcaatt tcaacagacc aaattgaata taaaaaagat    4140
ggaaaagtat tagttaatat tgacgcaaaa gataaaatga tcaccaaaga gagaattgaa    4200
cagatgagag ataaggtaaa aaattggaga actccaacaa atagtgcgga aaaattaatc    4260
taa                                                                  4263

SEQ ID NO: 79           moltype = AA  length = 736
FEATURE                 Location/Qualifiers
source                  1..736
                        mol_type = protein
                        organism = Fusobacterium necrophorum
SEQUENCE: 79
MKKILFLVGA LFSISAFAEQ TIELGSTSIK GNRKTDYTLT PKEYKNTYTI TQEKIRERNY    60
KNVEDVLRDA PGVVVQNTAF GPRIDMRGSG EKSLSRVKVL VDGISINPTE ETMASLPINS    120
IPIESVKKIE IIPGGGATLY GSGSVGGVVS ISTNSNVTKN NFFMDLNYGS FDNRNFGFAG    180
GYNVSDKLYV NYGFNYLNSE DYREHEEKEN KIYLLGFDYK INPKNRFRVQ TRYSKMKHDG    240
SNWLSQEELK ISRKKAGLNL DLDTTDKSYT FDYEYRPSQN LTLAATAYKQ QQDRDITTDD    300
IRDIEIIASN RNYTDLKEYM TFYDVKSTLK AKFKEKKYGL KLKGKYEYGR GEVIFGYDYQ    360
DSNNKRNSLV QSETLKTYND KISDNLSPE DRKPIINRVN IDLTKKSHGF YVFNKLELTD    420
KWDFTTGFRT EITKYNGYRK NGPNTMPIVS PKVNEIRTDE KMTNYAGEAG MLYKYSDTGR    480
APVRYERGFV TPFANQLTDK IHDTKLKSPA GFFTPPIVNV SSLYVANNLK SEITDTIEVG    540
FRDYIFNSLI SASFFATDTT DEITLISSGI TNPAVNRWKF RNIGKTRRLG IELEAEQKWG    600
KFDFSQSLTF VDTKVLKTDA ESRIFRGDKV PMVPRIKATL GLKYNVTDNL ALIGTYTYLS    660
KRETRELDEK DKVYKHTIKG YGTADLGILY KVDKYSNFKV GAKNIFGKKY NLRETKLEAL    720
PAPERNYYLE FNVKFN                                                    736

SEQ ID NO: 80           moltype = AA  length = 694
FEATURE                 Location/Qualifiers
source                  1..694
                        mol_type = protein
                        organism = Fusobacterium necrophorum
SEQUENCE: 80
LKVNFIMKRE SEKMKKILFL VGALFSISAF AEQTIELGST SIKGNRKTDY TLTPKEYKNT    60
YTITQEKIRE RNYKNVEDVL RDAPGVVVQN TAFGPRIDMR GSGEKSLSRV KVLVDGISIN    120
PTEETMASLP INSIPIESVK KIEIIPGGGA TLYGSGSVGG VVSISTNSNV TKNNFFMDLN    180
YGSFDNRNFG FAGGYNVSDK LYVNYGFNYL NSEDYREHEE KENKIYLLGF DYKINPKNRF    240
RVQTRYSKMK HDGSNWLSQE ELKISRKKAG LNLDLDTTDK SYTFDYEYRP SQNLTLAATA    300
YKQQQDRDIT TDDIRDIEII ASNRNYTDLK EYMTFYDVKS TLKAKFKEKK YGLKLKGKNID    360
LTKKSHGFYV FNKLELTDKW DFTTGFRTEI TKYNGYRKNG PNTMPIVSPK VNEIRTDEKM    420
TNYAGEAGML YKYSDTGRAF VRYERGFVTP FANQLTDKIH DTKLKSPAGF FTPPIVNVSS    480
LYVANNLKSE ITDTIEVGFR DYIFNSLISA SFFATDTTDE ITLISSGITN PAVNRWKFRN    540
IGKTRRLGIE LEAEQKWGKF DFSQSLTFVD TKVLKTDAES RIFRGDKVPM VPRIKATLGL    600
KYNVTDNLAL IGTYTYLSKR ETRELDEKDK VYKHTIKGYG TADLGILYKV DKYSNFKVGA    660
KNIFGKKYNL RETKLEALPA PERNYYLEFN VKFN                                694

SEQ ID NO: 81           moltype = AA  length = 680
FEATURE                 Location/Qualifiers
source                  1..680
                        mol_type = protein
                        organism = Fusobacterium gonidiaformans
SEQUENCE: 81
MRKMLFLIGA LLSISAFAEQ TVELGSTSIK GNRKADYTLT PKEYKNTYTI TQEKIQERNY    60
KNVEDVLRDA PGVVIQNTAF GPRIDMRGSG EKSLSRVKVL VDGVSINPTE ETMASLPINS    120
IPIETVKKIE IIPGGGATLY GSGSVGGVVS ITTNSNATKN NFFMDLNYGS FDNRNFGFAG    180
GYNVTDKLYV NYGFNYLNSE DYREHEEKEN KIYLLGFDYK INAKNRFRVQ TRYSKMKHDG    240
SNWLSQDELK TSRKKAGLNL DLDTTDKSYT FDYEYRPTEN LTLAATAYKQ QQDRDITTDD    300
IRDIEIVASN RNYTDLKEYM TFYDVKSTLK AKFKEEKHGI KLKGDIDLTK KSHGFYAFNK    360
LELGKKFDFT TGFRTEITEY NGYRKNGPNT MPIISPKTNE IKTNEKMTNY AGEAGMLYK    420
SDTGRAFVRY ERGFVTPFAN QLTDKIHDTE LKNPGGFFTP PIVNVASLYV ANNLKSEITD    480
TIEVGFRDYI FDSLVSASFF ATDTTDEITL ISSGITNPAV NRWKFRNIGK TRRLGIELEA    540
EQKWGDFEFS QSLTFVDTKV LKTDKESNIY RGDKVPMVPN IKATLGLKYN VTDNLSLIGT    600
YTYLSKRETR ELDEKDKVYK HTIKGYGTAD LGVLYKVDKY SNFKVGAKNL FGKKYNLRET    660
KLEALPAPER NYYLEFNVKF                                                680

SEQ ID NO: 82           moltype = AA  length = 736
FEATURE                 Location/Qualifiers
source                  1..736
                        mol_type = protein
                        organism = Fusobacterium necrophorum
SEQUENCE: 82
MRKTLLLFSI LATLAYAEQT VELGSSSIRS SAKKTDYTLI PKEYKNTYTI TQETIRERNY    60
KNVEDVLRDA PGVVIQNTAF GPRVDMRGSG EKSLARVKVL VDGISINPTE ETMASLPINS    120
IPIESVKKIE IIPGGGATLY GSGSVGGVVS ISTNSNVTKN NFFMDLNYGS FDNRNFGFAG    180
GYNVNKKLYV NYGFNYLNSE SYRKHEEKEN KIYLVGFDYK FNGKNRVRFQ TRQSDIMDHG    240
```

```
SNQLRKTELE GDRRAPGLAL NLDTKDQSYT MDYEYRPTEK LTLGATAYQQ QQDRDIYTED    300
IRDIEIVASD RNYTDIKEYM IFHDVKSTMK AKFKEKKHGI KLKGKYDYGK GEIIFGYDYY    360
DSNNRRDSHV RSETLKTYNT KYTDSVLSPE ERLPIINNVK IDLTKKSHGF YAFNKWNVNK    420
NFDFTTGFRI EKTKYNGYRK NGKNTMPIAV AKTDVIRTDE RHTNFAGEVG GLWKYSDTGR    480
FFTRYERGFV TPFSTQLTDK IHDTELKNPN GFFIPPIVNS ASKYVANHLQ PEITDTVEIG    540
FRDYFYNSLF SASFFVTDTK DEITLISSGI TNPAVNRWRY RNIGKTRRFG IELEAEQKFG    600
KFGLTESLTF VDSKVLKTDA NSNIFRGDRV PMVPRLKATL GIKYRMTDDL TLLANYTYLS    660
KREARELDEK DKIYRHTIKG HGVLDVGALY RIDKYSNVKV GAKNLFSKKY NLRETKVEAL    720
PAPERNYYLE FNVKFD                                                   736

SEQ ID NO: 83           moltype = AA  length = 744
FEATURE                 Location/Qualifiers
source                  1..744
                        mol_type = protein
                        organism = Fusobacterium nucleatum
SEQUENCE: 83
MKKLLVLLTI LSSIIAHAED TIELKETTVK SSPRSSDYTL IPKEQKNTYV ITQEKIRERN     60
YKNVEDVLRD APGVTIQNTA FGPRVDMRGS GEKSLSRVKV LIDGVSINPT EETMASLPIN    120
SIPIESVKKI EIIPGGGATL YGSGSVGGVI SITTNSNVTK NNFFADLNYG SFDNRNFGFA    180
GGYNVTKNLY VNYGFNYLNS EGYRREEEKE NKIYLLGFDY KINSKNRFRF QTRYSKFKDD    240
GSNQVTREVL EYDRRAIGLN LDMITKDKSY TFDYEYRPKN NLTLAATIYK QEQDRDIQTE    300
SIDDIRIVSS PAGYTYGSYK EEMNFYGVTS KMNAKFEEDK KGLKLKSKYD YSNGQIIFGY    360
DYQKAVNKRD SFVQSETLKS YNNGYSNKTL EGEDIQPVIN RVKVNMEKES HGFYVFNKFD    420
VTDKLDITTG FRTEITKYNG KRVNGPNTMP FVAAKTAEIN TDRKLENYAG EFGALYEYRD    480
TGRVFLRYEK GFVTPFANQL TDKVRDTTLP KKVGFFDPPQ VNVASKYVDN NLKSEKTDTV    540
ELGVRDYFFG SLFSASVFLT DTKDEITLIS SGVTNPAVNR WKYRNIGKTR RMGLELEAEQ    600
NFGNWSLSQS LTLLNTKVLK ANEEARLEKG DKVPLVPRVK ATLGVKYNFT DKIALIGTYT    660
YFSKRETREI RESEDLNKDD NIIKHTIGGY GITDLGVLYK ADAYSNIKVG AKNIFNKKYN    720
LRETSLEALP APEKTYYLEM NVRF                                          744

SEQ ID NO: 84           moltype = AA  length = 689
FEATURE                 Location/Qualifiers
source                  1..689
                        mol_type = protein
                        organism = Fusobacterium nucleatum
SEQUENCE: 84
MKKLLVLLTI LSSIIAYAED TIELNQTTVK SSPRSSDYTL IPKEQKNTYV ITQEKIRERN     60
YKNVEDVLRD APGVTIQNTA FGPRVDMRGS GEKSLSRVKV LIDGVSINPT EETMASLPIN    120
SIPIESVKKI EIIPGGGATL YGSGSVGGVI SITTNSNVTK NNFFADLNYG SFDNRNFGFA    180
GGYNVTKNLY VNYGFNYLNS EGYRREEEKE NKIYLLGFDY KINAKNRFRF QTRYSKFKDD    240
GSNQVAREVL EYDRRAVGLN LDMITKDKSY TFDYEYRPKN NLTLAATIYK QEQDRDIQTE    300
SIDDIRIVSS PAGYTYGSYK EEMNFYGVTS KMNAKFEEDK KGLKLKSKVN MEKESHGFYV    360
FNKFDATDKL DITTGFRTEI TKYNGKRVNG PNTMPFVAAK TAEINTDRKL ENYAGEFGAL    420
YKYRDTGRVF LRYEKGFVTP FANQLTDKVR DTTLPKKVGF FDPPQVNVAS KYVDNNLKSE    480
KTDTVELGVR DYFFGSLFSA SVFLTDTKDE ITLISSGVTN PAVNRWKYRN IGKTRRMGLE    540
LEAEQNFGNW SLSQSLTLLN TKVLKANEEA RLEKGDQVPL VPRVKATLGV KYNFTDKIAL    600
VGTYTYFSKR DTREIRESED LNKDDDIIKH TIGGYGVTDL GVLYKADAYS NIKVGAKNIF    660
NKKYNLRETS LEALPAPEKT YYLEMNVRF                                     689

SEQ ID NO: 85           moltype = AA  length = 747
FEATURE                 Location/Qualifiers
source                  1..747
                        mol_type = protein
                        organism = Fusobacterium periodonticum
SEQUENCE: 85
MKKLLVLLTI LTSIASFSED VIELGQTTVK GSKTSDYTAP PKEQKNTFVI TQERIREKNY     60
KNVEDILRDA PGVVVQNTAF GPRIDMRGSG EKSLSRVKVL VDGVSINPTE ETMASLPINA    120
IPVESIKKIE IIPGGGATLY GSGSVGGVVN ISTNSNVTKD NFFMDLNYGS FDNRNFGFAG    180
GYNFNKHLYV NYGFSYLNSE DYREHEEKEN KIYLLGFDYK INAKHRFRFQ TRFSDIKQDS    240
SNQIPVEELK NDRRKAGLNM DINTKDRSYT FDYEYRPTQN ATLSTTFYKQ KQERDIDTES    300
IDDIKIIASD RTHTWHKEEM NFYDIKSKMH ADFKEDKDGA KLKAKFDYNL VENLPSETII    360
GYDYQSATNK RNSLVQSETL KTYNNGYMDI NLSQSERLPV INRVDMEMKR KSQGIYVFNK    420
WGLANWLDVT LGGRMEKTKY NGYRENGPNV MPYVEPEVKR IETNRKLDNY AEELGFLFKY    480
NDTGRFYTRY ERGFVTPFGN QLTDKIHDTT LKNPNSGFII PPTVNVASKY VDNNLNAEKT    540
DTFEIGFRDY ILGSTLSTSF FLTNTKDEIT LISSGVTNPA VNRWKYRNIG KTRRFGLEFE    600
AEQNFGKFRF NQSLTLVRTK VLVANEEAKL ERGDQVPMVP RLKATLGLRY NFTDRLAGFV    660
NYTYLAKQES RELRENEDLN KDDIVVKHTI GGHGVVDAGF SYKPDAYSDI KIGAKNLFSK    720
KYNLRETSLE ALPAPERNYY LELNVRF                                       747
```

UNITED STATES PATENT AND TRADEMARK OFFICE
CERTIFICATE OF CORRECTION

PATENT NO. : 12,178,866 B2
APPLICATION NO. : 18/144568
DATED : December 31, 2024
INVENTOR(S) : Charles Nelson Carver, III et al.

Page 1 of 1

It is certified that error appears in the above-identified patent and that said Letters Patent is hereby corrected as shown below:

In the Specification

In Column 10, Line 48 delete "FIG 14-23, 24A, 24B, 48, 49A, 49B, and 50" and insert -- FIG 14-23, 24A, 24B, 25-48, 49A, 49B, and 50 -- therefor.

Signed and Sealed this
Twenty-ninth Day of July, 2025

Coke Morgan Stewart
*Acting Director of the United States Patent and Trademark Office*